United States Patent
Liu et al.

(10) Patent No.: US 10,836,743 B2
(45) Date of Patent: Nov. 17, 2020

(54) FLUORINATED CYCLOPROPYLAMINE COMPOUND, PREPARATION METHOD THEREFOR, PHARMACEUTICAL COMPOSITION THEREOF, AND USES THEREOF

(71) Applicant: SHANGHAI INSTITUTE OF MATERIA MEDICA, CHINESE ACADEMY OF SCIENCES, Shanghai (CN)

(72) Inventors: Hong Liu, Shanghai (CN); Jia Li, Shanghai (CN); Jiang Wang, Shanghai (CN); Mingbo Su, Shanghai (CN); Shuni Wang, Shanghai (CN); Yubo Zhou, Shanghai (CN); Wei Zhu, Shanghai (CN); Wei Xu, Shanghai (CN); Chunpu Li, Shanghai (CN); Hualiang Jiang, Shanghai (CN); Kaixian Chen, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 3 days.

(21) Appl. No.: 16/085,311

(22) PCT Filed: Mar. 16, 2017

(86) PCT No.: PCT/CN2017/076967
§ 371 (c)(1),
(2) Date: Dec. 11, 2018

(87) PCT Pub. No.: WO2017/157322
PCT Pub. Date: Sep. 21, 2017

(65) Prior Publication Data
US 2019/0100507 A1    Apr. 4, 2019

(30) Foreign Application Priority Data
Mar. 16, 2016  (CN) .......................... 2016 1 0149958

(51) Int. Cl.
| | |
|---|---|
| C07D 401/12 | (2006.01) |
| C07D 401/06 | (2006.01) |
| C07D 405/12 | (2006.01) |
| C07D 409/12 | (2006.01) |
| C07D 409/14 | (2006.01) |
| C07D 417/12 | (2006.01) |

(Continued)

(52) U.S. Cl.
CPC ............ *C07D 401/12* (2013.01); *A61P 35/00* (2018.01); *C07C 211/37* (2013.01); *C07C 233/41* (2013.01); *C07C 233/43* (2013.01); *C07C 271/24* (2013.01); *C07C 311/20* (2013.01); *C07D 205/04* (2013.01); *C07D 211/38* (2013.01); *C07D 211/46* (2013.01); *C07D 211/96* (2013.01); *C07D 265/30* (2013.01); *C07D 401/06* (2013.01); *C07D 401/14* (2013.01); *C07D 405/12* (2013.01); *C07D 409/06* (2013.01); *C07D 409/12* (2013.01); *C07D 409/14* (2013.01); *C07D 417/12* (2013.01); *C07D 417/14* (2013.01); *C07D 471/04* (2013.01); *C07B 2200/07* (2013.01); *C07C 2601/02* (2017.05); *C07C 2601/14* (2017.05); *Y02P 20/55* (2015.11)

(58) Field of Classification Search
CPC .. C07D 401/12; C07D 205/04; C07D 211/38; C07D 211/46; C07D 211/96; C07D 265/30; C07D 401/06; C07D 401/14; C07D 405/12; C07D 409/06; C07D 409/12; C07D 409/14; C07D 417/12; C07D 417/14; C07D 471/04; C07C 211/37; C07C 233/41; C07C 233/43; C07C 271/24; C07C 311/20; A61P 35/00
USPC ....................................... 514/210.2
See application file for complete search history.

(56) References Cited

FOREIGN PATENT DOCUMENTS

| | | |
|---|---|---|
| RU | 2013108702 A | 9/2014 |
| WO | 2012135113 A2 | 10/2012 |

(Continued)

OTHER PUBLICATIONS

Cancer [online], [retrieved on Jul. 6, 2007] Retrieved from the Internet, URL: http://www.nlm.nih.gov/medlineplus/cancer.html (Year: 2007).*

(Continued)

*Primary Examiner* — Kristin A Vajda
(74) *Attorney, Agent, or Firm* — Panitch Schwarze Belisario & Nadel LLP

(57) ABSTRACT

Provided is a fluorinated cyclopropylamine compound represented by formula I, a racemate thereof, an R-isomer thereof, an S-isomer thereof, a pharmaceutical salt thereof, and a mixture thereof. Also provided are pharmaceutical compositions containing the compound, a preparation method for the compound, and uses thereof as a lysine specific demethylase 1 (LSD1) inhibitor, and in the treatment of cancers.

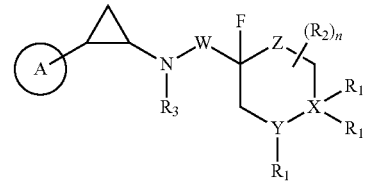

Formula I

12 Claims, No Drawings

(51) Int. Cl.

| | |
|---|---|
| *C07D 471/04* | (2006.01) |
| *C07D 205/04* | (2006.01) |
| *C07D 265/30* | (2006.01) |
| *C07D 211/38* | (2006.01) |
| *C07D 211/96* | (2006.01) |
| *A61P 35/00* | (2006.01) |
| *C07D 409/06* | (2006.01) |
| *C07C 233/41* | (2006.01) |
| *C07D 211/46* | (2006.01) |
| *C07C 311/20* | (2006.01) |
| *C07C 233/43* | (2006.01) |
| *C07C 271/24* | (2006.01) |
| *C07C 211/37* | (2006.01) |
| *C07D 417/14* | (2006.01) |
| *C07D 401/14* | (2006.01) |

(56) References Cited

FOREIGN PATENT DOCUMENTS

| WO | 2015123408 A1 | 8/2015 |
|---|---|---|
| WO | 2015123424 A1 | 8/2015 |
| WO | 2015123437 A1 | 8/2015 |
| WO | 2015123465 A1 | 8/2015 |

OTHER PUBLICATIONS

Lala et al., Role of nitric oxide in tumor progression: Lessons from experimental tumors, Cancer and Metastasis Reviews (1998), 17, 91-106 (Year: 1998).*

Golub et al., Molecular Classification of Cancer: Class Discovery and Class Prediction by Gene Expression Monitoring, Science (1999), vol. 286, 531-537 (Year: 1999).*

Int'l Search Report dated May 24, 2017 in Int'l Application No. PCT/CN2017/076967.

Database extract; compounds with the Registry Nos. 1865537-49-0 and 1865458-45-2 (Feb. 12, 2016).

Database extract; compounds with the Registry Nos. 1876875-02-3 and 1876889-76-7 (Mar. 1, 2016).

English Translation of Written Opinion dated Nov. 12, 2019 in SG Application No. 11201808017P.

Office Action dated Oct. 26, 2019 in KR Application No. 1020187029900.

Search Report dated Nov. 6, 2019 in RU Application No. 2018136336.

Supplementary European Search Report dated Sep. 12, 2019 in EP Application No. 17765864.8.

Zhou et al,, "Structure activity relationship and modeling studies of inhibitors of lysine specific demethylase 1," PLOS One, vol. 12, No. 2, pp. 1-12 (2017).

* cited by examiner

FLUORINATED CYCLOPROPYLAMINE COMPOUND, PREPARATION METHOD THEREFOR, PHARMACEUTICAL COMPOSITION THEREOF, AND USES THEREOF

CROSS-REFERENCE TO RELATED APPLICATION

This application is a Section 371 of International Application No. PCT/CN2017/076967, filed Mar. 16, 2017, which was published in the Chinese language on Sep. 21, 2017 under International Publication No. WO 2017/157322 A1, and claims priority under 35 U.S.C. § 119(b) to Chinese Application No. 201610149958.6, filed Mar. 16, 2016 and the disclosures of which are incorporated herein by reference.

FIELD OF THE INVENTION

The present invention relates to the field of medicinal chemistry and pharmaco-therapeutics, and in particular to a class of fluorine-substituted cyclopropylamine compounds, a process for the preparation thereof, a pharmaceutical composition containing the same, and the use as a lysine-specific demethylase 1 (LSD1) inhibitor, in particular for the preparation of a medicament for the treatment of diseases such as cancer, leukemia and the like.

BACKGROUND OF THE INVENTION

Epigenetics is a branch of genetics which studies the induction of heritable changes in gene expression by reversible modification of nucleotides or chromosomes without leading to changes in the DNA sequence of the studied gene. The regulation mechanisms of epigenetics mainly include DNA methylation, histone modification, and non-coding RNA action. In most cases, epigenetic information is stored by altering the chemical modification of cytosine and histones, which alter the structure of chromatin. The normal epigenetic process plays an important role in life activities such as embryonic development and cell differentiation. Studies have shown that the occurrence of many diseases is related to the abnormality of epigenetic modification. In recent years, epigenetics has become a research hotspot in the fields of biology and medicine. Epigenetic related research being carried out is of great significance in the prevention and treatment of many human diseases.

LSD1 (also known as BHC110, p110b and NPAO) was confirmed by Shi et al. in 2004, of which the structure is highly conserved from yeast to humans. In cells, the demethylation ability of LSD1 is highly specific for genes, substrates, and environments, and produces different (or even opposite) effects on gene expression at different locations. Studies found that LSD1 plays an important role in promoting normal cell differentiation, but it is also found that LSD1 is abnormally recruited to inappropriately inhibit abnormal gene targets downstream to leukemia-causing genes (e.g., MLL-AF9). In this case, LSD1 maintains the activity on leukemia stem cells (LSC) conferred by initial damage, and cellular effects downstream to LSD1 are also significantly different from normal cell states. No changes in gene expression were observed at the most primitive hematopoietic stem cell (HSC) levels during normal hematopoiesis, which is consistent with the exact opposite observation of cytopenia induced by LSD1 depletion. Therefore, LSD1 can be used as a potential target of drugs for the treatment of leukemia if it can produce controllable and reversible toxicity to normal hematopoietic cells.

The development of novel small-molecule LSD1 inhibitors has important research significance for the treatment of diseases such as malignant tumors and leukemia.

SUMMARY OF THE INVENTION

An object of the present invention to provide a fluorine-substituted cyclopropylamine compound of the formula I, a pharmaceutically acceptable salt, a racemate, an R-isomer, an S-isomer, or a mixture thereof.

Another object of the present invention is to provide a process for producing a fluorine-substituted cyclopropylamine compound of formula I.

Still another object of the present invention to provide a pharmaceutical composition comprising a therapeutically effective amount of one or more of a fluorosubstituted cyclopropylamine compound of formula I, pharmaceutically acceptable salt, racemate, R isomer, S-isomer, or mixtures thereof.

Still another object of the present invention is to provide a lysine-specific demethylase 1 (LSD1) inhibitor comprising one or more of a fluorine-substituted cyclopropylamine compound of formula I, pharmaceutically acceptable salt, racemate, R isomer, S-isomer, or the mixtures thereof.

Still another object of the present invention is to provide a use of fluorine-substituted cyclopropylamine compound of formula I, a pharmaceutically acceptable salt, a racemate, an R-isomer, an S-isomer, or a mixture thereof in the preparation of a medicament for the treatment of malignant tumor diseases associated with lysine-specific demethylase 1 (LSD1) inhibitor, such as cancer, leukemia or the like.

Still another object of the present invention provides a method of treating diseases associated with lysine-specific demethylase 1 (LSD1) inhibitor, such as cancer, leukemia, and the like, which include administering to a patient in need thereof with one or more of the fluorine-substituted cyclopropylamine compound of the above formula I, the pharmaceutically acceptable salts, isomers, or mixtures thereof.

Based on the above objects, the present invention provided a fluorine-substituted cyclopropylamine compound having a structure represented by the following general formula I, and a racemate, R-isomer, S-isomer, pharmaceutically acceptable salt, or mixtures thereof:

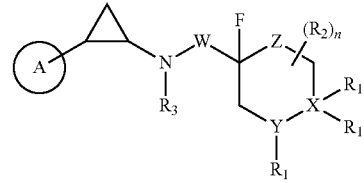

Formula I wherein:

A is selected from the group consisting of a substituted or unsubstituted benzene ring, or a substituted or unsubstituted C5-C12 aromatic heterocyclic ring containing 1 to 4 heteroatoms selected from the group consisting of oxygen, sulfur and nitrogen, wherein each of the substituted benzene ring or substituted aromatic heterocycles comprises 1 to 3 substituents;

Wherein the substituent on the substituted benzene ring or substituted aromatic heterocyclic ring is hydrogen, isotope of hydrogen, halogen, C1-C12 straight or branched alkyl which is unsubstituted or substituted by 1-3 halogens, C1-C12 straight or branched alkoxy which is unsubstituted or substituted by 1 to 3 halogens or phenyl groups, C2-C12 straight or branched unsaturated hydrocarbon group which is unsubstituted or substituted by 1 to 3 halogens, C3-C6 cycloalkyl group which is unsubstituted or substituted by 1 to 3 halogens, C1-C6 straight or branched alkyl substituted by C1-C6 alkoxy group, C1-C6 straight or branched alkyl substituted by C3-C6 cycloalkyl, hydroxy, cyano, nitro, C1-C6 straight or branched hydroxyalkyl or thiol;

Alternatively, any two substituents on the substituted benzene ring or substituted aromatic heterocyclic ring may be linked together with their adjacent carbon or heteroatom to form a 5-7 membered heterocyclic ring comprises 1 to 3 heteroatoms selected from N, O and S, and the 5-7 membered heterocyclic ring is optionally substituted by a substituent selected from the group consisting of hydrogen, hydrogen isotope, halogen, C1-C6 straight or branched alkyl unsubstituted or substituted with 1-3 halogens, C1-C6 straight or branched alkoxy unsubstituted or substituted by 1 to 3 halogens, and hydroxyl;

Each $R_1$ is independently selected from: a substituted or unsubstituted aryl, substituted or unsubstituted heteroaryl, hydrogen, substituted or unsubstituted C1-C6 alkyl, —$SO_2Ra$, —NC(O)Ra, —$CH_2C(O)ORa$, —C(O)ORa, —C(O)Ra, —C(O)NRaRb, —NRcRd, substituted or unsubstituted amino, urea, amide, sulfonamide, substituted or unsubstituted arylalkyl, and substituted or unsubstituted heteroarylalkyl;

Each Ra is independently hydrogen, phenyl, phenylmethyl, 3,5-dimethylisoxazol-4-yl, 1,2-dimethyl-1H-imidazol-4-yl, C3-C7 cycloalkyl, C1-C6 alkyl, C1-C4 alkoxy, C1-C3 alkylamino or —NHPh;

Rb is hydrogen or a C1-C3 alkyl, or when attached to the same atom,

Ra and Rb together form a 5- or 6-membered heterocycloalkyl ring;

Rc and Rd are each independently selected from hydrogen, a C1-C3 straight or branched alkyl, C3-C5 cycloalkyl, C1-C3 alkoxy, 4- to 6-membered heterocyclic group, C1-C3 alkylacyl, C5-C7 arylacyl, benzyl, C5-C7 aryl; the C1-C3 straight or branched alkyl is optionally substituted by one or more selected from the group consisting of methylsulfonyl, C1-C3 alkoxy, C1-C3 alkoxycarbonyl group; the heterocyclic group containing one heteroatom selected from the group consisting of oxygen, sulfur and nitrogen;

$R_2$ is hydrogen or COOH;

$R_3$ is C1-C4 alkyl, acyl, —C(O)CF3 or hydrogen;

W is —$(CH_2)_{1-4}$ or —$CH(Re)(CH_2)_{0-3}$, wherein Re is CN or C1-C4 alkyl;

Y is N or C;

X is N or C;

Z is O or $(CH_2)_q$, wherein q is 0-2, and when q is 0, Z represents a bond;

n is 0-3;

with the proviso that when Z is O, Y is N and X is C;

Moreover, when X is C, at least one $R_1$ group attached to X is not hydrogen.

In another preferred embodiment, when X is N, only one $R_1$ is connected to X.

In another preferred embodiment, W is —$CH_2$—.

In another preferred embodiment, Z is $(CH_2)_q$, wherein q is 1.

In another preferred embodiment, X is C, and at least one $R_1$ attached to X is —NRcRd, and Rc and Rd are each independently selected from hydrogen, a C1-C3 straight or branched alkyl, C3-C5 cycloalkyl, C1-C3 alkoxy, 4- to -6-membered heterocyclic group, C1-C3 alkylacyl, C5-C7 arylacyl, benzyl, C5-C7 aryl; the C1-C3 straight or branched alkyl is optionally substituted by one or more selected from the group consisting of methylsulfonyl, C1-C3 alkoxy, C1-C3 alkoxycarbonyl; the heterocyclic group contains one heteroatom selected from the group consisting of oxygen, sulfur and nitrogen.

In another preferred embodiment, X is N, and at least one $R_1$ attached to X is selected from a substituted or unsubstituted aryl, heteroaryl, aralkyl, and heteroarylalkyl.

In another preferred embodiment, X is N and at least one $R_1$ attached to (X) is selected from a substituted or unsubstituted aryl C1-C4 alkyl, or heteroaryl C1-C4 alkyl.

In another preferred embodiment, the structure of the compound is as shown by the formula (1R, 2S)-Ia or the formula (1S, 2R)-Ib:

formula (1R, 2S)-Ia formula (1S, 2R)-Ib

In the present invention, the halogen is F, Cl, Br or I.

In the present invention, unless otherwise specified, the terms used have the general meaning known by those skilled in the art.

In the present invention, the term "C1-C6 alkyl" refers to a straight or branched alkyl with 1 to 6 carbon atoms, non-limiting examples of which comprise methyl, ethyl, propyl, isopropyl, butyl, isobutyl, sec-butyl, tert-butyl, pentyl and hexyl, or the like; preferably ethyl, propyl, isopropyl, butyl, isobutyl, secbutyl and tert-butyl.

In the present invention, the term "C1-C6 alkoxy" refers to a straight or branched chain alkoxy group having 1 to 6 carbon atoms, non-limiting examples of which comprise methoxy, ethoxy, propoxy, isopropoxy, butoxy, iso-butoxy, butoxy, or the like.

In the present invention, the term "C2-C6 alkenyl" refers to a straight or branched alkenyl having one double bond and 2-6 carbon atoms, non-limiting examples of which comprise vinyl, propenyl, butenyl, isobutenyl, pentenyl and hexenyl.

In the present invention, the term "C2-C6 alkynyl" refers to a straight or branched alkynyl having one triple bond and 2 to 6 carbon atoms, including, without limitation, ethynyl, propynyl, butynyl, isobutynyl, pentynyl and hexynyl.

In the present invention, the term "C3-C10 cycloalkyl" refers to a cyclic alkyl having 3 to 10 carbon atoms on the ring, non-limiting examples of which comprise cyclopropyl, cyclobutyl, cyclopentyl, cyclohexyl, cycloheptyl, cyclooctyl and cyclodecyl. The terms "C3-C8 cycloalkyl", "C3-C7 cycloalkyl" and "C3-C6 cycloalkyl" have similar meanings.

In the present invention, the term "C3-C10 cycloalkenyl" refers to a cyclic alkenyl having 3 to 10 carbon atoms on the ring, non-limiting examples of which comprise cyclopropenyl, cyclobutenyl, cyclopentenyl, cyclohexenyl, cycloheptenyl, cyclooctenyl and cyclodecenyl. The term "C3-C7 cycloalkenyl" has a similar meaning.

In the present invention, the term "aromatic ring" or "aryl" has the same meaning, and preferably, "aryl" is "C6-C12 aryl" or "C6-C10 aryl". The term "C6-C12 aryl" refers to an aryl having 6 to 12 carbon atoms which do not comprises a heteroatom on the ring, such as phenyl, naphthyl and the like. The term "C6-C10 aryl" has a similar meaning.

In the present invention, the term "aromatic heterocyclic ring" or "heteroaryl" has the same meaning, which refers to a heteroaromatic group containing one or more heteroatoms. The heteroatoms herein include oxygen, sulfur, and nitrogen. Such as furyl, thienyl, pyridyl, pyrazolyl, pyrrolyl, N-alkylpyrrolyl, pyrimidinyl, pyrazinyl, imidazolyl, tetrazolyl, and the like. The heteroaryl ring can be fused to aryl, heterocyclic group or cycloalkyl ring, wherein the ring to which the parent structure is attached is a heteroaryl ring. The heteroaryl may optionally be substituted or unsubstituted.

In the present invention, the term "3-12 membered heterocyclyl" refers to a saturated or unsaturated 3-12 membered ring group having 1 to 3 heteroatoms selected from oxygen, sulfur and nitrogen on the ring, such as oxepanyl. The term "3-7 membered heterocyclyl" has a similar meaning.

In the present invention, the term "substituted" means that one or more hydrogen atom s on a particular group are replaced by a specific substituent. The specific substituent is a substituent which is correspondingly described in the foregoing, or a substituent which app ears in each embodiment. Unless otherwise indicated, a substituted group may have a substituent selected from a particular group at any substitutable position of the group, wherein the substituents may be the same or different at each position. A cyclic substituent, such as a heterocycloalkyl, may be attached to another ring, such as a cycloalkyl, to form a spiro bicyclic ring system, for example, two rings having a common carbon atom. Those skilled in the art will appreciate that the combinations of substituents contemplated in the present invention are those that are stable or chemically achievable. The substituents are, for example but not limited to, $C_{1-8}$ alkyl, $C_{2-8}$ alkenyl, $C_{2-8}$ alkynyl, $C_{3-8}$ cycloalkyl, 3- to 12-membered heterocyclic group, aryl, heteroaryl, halogen, hydroxy, carboxy (—COOH), $C_{1-8}$ aldehyde group, $C_{2-10}$ acyl, $C_{2-10}$ ester group, amino, alkoxy, $C_{1-10}$ sulfonyl, etc.

In a more preferred embodiment of the present invention, the compounds of general formula (I) of the present invention are preferably specific compounds as follows:

| No. | Name | Structure |
| --- | --- | --- |
| A1 | Benzyl 4-fluoro-4-((trans-2-phenylcyclopropyl)amino)methyl)piperidine-1-carboxylate | 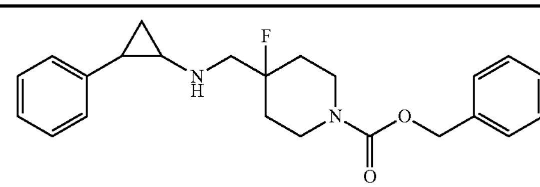 |
| A2 | N-((4-fluoropiperidin-4-yl)methyl)-trans-2-phenylcyclopropylamine | 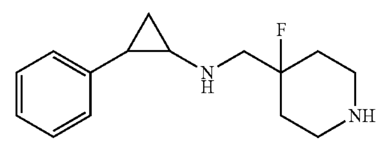 [SMILES: FC1(CNC2CC2c2ccccc2)CCNCC1] |
| A3 | Methyl 4-((4-fluoro-4-(((trans-2-phenylcyclopropyl)amino)methyl)piperidin-1-yl)methyl)benzoate | 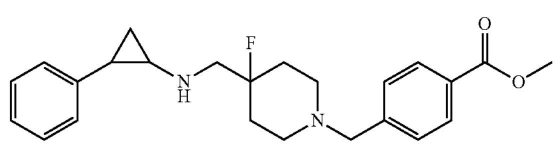 [SMILES: COC(=O)c1ccc(CN2CCC(F)(CNC3CC3c3ccccc3)CC2)cc1] |
| A4 | (1s,4s)-4-fluoro-4-(((trans-2-phenylcyclopropyl)amino)methyl)cyclohexylamine | 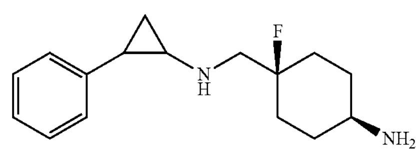 [SMILES: N[C@H]1CC[C@](F)(CNC2CC2c2ccccc2)CC1] |
| A5 | 4-((4-fluoro-4-(((trans-2-phenylcyclopropyl)amino)methyl)piperidin-1-yl)methyl)benzoic acid | 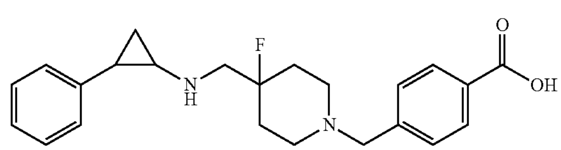 [SMILES: O=C(O)c1ccc(CN2CCC(F)(CNC3CC3c3ccccc3)CC2)cc1] |
| A6 | N-((1-benzyl-4-fluoropiperidin-4-yl)methyl)-trans-2-phenylcyclopropylamine | 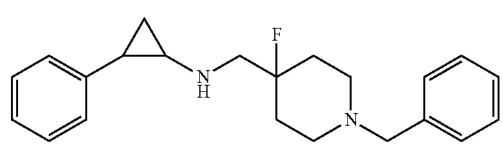 [SMILES: FC1(CNC2CC2c2ccccc2)CCN(Cc2ccccc2)CC1] |

-continued

| No. | Name | Structure |
|---|---|---|
| A7 | Methyl 3-(4-fluoro-4-(((trans-2-phenylcyclopropyl)amino)methyl)piperidin-1-yl)-propionate | 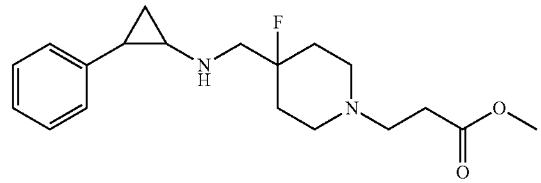 [SMILES: COC(=O)CCN1CCC(F)(CNC2CC2c2ccccc2)CC1] |
| A8 | 1-(4-fluoro-4-(((trans-2-phenylcyclopropyl)amino)methyl)piperidin-1-yl)-3-phenyl-1-propanone | 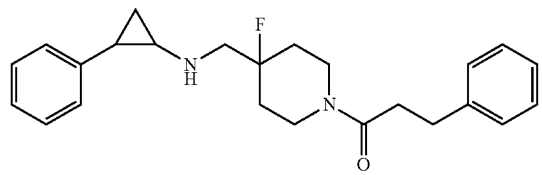 |
| A9 | Phenyl 4-fluoro-4-((trans-2-phenylcyclopropyl)amino)methyl)piperidine-1-carboxylate | 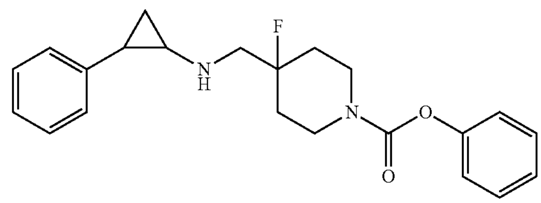 [SMILES: O=C(Oc1ccccc1)N1CCC(F)(CNC2CC2c2ccccc2)CC1] |
| A10 | 3-cyclohexyl-1-(4-fluoro-4-(((trans-2-phenylcyclopropyl)amino)methyl)piperidin-1-yl)-1-propanone | 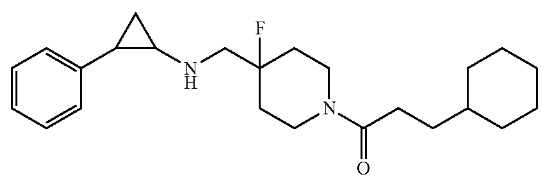 |
| A11 | 4-fluoro-N-methyl-4-(((trans-2-phenylcyclopropyl)amino)methyl)cyclohexane-1-amine | 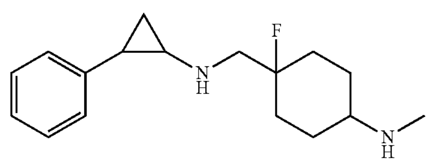 [SMILES: CNC1CCC(F)(CNC2CC2c2ccccc2)CC1] |
| A12 | N-((4-fluoro-1-(3-phenylpropyl)piperidin-4-yl)methyl)-trans-2-phenylcyclopropylamine | 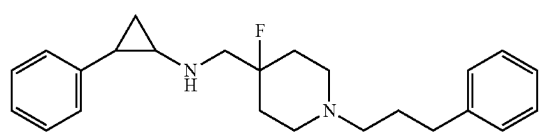 [SMILES: FC1(CNC2CC2c2ccccc2)CCN(CCCc2ccccc2)CC1] |
| A13 | N-((1-([1,1'-biphenyl]-4-methyl)-4-fluoropiperidin-4-yl)methyl)-trans-2-phenylcyclopropylamine | 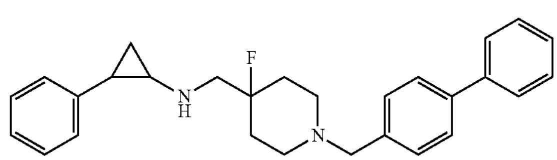 [SMILES: FC1(CNC2CC2c2ccccc2)CCN(Cc2ccc(-c3ccccc3)cc2)CC1] |
| A14 | N-((1-(3-cyclohexylpropyl)-4-fluoropiperidin-4-yl)methyl)-trans-2-phenylcyclopropylamine | 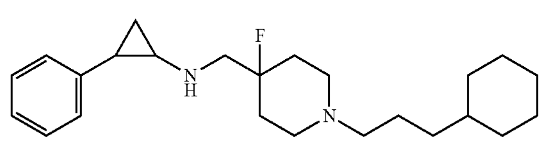 [SMILES: FC1(CNC2CC2c2ccccc2)CCN(CCCC2CCCCC2)CC1] |
| A15 | N-((4-fluoro-1-methylpiperidin-4-yl)methyl)-trans-2-phenylcyclopropyl-amine | 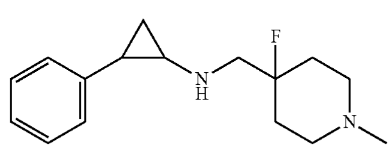 [SMILES: CN1CCC(F)(CNC2CC2c2ccccc2)CC1] |

-continued

| No. | Name | Structure |
|---|---|---|
| A16 | N-((4-fluoro-1-(4-(methylsulfonyl) benzyl)piperidin-4-yl)methyl)-trans-2-phenylcyclopropylamine | 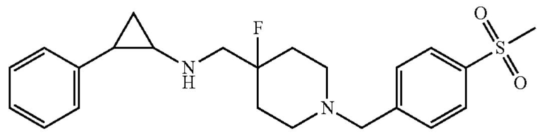 [SMILES: CS(=O)(=O)c1ccc(CN2CCC(F)(CNC3CC3c3ccccc3)CC2)cc1] |
| A17 | N-((4-fluoro-1-(naphthyl-2-methyl) piperidin-4-yl)methyl)-trans-2-phenylcyclopropylamine | 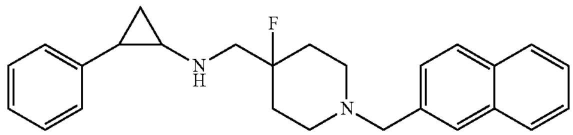 [SMILES: FC1(CNC2CC2c2ccccc2)CCN(Cc2ccc3ccccc3c2)CC1] |
| A18 | N-((1-fluorocyclohexyl)methyl)-trans-2-phenylcyclopropylamine | 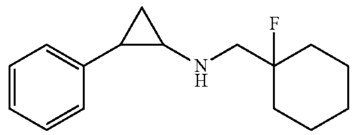 [SMILES: FC1(CNC2CC2c2ccccc2)CCCCC1] |
| A19 | Benzyl (4-fluoro-4-((trans-2-phenylcyclopropyl)amino)methyl)cyclohexyl) carbamate | 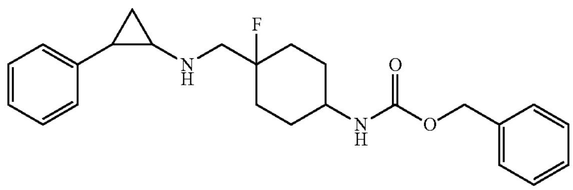 [SMILES: O=C(NC1CCC(F)(CNC2CC2c2ccccc2)CC1)OCc1ccccc1] |
| A20 | N-((4-fluoro-1-phenylpiperidin-4-yl)methyl)-trans-2-phenylcyclopropylamine | 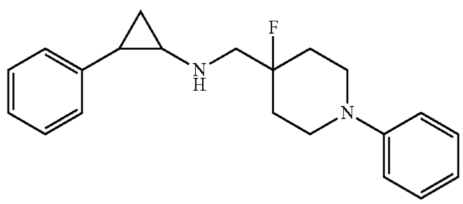 [SMILES: FC1(CNC2CC2c2ccccc2)CCN(c2ccccc2)CC1] |
| A21 | Cyclohexylmethyl 4-fluoro-4-(((trans-2-phenylcyclopropyl)amino)methyl)piperidine-1-carboxylate | 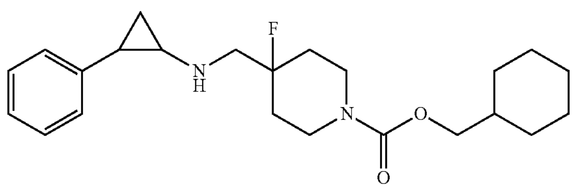 [SMILES: O=C(OCC1CCCCC1)N1CCC(F)(CNC2CC2c2ccccc2)CC1] |
| A22 | Pyridin-4-ylmethyl 4-fluoro-4-(((trans-2-phenylcyclopropyl)amino)methyl)piperidine-1-carboxylate | 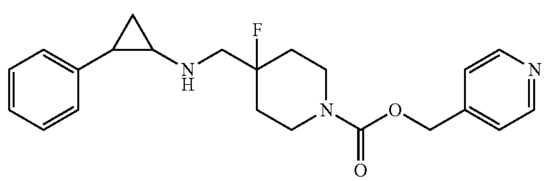 [SMILES: O=C(OCc1ccncc1)N1CCC(F)(CNC2CC2c2ccccc2)CC1] |
| A23 | Phenethyl 4-fluoro-4-(((trans-2-phenylcyclopropyl)amino)methyl)piperidine-1-carboxylate | 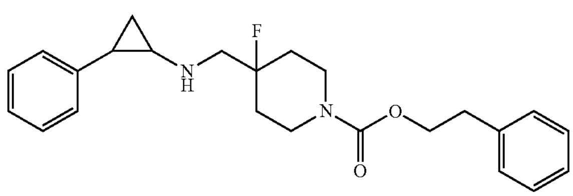 [SMILES: O=C(OCCc1ccccc1)N1CCC(F)(CNC2CC2c2ccccc2)CC1] |
| A24 | Ethyl 4-fluoro-4-(((trans-2-phenylcyclopropyl)amino)methyl)piperidine-1-carboxylate | 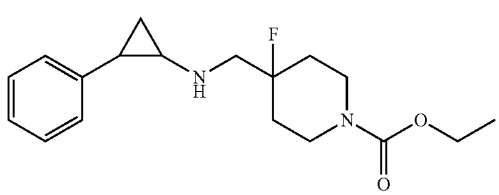 [SMILES: CCOC(=O)N1CCC(F)(CNC2CC2c2ccccc2)CC1] |

-continued

| No. | Name | Structure |
|---|---|---|
| A25 | (1H-indol-5-yl)methyl 4-fluoro-4-(((trans-2-phenylcyclo-propyl)amino)methyl)piperidine-1-carboxylate | 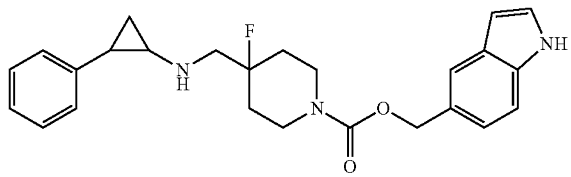 [SMILES: O=C(OCc1ccc2[nH]ccc2c1)N1CCC(F)(CNC2CC2c2ccccc2)CC1] |
| A26 | 1-(4-Fluoro-4-(((trans-2-phenyl-cyclopropyl)amino)methyl)pyridin-1-yl)-1-ethanone) | 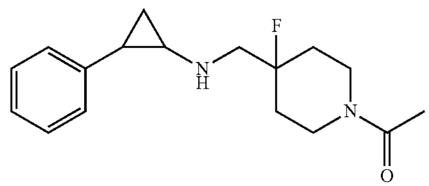 [SMILES: CC(=O)N1CCC(F)(CNC2CC2c2ccccc2)CC1] |
| A27 | Thiophen-2-ylmethyl-4-fluoro-4-(((trans-2-phenylcyclopropyl)amino)methyl)piperidine-1-carboxylate | 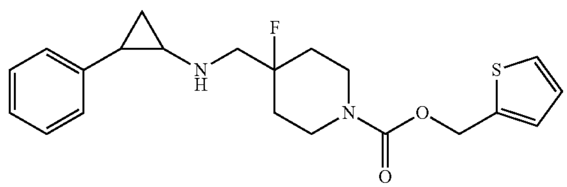 |
| A28 | Furan-2-ylmethyl-4-fluoro-4-(((trans-2-phenylcyclopropyl)amino)methyl)piperidine-1-carboxylate | 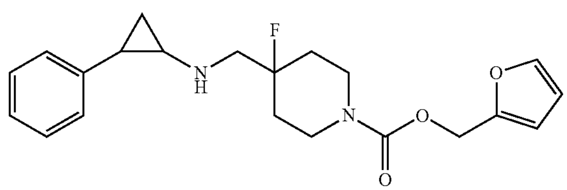 [SMILES: O=C(OCc1ccco1)N1CCC(F)(CNC2CC2c2ccccc2)CC1] |
| A29 | 4-fluorobenzyl-4-fluoro-4-(((trans-2-phenylcyclopropyl)amino)methyl)piperidine-1-carboxylate | 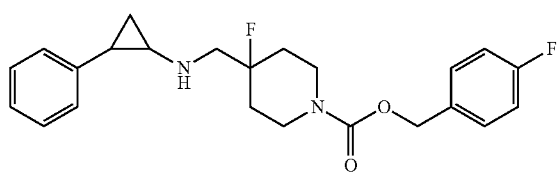 [SMILES: O=C(OCc1ccc(F)cc1)N1CCC(F)(CNC2CC2c2ccccc2)CC1] |
| A30 | 4-chlorobenzyl-4-fluoro-4-(((trans-2-phenylcyclopropyl)amino)methyl)piperidine-1-carboxylate | 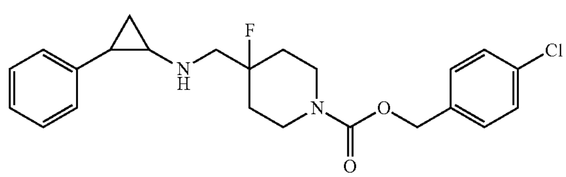 [SMILES: O=C(OCc1ccc(Cl)cc1)N1CCC(F)(CNC2CC2c2ccccc2)CC1] |
| A31 | 4-bromobenzyl-4-fluoro-4-(((trans-2-phenylcyclopropyl)amino)methyl)piperidine-1-carboxylate | 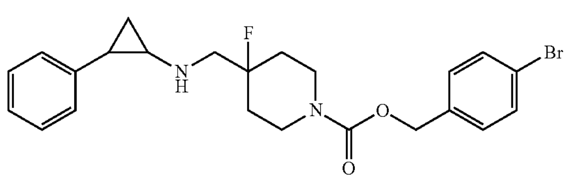 [SMILES: O=C(OCc1ccc(Br)cc1)N1CCC(F)(CNC2CC2c2ccccc2)CC1] |
| A32 | 4-methoxybenzyl-4-fluoro-4-(((trans-2-phenylcyclopropyl)amino)methyl)piperidine-1-carboxylate | 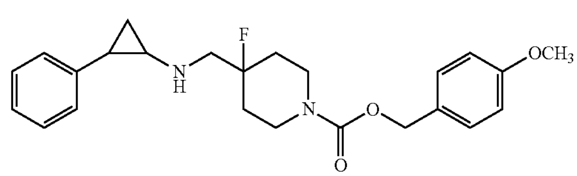 |

-continued

| No. | Name | Structure |
|---|---|---|
| A33 | 4-trifluoromethylbenzyl-4-fluoro-4-(((trans-2-phenylcyclopropyl)amino)methyl)piperidine-1-carboxylate | 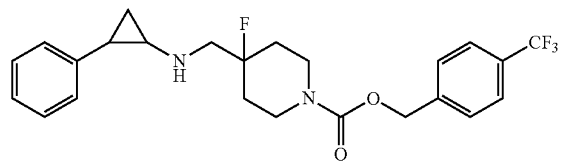 [SMILES: O=C(OCc1ccc(C(F)(F)F)cc1)N1CCC(F)(CNC2CC2c2ccccc2)CC1] |
| A34 | 3,5-Dimethoxybenzyl-4-fluoro-4-(((trans-2-phenylcyclopropyl)amino)methyl)piperidine-1-carboxylate | 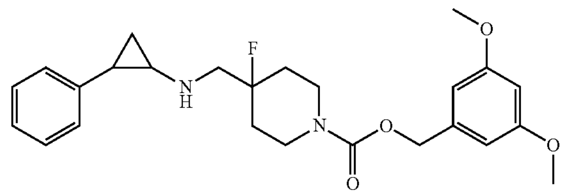 [SMILES: COc1cc(COC(=O)N2CCC(F)(CNC3CC3c3ccccc3)CC2)cc(OC)c1] |
| A35 | 4-((4-Fluoro-4-(((trans-2-phenyl-cyclopropyl)amino)methyl)piperidine-1-carbonyloxy)methyl)benzoic acid | 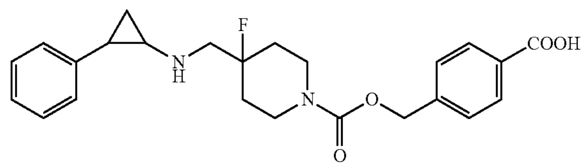 [SMILES: O=C(O)c1ccc(COC(=O)N2CCC(F)(CNC3CC3c3ccccc3)CC2)cc1] |
| A36 | (E)-1-(4-fluoro-4-(((trans-2-phenyl-cyclopropyl)amino)methyl)piperidin-1-yl)-3-phenyl-2-ene-1-propanone | 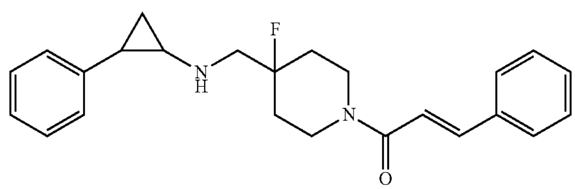 [SMILES: O=C(/C=C/c1ccccc1)N1CCC(F)(CNC2CC2c2ccccc2)CC1] |
| A37 | N-benzyl-4-fluoro-4-(((trans-2-phenylcyclopropyl)amino)methyl)piperidine-1-thioamide | 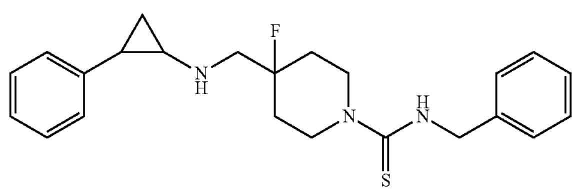 [SMILES: FC1(CNC2CC2c2ccccc2)CCN(C(=S)NCc2ccccc2)CC1] |
| A38 | N-benzyl-4-fluoro-4-(((trans-2-phenylcyclopropyl)amino)methyl)piperidine-1-carboxamide | 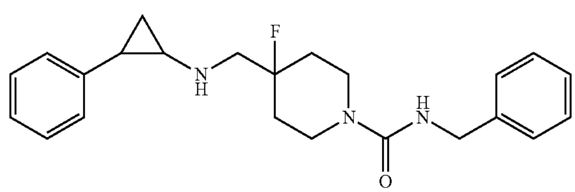 [SMILES: O=C(NCc1ccccc1)N1CCC(F)(CNC2CC2c2ccccc2)CC1] |
| A39 | N-((1-((benzyloxy)methyl)-4-fluoropiperidin-4-yl)methyl)-trans-2-phenylcyclopropylamine | 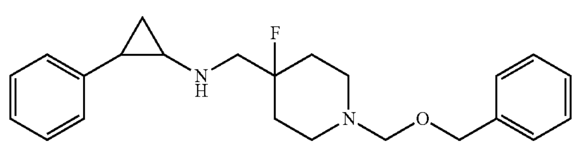 [SMILES: FC1(CNC2CC2c2ccccc2)CCN(COCc2ccccc2)CC1] |
| A40 | Benzyl 4-fluoro-4-(((trans-2-phenylcyclopropyl)amino)methyl)cyclohexane-1-carboxylate | 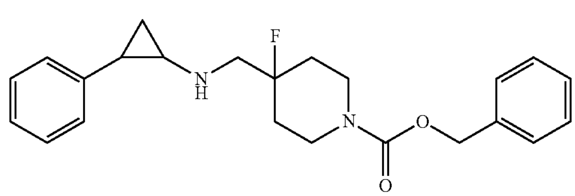 [SMILES: O=C(OCc1ccccc1)N1CCC(F)(CNC2CC2c2ccccc2)CC1] |

-continued

| No. | Name | Structure |
|---|---|---|
| A41 | Cyclopentylmethyl-4-fluoro-4-(((trans-2-phenylcyclopropyl)amino)methyl)piperidine-1-carboxylate | 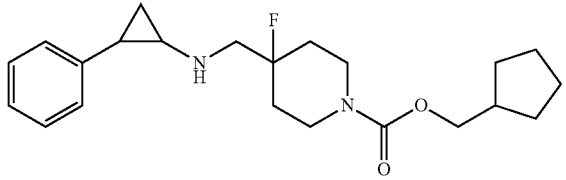 [SMILES: O=C(OCC1CCCC1)N1CCC(F)(CNC2CC2c2ccccc2)CC1] |
| A42 | Cyclobutylmethyl-4-fluoro-4-(((trans-2-phenylcyclopropylamino)methyl)piperidine-1-carboxylate | 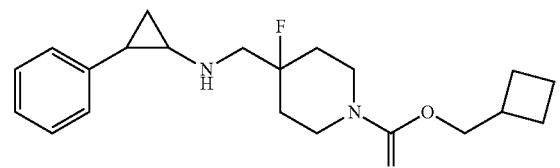 |
| A43 | Piperidin-4-ylmethyl-4-fluoro-4-(((trans-2-phenylcyclopropyl)amino)methyl)piperidine-1-carboxylate | 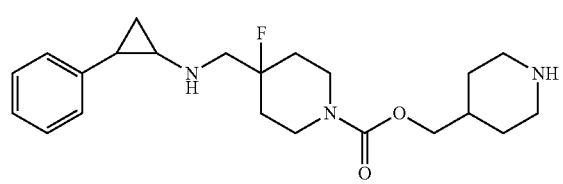 [SMILES: O=C(OCC1CCNCC1)N1CCC(F)(CNC2CC2c2ccccc2)CC1] |
| A44 | 3-chlorobenzyl-4-fluoro-4-(((trans-2-phenylcyclopropyl)amino)methyl)piperidine-1-carboxylate | 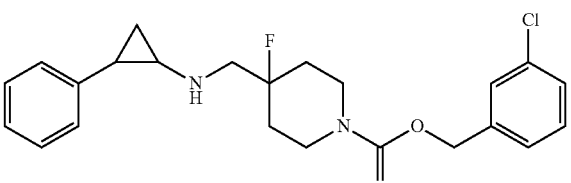 |
| A45 | 2-chlorobenzyl-4-fluoro-4-(((trans-2-phenylcyclopropyl)amino)methyl)piperidine-1-carboxylate | 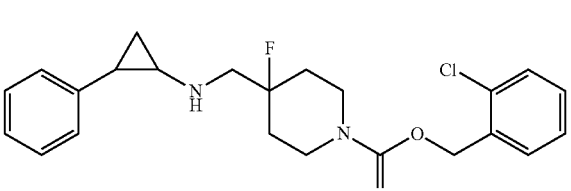 |
| A46 | (4-fluoro-4-((trans-2-phenylcyclopropyl)amino)methyl)piperidin-1-yl)(phenyl)methanone | 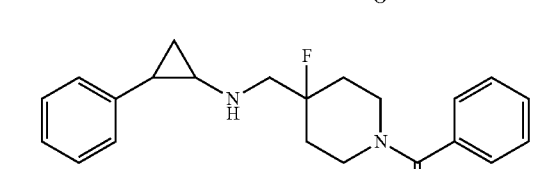 |
| A47 | 4-tert-butylbenzyl 4-fluoro-4-(((trans-2-phenylcyclopropyl)amino)methyl)piperidine-1-carboxylate | 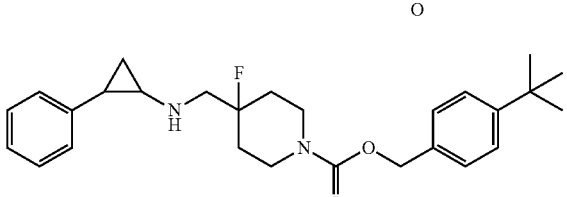 |
| A48 | Benzyl 4-fluoro-2-methyl-4-((trans-2-phenylcyclopropyl)amino)methyl)piperidine-1-carboxylate | 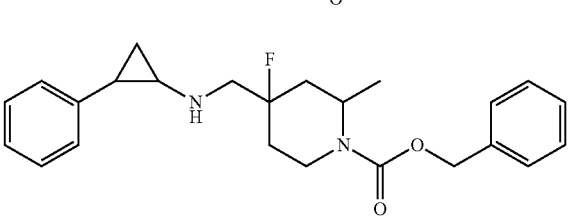 |

| No. | Name | Structure |
|---|---|---|
| A49 | Benzyl 4-fluoro-2,6-dimethyl-4-((trans-2-phenylcyclopropyl)amino)methyl)piperidine-1-carboxylate | 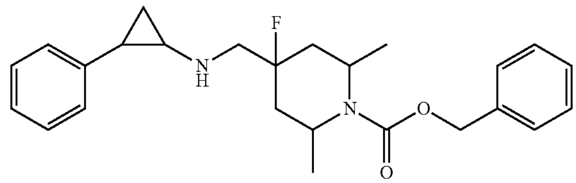 [SMILES: CC1CC(F)(CNC2CC2c2ccccc2)CC(C)N1C(=O)OCc1ccccc1] |
| A50 | Benzyl 4-fluoro-4-((trans-2-(naphthalen-2-yl)cyclopropyl)amino)methyl)piperidine-1-carboxylate | 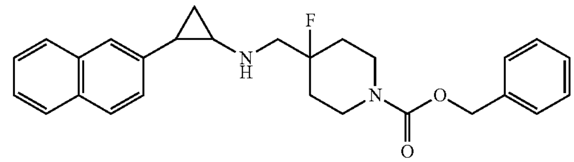 [SMILES: O=C(OCc1ccccc1)N1CCC(F)(CNC2CC2c2ccc3ccccc3c2)CC1] |
| A51 | Benzyl 4-fluoro-4-((trans-2-(benzothiophen-5-yl)cyclopropyl)amino)methyl)piperidine-1-carboxylate | 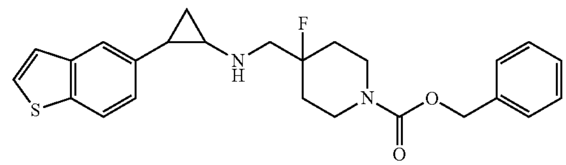 |
| A52 | Benzyl 4-fluoro-4-((trans-2-(pyridin-4-yl)cyclopropyl)amino)methyl)piperidine-1-carboxylate | 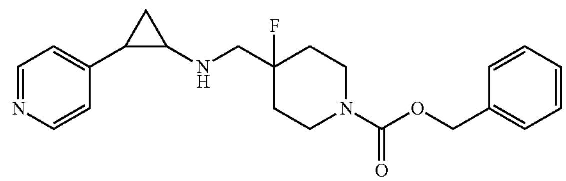 [SMILES: O=C(OCc1ccccc1)N1CCC(F)(CNC2CC2c2ccncc2)CC1] |
| A53 | Benzyl 4-fluoro-4-((trans-2-(1H-indol-5-yl)cyclopropyl)amino)methyl)piperidine-1-carboxylate | 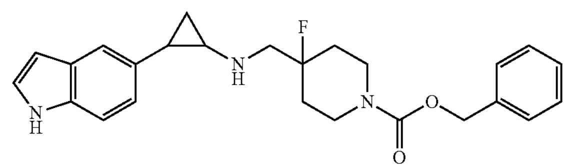 [SMILES: O=C(OCc1ccccc1)N1CCC(F)(CNC2CC2c2ccc3[nH]ccc3c2)CC1] |
| A54 | Benzyl 4-fluoro-4-((trans-2-(1-methyl-1H-indol-5-yl)cyclopropyl)amino)methyl)piperidine-1-carboxylate | 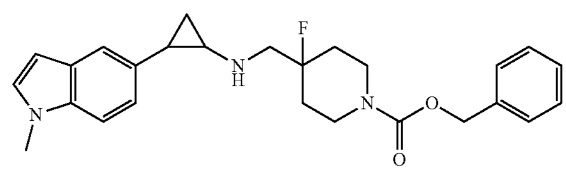 [SMILES: Cn1ccc2cc(C3CC3NCC3(F)CCN(C(=O)OCc4ccccc4)CC3)ccc21] |
| A55 | Benzyl 4-fluoro-4-((trans-2-(indoline-5-yl)cyclopropyl)amino)methyl)piperidine-1-carboxylate | 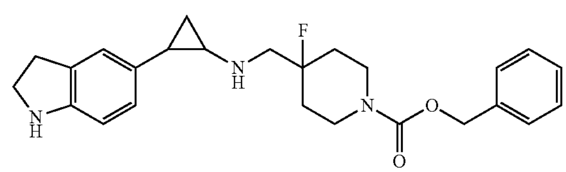 |
| A56 | Benzyl 4-fluoro-4-((trans-2-(1-(phenylsulfonyl)indoline-5-yl)cyclopropyl)amino)methyl)piperidine-1-carboxylate | 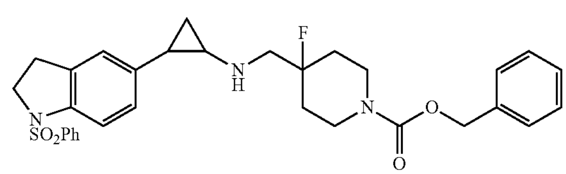 |
| A57 | Benzyl 4-fluoro-4-((trans-2-(1H-indol-3-yl)cyclopropyl)amino)methyl)piperidine-1-carboxylate | 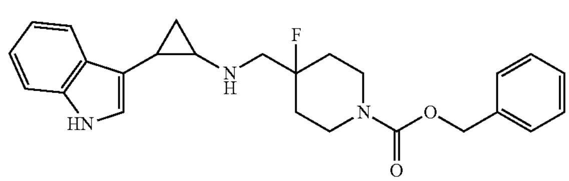 [SMILES: O=C(OCc1ccccc1)N1CCC(F)(CNC2CC2c2c[nH]c3ccccc23)CC1] |

-continued

| No. | Name | Structure |
|---|---|---|
| A58 | Benzyl 4-fluoro-4-((trans-2-(imidazo[1,2-α]pyridin-3-yl)cyclopropyl)amino)methyl)piperidine-1-carboxylate | 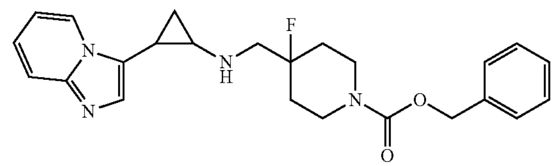 [SMILES: O=C(OCc1ccccc1)N1CCC(F)(CNC2CC2c2cnc3ccccn23)CC1] |
| A59 | Benzyl 4-fluoro-4-((trans-2-(2,3-dihydro-benzofuran-5-yl)cyclopropyl)amino)methyl)piperidine-1-carboxylate | 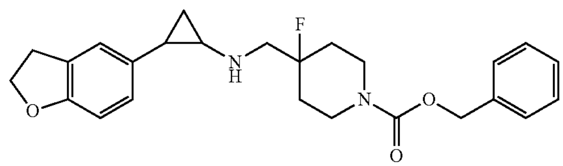 [SMILES: O=C(OCc1ccccc1)N1CCC(F)(CNC2CC2c2ccc3c(c2)CCO3)CC1] |
| A60 | benzyl 4-fluoro-4-((trans-2-(chroman-6-yl)cyclopropyl)amino)methyl)piperidine-1-carboxylate | 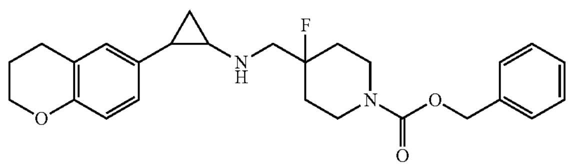 [SMILES: O=C(OCc1ccccc1)N1CCC(F)(CNC2CC2c2ccc3c(c2)CCCO3)CC1] |
| A61 | benzyl 4-fluoro-4-(((trans-2-(2-oxo-1,2,3,4-tetrahydroquinolin-6-yl)cyclopropyl)amino)methyl)piperidine-1-carboxylate | 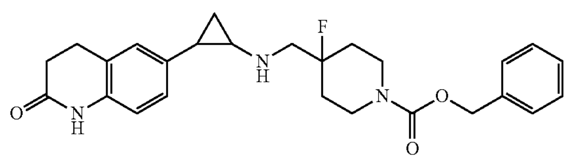 [SMILES: O=C1CCc2cc(C3CC3NCC3(F)CCN(C(=O)OCc4ccccc4)CC3)ccc2N1] |
| A62 | Benzyl 4-fluoro-4-((trans-2-(thiophen-3-yl)cyclopropyl)amino)methyl)piperidine-1-carboxylate | 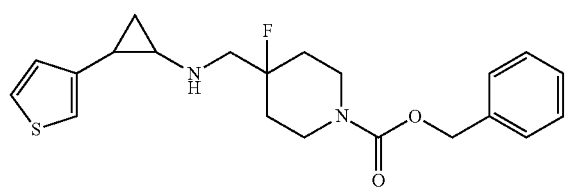 |
| A63 | Benzyl 4-fluoro-4-((trans-2-(furan-3-yl)cyclopropyl)amino)methyl)piperidine-1-carboxylate | 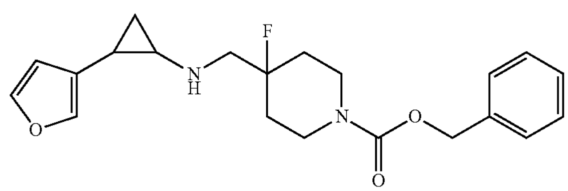 |
| A64 | Benzyl 4-fluoro-4-((trans-2-(thiazol-2-yl)cyclopropyl)amino)methyl)piperidine-1-carboxylate | 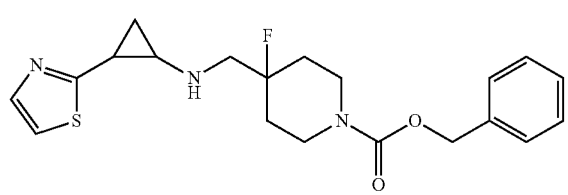 [SMILES: O=C(OCc1ccccc1)N1CCC(F)(CNC2CC2c2nccs2)CC1] |
| A65 | Benzyl 4-fluoro-4-((trans-2-(4-fluoro-phenyl)cyclopropyl)amino)methyl)piperidine-1-carboxylate | 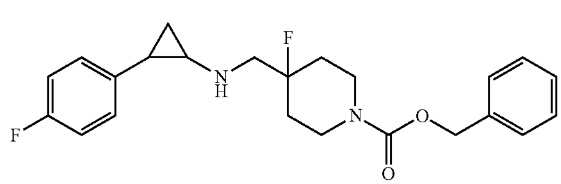 [SMILES: O=C(OCc1ccccc1)N1CCC(F)(CNC2CC2c2ccc(F)cc2)CC1] |

| No. | Name | Structure |
|---|---|---|
| A66 | Benzyl 4-fluoro-4-((trans-2-(4-cyano-phenyl)cyclopropyl)amino)methyl)piperidine-1-carboxylate | 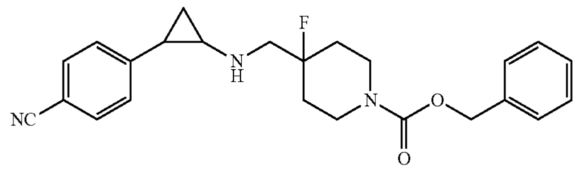 [SMILES: N#Cc1ccc(C2CC2NCC2(F)CCN(C(=O)OCc3ccccc3)CC2)cc1] |
| A67 | Benzyl 4-fluoro-4-((trans-2-(4-methoxy-phenyl)cyclopropyl)amino)methyl)piperidine-1-carboxylate | 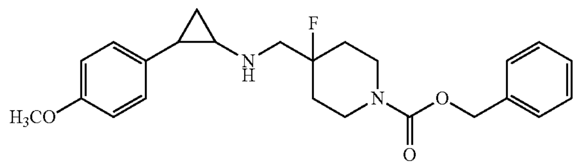 [SMILES: COc1ccc(C2CC2NCC2(F)CCN(C(=O)OCc3ccccc3)CC2)cc1] |
| A68 | Benzyl 4-fluoro-4-((trans-2-(2-acetyl-phenyl)cyclopropyl)amino)methyl)piperidine-1-carboxylate | 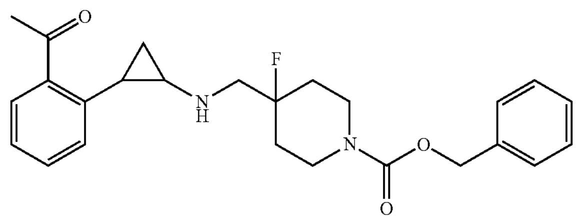 [SMILES: CC(=O)c1ccccc1C1CC1NCC1(F)CCN(C(=O)OCc2ccccc2)CC1] |
| A69 | Benzyl 4-fluoro-4-((trans-2-([1,1'-biphenyl]-4-yl)cyclopropyl)amino)methyl)piperidine-1-carboxylate | 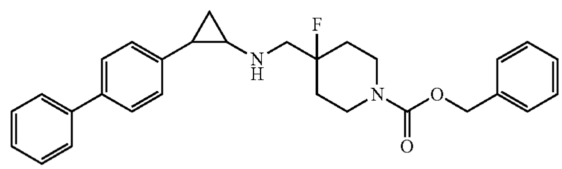 [SMILES: O=C(OCc1ccccc1)N1CCC(F)(CNC2CC2c2ccc(-c3ccccc3)cc2)CC1] |
| A70 | Benzyl 4-fluoro-4-((trans-2-(4-methyl-phenyl)cyclopropyl)amino)methyl)piperidine-1-carboxylate | 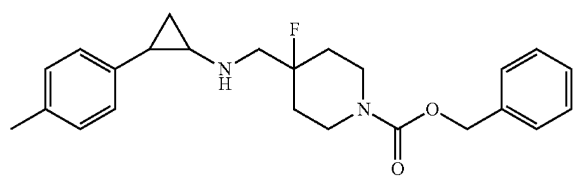 [SMILES: Cc1ccc(C2CC2NCC2(F)CCN(C(=O)OCc3ccccc3)CC2)cc1] |
| A71 | Benzyl 4-fluoro-4-((trans-2-(4-nitrophenyl)cyclopropyl)amino)methyl)piperidine-1-carboxylate | 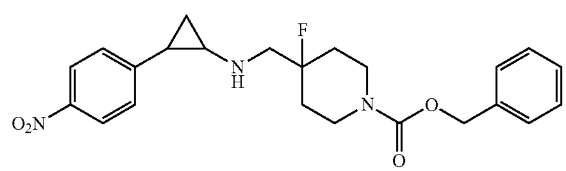 [SMILES: O=C(OCc1ccccc1)N1CCC(F)(CNC2CC2c2ccc([N+](=O)[O-])cc2)CC1] |
| A72 | 4-(trans-2-((1-((benzyloxy))carbonyl)-4-fluoropiperidin-4-yl)methyl)amino)cyclopropyl)benzoic acid | 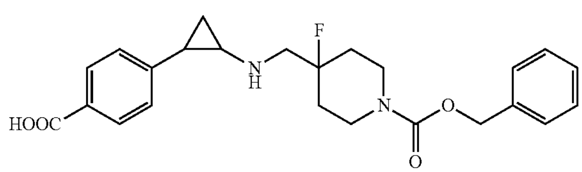 [SMILES: O=C(O)c1ccc(C2CC2NCC2(F)CCN(C(=O)OCc3ccccc3)CC2)cc1] |
| A73 | Benzyl 4-fluoro-4-((trans-2-(3,4-difluoro-phenyl)cyclopropyl)amino)methyl)piperidine-1-carboxylate | 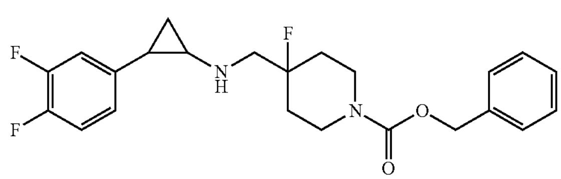 [SMILES: O=C(OCc1ccccc1)N1CCC(F)(CNC2CC2c2ccc(F)c(F)c2)CC1] |

| No. | Name | Structure |
|---|---|---|
| A74 | Benzyl 4-fluoro-4-((2,2,2-trifluoro-N-(trans-2-phenylcyclopropyl)acetamido)methyl)piperidine-1-carboxylate | 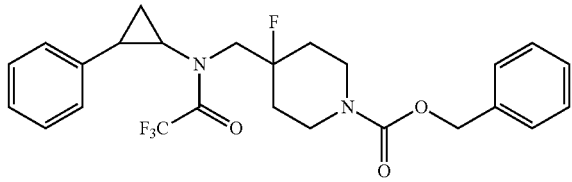 [SMILES: O=C(OCc1ccccc1)N1CCC(F)(CN(C(=O)C(F)(F)F)C2CC2c2ccccc2)CC1] |
| A75 | Benzyl 4-fluoro-4-((methyl(trans-2-phenyl-cyclopropyl)amino)methyl)piperidine-1-carboxylate | 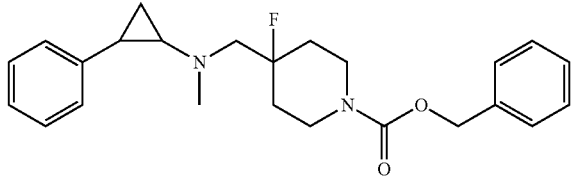 |
| A76 | Benzyl 4-fluoro-4-(1-((trans-2-phenyl-cyclopropyl)amino)ethyl)piperidine-1-carboxylate | 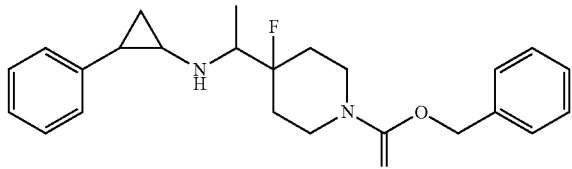 |
| A77 | Benzyl 4-fluoro-4-((N-(trans-2-phenyl-cyclopropyl)acetamido)methyl)piperidine-1-carboxylate | 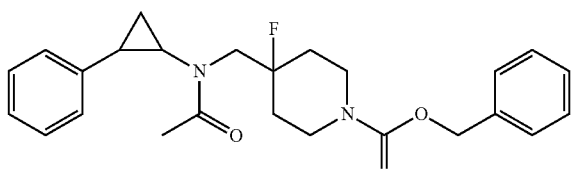 |
| A78 | 3-fluoro-3-(((trans-2-phenylcyclo-propyl)amino)methyl)azetidin-1-carboxylate | 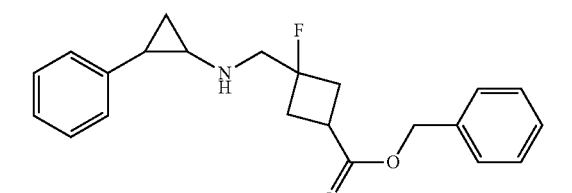 |
| A79 | 2-fluoro-2-(((trans-2-phenylcyclo-propyl)amino)methyl)morpholine-4-carboxylate | 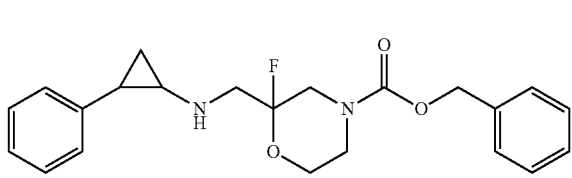 |
| A80 | Benzyl 4-fluoro-4-(2-((trans-2-phenylcyclo-propyl)amino)ethyl)piperidine-1-carboxylate | 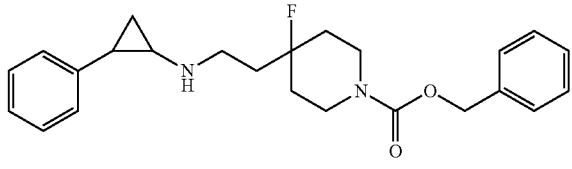 [SMILES: O=C(OCc1ccccc1)N1CCC(F)(CCNC2CC2c2ccccc2)CC1] |
| A81 | Benzyl 3-fluoro-3-((trans-2-phenylcyclo-propyl)amino)methyl)piperidine-1-carboxylate | 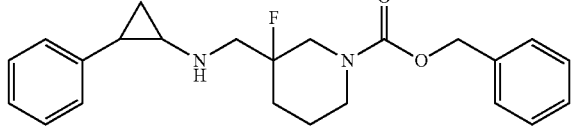 |

-continued

| No. | Name | Structure |
|---|---|---|
| A82 | N-((4-fluoro-1-(phenylsulfonyl) piperidin-4-yl)methyl)-trans-2-phenylcyclopropylamine | 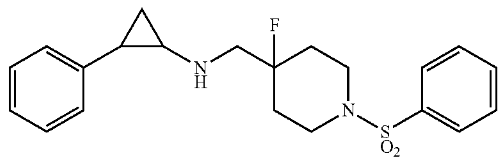 [SMILES: O=S(=O)(c1ccccc1)N1CCC(F)(CNC2CC2c2ccccc2)CC1] |
| A83 | 2-(4-Fluoro-4-(((trans-2-phenyl-cyclohexyl)amino)methyl) piperidin-1-yl)ethanol | 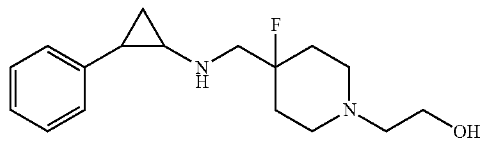 [SMILES: OCCN1CCC(F)(CNC2CC2c2ccccc2)CC1] |
| A84 | N-(4-fluoro-4-(((trans-2-phenyl-cyclopropyl)amino)methyl) cyclohexyl)acetamide | 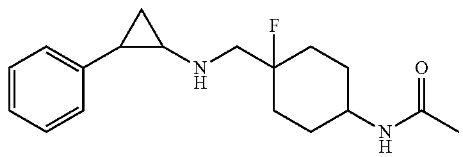 [SMILES: CC(=O)NC1CCC(F)(CNC2CC2c2ccccc2)CC1] |
| A85 | N-benzyl-4-fluoro-4-(((trans-2-phenylcyclopropyl)amino)methyl) cyclohexylamine | 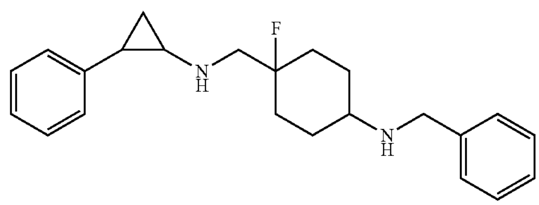 [SMILES: FC1(CNC2CC2c2ccccc2)CCC(NCc2ccccc2)CC1] |
| A86 | N-(4-fluoro-4-(((trans-2-phenyl-cyclopropyl)amino)methyl) cyclohexyl)aniline | 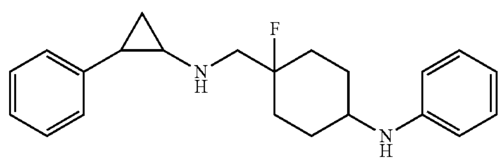 [SMILES: FC1(CNC2CC2c2ccccc2)CCC(Nc2ccccc2)CC1] |
| A87 | N-(4-Fluoro-4-(((trans-2-phenyl-cyclopropyl)amino)methyl)cyclo-hexyl)benzenesulfonamide | 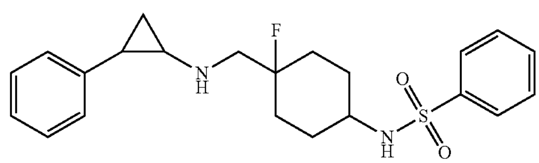 [SMILES: O=S(=O)(NC1CCC(F)(CNC2CC2c2ccccc2)CC1)c1ccccc1] |
| A88 | (1r,4r)-4-fluoro-4-(((trans-2-phenylcyclopropyl)amino)methyl) cyclohexylamine | 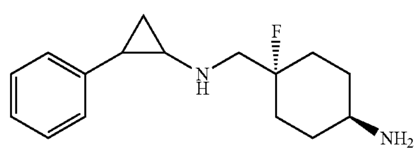 [SMILES: N[C@H]1CC[C@@](F)(CNC2CC2c2ccccc2)CC1] |
| A89 | (1-methylpiperidin-4-yl)methyl 4-fluoro-4-(((trans-2-phenylcyclo-propyl)amino)methyl)piperidine-1-carboxylate | 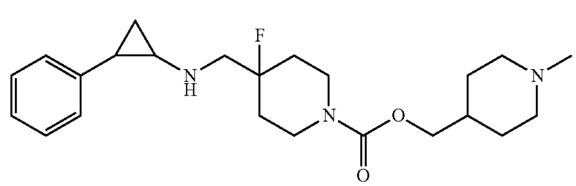 [SMILES: CN1CCC(COC(=O)N2CCC(F)(CNC3CC3c3ccccc3)CC2)CC1] |
| A90 | (1-benzylpiperidin-4-yl)methyl 4-fluoro-4-(((trans-2-phenyl-cyclopropyl)amino)methyl) piperidine-1-carboxylate | 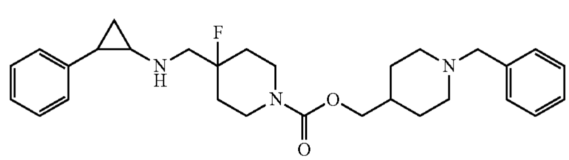 [SMILES: O=C(OCC1CCN(Cc2ccccc2)CC1)N1CCC(F)(CNC2CC2c2ccccc2)CC1] |

-continued

| No. | Name | Structure |
|---|---|---|
| A91 | 4-((4-(((4-Fluoro-4-(((trans-2-phenylcyclopropyl)amino)methyl)piperidine-1-carbonyl)oxo)methyl)piperdin-1-yl)methyl)benzoic acid | 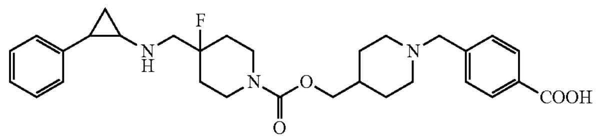 [SMILES: O=C(O)c1ccc(CN2CCC(COC(=O)N3CCC(F)(CNC4CC4c4ccccc4)CC3)CC2)cc1] |
| A92 | N-((4-fluoro-1-(piperidin-4-ylmethyl)sulfonyl)piperidin-4-yl)methyl)-trans-2-phenylcyclopropylamine | 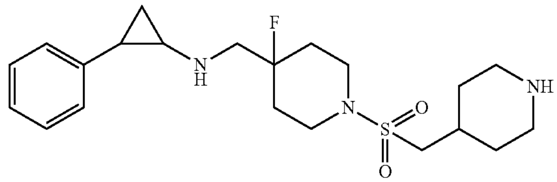 [SMILES: O=S(=O)(CC1CCNCC1)N1CCC(F)(CNC2CC2c2ccccc2)CC1] |
| A93 | N-((4-fluoro-1-(methylsulfonyl)piperidin-4-yl)methyl)-trans-2-phenylcyclopropylamine | 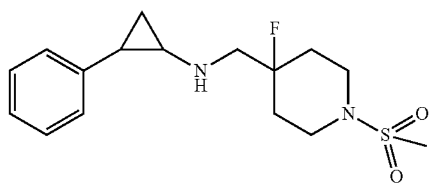 [SMILES: CS(=O)(=O)N1CCC(F)(CNC2CC2c2ccccc2)CC1] |
| A94 | Azetidin-3-ylmethyl 4-fluoro-4-(((trans-2-phenylcyclopropyl)amino)methyl)piperidine-1-carboxylate | 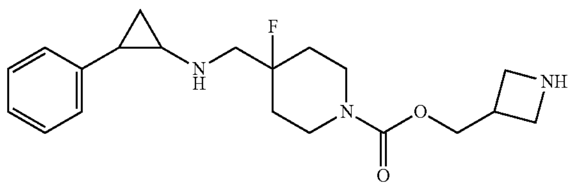 [SMILES: O=C(OCC1CNC1)N1CCC(F)(CNC2CC2c2ccccc2)CC1] |
| A95 | Piperidin-4-yl 4-fluoro-4-(((trans-2-phenylcyclopropyl)amino)methyl)piperidine-1-carboxylate | 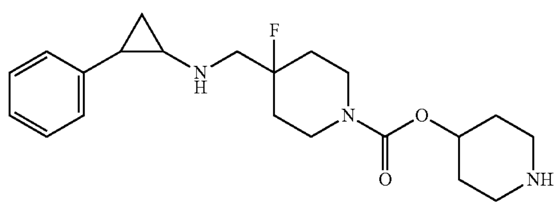 [SMILES: O=C(OC1CCNCC1)N1CCC(F)(CNC2CC2c2ccccc2)CC1] |
| A96 | 4-((4-Fluoro-4-(((trans-2-phenylcyclopropyl)amino)methyl)piperidin-1-yl)methyl)benzonitrile | 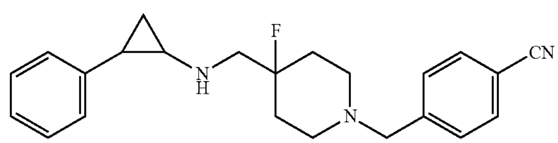 [SMILES: N#Cc1ccc(CN2CCC(F)(CNC3CC3c3ccccc3)CC2)cc1] |
| A97 | N-((4-fluoro-1-(piperidin-4-ylmethyl)piperidin-4-yl)methyl)-trans-2-phenylcyclopropylamine | 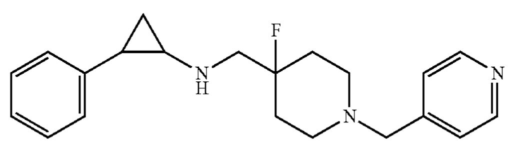 [SMILES: FC1(CNC2CC2c2ccccc2)CCN(Cc2ccncc2)CC1] |
| A98 | N-((4-fluoro-1-(thien-3-ylmethyl)piperidin-4-yl)methyl)-trans-2-phenylcyclopropylamine | 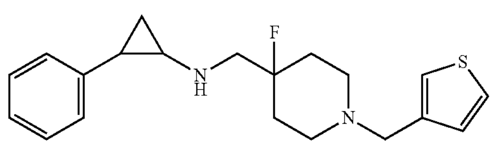 [SMILES: FC1(CNC2CC2c2ccccc2)CCN(Cc2ccsc2)CC1] |
| A99 | (1-(cyclopropylmethyl)piperidin-4-yl)methyl 4-fluoro-4-(((trans-2-phenylcyclopropyl)amino)methyl)piperidine-1-carboxylate | 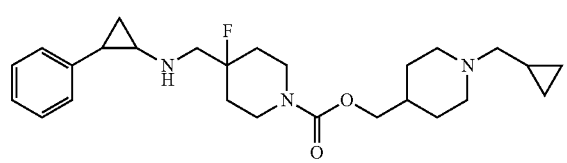 [SMILES: O=C(OCC1CCN(CC2CC2)CC1)N1CCC(F)(CNC2CC2c2ccccc2)CC1] |

| No. | Name | Structure |
|---|---|---|
| A100 | N-(2-Aminophenyl)-4-((4-fluoro-4-(((trans-2-phenylcyclopropyl)amino)methyl)piperidin-1-yl)methyl)benzamide | 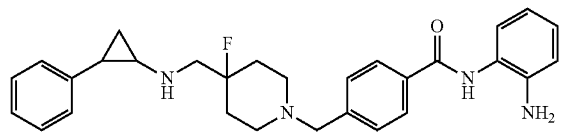 [SMILES: Nc1ccccc1NC(=O)c1ccc(CN2CCC(F)(CNC3CC3c3ccccc3)CC2)cc1] |
| A101 | tert-Butyl 4-((4-((2-(5-bromothien-2-yl))cyclopropyl)amino)methyl)-4-fluoropiperidin-1-yl)methyl)benzoate | 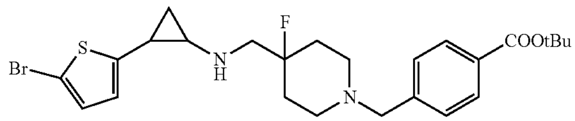 |
| A102 | 4-((4-(((2-(5-Bromothiophen-2-yl))cyclopropyl)amino)methyl)-4-fluoropiperidin-1-yl)methyl)benzoic acid | 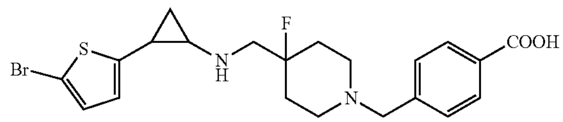 [SMILES: O=C(O)c1ccc(CN2CCC(F)(CNC3CC3c3ccc(Br)s3)CC2)cc1] |
| A103 | Methyl 4-((4-(((2-(5-bromothiophen-2-yl))cyclopropyl)amino)methyl)-4-fluoropiperidin-1-yl)methyl)benzoate | 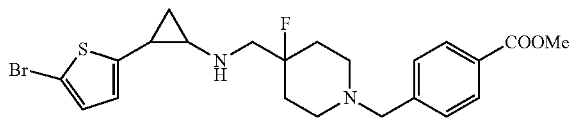 [SMILES: COC(=O)c1ccc(CN2CCC(F)(CNC3CC3c3ccc(Br)s3)CC2)cc1] |
| A104 | Ethyl 4-((4-(((2-(5-bromothiophen-2-yl))cyclopropyl)amino)methyl)-4-fluoropiperidin-1-yl)methyl)benzoate | 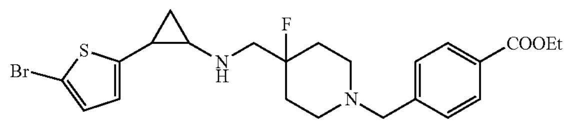 [SMILES: CCOC(=O)c1ccc(CN2CCC(F)(CNC3CC3c3ccc(Br)s3)CC2)cc1] |
| A105 | tert-Butyl 4-((4-fluoro-4-(((2-(5-(4-fluorophenyl)thiophen-2-yl)cyclopropyl)amino)methyl)piperidin-1-yl)methyl)benzoate | 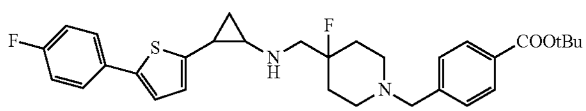 |
| A106 | tert-Butyl 4-((4-(((2-(5-(4-chlorophenyl)thiophen-2-yl)cyclopropyl)amino)methyl)-4-fluoropiperidin-1-yl)methyl)benzoate | 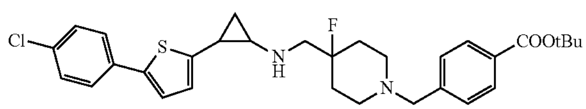 |
| A107 | tert-Butyl 4-((4-fluoro-4-(((2-(5-(4-(trifluoromethyl)phenyl)thiophen-2-yl)cyclopropyl)amino)methyl)piperidine-1-yl)methyl)benzoate | 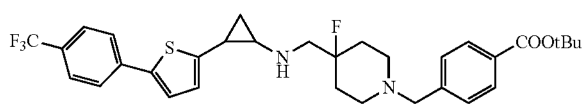 |
| A108 | tert-Butyl 4-((4-fluoro-4-(((2-(5-phenyl-thiophen-2-yl)cyclopropyl)amino)methyl)piperidin-1-yl)methyl)benzoic acid | 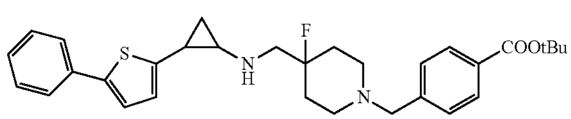 |
| A109 | tert-Butyl 4-((4-fluoro-4-(((2-(5-(naphthalen-1-yl)thiophen-2-yl)cyclopropyl)amino)methyl)piperidin-1-yl)methyl)benzoate | 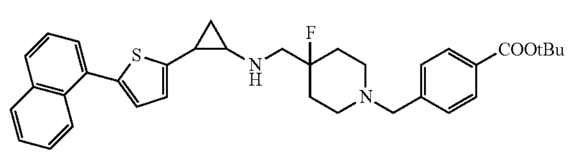 |
| A110 | Piperidin-4-ylmethyl 4-fluoro-4-(((2-(5-(4-(trifluoromethyl)phenyl)thiophen-2-yl)cyclopropyl)amino)methyl)piperdine-1-carboxylate | 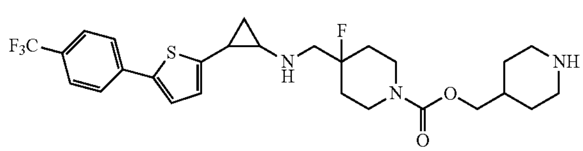 [SMILES: O=C(OCC1CCNCC1)N1CCC(F)(CNC2CC2c2ccc(-c3ccc(C(F)(F)F)cc3)s2)CC1] |

-continued

| No. | Name | Structure |
|---|---|---|
| A111 | Piperidin-4-ylmethyl 4-(((2-(5-bromothien-2-yl)cyclopropyl)amino)methyl)-4-fluoropiperidine-1-carboxylate | 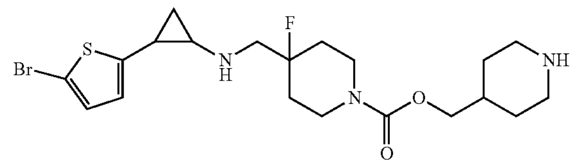 [SMILES: O=C(OCC1CCNCC1)N1CCC(F)(CNC2CC2c2ccc(Br)s2)CC1] |
| A112 | Piperidin-4-ylmethyl 4-fluoro-4-(((2-(6-(4-methoxyphenyl)pyridin-3-yl)cyclopropyl)amino)methyl)piperidin-1-carboxylate | 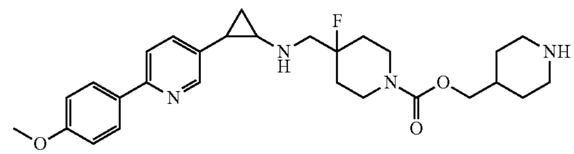 [SMILES: COc1ccc(-c2ccc(C3CC3NCC3(F)CCN(C(=O)OCC4CCNCC4)CC3)cn2)cc1] |
| A113 | Piperidin-4-ylmethyl 4-(((2-(5-cyclopropylthiophen-2-yl)cyclopropyl)amino)methyl)-4-fluoropiperidine-1-carboxylate | 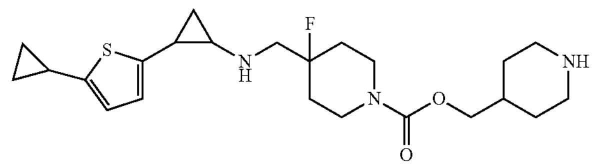 [SMILES: O=C(OCC1CCNCC1)N1CCC(F)(CNC2CC2c2ccc(C3CC3)s2)CC1] |
| A114 | Piperidin-4-ylmethyl 4-(((2-(5-((4-cyanophenyl)ethynyl)thiophen-2-yl)cyclopropyl)amino)methyl)-4-fluoropiperidine-1-carboxylate | 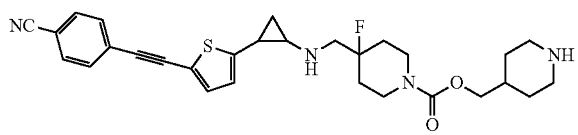 [SMILES: N#Cc1ccc(C#Cc2ccc(C3CC3NCC3(F)CCN(C(=O)OCC4CCNCC4)CC3)s2)cc1] |
| A115 | Piperidin-4-ylmethyl 4-fluoro-4-(((2-(6-phenylpyridin-3-yl)cyclopropyl)amino)methyl)piperidine-1-carboxylate | 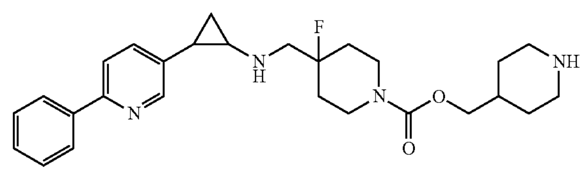 [SMILES: O=C(OCC1CCNCC1)N1CCC(F)(CNC2CC2c2ccc(-c3ccccc3)nc2)CC1] |
| A116 | Piperidin-4-ylmethyl 4-(((2-(6-(4-ethylphenoxy)pyridin-3-yl)cyclopropyl)amino)methyl)-4-fluoropiperidine-1-carboxylate | 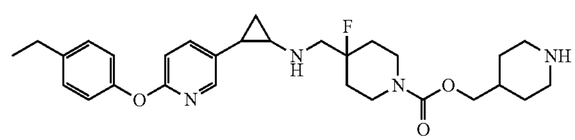 [SMILES: CCc1ccc(Oc2ccc(C3CC3NCC3(F)CCN(C(=O)OCC4CCNCC4)CC3)cn2)cc1] |
| A117 | Piperidin-4-ylmethyl 4-fluoro-4-(((2-(6-(3-(trifluoromethyl)phenyl)pyridin-3-yl)cyclopropyl)amino)methyl)piperidine-1-carboxylate | 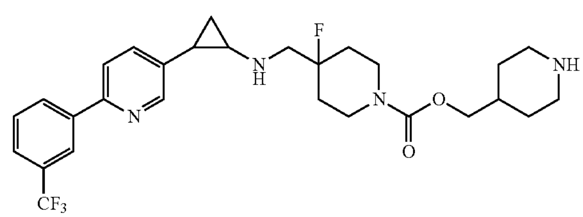 [SMILES: O=C(OCC1CCNCC1)N1CCC(F)(CNC2CC2c2ccc(-c3cccc(C(F)(F)F)c3)nc2)CC1] |
| A118 | Piperidin-4-ylmethyl 4-fluoro-4-(((2-(6-(4-fluorophenyl)pyridin-3-yl)cyclopropyl)amino)methyl)piperidine-1-carboxylate | 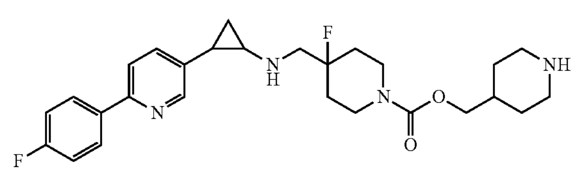 [SMILES: O=C(OCC1CCNCC1)N1CCC(F)(CNC2CC2c2ccc(-c3ccc(F)cc3)nc2)CC1] |
| A119 | Piperidin-4-ylmethyl 4-(((2-(6-(4-chlorophenyl)pyridin-3-yl)cyclopropyl)amino)methyl)-4-fluoropiperidine-1-carboxylate | 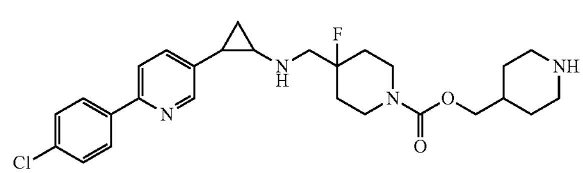 [SMILES: O=C(OCC1CCNCC1)N1CCC(F)(CNC2CC2c2ccc(-c3ccc(Cl)cc3)nc2)CC1] |

-continued

| No. | Name | Structure |
|---|---|---|
| A120 | Piperidin-4-ylmethyl 4-(((2-(6-(3,5-dimethoxyphenyl)pyridin-3-yl)cyclopropyl)amino)methyl)-4-fluoropiperidine 1-carboxylate | 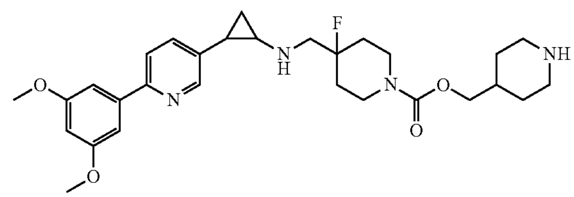 [SMILES: COc1cc(OC)cc(-c2ccc(C3CC3NCC3(F)CCN(C(=O)OCC4CCNCC4)CC3)cn2)c1] |
| A121 | Piperidin-4-ylmethyl 4-(((2-(6-bromopyridin-3-yl)cyclopropyl)amino)methyl)-4-fluoropiperidine-1-carboxylate | 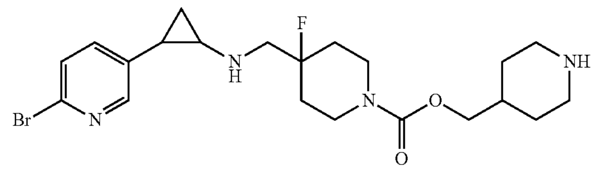 [SMILES: O=C(OCC1CCNCC1)N1CCC(F)(CNC2CC2c2ccc(Br)nc2)CC1] |
| A122 | Piperidin-4-ylmethyl 4-(((2-(2-chlorothiazol-5-yl)cyclopropyl)amino)methyl)-4-fluoropiperidine-1-carboxylate | 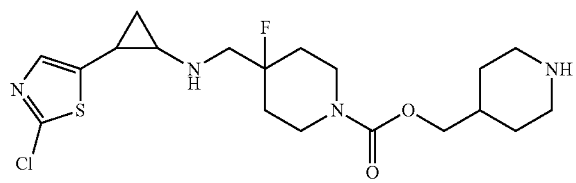 [SMILES: O=C(OCC1CCNCC1)N1CCC(F)(CNC2CC2c2cnc(Cl)s2)CC1] |
| A123 | Piperidin-4-ylmethyl 4-fluoro-4-(((2-(2-(4-fluorophenyl)thiazol-5-yl)cyclopropyl)amino)methyl)piperidine-1-carboxylate | 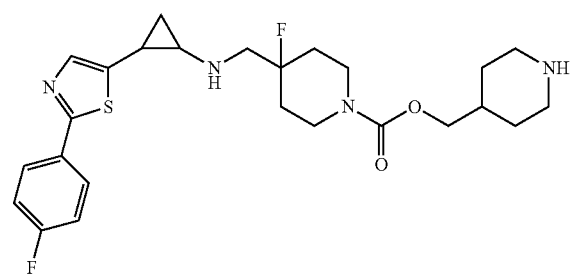 [SMILES: O=C(OCC1CCNCC1)N1CCC(F)(CNC2CC2c2cnc(-c3ccc(F)cc3)s2)CC1] |
| A124 | Piperidin-4-ylmethyl 4-(((2-(2-(4-chlorophenyl)thiazol-5-yl)cyclopropyl)amino)methyl)-4-fluoropiperidine-1-carboxylate | 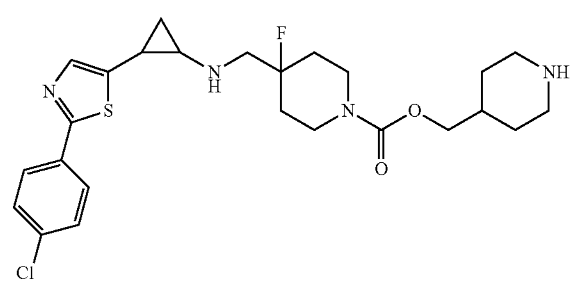 [SMILES: O=C(OCC1CCNCC1)N1CCC(F)(CNC2CC2c2cnc(-c3ccc(Cl)cc3)s2)CC1] |
| A125 | Piperidin-4-ylmethyl 4-fluoro-4-(((2-(2-phenylthiazol-5-yl)cyclopropyl)amino)methyl)piperidine-1-carboxylate | 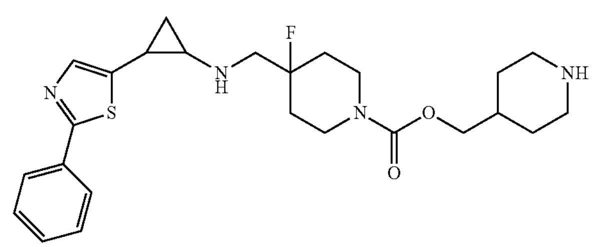 [SMILES: O=C(OCC1CCNCC1)N1CCC(F)(CNC2CC2c2cnc(-c3ccccc3)s2)CC1] |

| No. | Name | Structure |
|---|---|---|
| A126 | Piperidin-4-ylmethyl 4-fluoro-4-(((2-(2-(4-methoxy-phenyl)thiazol-5-yl)cyclopropyl)amino)methyl)piperidin-1-carboxylate | 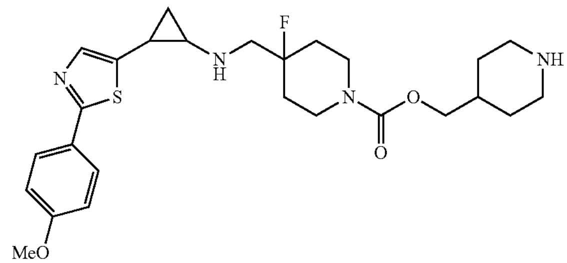 [SMILES: COc1ccc(-c2ncc(C3CC3NCC3(F)CCN(C(=O)OCC4CCNCC4)CC3)s2)cc1] |
| A127 | Piperidin-4-ylmethyl 4-(((2-(2-(3,5-dimethoxyphenyl)thiazol-5-yl)cyclopropyl)amino)methyl)-4-fluoropiperidine-1-carboxylate | 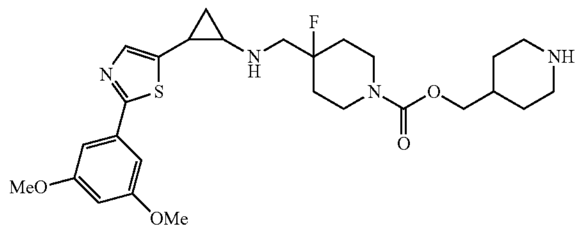 [SMILES: COc1cc(OC)cc(-c2ncc(C3CC3NCC3(F)CCN(C(=O)OCC4CCNCC4)CC3)s2)c1] |
| (1R,2S)-A43 | Piperidin-4-ylmethyl 4-fluoro-4-((((1R,2S)-2-phenyl-cyclopropyl)amino)methyl)piperidine-1-carboxylate | 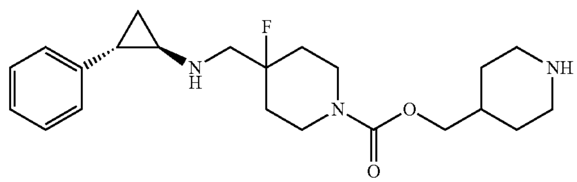 [SMILES: O=C(OCC1CCNCC1)N1CCC(F)(CN[C@@H]2C[C@H]2c2ccccc2)CC1] |
| (1S,2R)-A43 | Piperidin-4-ylmethyl 4-fluoro-4-((((1S,2R)-2-phenyl-cyclopropyl)amino)methyl)piperidine-1-carboxylate | 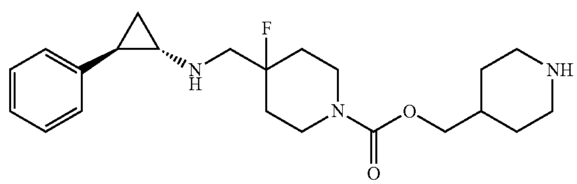 [SMILES: O=C(OCC1CCNCC1)N1CCC(F)(CN[C@H]2C[C@@H]2c2ccccc2)CC1] |
| (1R,2S)-A90 | (1-Benzylpiperidin-4-yl)methyl 4-fluoro-4-((((1R,2S)-2-phenyl-cyclopropyl)amino)methyl)piperidine-1-carboxylate | 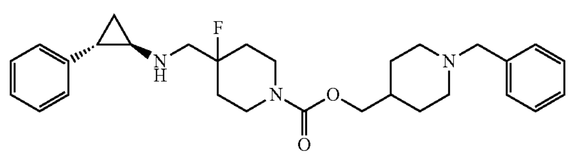 [SMILES: O=C(OCC1CCN(Cc2ccccc2)CC1)N1CCC(F)(CN[C@@H]2C[C@H]2c2ccccc2)CC1] |
| (1R,2S)-A5 | 4-((4-fluoro-4-((((1R,2S)-2-phenylcyclopropyl)amino)methyl)piperidin-1-yl)methyl)benzoic acid | 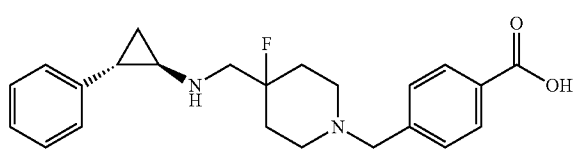 [SMILES: O=C(O)c1ccc(CN2CCC(F)(CN[C@@H]3C[C@H]3c3ccccc3)CC2)cc1] |
| (1S,2R)-A5 | 4-((4-fluoro-4-((((1S,2R)-2-phenyl-cyclopropyl)amino)methyl)piperidin-1-yl)methyl)benzoic acid | 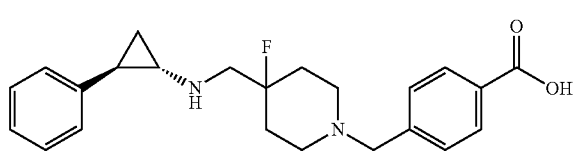 [SMILES: O=C(O)c1ccc(CN2CCC(F)(CN[C@H]3C[C@@H]3c3ccccc3)CC2)cc1] |

The compounds of the invention have asymmetric centers, chiral axes and chiral planes, and may exist in the form of racemates, R-isomers or S-isomers. Those skilled in the art will be able to resolve the R-isomer and/or the S-isomer from the racemate by conventional techniques.

The present invention provides a pharmaceutically acceptable salt of a compound of formula I, in particular a conventional pharmaceutically acceptable salt formed from a compound of formula I with an inorganic or organic acid. For example, conventional pharmaceutically acceptable salts may be prepared by reacting a compound of formula I with an inorganic mineral acid, such as hydrochloric acid, hydrobromic acid, sulfuric acid, nitric acid, aminosulfonic acid and phosphoric acid, and the like, and organic acids include citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalene disulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, p-anilinesulfonic acid, 2-acetoxybenzoic acid and isethionic acid; or sodium, potassium, calcium, aluminum or ammonium salts of the compound of formula I with an inorganic base; or a salt formed by compound of formula I with an organic base, such as methanamine salt, ethylamine salt or ethanolamine salt.

In another aspect of the present invention, a process for the preparation of a compound of formula I is provided, which is carried out according to the following scheme 1, scheme 2 or scheme 3:

The compound of formula (I) can be prepared by the following scheme 1:

The structural formula and R group labels used in the following schemes are only used in this section. Compounds of formula (II) and (III) are commercially available or can be synthesized using conventional techniques in the art. Those skilled in the art should understand that when HCl is used in the final step of the preparation, the compounds exemplified below may be present in the form of the hydrochloride salt.

The compounds of formula (II) and (III) can be reacted under conventional reductive amination conditions to provide compounds of formula (I). The addition reaction is usually carried out in the presence of a polar solvent such as methanol and an acid such as acetic acid. The acid is usually present in 100 mol % amount relative to formula (I). The reducing agent is usually borohydrides (e.g., sodium cyanoborohydride).

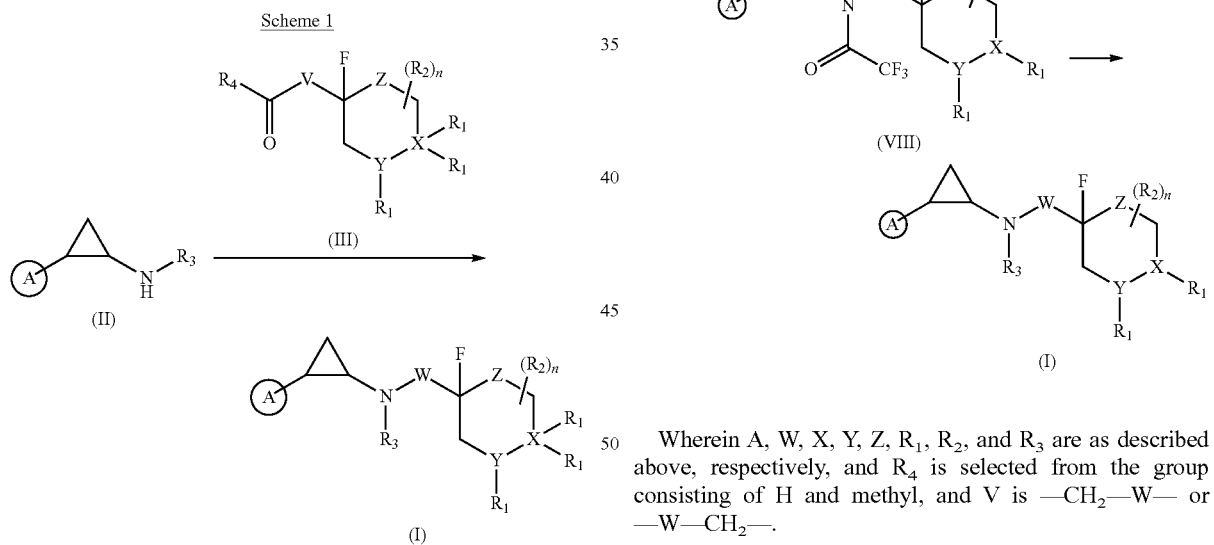

Wherein A, W, X, Y, Z, $R_1$, $R_2$, and $R_3$ are as described above, respectively, and $R_4$ is selected from the group consisting of H and methyl, and V is —$CH_2$—W— or —W—$CH_2$—.

The compound of formula (I) can be conveniently prepared by the procedure shown in Scheme 2 starting from the synthetic cyclopropylamine (IV) and suitably protected aldehyde (V). The amine (IV) and the aldehyde (V) are subjected to reductive amination to give the formula (VI) intermediate. Then the amine group can be protected. The protecting group of the X or Y group is then removed to give compound of formula (VII) to functionalize the appropriate $R_1$ substituent to provide a compound of formula (VIII). Then the amine can then be deprotected and functionalized with an $R_3$ group;

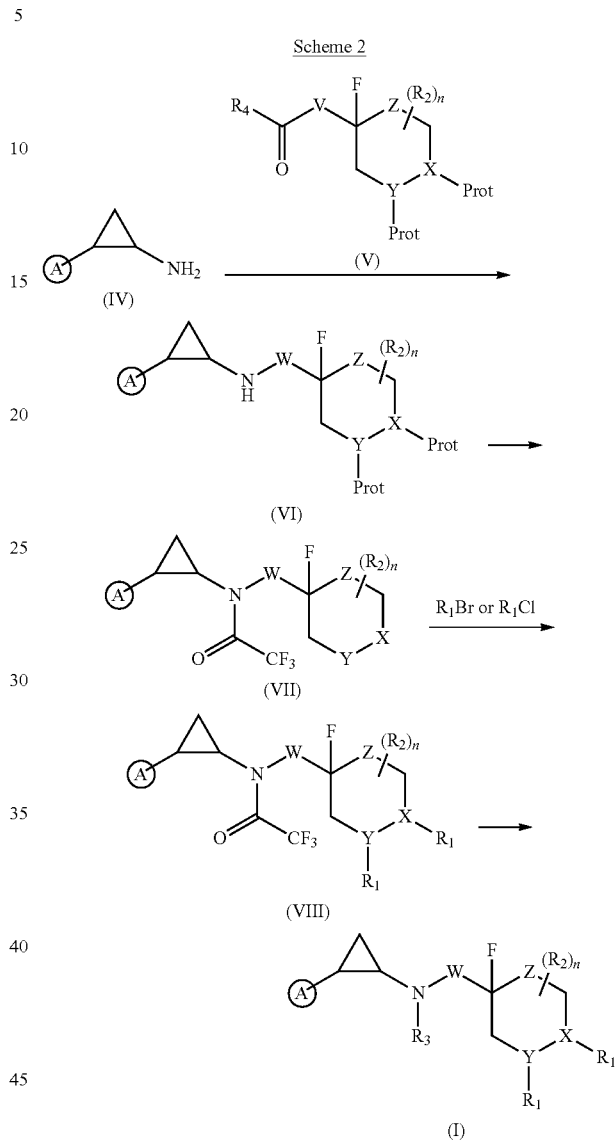

Wherein A, W, X, Y, Z, $R_1$, $R_2$, and $R_3$ are as described above, respectively, and $R_4$ is selected from the group consisting of H and methyl, and V is —$CH_2$—W— or —W—$CH_2$—.

Compounds of formula (II) and (IV) can be synthesized as shown in Scheme 3, starting from cinnamic acid (IX), and condensed with dimethylhydroxylamine in the presence of condensing agent (for example, HATU) and base (for example, DIPEA) to give the amide (X). The cyclopropylation is then carried out in the presence of standard conditions (e.g., trimethylsulfoxide iodide and sodium hydride) to give the compound of formula (XI). The amide is then hydrolyzed to give the formula (XII) acid. It is then reacted under standard Curtius rearrangement conditions to give the desired formula (IV) compound. The compound of formula (IV) can be converted to the compound of formula (II) under standard conditions.

Scheme 3
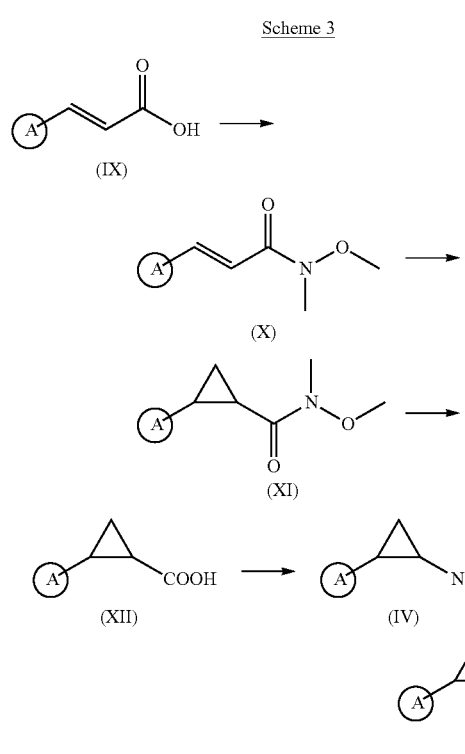
The compounds of formula (1R, 2S)-I and (1S, 2R)-I can be obtained by the preparation methods described in Scheme 4 and Scheme 5, respectively, and the specific operation steps are the same as Scheme 2.
Scheme 4
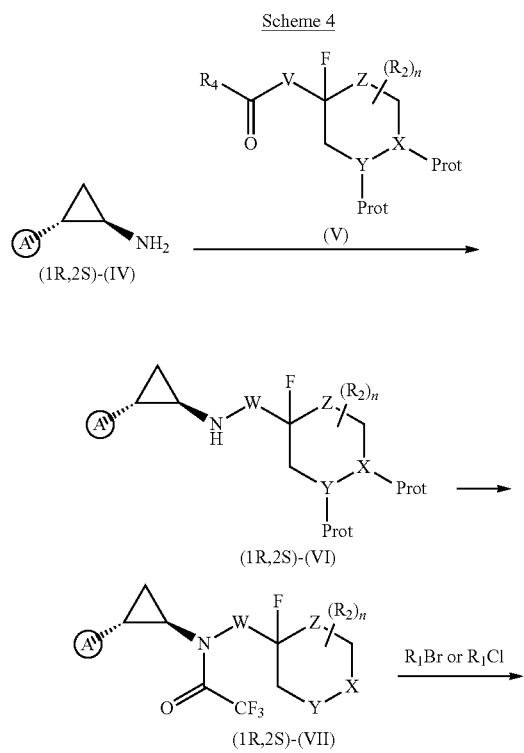
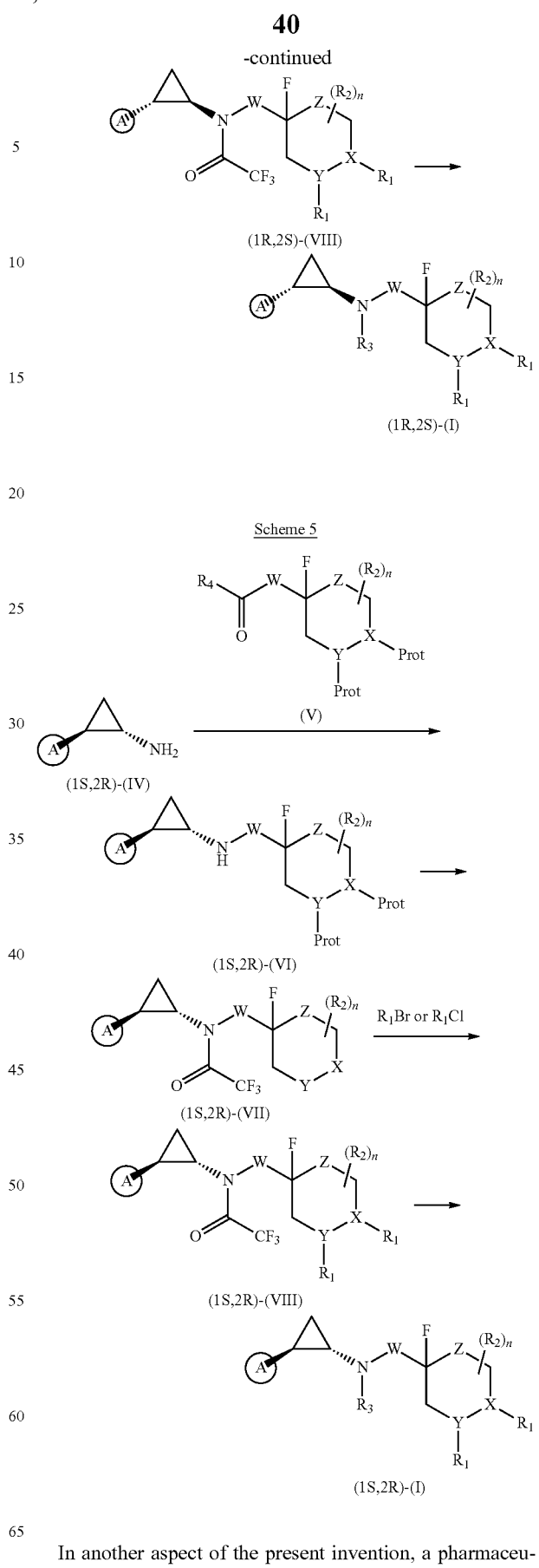
In another aspect of the present invention, a pharmaceutical composition is provided, comprising a therapeutically effective amount of a compound selected from the above general formula (I), pharmaceutically acceptable salts, enantiomers, diastereomers or racemates thereof, and optionally one or more pharmaceutically acceptable carriers, excipients, adjuvants, auxiliary substances and/or diluents. The auxiliary substances are, for example, odorants, flavoring agents, sweeteners, and the like.

The pharmaceutical composition provided in the present invention preferably contains the active ingredient in a weight ratio of 1 to 99%. The preferable proportion thereof is that the compound of the general formula I accounts for 65 wt % to 99 wt % of the total weight as the active ingredient, and the rest is pharmaceutically acceptable carriers, diluents, solutions or salt solutions.

The compounds and pharmaceutical compositions provided in the present invention may be in various forms, such as tablets, capsules, powders, syrups, solutions, suspensions, aerosols, etc., and may be present in suitable solid or liquid carriers or diluents, and in disinfectors suitable for injection or instillation.

Various dosage forms of the pharmaceutical composition of the present invention can be prepared according to the conventional preparation methods in the pharmaceutical field. The unit dosage of its formulation formula comprises 0.05-200 mg of the compound of formula I, preferably, the unit dosage of the formulation contains 0.1 mg-100 mg of the compound of formula I.

The compounds and pharmaceutical compositions of the present invention can be used clinically in mammals, including humans and animals, and can be administered via mouth, nose, skin, lungs or gastrointestinal tract, and most preferably oral. The most preferred daily dose is 0.01-200 mg/kg body weight, taken once, or 0.01-100 mg/kg body weight in divided doses. Regardless of the method of administration, the individual's optimal dose should be based on the specific treatment. Usually, it starts with a small dose, and gradually increase the dose until the most suitable dose is found.

In a further aspect of the present invention, an Lysine specific demethylase 1 (LSD1) inhibitor is provided, comprising one or more selected from the group consisting of the compounds represented by Formula I, the pharmaceutically acceptable salts, racemate, R-isomer, S-isomer thereof, and mixtures thereof, and optionally one or more pharmaceutically acceptable carriers, excipients, adjuvants, auxiliary substances and/or diluents.

The compounds and compositions of the invention are useful in the treatment and prevention of malignant tumor diseases associated with lysine-specific demethylase 1 (LSD1) inhibitors, including, but not limited to, diseases such as cancer, leukemia, and the like.

Therefore, another aspect of the present invention is to provide a use of compound of formula I, a pharmaceutically acceptable salt, a racemate, an R-isomer, an S-isomer, or a mixture thereof in the preparation of a medicament for the treatment of malignant tumor diseases associated with lysine-specific demethylase 1 (LSD1) inhibitor, such as cancer, leukemia or the like.

Still in another aspect of the present invention, a method of treating diseases associated with lysine-specific demethylase 1 (LSD1) inhibitor, such as cancer, leukemia, and the like is provided, which include administering to a patient in need thereof with one or more of the compound of the above formula I, the pharmaceutically acceptable salts, racemate, R-isomer, S-isomer, or mixtures thereof.

EMBODIMENTS FOR CARRYING OUT THE INVENTION

Active Ingredients

The present invention provided a fluorine-substituted cyclopropylamine compound having a structure represented by the following general formula I, or a racemate, R-isomer, S-isomer, pharmaceutically acceptable salt thereof, or a mixture thereof:

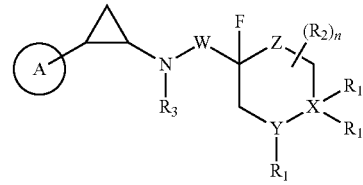

Formula I wherein,

A is selected from the group consisting of a substituted or unsubstituted aromatic ring (preferably benzene ring), or a substituted or unsubstituted 5-12 membered aromatic heterocyclic ring containing 1 to 4 heteroatoms selected from the group consisting of oxygen, sulfur and nitrogen, wherein each of the substituted benzene ring or substituted aromatic heterocycles comprises 1 to 3 substituents;

Wherein the substituent on the substituted aromatic ring or substituted aromatic heterocyclic ring is independently selected from hydrogen, isotope of hydrogen, halogen, an unsubstituted or substituted C1-C12 straight or branched alkyl group, unsubstituted or substituted C1-C12 straight or branched alkoxy, unsubstituted or substituted C2-C12 straight or branched unsaturated hydrocarbon group, unsubstituted C3-C6 cycloalkyl, C1-C6 straight or branched alkyl substituted by C1-C6 alkoxy, C1-C6 straight or branched alkyl substituted by C3-C6 cycloalkyl, hydroxy, cyano, nitro, C1-C6 straight or branched hydroxyalkyl or thiol, oxygen (=O), unsubstituted or substituted C6-C12 aryl (such as phenyl, naphthyl), unsubstituted or substituted C6-C12 aryloxy (such as phenyl, naphthyl), unsubstituted or substituted phenyloxy, carboxy, acyl (such as acetyl), and sulfonyl (including phenylsulfonyl, alkylsulfonyl); preferably the substituent is selected from the group consisting of halogen, a C1-C4 straight or branched alkyl, halogen-substituted C1-C4 straight or branched alkyl, C1-C4 alkyloxy, cyano-substituted phenyl;

Alternatively, any two substituents on the substituted aromatic ring or substituted aromatic heterocyclic ring may be linked together with their adjacent carbon or hetero atom to form a 5-7 membered heterocyclic ring comprising 1 to 3 heteroatoms selected from N, O and S, and the 5-7 membered heterocyclic ring is optionally substituted by substituents selected from the group consisting of hydrogen, hydrogen isotope, halogen, C1-C6 straight or branched alkyl unsubstituted or substituted with 1-3 halogens, C1-C6 straight or branched alkoxy unsubstituted or substituted by 1 to 3 halogens, and hydroxyl;

Each $R_1$ is independently selected from the group consisting of a substituted or unsubstituted aryl, substituted or unsubstituted heteroaryl, hydrogen, substituted or unsubstituted C1-C6 alkyl group, —SO$_2$Ra, —NC(O)Ra, —(CH$_2$)$_m$C(O)ORa, —C(O)O(CH$_2$)$_m$Ra, —C(O)ORa, —C(O)Ra, —(CH$_2$)$_m$ORa, —C(O)NRaRb, —C(S)NRaRb, —CORa, —NRcRd, substituted or unsubstituted amino, substituted or unsubstituted urea, substituted or unsubstituted amide, substituted or unsubstituted sulfonamide, substituted or unsubstituted arylalkyl and substituted or unsubstituted heteroarylalkyl, wherein m is an integer from 1 to 3; preferably, the substituent is selected from the group consisting of halogen, hydroxy, carboxy, cyano, amino, a C1-C4 alkyl, halogen-substituted C1-C4 alkyl, C1-C4 alkyl ester group, C1-C4 alkylsulfonyl, aminophenylamide group ( 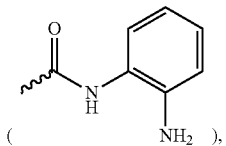 ), arylalkyl, and aryl;

Each Ra is independently hydrogen, a substituted or unsubstituted phenyl, substituted or unsubstituted phenylmethyl, 3,5-dimethylisoxazol-4-yl, 1,2-dimethyl-1H-imidazol-4-yl, substituted or unsubstituted C3-C7 cycloalkyl, substituted or unsubstituted C3-C7 heterocyclic group, substituted or unsubstituted C3-C7 heterocycloalkyl, substituted or unsubstituted C1-C6 alkyl, substituted or unsubstituted C1-C6 alkenyl, substituted or unsubstituted C1-C4 alkoxy, substituted or unsubstituted C1-C3 alkylamino, —NHPh, substituted or unsubstituted 5-10 membered heteroaryl, substituted or unsubstituted arylalkyl group, or substituted or unsubstituted heteroarylalkyl group; preferably the substituent group is selected from the group consisting of: C1-C4 alkyl, halogen-substituted C1-C4 alkyl, phenyl-substituted C1-C4 alkyl, C1-C4 alkyl ester, C3-C7 cyclic group, C3-C7 cyclic group, C3-C7 heterocyclic group, benzyl-substituted C3-C7 heterocycloalkyl, aryl, halogen, C1-C4 alkoxy, C1-C4 halogenoalkyl, carboxyl, and a carboxyl-substituted benzyl;

Rb is hydrogen or a C1-C3 alkyl, or when attached to the same atom,

Ra and Rb together form a 5- or 6-membered heterocycloalkyl ring;

Rc and Rd are each independently selected from hydrogen, a substituted or unsubstituted C1-C3 straight or branched alkyl, substituted or unsubstituted C3-C5 cycloalkyl, substituted or unsubstituted C1-C3 alkoxy, substituted or unsubstituted 4- to -6-membered heterocyclic group, substituted or unsubstituted C1-C3 alkylacyl, substituted or unsubstituted arylacyl, substituted or unsubstituted arylsulfonyl, substituted or unsubstituted benzyl, substituted or unsubstituted aryl; the C1-C3 straight or branched alkyl is optionally substituted by one or more selected from the group consisting of methylsulfonyl, C1-C3 alkoxy, C1-C3 alkoxycarbonyl group, aryl; the heterocyclic group containing one heteroatom selected from the group consisting of oxygen, sulfur and nitrogen;

$R_2$ is hydrogen or COOH;

$R_3$ is C1-C4 alkyl, acyl, —C(O)CF3 or hydrogen;

W is —$(CH_2)_{1-4}$ or —$CH(Re)(CH_2)_{0-3}$, wherein Re is CN or C1-C4 alkyl;

Y is N, C or none;

X is N or C;

Z is O or $(CH_2)_q$, wherein q is 0-2, and when q is 0, Z represents a bond;

n is 0-3;

with the proviso that when Z is O, Y is N and X is C.

In a preferred embodiment of the present invention, A is a substituted or unsubstituted benzene ring, or a substituted or unsubstituted 5-12 membered aromatic heterocyclic ring containing 1 to 4 heteroatoms selected from the group consisting of oxygen, sulfur and nitrogen, wherein each of the substituted benzene ring or substituted aromatic heterocycles comprises 1 to 3 substituents;

Wherein the substituent on the substituted aromatic ring or substituted aromatic heterocyclic ring is independently selected from the group consisting of hydrogen, hydrogen isotope, halogen, carboxyl, nitro, a C1-C4 alkyl, C1-C4 alkanoyl, C1-C4 alkoxy, cyano, oxygen (═O), sulfonyl.

In a preferred embodiment of the present invention, each $R_1$ is independently selected from: a substituted or unsubstituted aryl, substituted or unsubstituted heteroaryl, hydrogen, substituted or unsubstituted C1-C4 alkyl, —$SO_2Ra$, —NC(O)Ra, —$(CH_2)_mC(O)ORa$, —C(O)ORa, —C(O)Ra, —$(CH_2)_mORa$, —C(O)NRaRb, —NRcRd, substituted or unsubstituted arylalkyl, and substituted or unsubstituted heteroarylalkyl, wherein m is an integer of 1-3;

Each Ra is independently hydrogen, a substituted or unsubstituted phenyl, substituted or unsubstituted phenylmethyl, substituted or unsubstituted C3-C7 cycloalkyl, substituted or unsubstituted C1-C4 alkyl, substituted or unsubstituted C1-C4 alkenyl, substituted or unsubstituted C1-C4 alkoxy, substituted or unsubstituted C1-C3 alkylamino, —NHPh, or substituted or unsubstituted 5-10 membered heteroaryl;

Rb is hydrogen or C1-C3 alkyl;

Rc and Rd are each independently selected from hydrogen, a C1-C3 straight or branched alkyl, substituted or unsubstituted C3-C5 cycloalkyl, substituted or unsubstituted C1-C3 alkoxy, substituted or unsubstituted 4- to -6-membered heterocyclic group, substituted or unsubstituted C1-C3 alkylacyl, substituted or unsubstituted arylacyl, substituted or unsubstituted arylsulfonyl, substituted or unsubstituted benzyl, substituted or unsubstituted aryl; the heterocyclic group containing one heteroatom selected from the group consisting of oxygen, sulfur and nitrogen;

The substituents are selected from the group consisting of C1-C8 alkyl, C2-C8 alkenyl, C2-C8 alkynyl, C3-C8 cycloalkyl, 3- to 12-membered heterocyclic group, aryl, heteroaryl, halogen, hydroxy, carboxy (—COOH), C1-C8 aldehyde, C2-C10 acyl, C2-C10 ester group, amino, and alkoxy.

In another preferred embodiment of the invention, X is N, and $R_1$ attached to X is selected from: a substituted or unsubstituted: aryl, heteroaryl, aralkyl, and heteroarylalkyl, wherein the substituent is selected from the group consisting of a C1-C8 alkyl, C2-C8 alkenyl, C2-C8 alkynyl, C3-C8 cycloalkyl, 3- to 12-membered heterocyclic group, aryl, heteroaryl, halogen, hydroxy, carboxy (—COOH), C1-C8 aldehyde group, C2-C10 acyl, C2-C10 ester group, amino, and alkoxy.

In another preferred embodiment of the invention, X is N, and $R_1$ attached to X is selected from a substituted or unsubstituted: aryl C1-C4 alkyl, and heteroaryl C1-C4 alkyl, wherein the substituent is selected from the group consisting of a C1-C8 alkyl, C2-C8 alkenyl, C2-C8 alkynyl, C3-C8 cycloalkyl, 3- to 12-membered heterocyclic group, aryl, heteroaryl, halogen, hydroxy, carboxy (—COOH), C1-C8 aldehyde, C2-C10 acyl, C2-C10 ester group, amino, and alkoxy.

In a preferred embodiment of the invention, W is —$(CH_2)_{1-2}$.

In a preferred embodiment of the invention, the structure of the compound is as shown by the formula (1R, 2S)-Ia or the formula (1S, 2R)-Ib:

Formula (1R, 2S)-Ia

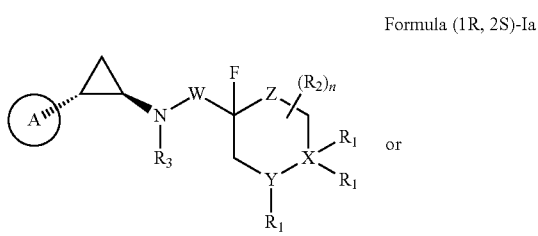

formula (1S, 2R)-Ib

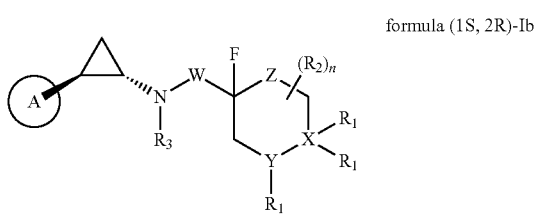

Preparation Method

The preparation method of fluorine-substituted cyclic amine compound as an active ingredient of the present invention can be chosen from the following scheme 1 or scheme 2:

Scheme 1

The compounds of formula (II) and (III) were reacted under reductive amination conditions to provide compounds of formula (I).

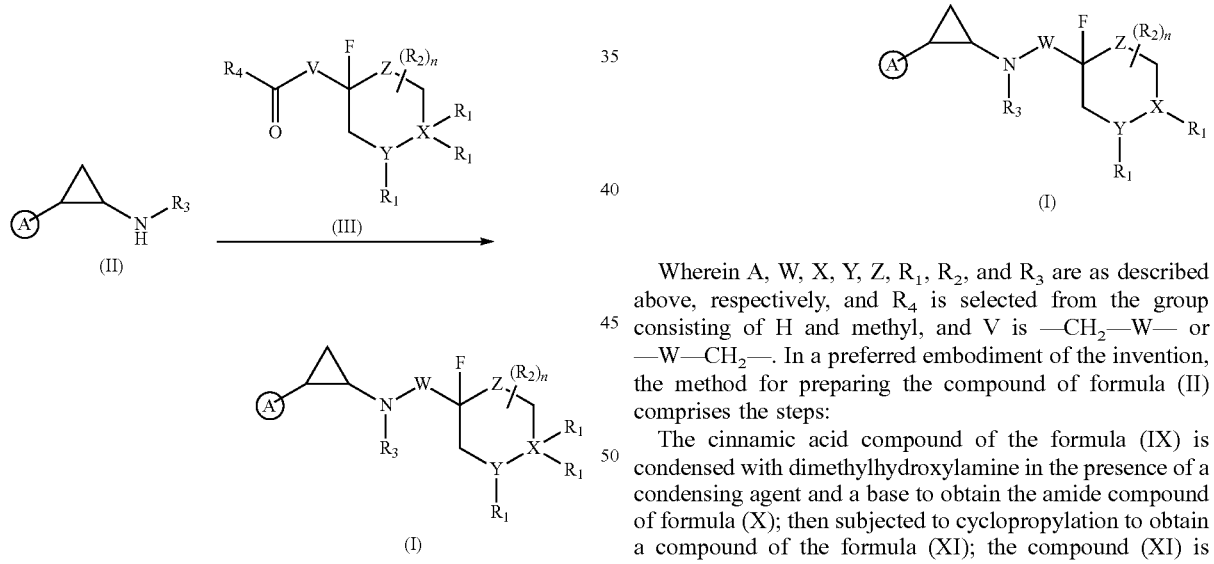

Scheme 2

The compound of formula (IV) and compound of formula (V) were subjected to a reaction to afford the compound of formula (VI), and then the amino can be protected, and compound of formula (VII) was obtained by removal of the protecting group of the X and/or Y group. The compound of formula (VII) is functionalized with $R_1$ substituent to give a compound of formula (VIII), the deprotecting group of amine is removed and the compound of formula (VIII) is functionalized with an $R_3$ group to give a compound of formula (I);

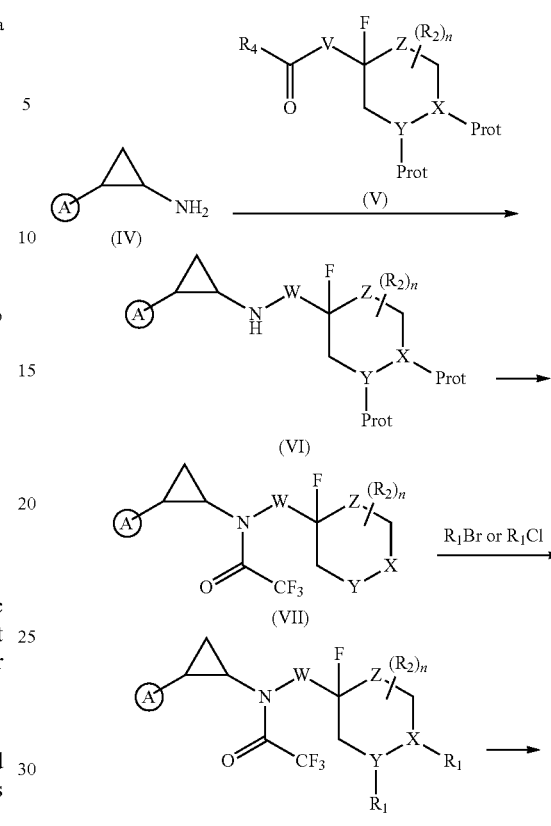

Wherein A, W, X, Y, Z, $R_1$, $R_2$, and $R_3$ are as described above, respectively, and $R_4$ is selected from the group consisting of H and methyl, and V is —$CH_2$—W— or —W—$CH_2$—. In a preferred embodiment of the invention, the method for preparing the compound of formula (II) comprises the steps:

The cinnamic acid compound of the formula (IX) is condensed with dimethylhydroxylamine in the presence of a condensing agent and a base to obtain the amide compound of formula (X); then subjected to cyclopropylation to obtain a compound of the formula (XI); the compound (XI) is hydrolysised to give compound of formula (XII), and then reacted under Curtius rearrangement conditions to provide a compound of formula (IV), and then compound of formula (IV) is functionalized with $R_3$ group to provide a compound of formula (II);

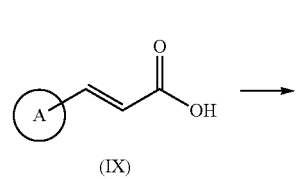

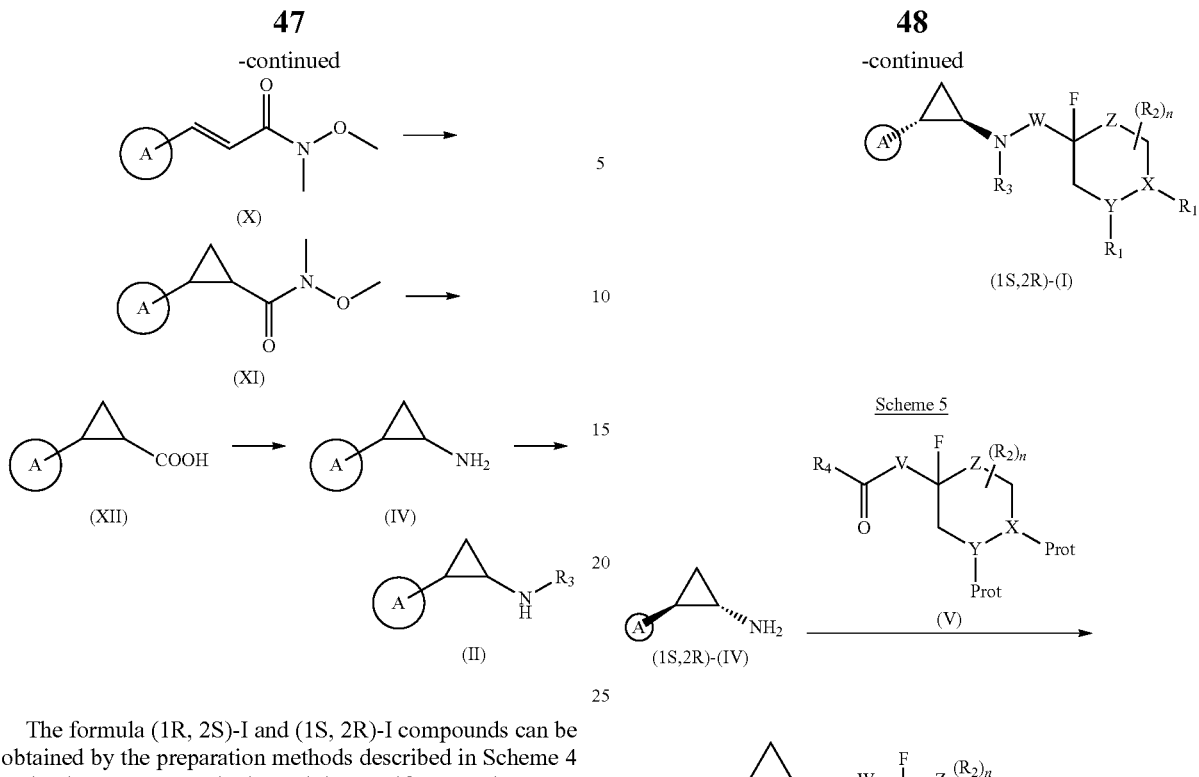
The formula (1R, 2S)-I and (1S, 2R)-I compounds can be obtained by the preparation methods described in Scheme 4 and Scheme 5, respectively, and the specific operation steps are the same as Scheme 2.
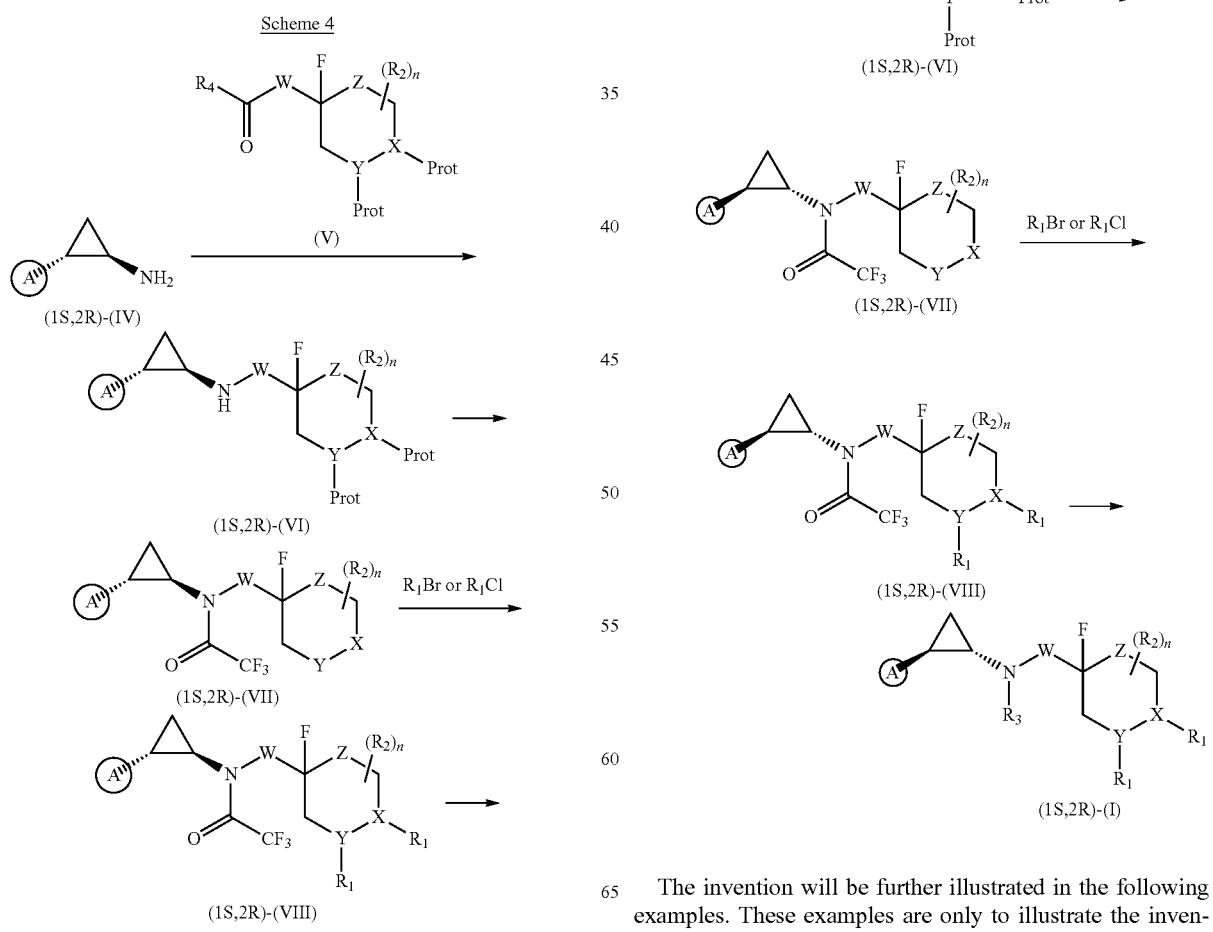
The invention will be further illustrated in the following examples. These examples are only to illustrate the invention but not to limit the scope of the invention by any means.

Example 1 Benzyl 4-fluoro-4-((trans-2-phenylcyclopropyl)amino)methyl)piperidine-1-carboxylate (A1)

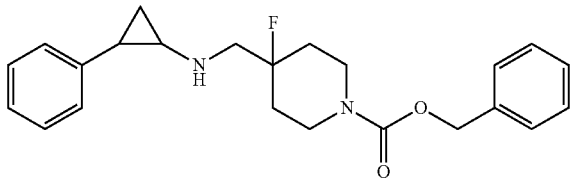 [SMILES: O=C(OCc1ccccc1)N1CCC(F)(CNC2CC2c2ccccc2)CC1]

20 mL of anhydrous methanol was added into a 100 mL eggplant bottle, and 167 mg of trans-2-phenylcyclopropylamine and 300 mg of benzyl 4-fluoro-4-formylpiperidine-1-carboxylate were weighted and added into the methanol solution. Then, 72 µl of acetic acid was added to the system, heated and refluxed for 10 minutes under nitrogen atmosphere, and then cooled to room temperature. 142 mg of sodium cyanoborohydride was added to the solution, and stirred at room temperature for 5 hours. The reaction was monitored with thin layer chromatography (TLC). After the reaction was completed, the methanol was vacuum-evaporated, 50 mL of water was added, and 50 mL of dichloromethane was used for extraction for 3 times. The organic layer was vacuum-evaporated to dryness, and purified through column chromatography with methylene chloride: methanol=50:1 to provide product A1 (310 mg, yield 72%). $^1$H NMR (600 MHz, MeOD) δ 7.41-7.34 (m, 4H), 7.36-7.30 (m, 3H), 7.27-7.24 (m, 1H), 7.22-7.19 (m, 2H), 5.15 (s, 2H), 4.14-4.08 (m, 2H), 3.54 (d, J=20.1 Hz, 2H), 3.27-3.14 (m, 2H), 3.07 (dt, J=8.0, 4.1 Hz, 1H), 2.60 (ddd, J=10.3, 6.6, 3.6 Hz, 1H), 2.02-1.95 (m, 2H), 1.87-1.72 (m, 2H), 1.60 (ddd, J=10.4, 6.8, 4.4 Hz, 1H), 1.41 (dt, J=7.8, 6.7 Hz, 1H); LRMS (ESI): 383.21 [M+H]$^+$.

Example 2 N-((4-fluoropiperidin-4-yl)methyl)-trans-2-phenylcyclopropylamine (A2)

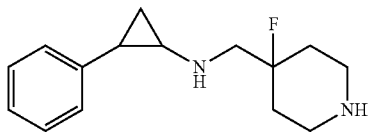 [SMILES: FC1(CNC2CC2c2ccccc2)CCNCC1]

2.1 Synthesis of tert-butyl 4-fluoro-4-((trans-2-phenylcyclopropyl)amino)methyl)piperidine-1-carboxylate

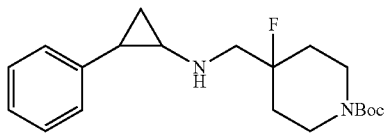 [SMILES: CC(C)(C)OC(=O)N1CCC(F)(CNC2CC2c2ccccc2)CC1]

The benzyl 4-fluoro-4-formylpiperidine-1-carboxylate was replaced with tert-butyl 4-fluoro-4-formylpiperidine-1-carboxylate, and the other raw materials, reagents and preparation methods were the same as those in example 1 to obtain tert-butyl 4-fluoro-4-((trans-2-phenylcyclopropyl)amino)methyl)piperidine-1-carboxylate (yield: 75%).

2.2 Synthesis of Final Product A2

3.5 g of tert-butyl 4-fluoro-4-((trans-2-phenylcyclopropyl)amino)methyl)piperidine-1-carboxylate was dissolved in 30 mL of 2M hydrochloric acid 1,4-dioxane, and stirred at room temperature for 10 hours. After the reaction was completed, the solvent was evaporated to give white solids. The solids were dissolved in a small amount of methanol, large amount of ethyl acetate was added, and white solids were obtained by ultrasonication. After suction filtration, the cake was dried to give 4.4 g of the bihydrochloride of desired product A2 (yield: 97%). $^1$H NMR (400 MHz, D$_2$O) δ 7.30 (t, J=7.4 Hz, 2H), 7.22 (t, J=7.3 Hz, 1H), 7.14 (d, J=7.5 Hz, 2H), 3.55 (d, J=20.3 Hz, 2H), 3.38 (dd, J=13.4, 4.7 Hz, 2H), 3.21 (td, J=13.2, 3.1 Hz, 2H), 2.97 (dt, J=8.0, 4.1 Hz, 1H), 2.52 (ddd, J=10.4, 6.7, 3.6 Hz, 1H), 2.25-2.10 (m, 2H), 1.96 (dtd, J=37.8, 14.7, 4.9 Hz, 2H), 1.50 (ddd, J=10.9, 7.1, 4.4 Hz, 1H), 1.36 (q, J=7.2 Hz, 1H); LRMS (ESI): 249.17 [M+H]$^+$.

Example 3 Methyl 4-((4-fluoro-4-(((trans-2-phenylcyclopropyl)amino)methyl)piperidin-1-yl)methyl)benzoate (A3)

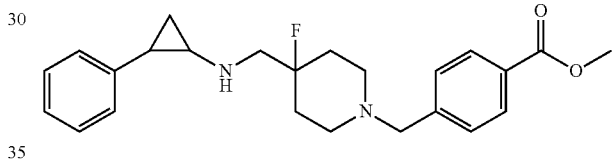

The benzyl 4-fluoro-4-formylpiperidine-1-carboxylate was replaced with methyl 4-((4-fluoro-4-formylpiperidin-1-yl)methyl)benzoate, while other raw materials, reagents and the preparation method were the same as those in example 1 to provide product A3 (yield: 63%). $^1$H NMR (400 MHz, D$_2$O) δ 7.95 (d, J=8.3 Hz, 2H), 7.48 (d, J=8.2 Hz, 2H), 7.27-7.18 (m, 2H), 7.18-7.12 (m, 1H), 7.08-7.04 (m, 2H), 4.31 (s, 2H), 3.79 (s, 3H), 3.48 (d, J=20.2 Hz, 2H), 3.39 (d, J=12.5 Hz, 2H), 3.23 (t, J=12.2 Hz, 2H), 2.90 (dt, J=7.9, 4.0 Hz, 1H), 2.44 (ddd, J=10.4, 6.7, 3.6 Hz, 1H), 2.21-2.07 (m, 2H), 2.04-1.81 (m, 2H), 1.43 (ddd, J=10.9, 7.2, 4.4 Hz, 1H), 1.29 (q, J=7.3 Hz, 1H); LRMS (ESI): 397.22 [M+H]$^+$.

Example 4 (1s, 4s)-4-fluoro-4-(((trans-2-phenylcyclopropyl)amino)methyl)cyclohexylamine (A4)

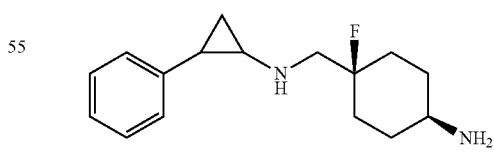

tert-butyl 4-fluoro-4-formylpiperidine-1-carboxylate was replaced with tert-butyl ((1s,4s)-4-fluoro-4-formylcyclohexyl)carbamate, while other raw materials, reagents and the preparation method were the same as those in example 1 to provide product A3 (yield: 70%). $^1$H NMR (400 MHz, DMSO-d$_6$) δ 7.33-7.27 (m, 2H), 7.25-7.16 (m, 3H), 3.51 (d, J=19.8 Hz, 2H), 3.28-3.18 (m, 1H), 3.05 (dt, J=7.9, 4.1 Hz, 1H), 2.61 (ddd, J=10.3, 6.6, 3.6 Hz, 1H), 2.21-2.10 (m, 2H), 2.08-1.97 (m, 2H), 1.87-1.66 (m, 4H), 1.60 (ddd, J=10.5, 6.8, 4.4 Hz, 1H), 1.38 (dt, J=7.9, 6.7 Hz, 1H); LRMS (ESI): 263.18 [M+H]+.

Example 5 4-((4-fluoro-4-((((trans-2-phenylcyclopropyl)amino)methyl)piperidin-1-yl)methyl)benzoate (A5)

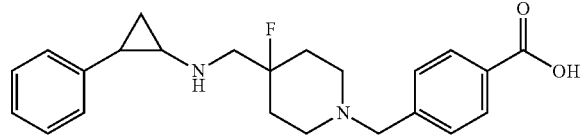 [SMILES: O=C(O)c1ccc(CN2CCC(F)(CNC3CC3c3ccccc3)CC2)cc1]

5.1 Synthesis of tert-butyl 4-fluoro-4-((2,2,2-trifluoro-N-(trans-2-phenylcyclopropyl)acetamido)methyl)piperidine-1-carboxylate

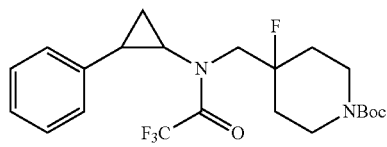 [SMILES: CC(C)(C)OC(=O)N1CCC(F)(CN(C(=O)C(F)(F)F)C2CC2c2ccccc2)CC1]

210 mg of the product tert-butyl 4-fluoro-4-((trans-2-phenylcyclopropyl)amino)methyl)piperidine-1-carboxylate obtained in Example 2.1 was dissolved in 15 ml of chloroform. 1.2 ml of triethylamine was added, then 0.44 ml of trifluoroacetic anhydride was slowly added dropwise to the solution, and stirred at room temperature for 30 minutes, and then quenched by adding 6 ml of 1M sodium carbonate solution, and the organic layer was separated. The aqueous layer was extracted with 5 ml of dichloromethane twice, the organic layers were combined and the solution was vacuum-dried, and purified by column chromatography (petroleum: EtOAc=10:1) so as to obtain 1.09 g of yellow oil, which is tert-butyl 4-fluorine-N-(4-((2,2,2-trifluorine-N-(trans-2-phenylcyclopropyl)acetamido)methyl)piperidine-1-carboxylate (yield 85%)

5.2 Synthesis of 2,2,2-trifluoro-N-((4-fluoropiperidin-4-yl)methyl)-N-(trans-2-phenylcyclopropyl)acetamide Hydrochloride

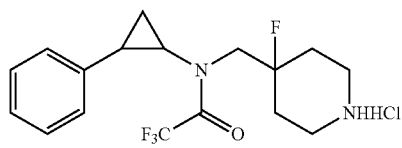

1.09 g of tert-butyl 4-Fluoro-4-((2,2,2-trifluoro-N-(trans-2-phenylcyclopropyl)acetamido)methyl)piperidine-1-carboxylate was dissolved in 15 ml of 2M 1,4-dioxane hydrochloride, stirred at room temperature for 4 hours to complete the reaction, and the solvent was evaporated to give 2,2,2-trifluoro-N-((4-fluoropiperidine) 4-yl)methyl)-N-(trans-2-phenylcyclopropyl)acetamide hydrochloride (yield 99%) as yellow solids.

5.3 Synthesis of tert-butyl 4-((4-Fluoro-4-((2,2,2-trifluoro-N-(trans-2-phenylcyclopropyl)acetamido)methyl)piperidin-1-yl methyl)benzoate

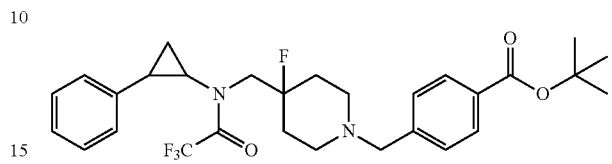

1.1 g of 2,2,2-trifluoro-N-((4-fluoropiperidin-4-yl)methyl)-N-(trans-2-phenylcyclopropyl)acetamide hydrochloride was dissolved in 20 ml of acetonitrile, and 784 mg of t-butyl 4-bromomethylbenzoate and 1.2 g of potassium carbonate were successively added into the system, and was heated to reflux for 2 hours. The reaction was monitored by thin layer chromatography (TLC). The acetonitrile was removed in vacuo after the reaction was completed, and then 30 mL of water was added, and was extracted for three times with 20 mL of dichloromethane. The organic layer was dried and separated by column chromatography (petroleum ether: ethyl acetate=2:1) to give tert-butyl 4-((4-fluoro-4-((2,2,2-trifluoro-N-(2-phenylcyclopropyl)acetamido)methyl)piperidine 1-ylmethyl)benzoate 720 mg (yield 47%).

5.4 Synthesis of Final Product A5

720 mg of Tert-butyl 4-((4-fluoro-4-((2,2,2-trifluoro-N-(2-phenylcyclopropyl)acetamido)methyl)piperidine1-ylmethyl)benzoate was dissolved in 20 ml of ethanol, and 10 ml of 1M sodium hydroxide solution was added heated to reflux for 2 hours, and cooled to room temperature after heating was stopped. The solvent was evaporated, 30 mL of water was added and 20 mL of dichloromethane was used to extract the organic layer for 3 times. The organic layer was dried over anhydrous sodium sulfate and then evaporated to dryness. The obtained pale yellow oil was dissolved in 1M hydrochloric acid solution, heated at 90° C. for 1 hour, and quenched. The reaction mixture was stirred in an ice bath for 1 hour to precipitate solids. The filter cake obtained from suction filtration was dried to give white solids, the dihydrochloride of A5, 540 mg (yield 88%). $^1$H NMR (400 MHz, DMSO-d$_6$) δ 8.00-7.93 (m, 2H), 7.44 (dt, J=7.4, 1.2 Hz, 2H), 7.26-7.11 (m, 5H), 3.54 (d, J=1.5 Hz, 2H), 3.11 (dt, J=12.6, 7.2 Hz, 2H), 2.76-2.64 (m, 2H), 2.62-2.49 (m, 3H), 2.05-1.85 (m, 3H), 1.45 (ddt, J=25.1, 13.2, 7.2 Hz, 2H), 0.95 (td, J=7.0, 4.9 Hz, 1H), 0.71 (td, J=7.0, 5.0 Hz, 1H); LRMS (ESI): 383.21 [M+H]+.

Example 6 N-((1-Benzyl-4-fluoropiperidin-4-yl)methyl)-trans-2-phenylcyclopropylamine (A6)

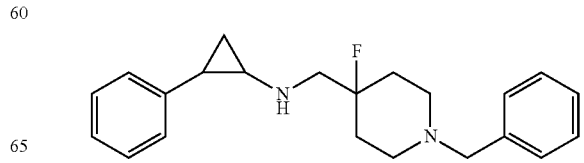

6.1 Synthesis of N-((1-Benzyl-4-fluoropiperidin-4-yl)methyl)-2,2,2-trifluoro-N-(trans-2-phenylcyclopropyl)acetamide

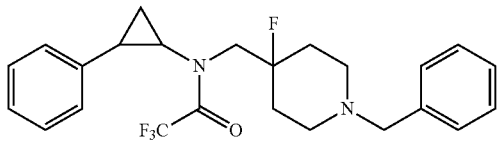 [SMILES: O=C(N(CC1(F)CCN(Cc2ccccc2)CC1)C1CC1c1ccccc1)C(F)(F)F]

The tert-butyl 4-bromomethylbenzoate was replaced with bromomethylbenzene, and the other starting materials, reagents and preparation methods were the same as those in Example 5.3 to obtain 210 mg of the product N-((1-benzyl-4-fluoropiperidin-4-yl)methyl)-2,2,2-trifluoro-N-(2-phenylcyclopropyl)acetamide (yield 70%)

6.2 Synthesis of Final Product A6

210 mg of N-((1-benzyl-4-fluoropiperidin-4-yl)methyl)-2,2,2-trifluoro-N-(2-phenylcyclopropyl)acetamide was dissolved in 10 ml of ethanol, and 5 ml of 1M sodium hydroxide solution was added and heated to reflux for 2 hours. The mixture was cooled to room temperature after heating was stopped, and the solvent was evaporated, and 30 mL of water was added and 20 mL of dichloromethane was used to extract the organic layer for 3 times. The organic layer was dried in vacuo, separated by column chromatography (dichloromethane:methanol=40:1) to provide A6 149 mg (yield: 91%). $^1$H NMR (500 MHz, D$_2$O) δ 7.50-7.41 (m, 5H), 7.35-7.28 (m, 2H), 7.27-7.22 (m, 1H), 7.18-7.12 (m, 2H), 4.32 (s, 2H), 3.54 (d, J=20.3 Hz, 2H), 3.47 (d, J=8.3 Hz, 2H), 3.28 (t, J=12.7 Hz, 2H), 2.97 (dt, J=8.0, 4.1 Hz, 1H), 2.52 (ddd, J=10.4, 6.7, 3.6 Hz, 1H), 2.22 (dd, J=15.3, 8.4 Hz, 2H), 2.11-1.86 (m, 2H), 1.50 (ddd, J=10.9, 7.2, 4.4 Hz, 1H), 1.37 (q, J=7.2 Hz, 1H); LRMS (ESI): 339.22 [M+H]$^+$.

Example 7 Methyl 3-(4-Fluoro-4-(((((trans-2-phenylcyclopropyl)amino)methyl)piperidin-1-yl)-propionate (A7)

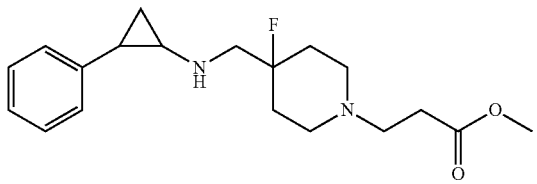 [SMILES: COC(=O)CCN1CCC(F)(CNC2CC2c2ccccc2)CC1]

The benzyl 4-fluoro-4-formylpiperidine-1-carboxylate was replaced with methyl 3-(4-fluoro-4-formylpiperidin-1-yl)-propionate, while other raw materials, reagents and the preparation method were the same as those in example 1 to provide product A7 (yield: 57%).

$^1$H NMR (500 MHz, D$_2$O) δ 7.32 (t, J=7.5 Hz, 2H), 7.25 (t, J=7.4 Hz, 1H), 7.16 (d, J=7.5 Hz, 2H), 3.68 (s, 3H), 3.61-3.54 (m, 4H), 3.46 (t, J=7.0 Hz, 2H), 3.32-3.23 (m, 2H), 3.00 (dt, J=8.0, 4.1 Hz, 1H), 2.93-2.85 (m, 2H), 2.55 (ddd, J=10.4, 6.7, 3.6 Hz, 1H), 2.30-2.20 (m, 2H), 2.16-1.94 (m, 2H), 1.52 (ddd, J=11.1, 7.2, 4.4 Hz, 1H), 1.38 (q, J=7.3 Hz, 1H); LRMS (ESI): 335.21 [M+H]$^+$.

Example 8 1-(4-fluoro-4-(((trans-2-phenylcyclopropyl)amino)methyl)piperidin-1-yl)-3-phenyl-1-propanone (A8)

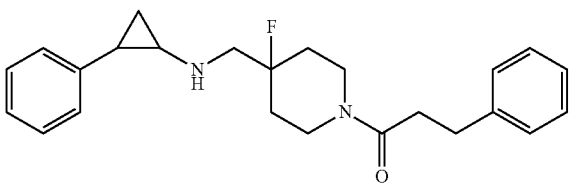

8.1 Synthesis of 2,2,2-trifluoro-N-((4-fluoro-1-(3-phenylpropanoyl)piperidin-4-yl)methyl)-N-(trans-2-phenylcyclopropyl)acetamide

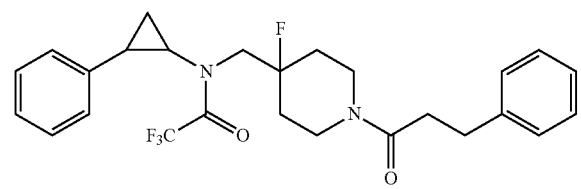

200 mg of the product obtained in Example 5.2, 2,2,2-trifluoro-N-((4-fluoropiperidin-4-yl)methyl)-N-(trans-2-phenylcyclopropyl)acetamide hydrochloride was dissolved in 10 ml of dry dichloromethane, and 0.22 ml of triethylamine was added, and 106 mg of 3-phenylpropionyl chloride in dichloromethane was added dropwise under ice-cooling, and the mixture was stirred at room temperature for 2 h. At the end of the reaction, 15 ml of water and 15 ml of dichloromethane were added for extraction. The organic layer was collected and dried in vacuo to give crude 2,2,2-trifluoro-N-((4-fluoro-1-(3-phenyl) propionyl)piperidin-4-yl)methyl)-N-(trans-2-phenylcyclopropyl)acetamide as a colorless oil. 8.2 Synthesis of final product A8

N-((1-benzyl-4-fluoropiperidin-4-yl)methyl)-2,2,2-trifluoro-N-(2-phenylcyclopropyl)acetamide was replaced with 2,2,2-trifluoro-N-((4-fluoro-1-(3-phenylpropanoyl)piperidin-4-yl)methyl)-N-(trans-2-phenylcyclopropyl)acetamide, while other raw materials, reagents and the preparation method were the same as those in example 6.2 to give the product A8 (yield: 72%). $^1$H NMR (400 MHz, D$_2$O) δ 7.28-7.12 (m, 5H), 7.14-7.04 (m, 5H), 4.14 (d, J=13.5 Hz, 1H), 3.61 (d, J=14.1 Hz, 1H), 3.21 (d, J=20.3 Hz, 2H), 3.06 (t, J=13.2 Hz, 1H), 2.90-2.62 (m, 5H), 2.57-2.47 (m, 1H), 2.46-2.37 (m, 1H), 1.78 (t, J=12.4 Hz, 1H), 1.62 (t, J=12.5 Hz, 1H), 1.48-1.21 (m, 3H), 0.81 (dt, J=39.9, 13.9 Hz, 1H); LRMS (ESI): 381.23 [M+H]$^+$.

Example 9 Phenyl 4-Fluoro-4-((trans-2-phenylcyclopropyl)amino)methyl)piperidine-1-carboxylate (A9)

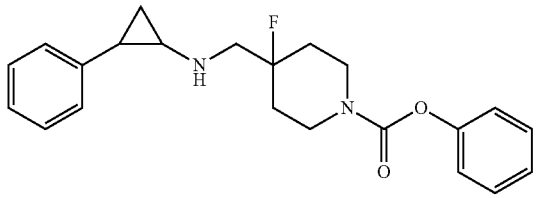 [SMILES: O=C(Oc1ccccc1)N1CCC(F)(CNC2CC2c2ccccc2)CC1]

benzyl 4-fluoro-4-formylpiperidine-1-carboxylate was replaced with phenyl 4-fluoro-4-formylpiperidin-1-carboxylate, while other raw materials, reagents and the preparation method were the same as those in example 1 to provide product A9 (yield: 79%).

$^1$H NMR (400 MHz, D$_2$O) δ 7.30 (t, J=7.4 Hz, 2H), 7.24 (t, J=7.2 Hz, 2H), 7.16 (t, J=7.1 Hz, 2H), 7.08 (d, J=7.4 Hz, 2H), 6.98 (d, J=7.6 Hz, 2H), 4.11 (d, J=13.8 Hz, 1H), 3.87 (d, J=13.6 Hz, 1H), 3.41 (d, J=20.4 Hz, 2H), 3.23 (t, J=12.7 Hz, 1H), 3.10 (t, J=12.9 Hz, 1H), 2.94-2.85 (m, 1H), 2.49-2.40 (m, 1H), 1.94-1.83 (m, 2H), 1.83-1.58 (m, 2H), 1.43 (ddd, J=10.8, 7.1, 4.0 Hz, 1H), 1.35-1.22 (m, 1H); LRMS (ESI): 369.19 [M+H]$^+$.

Example 10 3-Cyclohexyl-1-(4-fluoro-4-(((trans-2-phenylcyclopropyl)amino)methyl)piperidin-1-yl)-3-phenyl-1-propanone (A10)

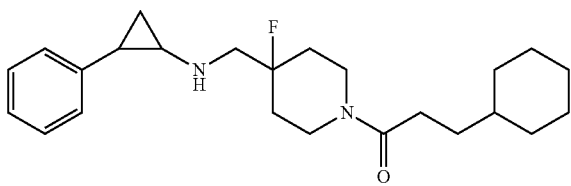 [SMILES: O=C(CCC1CCCCC1)N1CCC(F)(CNC2CC2c2ccccc2)CC1]

3-phenylpropionyl chloride was replaced with 3-cyclohexylpropanoyl chloride, while other raw materials, reagents and the preparation method were the same as those in example 8 to provide product A10 (yield: 54%). $^1$H NMR (400 MHz, DMSO) δ 7.34-7.27 (m, 2H), 7.25-7.16 (m, 3H), 4.48-4.41 (m, 1H), 3.95-3.88 (m, 1H), 3.53 (d, J=20.1 Hz, 2H), 3.40 (ddd, J=14.2, 12.4, 2.9 Hz, 1H), 3.05 (dt, J=7.9, 4.1 Hz, 1H), 2.96 (td, J=12.8, 3.0 Hz, 1H), 2.58 (ddd, J=10.3, 6.5, 3.5 Hz, 1H), 2.42 (td, J=7.5, 3.6 Hz, 2H), 2.11-1.93 (m, 2H), 1.93-1.54 (m, 8H), 1.53-1.34 (m, 3H), 1.33-1.09 (m, 4H), 1.01-0.82 (m, 2H); LRMS (ESI): 387.27 [M+H]$^+$.

Example 11 4-fluoro-N-methyl-4-(((trans-2-phenylcyclopropyl)amino)methyl)cyclohexane-1-amine (A11)

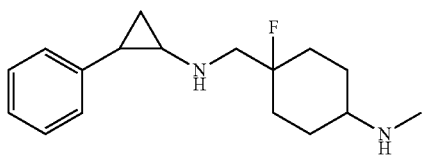 [SMILES: CNC1CCC(F)(CNC2CC2c2ccccc2)CC1]

11.1 Synthesis of N-((4-amino-1-fluorocyclohexyl)methyl)-2,2,2-trifluoro-N-(trans-2-phenylcyclopropyl)acetamide Hydrochloride

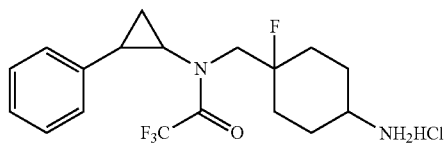

4-fluoro-4-formylpiperidine-1-carboxylic acid benzyl ester was replaced with (4-fluoro-4-formylcyclohexyl)carbamic acid tert-butyl ester, and the other raw materials, reagents and preparation methods were the same as those in Example 1, 5.1 and 5.2 to obtain the product N-((4-amino-1-fluorocyclohexyl)methyl)-2,2,2-trifluoro-N-(trans-2-phenylcyclopropyl)acetamide hydrochloride (yield 39%)

11.2 Synthesis of Final Product A11 benzyl 4-fluoro-4-formylpiperidine-1-carboxylate was replaced with formaldehyde solution (containing 8%-14% methanol), and trans-2-phenylcyclopropyl-1-amine was replaced with N-((4-amino-1-fluorocyclohexyl)methyl)-2,2,2-trifluoro-N-(trans-2-phenylcyclopropyl)acetamide, while other raw materials, reagents and the preparation method were the same as those in Examples 1 and 6.2 to give the product A11 (yield: 64%). $^1$H NMR (400 MHz, D$_2$O) δ 7.24-7.17 (m, 2H), 7.16-7.10 (m, 1H), 7.07-7.02 (m, 2H), 3.34 (d, J=20.4 Hz, 2H), 3.06-2.9 D$_2$O 5 (m, 1H), 2.85 (dt, J=8.0, 4.1 Hz, 1H), 2.54 (s, 3H), 2.41 (ddd, J=10.4, 6.7, 3.6 Hz, 1H), 2.01-1.89 (m, 4H), 1.64-1.43 (m, 4H), 1.39 (ddd, J=10.5, 7.2, 4.4 Hz, 1H), 1.30-1.19 (m, 1H); LRMS (ESI): 277.20 [M+H]$^+$.

Example 12 N-((4-fluoro-1-(3-phenylpropyl)piperidin-4-yl)methyl)-trans-2-phenylcyclopropylamine (A12)

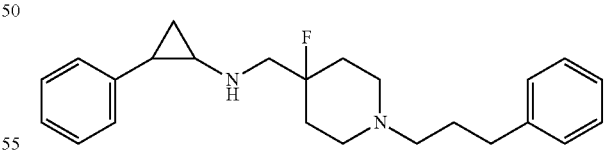

bromomethylbenzene was replaced with bromopropylbenzene, while other raw materials, reagents and the preparation method were the same as those in example 6 to provide product A12 (yield: 75%). $^1$H NMR (400 MHz, D$_2$O) δ 7.45-7.39 (m, 4H), 7.38-7.31 (m, 4H), 7.28-7.23 (m, 2H), 3.71-3.58 (m, 4H), 3.33-3.16 (m, 4H), 3.09 (dt, J=8.0, 4.1 Hz, 1H), 2.77 (t, J=7.4 Hz, 2H), 2.64 (ddd, J=10.4, 6.7, 3.6 Hz, 1H), 2.38-2.26 (m, 2H), 2.22-2.01 (m, 4H), 1.62 (ddd, J=10.5, 7.2, 4.4 Hz, 1H), 1.48 (q, J=7.2 Hz, 1H); LRMS (ESI): 367.25 [M+H]$^+$.

Example 13 N-((1-([1,1'-Biphenyl]-4-methyl)-4-fluoropiperidin-4-yl)methyl)-trans-2-phenylcyclopropylamine (A13)

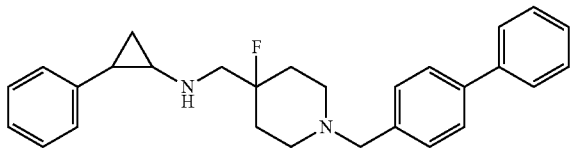 [SMILES: FC1(CNC2CC2c2ccccc2)CCN(Cc2ccc(-c3ccccc3)cc2)CC1]

bromomethylbenzene was replaced by 4-bromomethyl-1,1'-biphenyl, while other raw materials, reagents and the preparation method were the same as those in example 6 to provide product A12 (yield: 80%). $^1$H NMR (400 MHz, MeOD) δ 7.78 (d, J=8.1 Hz, 2H), 7.74-7.64 (m, 4H), 7.49 (t, J=7.6 Hz, 2H), 7.44-7.38 (m, 1H), 7.33 (t, J=7.4 Hz, 2H), 7.29-7.14 (m, 3H), 4.48 (s, 2H), 3.72-3.54 (m, 4H), 3.38 (d, J=13.2 Hz, 2H), 3.09 (t, J=4.6 Hz, 1H), 2.64 (t, J=9.6 Hz, 1H), 2.40-2.13 (m, 4H), 1.67-1.59 (m, 1H), 1.42 (q, J=7.0 Hz, 1H); LRMS ESI): 415.27 [M+H]$^+$.

Example 14 N-((1-(3-Cyclohexylpropyl)-4-fluoropiperidin-4-yl)methyl)-trans-2-phenylcyclopropylamine (A14)

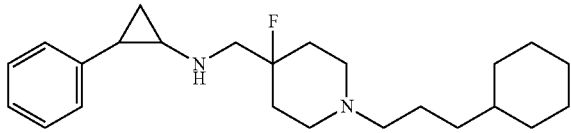 [SMILES: FC1(CNC2CC2c2ccccc2)CCN(CCCC2CCCCC2)CC1]

The bromomethylbenzene was replaced with bromopropylcyclohexane, while other raw materials, reagents and the preparation method were the same as those in example 6 to provide product A14 (yield: 74%). $^1$H NMR (400 MHz, D$_2$O) δ 7.45-7.39 (m, 2H), 7.38-7.32 (m, 1H), 7.28-7.23 (m, 2H), 3.73-3.58 (m, 4H), 3.29 (td, J=13.2, 2.9 Hz, 2H), 3.22-3.15 (m, 2H), 3.10 (dt, J=8.0, 4.0 Hz, 1H), 2.64 (ddd, J=10.5, 6.9, 3.7 Hz, 1H), 2.41-2.30 (m, 2H), 2.25-2.02 (m, 2H), 1.86-1.55 (m, 8H), 1.49 (q, J=7.3 Hz, 1H), 1.35-1.04 (m, 6H), 0.99-0.82 (m, 2H); LRMS (ESI): 373.29 [M+H]$^+$.

Example 15 N-((4-Fluoro-1-methylpiperidin-4-yl)methyl)-trans-2-phenylcyclopropylamine (A15)

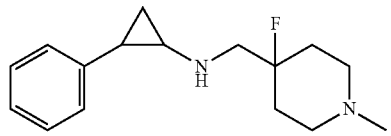 [SMILES: CN1CCC(F)(CNC2CC2c2ccccc2)CC1]

tert-butyl (4-fluoro-4-formylcyclohexyl)carbamate was replaced with tert-butyl 4-fluoro-4-formylpiperidine-1-carboxylate, while other raw materials, reagents and the preparation method were the same as those in example 11 to provide product A15 (yield: 34%). $^1$H NMR (400 MHz, D$_2$O) δ 7.30-7.24 (m, 2H), 7.22-7.17 (m, 1H), 7.11 (dd, J=7.1, 1.8 Hz, 2H), 3.52 (d, J=20.3 Hz, 2H), 3.43 (dd, J=12.7, 4.5 Hz, 2H), 3.20 (td, J=13.2, 3.1 Hz, 2H), 2.94 (dt, J=8.0, 4.1 Hz, 1H), 2.81 (s, 3H), 2.49 (ddd, J=10.4, 6.7, 3.6 Hz, 1H), 2.19 (dd, J=15.1, 8.6 Hz, 2H), 2.03 (td, J=15.1, 14.7, 4.9 Hz, 1H), 1.93 (td, J=14.5, 4.8 Hz, 1H), 1.47 (ddd, J=10.5, 7.2, 4.4 Hz, 1H), 1.33 (q, J=7.2 Hz, 1H); LRMS (ESI): 263.18 [M+H]$^+$.

Example 16 N-((4-Fluoro-1-(4-(methylsulfonyl)benzyl)piperidin-4-yl)methyl)-trans-2-phenylcyclopropylamine (A16)

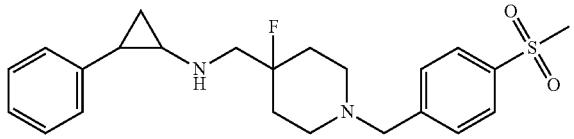 [SMILES: CS(=O)(=O)c1ccc(CN2CCC(F)(CNC3CC3c3ccccc3)CC2)cc1]

bromomethylbenzene was replaced with 1-bromomethyl-4-methanesulfonylbenzene, while other raw materials, reagents and the preparation method were the same as those in example 6 to provide product A16 (yield: 72%). $^1$H NMR (400 MHz, MeOD) δ 8.10-8.06 (m, 2H), 7.92-7.87 (m, 2H), 7.33-7.28 (m, 2H), 7.25-7.16 (m, 3H), 4.53 (s, 2H), 3.65 (d, J=20.1 Hz, 2H), 3.53 (d, J=12.5 Hz, 2H), 3.42-3.30 (m, 2H), 3.16 (s, 3H), 3.10-3.05 (m, 1H), 2.66-2.56 (m, 1H), 2.37-2.16 (m, 4H), 1.61 (dt, J=11.0, 6.2 Hz, 1H), 1.40 (q, J=7.1 Hz, 1H); LRMS (ESI): 417.19 [M+H]$^+$.

Example 17 N-((4-Fluoro-1-(naphthyl-2-methyl)piperidin-4-yl)methyl)-trans-2-phenylcyclopropylamine (A17)

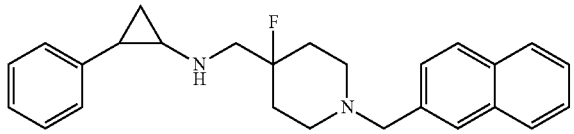 [SMILES: FC1(CNC2CC2c2ccccc2)CCN(Cc2ccc3ccccc3c2)CC1]

bromomethylbenzene was replaced with 2-bromomethylnaphthalene, while other raw materials, reagents and the preparation method were the same as those in example 6 to provide product A17 (yield: 60%). $^1$H NMR (400 MHz, DMSO-d$_6$) δ 7.95-7.77 (m, 3H), 7.69 (d, J=1.5 Hz, 1H), 7.61-7.47 (m, 3H), 7.26-7.11 (m, 5H), 3.66 (s, 2H), 3.00 (dt, J=12.6, 7.2 Hz, 2H), 2.66 (s, 1H), 2.60 (s, 1H), 2.46 (dt, J=12.6, 7.2 Hz, 2H), 1.93 (ddt, J=25.1, 14.2, 7.2 Hz, 3H), 1.53 (ddt, J=25.1, 13.1, 7.0 Hz, 2H), 0.95 (td, J=7.0, 5.1 Hz, 1H), 0.70 (td, J=7.0, 5.1 Hz, 1H); LRMS (ESI): 389.23 [M+H]$^+$.

Example 18 N-((1-Fluorocyclohexyl)methyl)-trans-2-phenylcyclopropylamine (A18)

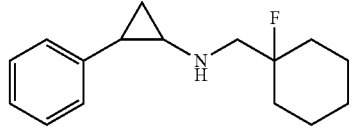 [SMILES: FC1(CNC2CC2c2ccccc2)CCCCC1]

benzyl 4-fluoro-4-formylpiperidine-1-carboxylate was replaced with methyl 1-fluorocyclohexane-1-carbaldehyde, while other raw materials, reagents and the preparation method were the same as those in example 1 to provide product A18 (yield: 82%). ¹H NMR (400 MHz, MeOD) δ 7.36-7.30 (m, 2H), 7.28-7.24 (m, 1H), 7.22 (tt, J=5.9, 1.2 Hz, 2H), 3.47 (d, J=20.0 Hz, 2H), 3.06 (dt, J=8.0, 4.1 Hz, 1H), 2.59 (ddd, J=10.3, 6.6, 3.6 Hz, 1H), 1.99-1.88 (m, 2H), 1.74-1.62 (m, 6H), 1.59 (ddd, J=10.3, 6.8, 4.4 Hz, 2H), 1.40 (dt, J=7.9, 6.7 Hz, 2H); LRMS (ESI): 248.17 [M+H]⁺.

Example 19 Benzyl 4-fluoro-4-((trans-2-phenylcyclopropyl)amino)methyl)cyclohexyl)carbamate (A19)

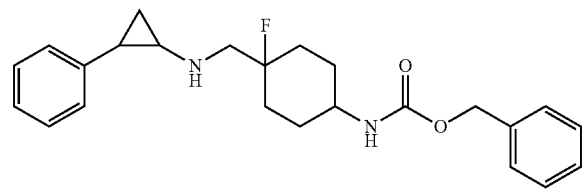 [SMILES: O=C(NC1CCC(F)(CNC2CC2c2ccccc2)CC1)OCc1ccccc1]

benzyl 4-fluoro-4-formylpiperidine-1-carboxylate was replaced with methyl benzyl (4-fluoro-4-formylcyclohexyl) carbamate, while other raw materials, reagents and the preparation method were the same as those in example 1 to provide product A19 (yield: 64%). ¹H NMR (400 MHz, DMSO-$d_6$) δ 7.39-7.26 (m, 5H), 7.26-7.11 (m, 5H), 5.02 (s, 2H), 4.11 (p, J=7.0 Hz, 1H), 2.73-2.64 (m, 2H), 1.94-1.72 (m, 5H), 1.65-1.50 (m, 2H), 1.54-1.43 (m, 2H), 0.99 (td, J=6.9, 5.0 Hz, 1H), 0.67 (td, J=7.0, 5.0 Hz, 1H); LRMS (ESI): 397.22 [M+H]⁺.

Example 20 N-((4-Fluoro-1-phenylpiperidin-4-yl)methyl)-trans-2-phenylcyclopropylamine (A20)

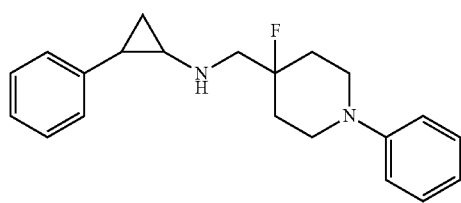 [SMILES: FC1(CNC2CC2c2ccccc2)CCN(c2ccccc2)CC1]

bromomethylbenzene was replaced with bromobenzene, while other raw materials, reagents and the preparation method were the same as those in example 6 to provide product A20 (yield: 41%). ¹H NMR (400 MHz, DMSO-$d_6$) δ 7.30-7.11 (m, 7H), 7.07-6.99 (m, 2H), 6.80 (tt, J=7.4, 2.0 Hz, 1H), 4.00 (dt, J=12.6, 7.2 Hz, 2H), 3.33 (dt, J=12.4, 7.0 Hz, 2H), 2.77-2.64 (m, 2H), 2.60 (s, 1H), 2.06-1.84 (m, 3H), 1.50 (ddt, J=25.2, 13.2, 7.1 Hz, 2H), 0.97 (td, J=7.0, 5.1 Hz, 1H), 0.69 (td, J=7.0, 5.0 Hz, 1H); LRMS (ESI): 325.20 [M+H]⁺.

Example 21 Cyclohexylmethyl 4-fluoro-4-(((trans-2-phenylcyclopropyl)amino)methyl)piperidine-1-carboxylate (A21)

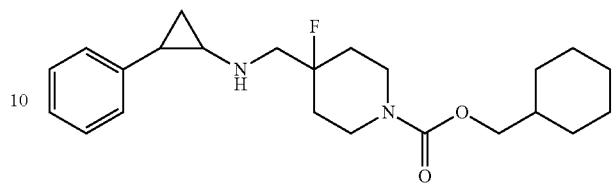

3-phenylpropionyl chloride was replaced with cyclohexylmethyl chloroformate, while other raw materials, reagents and the preparation method were the same as those in example 8 to provide product A21 (yield: 63%). ¹H NMR (400 MHz, DMSO-$d_6$) δ 7.26-7.11 (m, 5H), 4.02 (dt, J=12.4, 7.1 Hz, 2H), 3.91-3.85 (m, 2H), 3.27 (dt, J=12.4, 7.1 Hz, 2H), 2.76-2.64 (m, 2H), 2.04-1.85 (m, 3H), 1.77-1.65 (m, 2H), 1.70-1.56 (m, 4H), 1.60-1.42 (m, 2H), 1.34-1.12 (m, 6H), 0.95 (td, J=7.0, 5.0 Hz, 1H), 0.71 (td, J=6.9, 5.0 Hz, 1H); LRMS (ESI): 389.25 [M+H]⁺.

Example 22 Pyridin-4-ylmethyl 4-fluoro-4-(((trans-2-phenylcyclopropyl)amino)methyl)piperidine-1-carboxylate (A22)

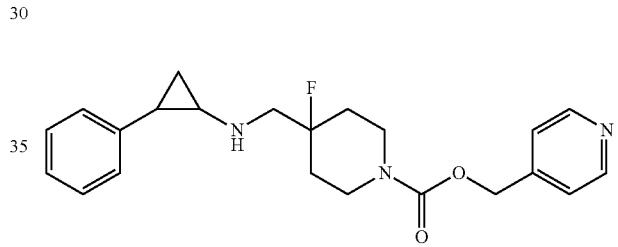

3-phenylpropionyl chloride was replaced with pyridin-4-ylmethyl chloroformate, while other raw materials, reagents and the preparation method were the same as those in example 8 to provide product A22 (yield: 53%). ¹H NMR (400 MHz, DMSO-$d_6$) δ 8.58 (d, J=5.1 Hz, 2H), 7.70 (d, J=5.1 Hz, 2H), 7.26-7.11 (m, 5H), 5.80 (s, 2H), 4.17 (dt, J=12.6, 7.2 Hz, 2H), 3.10 (dt, J=12.5, 7.0 Hz, 2H), 2.75-2.64 (m, 2H), 2.04-1.83 (m, 3H), 1.63 (ddt, J=25.2, 13.2, 7.1 Hz, 2H), 0.92 (td, J=6.9, 5.0 Hz, 1H), 0.70 (td, J=7.0, 5.0 Hz, 1H); LRMS (ESI): 384.20 [M+H]⁺.

Example 23 Phenethyl 4-fluoro-4-((trans-2-phenylcyclopropyl)amino)methyl)piperidine-1-carboxylate (A23)

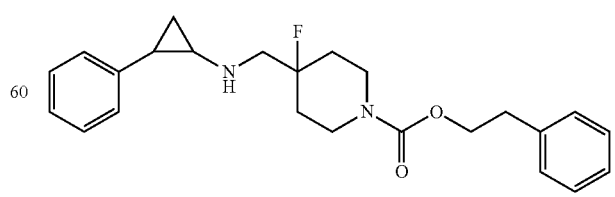

3-phenylpropionyl chloride was replaced with phenylethyl chloroformate, while other raw materials, reagents and the preparation method were the same as those in example 8 to provide product A23 (yield: 60%). ¹H NMR (400 MHz, DMSO-d₆) δ 7.27-7.11 (m, 10H), 4.41 (t, J=7.5 Hz, 2H), 4.05 (dt, J=12.4, 7.0 Hz, 2H), 3.30 (dt, J=12.6, 7.2 Hz, 2H), 2.86 (t, J=7.5 Hz, 2H), 2.78-2.64 (m, 2H), 2.05-1.86 (m, 3H), 1.65 (ddt, J=25.2, 13.2, 7.1 Hz, 2H), 0.96 (td, J=7.0, 5.0 Hz, 1H), 0.71 (td, J=7.0, 5.0 Hz, 1H); LRMS (ESI): 397.22 [M+H]⁺.

Example 24 Ethyl 4-fluoro-4-((trans-2-phenylcyclopropyl)amino)methyl)piperidine-1-carboxylate (A24)

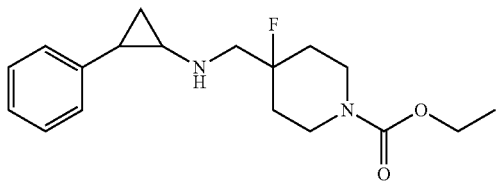 [SMILES: CCOC(=O)N1CCC(F)(CNC2CC2c2ccccc2)CC1]

3-phenylpropionyl chloride was replaced with ethyl chloroformate, while other raw materials, reagents and the preparation method were the same as those in example 8 to provide product A24 (yield: 74%). ¹H NMR (400 MHz, DMSO-d₆) δ 7.26-7.11 (m, 5H), 4.10-3.98 (m, 4H), 3.25 (dt, J=12.5, 7.1 Hz, 2H), 2.77-2.64 (m, 2H), 2.60 (s, 1H), 2.00-1.82 (m, 3H), 1.64 (ddt, J=25.2, 13.2, 7.1 Hz, 2H), 1.17 (t, J=8.0 Hz, 3H), 0.94 (td, J=7.0, 5.0 Hz, 1H), 0.71 (td, J=6.9, 5.0 Hz, 1H); LRMS (ESI): 321.19 [M+H]⁺.

Example 25 (1H-Indol-5-yl)methyl 4-fluoro-4-(((trans-2-phenylcyclopropyl)amino)methyl)piperidine-1-carboxylate (A25)

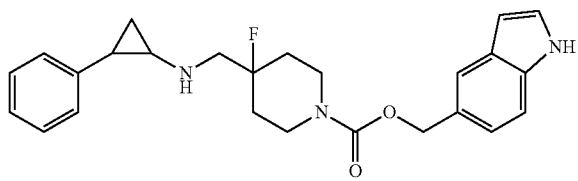 [SMILES: O=C(OCc1ccc2[nH]ccc2c1)N1CCC(F)(CNC2CC2c2ccccc2)CC1]

3-phenylpropionyl chloride was replaced with (1H-indol-5-yl)methyl chloroformate, while other raw materials, reagents and the preparation method were the same as those in example 8 to provide product A25 (yield: 36%). ¹H NMR (400 MHz, DMSO-d₆) δ 11.53 (s, 1H), 8.06 (t, J=1.5 Hz, 1H), 7.61 (d, J=7.5 Hz, 1H), 7.50-7.40 (m, 2H), 7.26-7.11 (m, 5H), 6.65 (dd, J=7.6, 1.5 Hz, 1H), 5.02 (s, 2H), 4.04 (dt, J=12.4, 7.1 Hz, 2H), 3.30 (dt, J=12.6, 7.2 Hz, 2H), 2.76-2.64 (m, 2H), 2.60 (s, 1H), 2.05-1.86 (m, 3H), 1.64 (ddt, J=25.2, 13.2, 7.1 Hz, 2H), 0.95 (td, J=7.0, 5.0 Hz, 1H), 0.71 (td, J=7.0, 5.0 Hz, 1H); LRMS (ESI): 422.22 [M+H]⁺.

Example 26 1-(4-Fluoro-4-(((trans-2-phenylcyclopropyl)amino)methyl)pyridin-1-yl)-1-ethanone (A26)

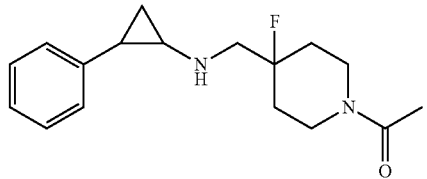 [SMILES: CC(=O)N1CCC(F)(CNC2CC2c2ccccc2)CC1]

3-phenylpropionyl chloride was replaced with acetyl chloride, while other raw materials, reagents and the preparation method were the same as those in example 8 to provide product A26 (yield: 76%). ¹H NMR (400 MHz, DMSO-d₆) δ 7.26-7.11 (m, 5H), 3.96 (dt, J=12.5, 7.1 Hz, 2H), 2.93 (dt, J=12.5, 7.1 Hz, 2H), 2.71-2.61 (m, 2H), 2.60 (s, 1H), 2.10 (s, 3H), 2.00-1.82 (m, 3H), 1.63 (ddt, J=25.3, 13.2, 7.2 Hz, 2H), 0.99 (td, J=7.0, 5.0 Hz, 1H), 0.66 (td, J=7.0, 5.1 Hz, 1H); LRMS (ESI): 291.18 [M+H]⁺.

Example 27 Thiophen-2-ylmethyl 4-fluoro-4-(((trans-2-phenylcyclopropyl)amino)methyl)piperidine-1-carboxylate (A27)

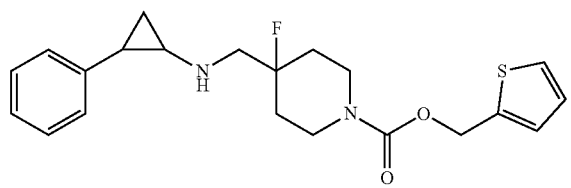

3-phenylpropionyl chloride was replaced with thiophen-2-ylmethyl chloroformate, while other raw materials, reagents and the preparation method were the same as those in example 8 to provide product A27 (yield: 70%). ¹H NMR (400 MHz, DMSO-d₆) δ 7.30 (dd, J=6.4, 2.5 Hz, 1H), 7.26-7.11 (m, 5H), 7.05-6.96 (m, 2H), 5.61 (s, 2H), 4.19 (dt, J=12.5, 7.1 Hz, 2H), 3.11 (dt, J=12.5, 7.1 Hz, 2H), 2.75-2.64 (m, 2H), 2.08-1.82 (m, 3H), 1.73-1.55 (m, 2H), 0.95 (td, J=7.0, 5.0 Hz, 1H), 0.70 (td, J=7.0, 5.1 Hz, 1H); LRMS (ESI): 389.16 [M+H]⁺.

Example 28 Furan-2-ylmethyl 4-fluoro-4-(((trans-2-phenylcyclopropyl)amino)methyl)piperidine-1-carboxylate (A28)

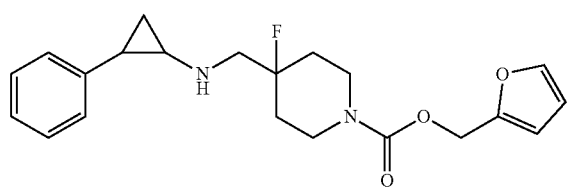 [SMILES: O=C(OCc1ccco1)N1CCC(F)(CNC2CC2c2ccccc2)CC1]

3-phenylpropionyl chloride was replaced with furan-2-ylmethyl chloroformate, while other raw materials, reagents and the preparation method were the same as those in example 8 to provide product A28 (yield: 76%). $^1$H NMR (400 MHz, DMSO-$d_6$) δ 7.45 (dd, J=7.0, 1.9 Hz, 1H), 7.26-7.11 (m, 5H), 6.44-6.32 (m, 2H), 5.09 (s, 2H), 4.06 (dt, J=12.5, 7.1 Hz, 2H), 3.31 (dt, J=12.5, 7.2 Hz, 2H), 2.76-2.64 (m, 2H), 2.60 (s, 1H), 1.99 (dt, J=10.9, 6.0 Hz, 1H), 1.98-1.86 (m, 2H), 1.65 (ddt, J=25.3, 13.3, 7.1 Hz, 2H), 0.95 (td, J=7.0, 5.0 Hz, 1H), 0.71 (td, J=7.0, 5.0 Hz, 1H); LRMS (ESI): 373.18 [M+H]$^+$.

Example 29 4-Fluorobenzyl 4-fluoro-4-(((trans-2-phenylcyclopropyl)amino)methyl)piperidine-1-carboxylate (A29)

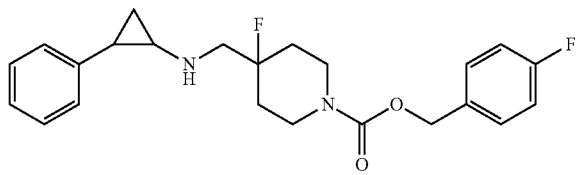 [SMILES: O=C(OCc1ccc(F)cc1)N1CCC(F)(CNC2CC2c2ccccc2)CC1]

3-phenylpropionyl chloride was replaced with 4-fluorobenzyl chloroformate, while other raw materials, reagents and the preparation method were the same as those in example 8 to provide product A29 (yield: 74%). $^1$H NMR (400 MHz, DMSO-$d_6$) δ 7.35 (dd, J=7.2, 5.7 Hz, 2H), 7.26-7.11 (m, 7H), 5.21-5.15 (m, 2H), 4.03 (dt, J=12.5, 7.1 Hz, 2H), 3.25 (dt, J=12.5, 7.1 Hz, 2H), 2.75-2.64 (m, 2H), 2.00-1.82 (m, 3H), 1.64 (ddt, J=25.1, 13.2, 7.0 Hz, 2H), 0.94 (td, J=7.0, 5.0 Hz, 1H), 0.71 (td, J=7.0, 5.0 Hz, 1H); LRMS (ESI): 401.20 [M+H]$^+$.

Example 30 4-Chlorobenzyl 4-fluoro-4-(((trans-2-phenylcyclopropyl)amino)methyl)piperidine-1-carboxylate (A30)

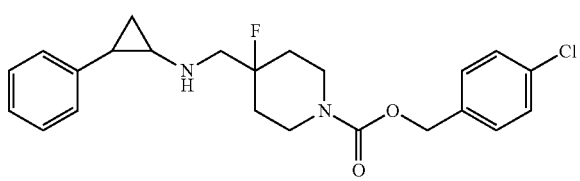 [SMILES: O=C(OCc1ccc(Cl)cc1)N1CCC(F)(CNC2CC2c2ccccc2)CC1]

3-phenylpropionyl chloride was replaced with 4-chlorobenzyl chloroformate, while other raw materials, reagents and the preparation method were the same as those in example 8 to provide product A30 (yield: 75%). $^1$H NMR (400 MHz, DMSO-$d_6$) δ 7.39 (d, J=7.5 Hz, 2H), 7.34-7.26 (m, 2H), 7.26-7.11 (m, 5H), 5.18 (s, 1H), 4.04 (dt, J=12.5, 7.1 Hz, 2H), 3.25 (dt, J=12.5, 7.1 Hz, 2H), 2.75-2.64 (m, 2H), 2.60 (s, 1H), 2.00-1.82 (m, 3H), 1.64 (ddt, J=25.3, 13.2, 7.2 Hz, 2H), 0.94 (td, J=6.9, 5.0 Hz, 1H), 0.71 (td, J=7.0, 5.0 Hz, 1H); LRMS (ESI): 417.17 [M+H]$^+$.

Example 31 4-Bromobenzyl 4-fluoro-4-(((trans-2-phenylcyclopropyl)amino)methyl)piperidine-1-carboxylate (A31)

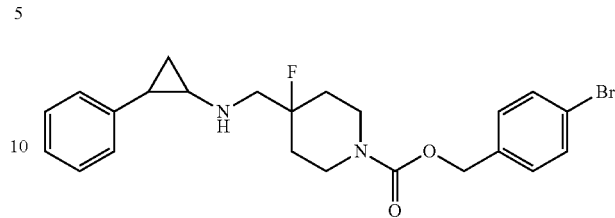

3-phenylpropionyl chloride was replaced with 4-bromobenzyl chloroformate, while other raw materials, reagents and the preparation method were the same as those in example 8 to provide product A31 (yield: 70%). $^1$H NMR (400 MHz, DMSO-$d_6$) δ 7.58 (d, J=7.6 Hz, 2H), 7.29-7.22 (m, 2H), 7.27-7.11 (m, 5H), 5.18 (s, 1H), 4.02 (dt, J=12.5, 7.1 Hz, 2H), 3.28 (dt, J=12.5, 7.1 Hz, 2H), 2.75-2.64 (m, 2H), 2.60 (s, 1H), 2.04-1.86 (m, 3H), 1.63 (ddt, J=25.3, 13.2, 7.2 Hz, 2H), 0.95 (td, J=7.0, 4.9 Hz, 1H), 0.71 (td, J=7.0, 5.0 Hz, 1H); LRMS (ESI): 461.12 [M+H]$^+$.

Example 32 4-Methoxybenzyl 4-fluoro-4-(((trans-2-phenylcyclopropyl)amino)methyl)piperidine-1-carboxylate (A32)

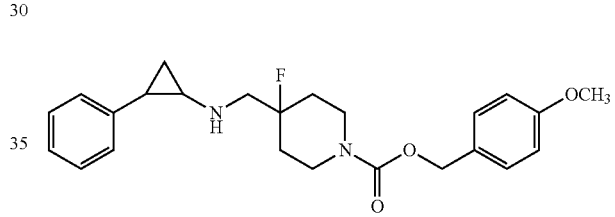

3-phenylpropionyl chloride was replaced with 4-methoxybenzyl chloroformate, while other raw materials, reagents and the preparation method were the same as those in example 8 to provide product A32 (yield: 76%). $^1$H NMR (400 MHz, DMSO-$d_6$) δ 7.26-7.11 (m, 5H), 7.03-6.96 (m, 2H), 6.94-6.87 (m, 2H), 5.18 (s, 1H), 4.03 (dt, J=12.5, 7.1 Hz, 2H), 3.79 (s, 3H), 3.28 (dt, J=12.5, 7.1 Hz, 2H), 2.76-2.64 (m, 2H), 2.60 (s, 1H), 2.04-1.85 (m, 3H), 1.72-1.54 (m, 2H), 0.95 (td, J=7.0, 5.0 Hz, 1H), 0.71 (td, J=7.0, 5.1 Hz, 1H); LRMS (ESI): 413.22 [M+H]$^+$.

Example 33 4-Trifluoromethylbenzyl 4-fluoro-4-(((trans-2-phenylcyclopropyl)amino)methyl)piperidine-1-carboxylate (A33)

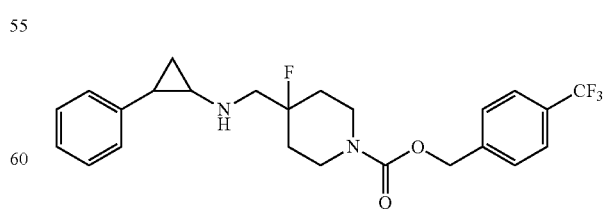

3-phenylpropionyl chloride was replaced with 4-trifluoromethylbenzyl chloroformate, while other raw materials, reagents and the preparation method were the same as those in example 8 to provide product A33 (yield: 68%). $^1$H NMR (400 MHz, DMSO-$d_6$) δ 7.69 (d, J=7.2 Hz, 2H), 7.58-7.52 (m, 2H), 7.26-7.11 (m, 5H), 5.18 (s, 1H), 4.03 (dt, J=12.5, 7.2 Hz, 2H), 3.27 (dt, J=12.5, 7.1 Hz, 2H), 2.74-2.64 (m, 2H), 2.60 (s, 1H), 1.94 (ddt, J=25.0, 14.1, 7.1 Hz, 3H), 1.73-1.54 (m, 2H), 0.96 (td, J=7.0, 5.0 Hz, 1H), 0.70 (td, J=7.0, 5.0 Hz, 1H); LRMS (ESI): 451.19 [M+H]$^+$.

Example 34 3,5-Dimethoxybenzyl 4-fluoro-4-(((trans-2-phenylcyclopropyl)amino)methyl)piperidine-1-carboxylate (A34)

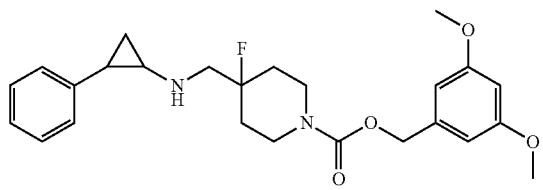 [SMILES: COc1cc(COC(=O)N2CCC(F)(CNC3CC3c3ccccc3)CC2)cc(OC)c1]

3-phenylpropionyl chloride was replaced with 3,5-dimethoxybenzyl chloroformate, while other raw materials, reagents and the preparation method were the same as those in example 8 to provide product A34 (yield: 77%). $^1$H NMR (400 MHz, DMSO-$d_6$) δ 7.26-7.11 (m, 5H), 6.59 (dt, J=2.2, 1.0 Hz, 2H), 6.33 (t, J=2.0 Hz, 1H), 5.02 (d, J=1.2 Hz, 2H), 4.16 (dt, J=12.6, 7.2 Hz, 2H), 3.66 (s, 6H), 3.09 (dt, J=12.5, 7.1 Hz, 2H), 2.77-2.64 (m, 2H), 2.60 (s, 1H), 2.05-1.81 (m, 3H), 1.61 (ddt, J=25.1, 13.2, 7.2 Hz, 2H), 0.94 (td, J=7.0, 5.0 Hz, 1H), 0.69 (td, J=7.0, 5.0 Hz, 1H); LRMS (ESI): 443.23 [M+H]$^+$.

Example 35

4-((4-Fluoro-4-(((trans-2-phenylcyclopropyl)amino) methyl)piperidine-1-carbonyloxy)methyl)benzoic Acid (A35)

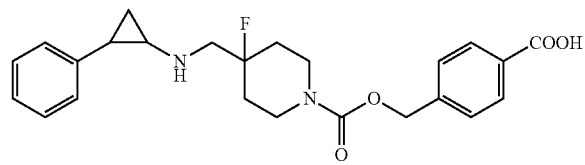 [SMILES: O=C(O)c1ccc(COC(=O)N2CCC(F)(CNC3CC3c3ccccc3)CC2)cc1]

35.1 Synthesis of 4-(tert-Butoxycarbonyl)benzyl 4-fluoro-4-((2,2,2-trifluoro-N-(trans-2-phenylcyclopropyl)acetamido)methyl)piperidine-1-formate

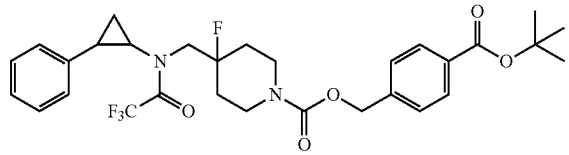 [SMILES: CC(C)(C)OC(=O)c1ccc(COC(=O)N2CCC(F)(CN(C(=O)C(F)(F)F)C3CC3c3ccccc3)CC2)cc1]

3-phenylpropionyl chloride was replaced with 4-((chloroformyloxy)methyl)benzoate, and the other raw materials, reagents and preparation methods were the same as those in examples 8.1 to obtain 4-(tert-butoxycarbonyl)benzyl 4-fluoro-4-((2,2,2-trifluoro-N-(trans-2-phenylcyclopropyl) acetamido)methyl)piperidine-1-formate (yield: 77%).

35.2 Synthesis of Final Product A35

Tert-butyl 4-((4-Fluoro-4-((2,2,2-trifluoro-N-(2-phenylcyclopropyl)acetamido)methyl)piperidine 1-ylmethyl)benzoate was replaced with 4-(tert-butoxycarbonyl)benzyl 4-fluoro-4-((2,2,2-trifluoro-N-(trans-2-phenylcyclopropyl) acetylamino)methyl piperidine-1-carboxylate, while other raw materials, reagents and the preparation method were the same as those in example 5.4 to provide hydrochloride salt of product A35 (yield 85%). $^1$H NMR (400 MHz, DMSO-$d_6$) δ 12.91 (s, 1H), 7.93-7.86 (m, 2H), 7.46-7.39 (m, 2H), 7.26-7.11 (m, 5H), 5.18 (s, 1H), 4.03 (dt, J=12.6, 7.2 Hz, 2H), 3.29 (dt, J=12.5, 7.2 Hz, 2H), 2.76-2.64 (m, 2H), 2.60 (s, 1H), 2.05-1.86 (m, 3H), 1.63 (ddt, J=25.3, 13.2, 7.2 Hz, 2H), 0.95 (td, J=7.0, 5.1 Hz, 1H), 0.71 (td, J=7.0, 5.0 Hz, 1H); LRMS (ESI): 427.20 [M+H]$^+$.

Example 36 (E)-1-(4-Fluoro-4-(((trans-2-phenylcyclopropyl)amino)methyl)piperidin-1-yl)-3-phenyl-2-ene-1-propanone (A36)

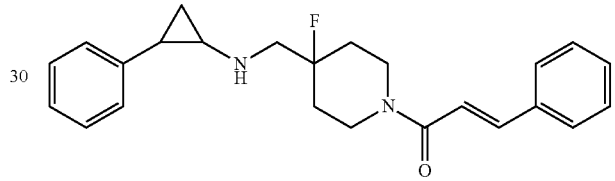

3-phenylpropionyl chloride was replaced with cinnamoyl chloride, while other raw materials, reagents and the preparation method were the same as those in example 8 to provide product A36 (yield: 88%). $^1$H NMR (400 MHz, CD$_3$OD) δ 7.66-7.54 (m, 3H), 7.43-7.34 (m, 3H), 7.31 (tt, J=6.9, 1.0 Hz, 2H), 7.25-7.16 (m, 4H), 4.56 (d, J=12.8 Hz, 1H), 4.27 (d, J=13.3 Hz, 1H), 3.61-3.45 (m, 3H), 3.17-3.09 (m, 1H), 3.06 (dt, J=7.9, 4.0 Hz, 1H), 2.58 (ddd, J=10.3, 6.6, 3.6 Hz, 1H), 2.07 (q, J=12.6, 11.4 Hz, 2H), 1.85 (tt, J=25.7, 13.1 Hz, 2H), 1.58 (ddd, J=10.6, 6.8, 4.4 Hz, 1H), 1.40 (dt, J=7.9, 6.7 Hz, 1H); LRMS (ESI): 379.21 [M+H]$^+$.

Example 37 N-Benzyl-4-fluoro-4-(((trans-2-phenylcyclopropyl)amino)methyl)piperidine-1-thioamide (A37)

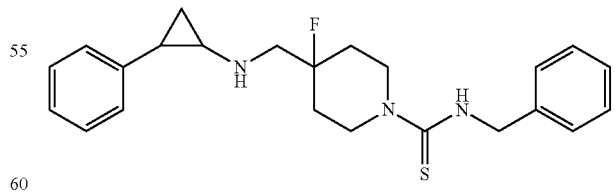

3-phenylpropionyl chloride was replaced with benzyl isothiocyanate, while other raw materials, reagents and the preparation method were the same as those in example 8 to provide product A37 (yield: 58%). $^1$H NMR (400 MHz, DMSO-$d_6$) δ 7.36-7.13 (m, 10H), 7.13 (s, 1H), 4.75 (s, 2H), 3.97 (dt, J=12.5, 7.1 Hz, 2H), 2.82 (q, J=7.0 Hz, 1H), 2.66

(s, 1H), 2.60 (s, 1H), 2.47 (dt, J=12.5, 7.0 Hz, 2H), 1.89 (q, J=7.0 Hz, 1H), 1.77 (ddt, J=25.3, 13.2, 7.2 Hz, 2H), 1.47 (ddt, J=25.3, 13.2, 7.2 Hz, 2H), 0.97 (td, J=7.0, 5.0 Hz, 1H), 0.71 (td, J=7.0, 5.0 Hz, 1H); LRMS (ESI): 398.20 [M+H]+.

Example 38 N-Benzyl-4-fluoro-4-(((trans-2-phenyl-cyclopropyl)amino)methyl)piperidine-1-carboxamide (A38)

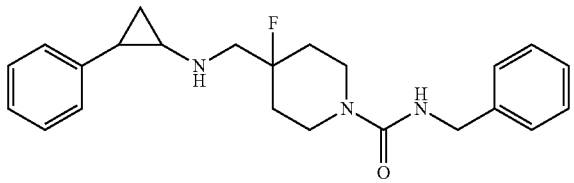

3-phenylpropionyl chloride was replaced with benzyl isocyanate, while other raw materials, reagents and the preparation method were the same as those in example 8 to provide product A38 (yield: 52%). 1H NMR (400 MHz, DMSO-d6) δ 7.30 (s, 3H), 7.34-7.23 (m, 2H), 7.27-7.11 (m, 5H), 4.27 (s, 2H), 4.11 (dt, J=12.5, 7.1 Hz, 2H), 3.09 (dt, J=12.5, 7.1 Hz, 2H), 2.72-2.57 (m, 3H), 2.04-1.85 (m, 3H), 1.59 (ddt, J=25.1, 13.2, 7.1 Hz, 2H), 0.94 (td, J=7.0, 5.0 Hz, 1H), 0.68 (td, J=7.0, 4.9 Hz, 1H); LRMS (ESI): 382.22 [M+H]+.

Example 39 N-((1-((Benzyloxy)methyl)-4-fluoropiperidin-4-yl)methyl)-trans-2-phenylcyclopropylamine (A39)

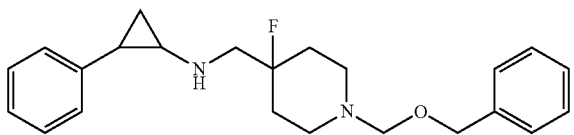 [SMILES: FC1(CNC2CC2c2ccccc2)CCN(COCc2ccccc2)CC1]

bromomethylbenzene was replaced with benzyl chloromethyl ether, while other raw materials, reagents and the preparation method were the same as those in example 6 to provide product A39 (yield: 64%). 1H NMR (400 MHz, DMSO-d6) δ 7.37-7.25 (m, 5H), 7.29-7.11 (m, 5H), 4.68 (s, 1H), 4.44 (s, 2H), 3.06 (dt, J=12.5, 7.2 Hz, 2H), 2.75-2.64 (m, 2H), 2.63-2.51 (m, 3H), 1.96-1.78 (m, 3H), 1.47 (ddt, J=25.3, 13.3, 7.1 Hz, 2H), 0.94 (td, J=7.0, 4.9 Hz, 1H), 0.69 (td, J=7.0, 5.0 Hz, 1H); LRMS (ESI): 369.23 [M+H]+.

Example 40 Benzyl 4-fluoro-4-(((trans-2-phenylcyclopropyl)amino)methyl)cyclohexane-1-carboxylate (A40)

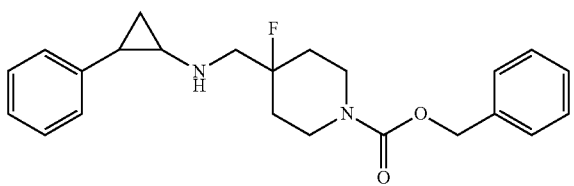 [SMILES: O=C(OCc1ccccc1)N1CCC(F)(CNC2CC2c2ccccc2)CC1]

benzyl 4-fluoro-4-formylpiperidine-1-carboxylate was replaced with benzyl 4-fluoro-4-formylcyclohexane-1-carboxylate, while other raw materials, reagents and the preparation method were the same as those in example 1 to provide product A40 (yield: 74%).

1H NMR (400 MHz, DMSO-d6) δ 7.38-7.26 (m, 5H), 7.26-7.11 (m, 5H), 5.11 (s, 2H), 2.74-2.64 (m, 2H), 2.27 (p, J=6.9 Hz, 1H), 2.18-2.05 (m, 2H), 1.98-1.74 (m, 6H), 1.61-1.42 (m, 2H), 0.95 (td, J=7.0, 5.0 Hz, 1H), 0.68 (td, J=7.0, 5.0 Hz, 1H); LRMS (ESI): 382.21 [M+H]+.

Example 41 Cyclopentylmethyl 4-fluoro-4-(((trans-2-phenylcyclopropyl)amino)methyl)piperidine-1-carboxylate (A41)

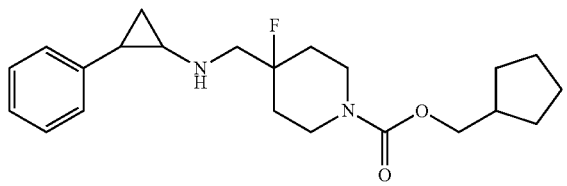 [SMILES: O=C(OCC1CCCC1)N1CCC(F)(CNC2CC2c2ccccc2)CC1]

3-phenylpropionyl chloride was replaced with cyclopentylmethyl chloroformate, while other raw materials, reagents and the preparation method were the same as those in example 8 to provide product A41 (yield: 69%). 1H NMR (400 MHz, DMSO-d6) δ 7.26-7.11 (m, 5H), 4.04 (dt, J=12.5, 7.1 Hz, 2H), 3.88 (s, 2H), 3.28 (dt, J=12.6, 7.2 Hz, 2H), 2.72 (s, 1H), 2.66 (s, 1H), 2.60 (s, 1H), 1.96 (ddt, J=25.1, 13.2, 7.0 Hz, 2H), 1.86 (s, 1H), 1.71-1.42 (m, 7H), 1.07 (tdd, J=7.8, 4.8, 1.5 Hz, 2H), 0.94 (s, 1H), 0.69 (s, 1H); LRMS (ESI): 375.24 [M+H]+.

Example 42 Cyclobutylmethyl 4-fluoro-4-(((trans-2-phenylcyclopropyl)amino)methyl)piperidine-1-carboxylate (A42)

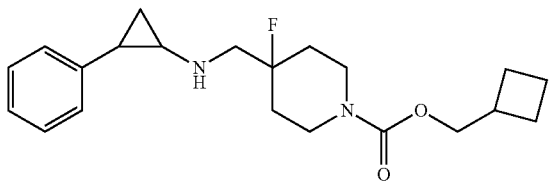 [SMILES: O=C(OCC1CCC1)N1CCC(F)(CNC2CC2c2ccccc2)CC1]

3-phenylpropionyl chloride was replaced with cyclobutylmethyl chloroformate, while other raw materials, reagents and the preparation method were the same as those in example 8 to provide product A42 (yield: 71%). 1H NMR (400 MHz, DMSO-d6) δ 7.26-7.11 (m, 5H), 4.13 (dt, J=12.5, 7.1 Hz, 2H), 3.88 (d, J=7.0 Hz, 2H), 3.11 (dt, J=12.5, 7.0 Hz, 2H), 2.90 (q, J=6.9 Hz, 1H), 2.62-2.47 (m, 2H), 2.14-1.96 (m, 4H), 1.90-1.77 (m, 2H), 1.80-1.68 (m, 2H), 1.71-1.58 (m, 4H), 0.93 (td, J=6.9, 5.0 Hz, 1H), 0.71 (td, J=7.0, 5.1 Hz, 1H); LRMS (ESI): 361.22 [M+H]+.

Example 43 Piperidin-4-ylmethyl 4-fluoro-4-(((trans-2-phenylcyclopropyl)amino)methyl)piperidine-1-carboxylate (A43)

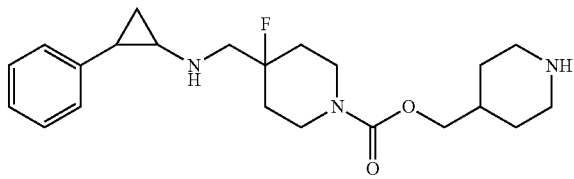 [SMILES: O=C(OCC1CCNCC1)N1CCC(F)(CNC2CC2c2ccccc2)CC1]

3-phenylpropionyl chloride was replaced with tert-butyl 4-((chloroformyloxy)methyl)piperidine-1-carboxylate, while other raw materials, reagents and the preparation method were the same as those in examples 8.1 and 5.4 to provide the dihydrochloride of product A43 (yield: 61%). $^1$H NMR (400 MHz, DMSO-$d_6$) δ 7.26-7.11 (m, 5H), 4.03 (dt, J=12.5, 7.1 Hz, 2H), 3.88 (s, 2H), 3.27 (dt, J=12.6, 7.2 Hz, 2H), 3.04 (dt, J=12.5, 7.2 Hz, 2H), 2.75-2.57 (m, 5H), 2.44 (s, 1H), 2.04-1.86 (m, 2H), 1.91 (s, 1H), 1.66 (s, 1H), 1.64 (ddt, J=25.3, 13.7, 7.1 Hz, 2H), 1.45 (dt, J=13.1, 7.1 Hz, 2H), 1.18 (dt, J=13.3, 7.2 Hz, 2H), 0.95 (s, 1H), 0.71 (s, 1H); LRMS (ESI): 390.25 [M+H]$^+$.

Example 44 3-Chlorobenzyl 4-fluoro-4-(((trans-2-phenylcyclopropyl)amino)methyl)piperidine-1-carboxylate (A44)

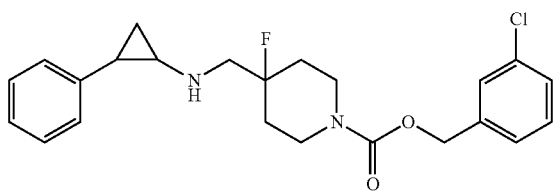 [SMILES: O=C(OCc1cccc(Cl)c1)N1CCC(F)(CNC2CC2c2ccccc2)CC1]

3-phenylpropionyl chloride was replaced with 3-chlorobenzyl chloroformate, while other raw materials, reagents and the preparation method were the same as those in example 8 to provide product A44 (yield: 74%). $^1$H NMR (400 MHz, DMSO-$d_6$) δ 7.51-7.45 (m, 1H), 7.39-7.26 (m, 3H), 7.26-7.11 (m, 5H), 5.02 (s, 2H), 4.04 (dt, J=12.5, 7.1 Hz, 2H), 3.26 (dt, J=12.5, 7.0 Hz, 2H), 2.76-2.64 (m, 2H), 2.01-1.83 (m, 3H), 1.64 (ddt, J=25.1, 13.2, 7.0 Hz, 2H), 0.93 (td, J=7.0, 5.1 Hz, 1H), 0.71 (td, J=7.0, 5.0 Hz, 1H); LRMS (ESI): 417.17 [M+H]$^+$.

Example 45 2-Chlorobenzyl 4-fluoro-4-(((trans-2-phenylcyclopropyl)amino)methyl)piperidine-1-carboxylate (A45)

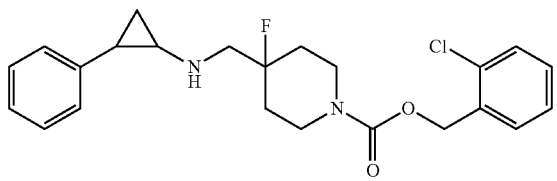 [SMILES: O=C(OCc1ccccc1Cl)N1CCC(F)(CNC2CC2c2ccccc2)CC1]

3-phenylpropionyl chloride was replaced with 2-chlorobenzyl chloroformate, while other raw materials, reagents and the preparation method were the same as those in example 8 to provide product A45 (yield: 70%). $^1$H NMR (400 MHz, DMSO-$d_6$) δ 7.45-7.31 (m, 2H), 7.26-7.05 (m, 7H), 5.09 (d, J=0.9 Hz, 2H), 4.03 (dt, J=12.5, 7.1 Hz, 2H), 3.26 (dt, J=12.5, 7.0 Hz, 2H), 2.75-2.64 (m, 2H), 2.00-1.82 (m, 3H), 1.73-1.55 (m, 2H), 0.94 (td, J=7.0, 5.0 Hz, 1H), 0.71 (td, J=7.0, 5.1 Hz, 1H); LRMS (ESI): 417.17 [M+H]$^+$.

Example 46 (4-Fluoro-4-(((trans-2-phenylcyclopropyl)amino)methyl)piperidin-1-yl)(phenyl)methanone (A46)

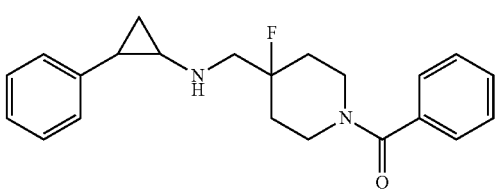 [SMILES: O=C(c1ccccc1)N1CCC(F)(CNC2CC2c2ccccc2)CC1]

3-phenylpropionyl chloride was replaced with benzoyl chloride, while other raw materials, reagents and the preparation method were the same as those in example 8 to provide product A46 (yield: 66%). $^1$H NMR (400 MHz, DMSO-$d_6$) δ 7.59 (tt, J=7.2, 2.2 Hz, 1H), 7.50-7.36 (m, 4H), 7.26-7.11 (m, 5H), 3.75 (dt, J=12.5, 7.1 Hz, 2H), 3.13 (dt, J=12.6, 7.2 Hz, 2H), 2.76-2.64 (m, 2H), 2.60 (s, 1H), 1.98-1.86 (m, 2H), 1.90-1.80 (m, 1H), 1.63 (ddt, J=25.1, 13.2, 7.0 Hz, 2H), 0.96 (td, J=6.9, 5.0 Hz, 1H), 0.70 (td, J=7.0, 5.0 Hz, 1H); LRMS (ESI): 353.20 [M+H]$^+$.

Example 47 4-tert-Butylbenzyl 4-fluoro-4-(((trans-2-phenylcyclopropyl)amino)methyl)piperidine-1-carboxylate (A47)

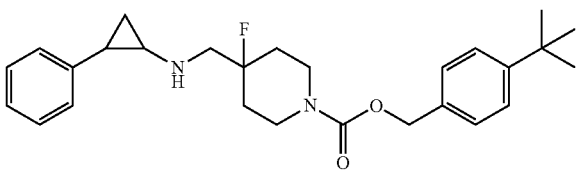 [SMILES: CC(C)(C)c1ccc(COC(=O)N2CCC(F)(CNC3CC3c3ccccc3)CC2)cc1]

3-phenylpropionyl chloride was replaced with 4-tert-butylbenzyl chloroformate, while other raw materials, reagents and the preparation method were the same as those in example 8 to provide product A47 (yield: 69%). $^1$H NMR (400 MHz, DMSO-$d_6$) δ 7.39 (t, J=6.3 Hz, 4H), 7.26-7.11 (m, 5H), 5.18 (d, J=1.2 Hz, 2H), 4.04 (dt, J=12.6, 7.2 Hz, 2H), 3.25 (dt, J=12.5, 7.1 Hz, 2H), 2.77-2.64 (m, 2H), 2.00-1.82 (m, 3H), 1.64 (ddt, J=25.1, 13.2, 7.2 Hz, 2H), 1.31 (s, 9H), 0.94 (td, J=7.0, 5.1 Hz, 1H), 0.70 (td, J=7.0, 5.1 Hz, 1H); LRMS (ESI): 439.27 [M+H]$^+$.

Example 48 Benzyl 4-fluoro-2-methyl-4-(((trans-2-phenylcyclopropyl)amino)methyl)piperidine-1-carboxylate (A48)

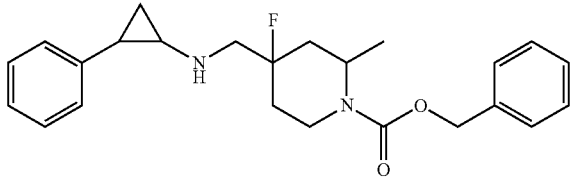 [SMILES: CC1CC(F)(CNC2CC2c2ccccc2)CCN1C(=O)OCc1ccccc1]

benzyl 4-fluoro-4-formylpiperidine-1-carboxylate was replaced with benzyl 4-fluoro-2-methyl-4-formylpiperidine-1-carboxylate, while other raw materials, reagents and the preparation method were the same as those in example 1 to provide product A48 (yield: 68%). $^1$H NMR (400 MHz, DMSO-$d_6$) δ 7.39-7.26 (m, 5H), 7.26-7.11 (m, 5H), 5.50 (d, J=12.3 Hz, 1H), 5.31 (d, J=12.4 Hz, 1H), 4.16 (dt, J=12.4, 7.1 Hz, 1H), 3.79 (h, J=6.8 Hz, 1H), 3.21 (dt, J=12.4, 7.1 Hz, 1H), 3.04 (dd, J=25.2, 12.4 Hz, 1H), 2.90-2.66 (m, 2H), 2.12-1.60 (m, 4H), 1.46 (ddd, J=25.3, 13.1, 7.0 Hz, 1H), 1.25 (d, J=6.8 Hz, 3H), 0.94 (td, J=7.0, 5.0 Hz, 1H), 0.69 (td, J=7.0, 4.9 Hz, 1H). LRMS (ESI): 397.22 [M+H]$^+$.

Example 49 Benzyl 4-fluoro-2,6-dimethyl-4-(((trans-2-phenylcyclopropyl)amino)methyl)piperidine-1-carboxylate (A49)

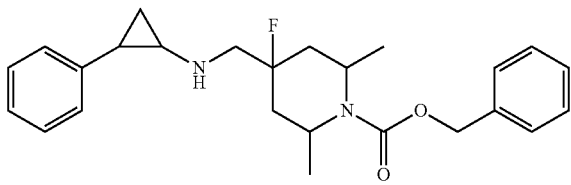 [SMILES: CC1CC(F)(CNC2CC2c2ccccc2)CC(C)N1C(=O)OCc1ccccc1]

benzyl 4-fluoro-4-formylpiperidine-1-carboxylate was replaced with benzyl 4-fluoro-2,6-dimethyl-4-formylpiperidine-1-carboxylate, the remaining raw materials, reagents and preparation method were the same as in Example 1 to give the product A49 (yield: 74%).

$^1$H NMR (400 MHz, DMSO-$d_6$) δ 7.39-7.26 (m, 5H), 7.26-7.11 (m, 5H), 5.35 (d, J=12.4 Hz, 1H), 3.88 (q, J=6.9 Hz, 2H), 2.74-2.64 (m, 2H), 2.60 (s, 1H), 1.94-1.78 (m, 3H), 1.51 (ddd, J=25.3, 13.2, 7.0 Hz, 2H), 1.25 (d, J=6.8 Hz, 6H), 0.95 (td, J=7.0, 5.0 Hz, 1H), 0.69 (td, J=7.0, 5.0 Hz, 1H); LRMS (ESI): 411.24 [M+H]$^+$.

Example 50 Benzyl 4-fluoro-4-(((trans-2-(naphthalen-2-yl)cyclopropyl)amino)methyl)piperidine-1-carboxylate (A50)

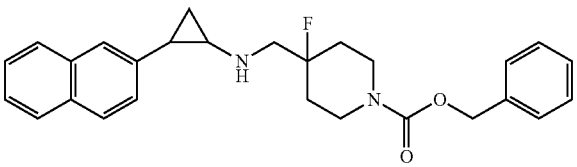 [SMILES: O=C(OCc1ccccc1)N1CCC(F)(CNC2CC2c2ccc3ccccc3c2)CC1]

trans-2-phenylpropionyl chloride was replaced with trans-2-(naphthalen-2-yl)cyclopropylamine, while other raw materials, reagents and the preparation method were the same as those in example 1 to provide product A50 (yield: 60%). $^1$H NMR (400 MHz, DMSO-$d_6$) δ 7.94-7.81 (m, 3H), 7.57-7.39 (m, 4H), 7.39-7.26 (m, 5H), 5.22 (s, 2H), 4.04 (dt, J=12.4, 7.2 Hz, 2H), 3.30 (dt, J=12.5, 7.1 Hz, 2H), 2.76 (q, J=7.0 Hz, 1H), 2.66 (s, 1H), 2.60 (s, 1H), 2.05-1.87 (m, 3H), 1.64 (ddt, J=25.1, 13.2, 7.2 Hz, 2H), 0.99 (td, J=7.0, 5.0 Hz, 1H), 0.75 (td, J=7.0, 5.0 Hz, 1H); LRMS (ESI): 433.22 [M+H]$^+$.

Example 51 Benzyl 4-fluoro-4-(((trans-2-(benzothiophen-5-yl)cyclopropyl)amino)methyl)piperidine-1-carboxylate (A51)

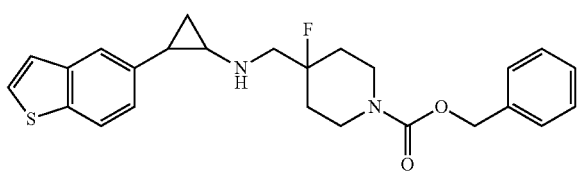 [SMILES: O=C(OCc1ccccc1)N1CCC(F)(CNC2CC2c2ccc3sccc3c2)CC1]

trans-2-phenyl cyclopropylamine was replaced with trans-2-(benzothiophen-5-yl)cyclopropylamine, while other raw materials, reagents and the preparation method were the same as those in example 1 to provide product A51 (yield: 55%). $^1$H NMR (400 MHz, DMSO-$d_6$) δ 7.96 (d, J=7.5 Hz, 1H), 7.68 (s, 1H), 7.55-7.44 (m, 2H), 7.32 (dtd, J=8.9, 7.4, 2.3 Hz, 6H), 5.22 (s, 2H), 4.03 (dt, J=12.6, 7.2 Hz, 2H), 3.30 (dt, J=12.5, 7.0 Hz, 2H), 2.77 (q, J=7.0 Hz, 1H), 2.66 (s, 1H), 2.60 (s, 1H), 2.05-1.87 (m, 3H), 1.73-1.55 (m, 2H), 0.99 (td, J=7.0, 4.9 Hz, 1H), 0.77 (td, J=7.0, 4.9 Hz, 1H); LRMS (ESI): 439.18 [M+H]$^+$.

Example 52 Benzyl 4-fluoro-4-(((trans-2-(pyridin-4-yl)cyclopropyl)amino)methyl)piperidine-1-carboxylate (A52)

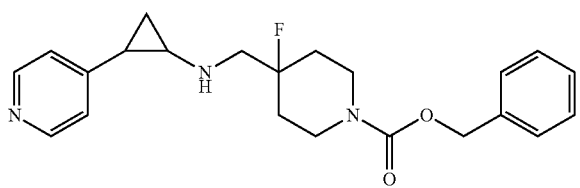

trans-2-phenyl cyclopropylamine was replaced with trans-2-(pyridin-4-yl)cyclopropylamine, while other raw materials, reagents and the preparation method were the same as those in example 1 to provide product A52 (yield: 65%). $^1$H NMR (400 MHz, DMSO-$d_6$) δ 8.50 (d, J=5.1 Hz, 2H), 7.39-7.26 (m, 5H), 7.22 (d, J=5.2 Hz, 2H), 5.22 (s, 2H), 4.02 (dt, J=12.5, 7.0 Hz, 2H), 3.34-3.13 (m, 3H), 2.66 (s, 1H), 2.60 (s, 1H), 1.94 (ddt, J=25.3, 13.9, 7.1 Hz, 2H), 1.79-1.54 (m, 3H), 0.86 (td, J=7.0, 4.9 Hz, 1H), 0.61 (td, J=7.0, 5.0 Hz, 1H); LRMS (ESI): 384.20 [M+H]$^+$.

Example 53 Benzyl 4-fluoro-4-(((trans-2-(1H-indol-5-yl)cyclopropyl)amino)methyl)piperidine-1-carboxylate (A53)

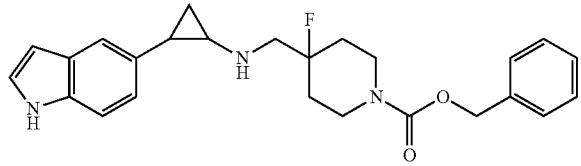

trans-2-phenyl cyclopropylamine was replaced with trans-2-(1H-indol-5-yl)cyclopropylamine, while other raw materials, reagents and the preparation method were the same as those in example 1 to provide product A53 (yield: 57%).

$^1$H NMR (400 MHz, DMSO-d$_6$) δ 11.53 (s, 1H), 7.82 (s, 1H), 7.56 (d, J=7.5 Hz, 1H), 7.43 (d, J=7.5 Hz, 1H), 7.39-7.24 (m, 6H), 6.64 (dd, J=7.4, 1.4 Hz, 1H), 5.22 (s, 2H), 4.03 (dt, J=12.5, 7.1 Hz, 2H), 3.29 (dt, J=12.5, 7.1 Hz, 2H), 2.76 (q, J=7.0 Hz, 1H), 2.66 (s, 1H), 2.60 (s, 1H), 2.05-1.87 (m, 3H), 1.64 (ddt, J=25.1, 13.2, 7.2 Hz, 2H), 0.99 (td, J=7.0, 4.9 Hz, 1H), 0.76 (td, J=6.9, 5.0 Hz, 1H); LRMS (ESI): 422.22 [M+H]$^+$.

Example 54 Benzyl 4-fluoro-4-(((trans-2-(1-methyl-1H-indol-5-yl)cyclopropyl)amino)methyl)piperidine-1-carboxylate (A54)

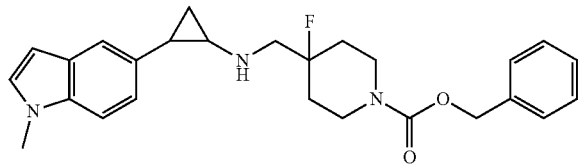

trans-2-phenyl cyclopropylamine was replaced with trans-2-(1-methyl-1H-indol-5-yl)cyclopropylamine, while other raw materials, reagents and the preparation method were the same as those in example 1 to provide product A54 (yield: 67%). $^1$H NMR (400 MHz, DMSO-d$_6$) δ 7.66 (t, J=1.5 Hz, 1H), 7.52 (d, J=7.5 Hz, 1H), 7.39-7.26 (m, 5H), 7.17 (d, J=7.5 Hz, 1H), 7.02 (dd, J=7.5, 1.5 Hz, 1H), 6.53 (dd, J=7.5, 1.6 Hz, 1H), 5.22 (s, 2H), 4.12 (dt, J=12.5, 7.1 Hz, 2H), 3.79 (s, 3H), 3.12 (dt, J=12.5, 7.1 Hz, 2H), 2.75 (q, J=6.9 Hz, 1H), 2.66 (s, 1H), 2.60 (s, 1H), 2.02-1.84 (m, 3H), 1.65 (ddt, J=25.1, 13.2, 7.2 Hz, 2H), 0.96 (td, J=7.0, 5.0 Hz, 1H), 0.72 (td, J=7.0, 5.0 Hz, 1H); LRMS (ESI): 436.23 [M+H]$^+$.

Example 55 Benzyl 4-fluoro-4-(((trans-2-(indolin-5-yl)cyclopropyl)amino)methyl)piperidine-1-carboxylate (A55)

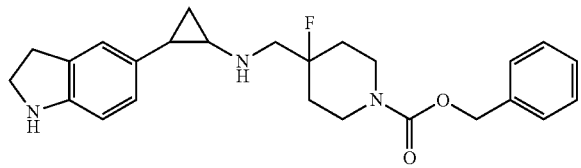

trans-2-phenyl cyclopropylamine was replaced with trans-2-(indolin-5-yl)cyclopropylamine, while other raw materials, reagents and the preparation method were the same as those in example 1 to provide product A55 (yield: 55%). $^1$H NMR (400 MHz, DMSO-d$_6$) δ 7.39-7.26 (m, 5H), 6.95 (d, J=2.0 Hz, 1H), 6.69 (dd, J=7.4, 2.0 Hz, 1H), 6.47 (d, J=7.5 Hz, 1H), 5.83 (s, 1H), 5.22 (s, 2H), 4.02 (dt, J=12.5, 7.2 Hz, 2H), 3.65-3.43 (m, 2H), 3.28 (dt, J=12.5, 7.1 Hz, 2H), 2.88 (ddd, J=18.5, 10.3, 8.0 Hz, 1H), 2.77-2.57 (m, 4H), 2.04-1.82 (m, 3H), 1.63 (ddt, J=25.1, 13.2, 7.1 Hz, 2H), 0.95 (td, J=7.0, 5.1 Hz, 1H), 0.71 (td, J=7.0, 5.0 Hz, 1H); LRMS (ESI): 424.23 [M+H]$^+$.

Example 56 Benzyl 4-fluoro-4-(((trans-2-(1-(phenylsulfonyl)indolin-5-yl)cyclopropyl)amino)methyl)piperidine-1-carboxylate (A56)

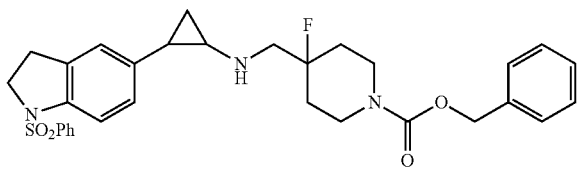

trans-2-phenyl cyclopropylamine was replaced with trans-2-(1-(phenylsulfonyl)indolin-5-yl)cyclopropylamine, while other raw materials, reagents and the preparation method were the same as those in example 1 to provide product A56 (yield: 70%). $^1$H NMR (400 MHz, DMSO-d$_6$) δ 7.68-7.51 (m, 5H), 7.39-7.26 (m, 5H), 7.17 (d, J=2.0 Hz, 1H), 6.75 (dd, J=7.5, 1.9 Hz, 1H), 6.63 (d, J=7.5 Hz, 1H), 5.22 (s, 2H), 4.43-4.22 (m, 2H), 4.19-4.09 (m, 1H), 3.99 (dt, J=12.5, 7.1 Hz, 1H), 3.32 (dt, J=12.5, 7.1 Hz, 1H), 3.08 (dt, J=12.5, 7.1 Hz, 1H), 2.97 (q, J=6.9 Hz, 1H), 2.92-2.83 (m, 2H), 2.66 (s, 1H), 2.60 (s, 1H), 2.09-1.72 (m, 4H), 1.63 (ddt, J=25.1, 13.2, 7.1 Hz, 1H), 0.90 (td, J=7.0, 5.0 Hz, 1H), 0.69 (td, J=7.0, 5.0 Hz, 1H); LRMS (ESI): 564.23 [M+H]$^+$.

Example 57 Benzyl 4-fluoro-4-(((trans-2-(1H-indol-3-yl)cyclopropyl)amino)methyl)piperidine-1-carboxylate (A57)

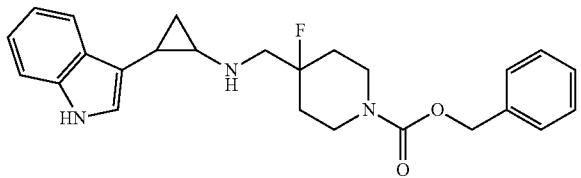 [SMILES: O=C(OCc1ccccc1)N1CCC(F)(CNC2CC2c2c[nH]c3ccccc23)CC1]

trans-2-phenyl cyclopropylamine was replaced with trans-2-(1H-indol-3-yl)cyclopropylamine, while other raw materials, reagents and the preparation method were the same as those in example 1 to provide product A57 (yield: 61%).

$^1$H NMR (400 MHz, DMSO-d$_6$) δ 10.75 (s, 1H), 7.58 (dd, J=7.4, 1.5 Hz, 1H), 7.39-7.26 (m, 3H), 7.32 (s, 3H), 7.17 (s, 1H), 7.02 (dtd, J=32.8, 7.4, 1.5 Hz, 2H), 5.22 (s, 2H), 3.89-3.71 (m, 3H), 2.89 (dt, J=12.5, 7.2 Hz, 2H), 2.66 (s, 1H), 2.60 (s, 1H), 1.88 (ddt, J=25.1, 12.3, 7.1 Hz, 2H), 1.72-1.46 (m, 3H), 0.71 (td, J=6.9, 5.0 Hz, 1H), 0.46 (td, J=7.0, 5.1 Hz, 1H);

Example 58 Benzyl 4-fluoro-4-(((trans-2-((imidazo[1,2-α]pyridin-3-yl)cyclopropyl)amino)methyl)piperidine-1-carboxylate (A58)

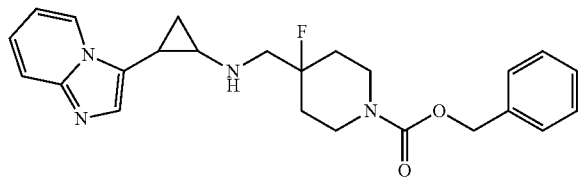 [SMILES: O=C(OCc1ccccc1)N1CCC(F)(CNC2CC2c2cnc3ccccn23)CC1]

trans-2-phenyl cyclopropylamine was replaced with trans-2-(imidazo[1,2-α]pyridin-3-yl)cyclopropylamine, while other raw materials, reagents and the preparation method were the same as those in example 1 to provide product A58 (yield: 51%). $^1$H NMR (400 MHz, DMSO-$d_6$) δ 8.47 (dd, J=7.4, 1.5 Hz, 1H), 7.89 (s, 1H), 7.47 (dd, J=7.5, 1.6 Hz, 1H), 7.39-7.26 (m, 5H), 7.21 (td, J=7.5, 1.5 Hz, 1H), 6.85 (td, J=7.4, 1.4 Hz, 1H), 5.22 (s, 2H), 3.83 (dt, J=12.4, 7.2 Hz, 2H), 3.76 (q, J=7.0 Hz, 1H), 2.89 (dt, J=12.5, 7.2 Hz, 2H), 2.66 (s, 1H), 2.60 (s, 1H), 1.88 (ddt, J=25.1, 12.3, 7.1 Hz, 2H), 1.72-1.46 (m, 3H), 0.82 (td, J=7.0, 4.9 Hz, 1H), 0.57 (td, J=7.0, 5.0 Hz, 1H); LRMS (ESI): 422.21 [M+H]$^+$.

Example 59 Benzyl 4-fluoro-4-(((trans-2-(2,3-dihydrobenzofuran-5-yl)cyclopropyl)amino)methyl)piperidine-1-carboxylate (A59)

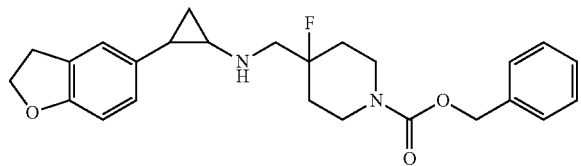

trans-2-phenyl cyclopropylamine was replaced with trans-2-(2,3-dihydrobenzofuran-5-yl)cyclopropylamine, while other raw materials, reagents and the preparation method were the same as those in example 1 to provide product A59 (yield: 65%). $^1$H NMR (400 MHz, DMSO-$d_6$) δ 7.39-7.26 (m, 5H), 7.05 (d, J=2.0 Hz, 1H), 6.96 (dd, J=7.5, 2.1 Hz, 1H), 6.78 (d, J=7.5 Hz, 1H), 5.22 (s, 2H), 4.47-4.37 (m, 2H), 4.03 (dt, J=12.5, 7.1 Hz, 2H), 3.29 (dt, J=12.5, 7.1 Hz, 2H), 2.99 (ddd, J=18.6, 6.2, 2.5 Hz, 1H), 2.77-2.57 (m, 4H), 2.04-1.84 (m, 3H), 1.63 (ddt, J=25.1, 13.2, 7.1 Hz, 2H), 0.95 (td, J=7.0, 5.0 Hz, 1H), 0.71 (td, J=7.0, 5.1 Hz, 1H); LRMS (ESI): 425.22 [M+H]$^+$.

Example 60 Benzyl 4-fluoro-4-(((trans-2-(chroman-6-yl)cyclopropyl)amino)methyl)piperidine-1-carboxylate (A60)

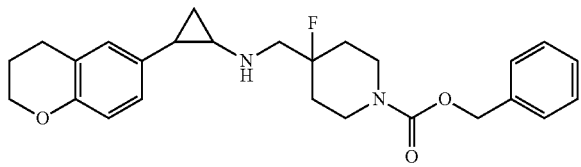 [SMILES: O=C(OCc1ccccc1)N1CCC(F)(CNC2CC2c2ccc3c(c2)CCCO3)CC1]

trans-2-phenyl cyclopropylamine was replaced with trans-2-(chroman-6-yl)cyclopropylamine, while other raw materials, reagents and the preparation method were the same as those in example 1 to provide product A60 (yield: 66%). $^1$H NMR (400 MHz, DMSO-$d_6$) δ 7.39-7.26 (m, 5H), 7.04-6.98 (m, 1H), 6.96-6.89 (m, 1H), 6.77 (d, J=7.4 Hz, 1H), 5.22 (s, 2H), 4.08-3.91 (m, 3H), 3.94-3.84 (m, 1H), 3.28 (dt, J=12.5, 7.1 Hz, 2H), 2.77-2.64 (m, 3H), 2.60 (s, 1H), 2.50-2.36 (m, 1H), 2.04-1.74 (m, 5H), 1.73-1.54 (m, 2H), 0.95 (td, J=7.0, 5.0 Hz, 1H), 0.71 (td, J=7.0, 4.9 Hz, 1H); LRMS (ESI): 439.23 [M+H]$^+$.

Example 61 Benzyl 4-fluoro-4-(((trans-2-(2-oxo-1,2,3,4-tetrahydroquinolin-6-yl)cyclopropyl)amino)methyl)piperidine-1-carboxylate (A61)

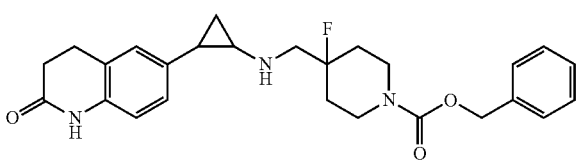 [SMILES: O=C1CCc2cc(C3CC3NCC3(F)CCN(C(=O)OCc4ccccc4)CC3)ccc2N1]

trans-2-phenyl cyclopropylamine was replaced with trans-2-(2-oxo-1,2,3,4-tetrahydroquinolin-6-yl)cyclopropylamine, while other raw materials, reagents and the preparation method were the same as those in example 1 to provide product A61 (yield: 69%). $^1$H NMR (400 MHz, DMSO-$d_6$) δ 10.01 (s, 1H), 7.39-7.26 (m, 5H), 7.20 (d, J=2.1 Hz, 1H), 7.11 (dd, J=7.5, 1.9 Hz, 1H), 6.98 (d, J=7.5 Hz, 1H), 5.22 (s, 2H), 4.14 (dt, J=12.5, 7.1 Hz, 2H), 3.31-3.07 (m, 4H), 2.89-2.70 (m, 2H), 2.66 (s, 1H), 2.60 (s, 1H), 2.48 (ddd, J=15.2, 4.4, 1.7 Hz, 1H), 2.11 (ddt, J=25.1, 13.2, 7.2 Hz, 2H), 1.89 (q, J=7.0 Hz, 1H), 1.67 (ddt, J=25.3, 13.2, 7.2 Hz, 2H), 0.96 (td, J=6.9, 5.0 Hz, 1H), 0.72 (td, J=7.0, 5.0 Hz, 1H); LRMS (ESI): 452.23 [M+H]$^+$.

Example 62 Benzyl 4-fluoro-4-(((trans-2-(thiophen-3-yl)cyclopropyl)amino)methyl)piperidine-1-carboxylate (A62)

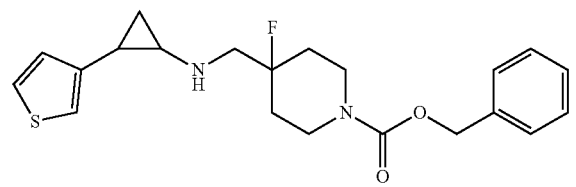 [SMILES: O=C(OCc1ccccc1)N1CCC(F)(CNC2CC2c2ccsc2)CC1]

trans-2-phenyl cyclopropylamine was replaced with trans-2-(thiophen-3-yl)cyclopropylamine, while other raw materials, reagents and the preparation method were the same as those in example 1 to provide product A62 (yield: 75%).

$^1$H NMR (400 MHz, DMSO-$d_6$) δ 7.39-7.26 (m, 5H), 7.22 (d, J=7.5 Hz, 1H), 6.95-6.86 (m, 2H), 5.22 (s, 2H), 3.83 (dt, J=12.4, 7.2 Hz, 2H), 3.76 (q, J=7.0 Hz, 1H), 2.89 (dt, J=12.5, 7.2 Hz, 2H), 2.66 (s, 1H), 2.60 (s, 1H), 1.88 (ddt, J=25.1, 12.3, 7.1 Hz, 2H), 1.63 (ddt, J=25.3, 12.5, 7.1 Hz, 2H), 1.51 (q, J=7.0 Hz, 1H), 0.69 (td, J=6.9, 5.0 Hz, 1H), 0.44 (td, J=7.0, 5.0 Hz, 1H); LRMS (ESI): 389.16 [M+H]$^+$.

Example 63 Benzyl 4-fluoro-4-(((trans-2-(furan-3-yl)cyclopropyl)amino)methyl)piperidine-1-carboxylate (A63)

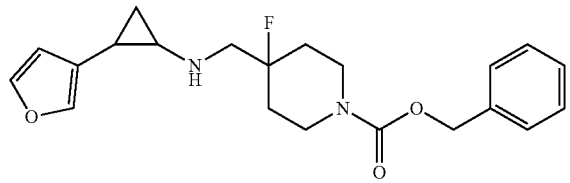 [SMILES: O=C(OCc1ccccc1)N1CCC(F)(CNC2CC2c2ccoc2)CC1]

trans-2-phenyl cyclopropylamine was replaced with trans-2-(furan-3-yl)cyclopropylamine, while other raw materials, reagents and the preparation method were the same as those in example 1 to provide product A63 (yield: 75%). $^1$H NMR (400 MHz, DMSO-$d_6$) δ 7.39-7.26 (m, 6H), 7.11 (d, J=1.5 Hz, 1H), 6.13 (dd, J=7.5, 1.5 Hz, 1H), 5.22 (s, 2H), 3.83 (dt, J=12.5, 7.2 Hz, 2H), 3.76 (q, J=7.0 Hz, 1H), 2.89 (dt, J=12.4, 7.2 Hz, 2H), 2.66 (s, 1H), 2.60 (s, 1H), 1.88 (ddt, J=25.1, 12.3, 7.1 Hz, 2H), 1.63 (ddt, J=25.3, 12.5, 7.1 Hz, 2H), 1.51 (q, J=7.0 Hz, 1H), 0.78 (td, J=7.0, 5.0 Hz, 1H), 0.53 (td, J=6.9, 5.0 Hz, 1H); LRMS (ESI): 373.18 [M+H]$^+$.

Example 64 Benzyl 4-fluoro-4-(((trans-2-(thiazol-2-yl)cyclopropyl)amino)methyl)piperidine-1-carboxylate (A64)

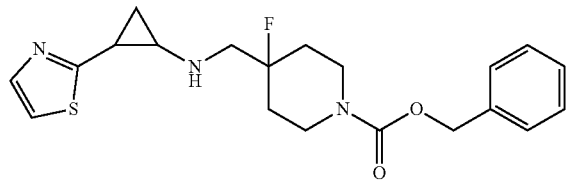 [SMILES: O=C(OCc1ccccc1)N1CCC(F)(CNC2CC2c2nccs2)CC1]

trans-2-phenyl cyclopropylamine was replaced with trans-2-(thiazol-2-yl)cyclopropylamine, while other raw materials, reagents and the preparation method were the same as those in example 1 to provide product A64 (yield: 70%). $^1$H NMR (400 MHz, DMSO-$d_6$) δ 7.69 (d, J=7.5 Hz, 1H), 7.58 (d, J=7.5 Hz, 1H), 7.39-7.26 (m, 5H), 5.22 (s, 2H), 3.83 (dt, J=12.4, 7.2 Hz, 2H), 3.76 (q, J=7.0 Hz, 1H), 2.89 (dt, J=12.5, 7.2 Hz, 2H), 2.66 (s, 1H), 2.60 (s, 1H), 1.88 (ddt, J=25.1, 12.3, 7.1 Hz, 2H), 1.63 (ddt, J=25.3, 12.5, 7.1 Hz, 2H), 1.51 (q, J=7.0 Hz, 1H), 0.78 (td, J=7.0, 4.9 Hz, 1H), 0.53 (td, J=6.9, 5.0 Hz, 1H); LRMS (ESI): 390.16 [M+H]$^+$.

Example 65 Benzyl 4-fluoro-4-(((trans-2-(4-fluorophenyl)cyclopropyl)amino)methyl)piperidine-1-carboxylate (A65)

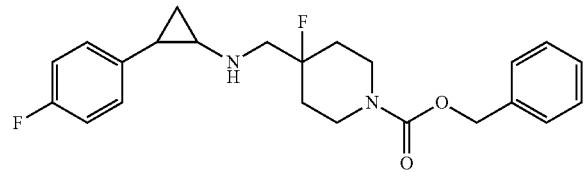 [SMILES: O=C(OCc1ccccc1)N1CCC(F)(CNC2CC2c2ccc(F)cc2)CC1]

trans-2-phenyl cyclopropylamine was replaced with trans-2-(4-fluorophenyl)cyclopropylamine, while other raw materials, reagents and the preparation method were the same as those in example 1 to provide product A65 (yield: 78%). $^1$H NMR (400 MHz, DMSO-$d_6$) δ 7.39-7.26 (m, 5H), 7.16 (ddd, J=7.0, 5.8, 1.1 Hz, 2H), 7.12-7.03 (m, 2H), 5.22 (s, 2H), 4.04 (dt, J=12.5, 7.1 Hz, 2H), 3.25 (dt, J=12.5, 7.1 Hz, 2H), 2.75-2.64 (m, 2H), 2.00-1.82 (m, 3H), 1.64 (ddt, J=25.1, 13.2, 7.2 Hz, 2H), 0.95 (td, J=7.0, 4.9 Hz, 1H), 0.71 (td, J=7.0, 5.1 Hz, 1H); LRMS (ESI): 401.20 [M+H]$^+$.

Example 66 Benzyl 4-fluoro-4-((trans-2-(4-cyanophenyl)cyclopropyl)amino)methyl)piperidine-1-carboxylate (A66)

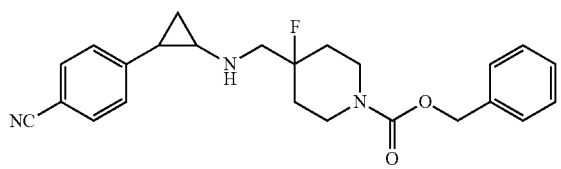 [SMILES: N#Cc1ccc(C2CC2NCC2(F)CCN(C(=O)OCc3ccccc3)CC2)cc1]

trans-2-phenyl cyclopropylamine was replaced with trans-2-(4-cyanophenyl)cyclopropylamine, while other raw materials, reagents and the preparation method were the same as those in example 1 to provide product A66 (yield: 72%).

$^1$H NMR (400 MHz, DMSO-$d_6$) δ 7.73-7.66 (m, 2H), 7.33 (tdd, J=8.7, 4.2, 2.8 Hz, 7H), 5.22 (s, 2H), 4.09 (dt, J=12.4, 7.1 Hz, 2H), 3.23 (dt, J=12.4, 7.1 Hz, 2H), 2.73-2.64 (m, 2H), 2.01-1.83 (m, 3H), 1.67 (ddt, J=25.3, 13.2, 7.2 Hz, 2H), 0.95 (td, J=7.0, 4.9 Hz, 1H), 0.69 (td, J=7.0, 5.0 Hz, 1H); LRMS (ESI): 408.20 [M+H]$^+$.

Example 67 Benzyl 4-fluoro-4-((trans-2-(4-methoxyphenyl)cyclopropyl)amino)methyl)piperidine-1-carboxylate (A67)

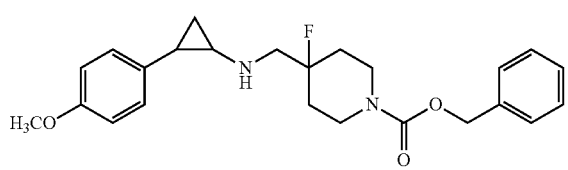 [SMILES: COc1ccc(C2CC2NCC2(F)CCN(C(=O)OCc3ccccc3)CC2)cc1]

trans-2-phenyl cyclopropylamine was replaced with trans-2-(4-methoxyphenyl)cyclopropylamine, while other raw materials, reagents and the preparation method were the same as those in example 1 to provide product A67 (yield: 70%).

$^1$H NMR (400 MHz, DMSO-$d_6$) δ 7.39-7.26 (m, 5H), 7.10-7.03 (m, 2H), 6.95-6.88 (m, 2H), 5.22 (s, 2H), 4.03 (dt, J=12.5, 7.1 Hz, 2H), 3.79 (s, 3H), 3.28 (dt, J=12.5, 7.2 Hz, 2H), 2.77-2.64 (m, 2H), 2.04-1.82 (m, 3H), 1.63 (ddt, J=25.1, 13.2, 7.1 Hz, 2H), 0.95 (td, J=7.0, 5.1 Hz, 1H), 0.71 (td, J=7.0, 5.0 Hz, 1H); LRMS (ESI): 413.22 [M+H]$^+$.

Example 68 Benzyl 4-fluoro-4-((trans-2-(2-acetylphenyl)cyclopropyl)amino)methyl)piperidine-1-carboxylate (A68)

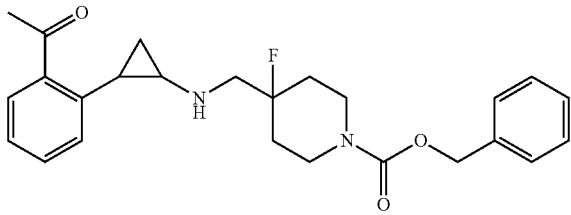 [SMILES: CC(=O)c1ccccc1C1CC1NCC1(F)CCN(C(=O)OCc2ccccc2)CC1]

trans-2-phenyl cyclopropylamine was replaced with trans-2-(2-acetylphenyl)cyclopropylamine, while other raw materials, reagents and the preparation method were the same as those in example 1 to provide product A68 (yield: 70%). $^1$H NMR (400 MHz, DMSO-$d_6$) δ 7.66 (dd, J=7.5, 2.0 Hz, 1H), 7.46 (td, J=7.5, 2.1 Hz, 1H), 7.39-7.26 (m, 5H), 7.27-7.12 (m, 2H), 5.22 (s, 2H), 4.04 (dt, J=12.6, 7.2 Hz, 2H), 3.24 (dt, J=12.5, 7.0 Hz, 2H), 2.73-2.64 (m, 2H), 2.60 (s, 1H), 2.50 (s, 3H), 2.08-1.82 (m, 3H), 1.72-1.54 (m, 2H), 0.85 (td, J=7.0, 5.0 Hz, 1H), 0.53 (td, J=7.0, 5.0 Hz, 1H). LRMS (ESI): 425.22 [M+H]$^+$.

Example 69 Benzyl 4-fluoro-4-((trans-2-([1,1'-biphenyl]-4-yl)cyclopropyl)amino)methyl)piperidine-1-carboxylate (A69)

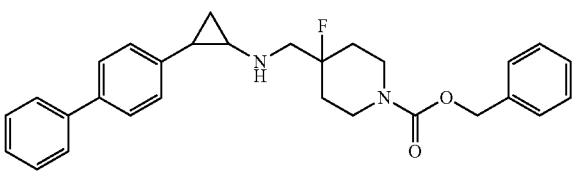 [SMILES: O=C(OCc1ccccc1)N1CCC(F)(CNC2CC2c2ccc(-c3ccccc3)cc2)CC1]

trans-2-phenyl cyclopropylamine was replaced with trans-2-([1,1'-biphenyl]-4-yl)cyclopropylamine, while other raw materials, reagents and the preparation method were the same as those in example 1 to provide product A69 (yield: 68%). $^1$H NMR (400 MHz, DMSO-$d_6$) δ 7.70 (dd, J=7.6, 2.0 Hz, 2H), 7.54-7.37 (m, 5H), 7.37-7.26 (m, 7H), 5.22 (s, 2H), 4.04 (dt, J=12.4, 7.1 Hz, 2H), 3.29 (dt, J=12.5, 7.1 Hz, 2H), 2.75 (q, J=6.9 Hz, 1H), 2.66 (s, 1H), 2.60 (s, 1H), 2.04-1.85 (m, 3H), 1.73-1.55 (m, 2H), 0.96 (td, J=7.0, 4.9 Hz, 1H), 0.72 (td, J=7.0, 5.1 Hz, 1H); LRMS (ESI): 459.24 [M+H]$^+$.

Example 70 Benzyl 4-fluoro-4-((trans-2-(4-methylphenyl)cyclopropyl)amino)methyl)piperidine-1-carboxylate (A70)

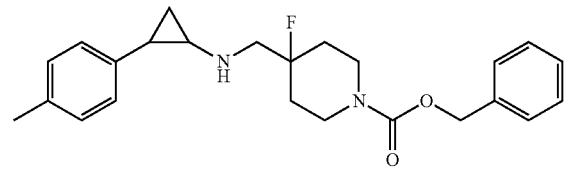 [SMILES: Cc1ccc(C2CC2NCC2(F)CCN(C(=O)OCc3ccccc3)CC2)cc1]

trans-2-phenyl cyclopropylamine was replaced with trans-2-(4-methylphenyl)cyclopropylamine, while other raw materials, reagents and the preparation method were the same as those in example 1 to provide product A70 (yield: 75%). $^1$H NMR (400 MHz, DMSO-$d_6$) δ 7.39-7.26 (m, 5H), 7.12-7.04 (m, 2H), 7.06-6.98 (m, 2H), 5.22 (s, 2H), 4.03 (dt, J=12.6, 7.2 Hz, 2H), 3.29 (dt, J=12.5, 7.1 Hz, 2H), 2.77-2.64 (m, 2H), 2.21 (s, 3H), 2.04-1.84 (m, 3H), 1.63 (ddt, J=25.1, 13.2, 7.0 Hz, 2H), 0.95 (td, J=7.0, 5.0 Hz, 1H), 0.71 (td, J=7.0, 5.1 Hz, 1H); LRMS (ESI): 397.22 [M+H]$^+$.

Example 71 Benzyl 4-fluoro-4-((trans-2-(4-nitrophenyl)cyclopropyl)amino)methyl)piperidine-1-carboxylate (A71)

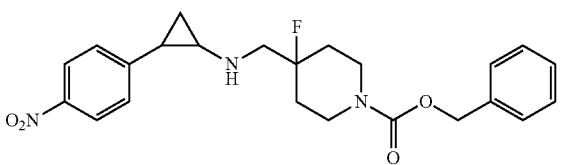 [SMILES: O=C(OCc1ccccc1)N1CCC(F)(CNC2CC2c2ccc([N+](=O)[O-])cc2)CC1]

trans-2-phenyl cyclopropylamine was replaced with trans-2-(4-nitrophenyl)cyclopropylamine, while other raw materials, reagents and the preparation method were the same as those in example 1 to provide product A71 (yield: 72%).

$^1$H NMR (400 MHz, DMSO-$d_6$) δ 8.22-8.13 (m, 2H), 7.39-7.26 (m, 7H), 5.22 (s, 2H), 3.95 (dt, J=12.6, 7.2 Hz, 2H), 3.19 (dt, J=12.4, 7.1 Hz, 2H), 2.81 (q, J=7.0 Hz, 1H), 2.66 (s, 1H), 2.60 (s, 1H), 1.96-1.72 (m, 3H), 1.56 (ddt, J=25.3, 13.7, 7.1 Hz, 2H), 0.95 (td, J=7.0, 4.9 Hz, 1H), 0.70 (td, J=7.0, 5.0 Hz, 1H); LRMS (ESI): 428.19 [M+H]$^+$.

Example 72 4-(trans-2-((1-((benzyloxy))carbonyl)-4-fluoropiperidin-4-yl)methyl)amino)cyclopropyl)benzoic Acid (A72)

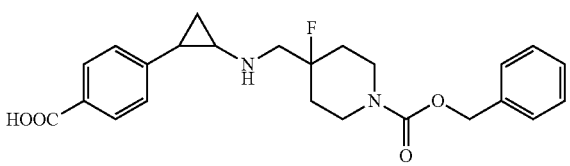

trans-2-phenyl cyclopropylamine was replaced with 4-(trans-2-aminocyclopropyl)benzoic acid, while other raw materials, reagents and the preparation method were the same as those in example 1 to provide product A72 (yield: 60%). $^1$H NMR (400 MHz, DMSO-$d_6$) δ 12.91 (s, 1H), 7.87-7.81 (m, 2H), 7.39-7.26 (m, 5H), 7.22 (dd, J=7.4, 1.1 Hz, 2H), 5.22 (s, 2H), 4.03 (dt, J=12.4, 7.1 Hz, 2H), 3.29 (dt, J=12.5, 7.1 Hz, 2H), 2.77-2.64 (m, 2H), 2.60 (s, 1H), 2.04-1.86 (m, 3H), 1.64 (ddt, J=25.1, 13.2, 7.1 Hz, 2H), 0.97 (td, J=7.0, 4.9 Hz, 1H), 0.72 (td, J=7.0, 5.1 Hz, 1H); LRMS (ESI): 427.20 [M+H]$^+$.

Example 73 Benzyl 4-fluoro-4-((trans-2-(3,4-difluorophenyl)cyclopropyl)amino)methyl)piperidine-1-carboxylate (A73)

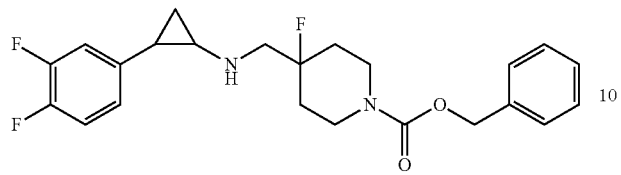

trans-2-phenyl cyclopropylamine was replaced with trans-2-(3,4-difluorophenyl)cyclopropylamine, while other raw materials, reagents and the preparation method were the same as those in example 1 to provide product A73 (yield: 75%). $^1$H NMR (400 MHz, DMSO-d$_6$) δ 7.39-7.22 (m, 6H), 7.01-6.88 (m, 2H), 5.22 (s, 2H), 4.03 (dt, J=12.4, 7.0 Hz, 2H), 3.29 (dt, J=12.6, 7.2 Hz, 2H), 2.77-2.64 (m, 2H), 2.03-1.85 (m, 3H), 1.64 (ddt, J=25.3, 13.7, 7.1 Hz, 2H), 0.98 (td, J=6.9, 5.0 Hz, 1H), 0.72 (td, J=7.0, 5.0 Hz, 1H); LRMS (ESI): 419.19 [M+H]$^+$.

Example 74 Benzyl 4-fluoro-4-((2,2,2-trifluoro-N-(trans-2-phenylcyclopropyl)acetamido)methyl)piperidine-1-carboxylate (A74)

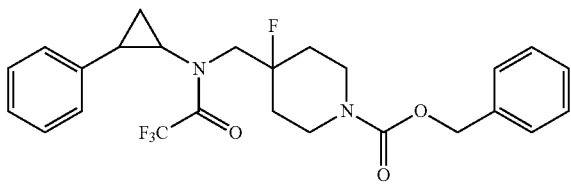

tert-butyl 4-fluoro-4-((trans-2-phenylcyclopropyl)amino)methyl)piperidine-1-carboxylate was replaced with the product A1 obtained in Example 1, while other raw materials, reagents and the preparation method were the same as those in example 5.1 to provide product A74 (yield: 80%). $^1$H NMR (400 MHz, DMSO-d$_6$) δ 7.39-7.26 (m, 5H), 7.26-7.11 (m, 5H), 5.22 (s, 2H), 3.99 (dt, J=12.4, 7.1 Hz, 2H), 3.31 (s, 1H), 3.25 (s, 1H), 3.16 (dt, J=12.5, 7.1 Hz, 2H), 2.85 (q, J=7.0 Hz, 1H), 2.10-1.86 (m, 3H), 1.67-1.48 (m, 2H), 1.04 (td, J=7.0, 4.9 Hz, 1H), 0.76 (td, J=7.0, 5.0 Hz, 1H); LRMS (ESI): 479.19 [M+H]$^+$.

Example 75 Benzyl 4-fluoro-4-(methyl(trans-2-phenylcyclopropyl)amino)methyl)piperidine-1-carboxylate (A75)

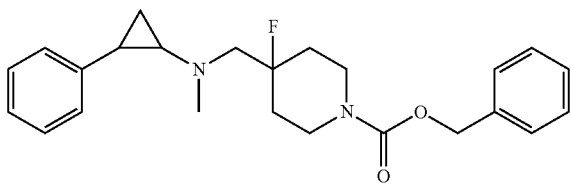 [SMILES: CN(CC1(F)CCN(C(=O)OCc2ccccc2)CC1)C1CC1c1ccccc1]

trans-2-phenyl cyclopropylamine was replaced with N-methyl-trans-2-phenylcyclopropylamine, while other raw materials, reagents and the preparation method were the same as those in example 1 to provide product A75 (yield: 74%).
$^1$H NMR (400 MHz, DMSO-d$_6$) δ 7.39-7.26 (m, 5H), 7.26-7.11 (m, 5H), 5.22 (s, 2H), 4.02 (dt, J=12.5, 7.1 Hz, 2H), 3.24 (dt, J=12.5, 7.1 Hz, 2H), 2.67 (q, J=7.0 Hz, 1H), 2.40 (d, J=6.3 Hz, 4H), 1.99-1.80 (m, 3H), 1.62 (ddt, J=25.1, 13.2, 7.0 Hz, 2H), 0.94 (td, J=6.9, 5.0 Hz, 1H), 0.70 (td, J=7.0, 5.0 Hz, 1H); LRMS (ESI): 397.22 [M+H]$^+$.

Example 76 Benzyl 4-fluoro-4-(1-((trans-2-phenylcyclopropyl)amino)ethyl)piperidine-1-carboxylate (A76)

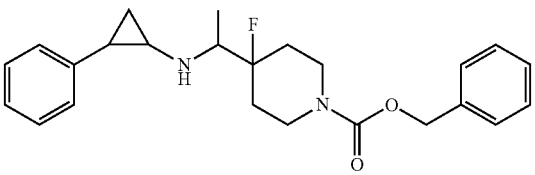 [SMILES: CC(NC1CC1c1ccccc1)C1(F)CCN(C(=O)OCc2ccccc2)CC1]

benzyl 4-fluoro-4-formylpiperidine-1-carboxylate was replaced with benzyl 4-acetyl-4-fluoropiperidine-1-carboxylate, the remaining raw materials, reagents The preparation method was the same as in Example 1 to give the product A76 (yield: 48%). $^1$H NMR (400 MHz, DMSO-d$_6$) δ 7.39-7.26 (m, 5H), 7.26-7.11 (m, 5H), 5.22 (s, 2H), 4.02 (dt, J=12.5, 7.1 Hz, 2H), 3.30 (dt, J=12.5, 7.1 Hz, 2H), 3.02 (dq, J=25.1, 6.8 Hz, 1H), 2.80 (q, J=7.0 Hz, 1H), 2.11 (s, 1H), 2.07-1.86 (m, 3H), 1.65 (ddt, J=25.1, 13.2, 7.0 Hz, 2H), 1.10 (d, J=6.7 Hz, 3H), 0.96 (td, J=7.0, 5.0 Hz, 1H), 0.71 (td, J=7.0, 5.1 Hz, 1H); LRMS (ESI):
397.22 [M+H]$^+$.

Example 77 Benzyl 4-Fluoro-4-((N-(trans-2-phenylcyclopropyl)acetamido)methyl)piperidine-1-carboxylate (A77)

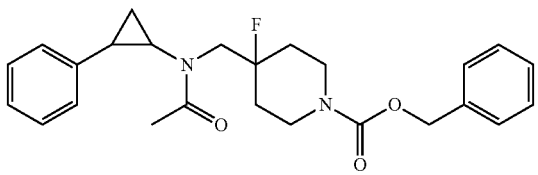 [SMILES: CC(=O)N(CC1(F)CCN(C(=O)OCc2ccccc2)CC1)C1CC1c1ccccc1]

tert-butyl 4-fluoro-4-((trans-2-phenylcyclopropyl)amino)methyl)piperidine-1-carboxylate was replaced with the product A1 obtained in Example 1, and the trifluoroacetic anhydride was replaced with acetic anhydride while other raw materials, reagents and the preparation method were the same as those in example 5.1 to provide product A77 (yield: 84%). $^1$H NMR (400 MHz, DMSO-d$_6$) δ 7.39-7.26 (m, 5H), 7.26-7.11 (m, 5H), 5.22 (s, 2H), 4.09 (dt, J=12.6, 7.2 Hz, 2H), 3.42-3.29 (m, 3H), 3.25 (s, 1H), 2.78 (q, J=7.0 Hz, 1H), 2.08 (s, 3H), 1.96-1.70 (m, 3H), 1.55 (ddt, J=25.1, 13.2, 7.1 Hz, 2H), 0.99 (td, J=7.0, 5.0 Hz, 1H), 0.69 (td, J=7.0, 5.0 Hz, 1H); LRMS (ESI): 425.22 [M+H]$^+$.

Example 78 Benzyl 3-fluoro-3-(((trans-2-phenylcyclopropyl)amino)methyl)azetidin-1-carboxylate (A78)

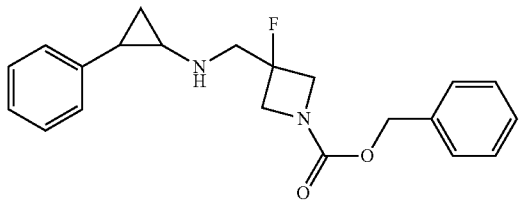 [SMILES: O=C(OCc1ccccc1)N1CC(F)(CNC2CC2c2ccccc2)C1]

benzyl 4-fluoro-4-formylpiperidine-1-carboxylate was replaced with benzyl 3-fluoro-3-formylazetidin-1-carboxylate, while other raw materials, reagents and the preparation method were the same as those in example 1 to provide product A78 (yield: 68%). $^1$H NMR (400 MHz, DMSO-$d_6$) δ 7.39-7.26 (m, 5H), 7.26-7.11 (m, 5H), 5.22 (s, 2H), 4.16 (d, J=11.3 Hz, 1H), 4.09 (d, J=11.1 Hz, 1H), 3.85 (d, J=11.1 Hz, 1H), 3.79 (d, J=11.2 Hz, 1H), 2.90 (q, J=7.0 Hz, 1H), 2.66 (s, 1H), 2.60 (s, 1H), 1.91 (q, J=6.9 Hz, 1H), 0.95 (td, J=7.0, 5.0 Hz, 1H), 0.72 (td, J=7.0, 5.0 Hz, 1H); LRMS (ESI): 355.17 [M+H]$^+$.

Example 79 Benzyl 2-fluoro-2-((trans-2-phenylcyclopropyl)amino)methyl)morpholine-4-carboxylate (A79)

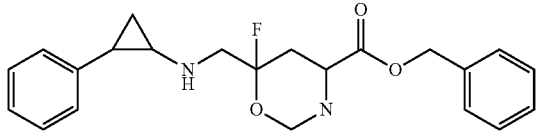 [SMILES: O=C(OCc1ccccc1)C1CC(F)(CNC2CC2c2ccccc2)OCN1]

benzyl 4-fluoro-4-formylpiperidine-1-carboxylate was replaced with benzyl 2-fluoro-2-formylmorpholine-4-carboxylate, while other raw materials, reagents and the preparation method were the same as those in example 1 to provide product A79 (yield: 60%).

$^1$H NMR (400 MHz, DMSO-$d_6$) δ 7.39-7.26 (m, 5H), 7.26-7.11 (m, 5H), 5.41 (d, J=1.2 Hz, 2H), 4.10 (dd, J=25.2, 12.6 Hz, 1H), 3.86-3.72 (m, 1H), 3.74-3.61 (m, 2H), 3.51-3.36 (m, 2H), 3.15 (dd, J=25.2, 12.4 Hz, 1H), 2.88 (dd, J=25.1, 12.5 Hz, 1H), 2.78 (q, J=7.0 Hz, 1H), 1.88 (q, J=7.0 Hz, 1H), 1.55 (s, 1H), 0.95 (td, J=7.0, 5.0 Hz, 1H), 0.69 (td, J=7.0, 4.9 Hz, 1H); LRMS (ESI): 385.18 [M+H]$^+$.

Example 80 Benzyl 4-fluoro-4-(2-(trans-2-phenylcyclopropyl)amino)ethyl)piperidine-1-carboxylate (A80)

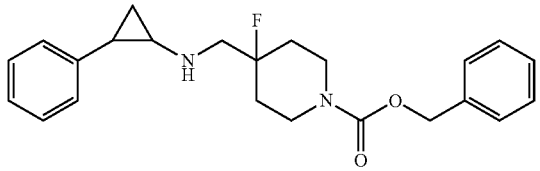

benzyl 4-fluoro-4-formylpiperidine-1-carboxylate was replaced with benzyl 4-fluoro-4-(2-oxoethyl)piperidine-1-carboxylate, the remaining raw materials, reagents and preparation method were the same as in Example 1 to give the product A80 (yield: 78%). $^1$H NMR (400 MHz, DMSO-$d_6$) δ 7.39-7.26 (m, 5H), 7.26-7.11 (m, 5H), 5.22 (s, 2H), 4.11 (dt, J=12.4, 7.0 Hz, 2H), 3.11 (tt, J=12.0, 7.4 Hz, 3H), 2.97 (dt, J=12.3, 7.8 Hz, 1H), 2.71 (q, J=7.0 Hz, 1H), 1.96-1.77 (m, 3H), 1.72-1.41 (m, 4H), 0.89 (td, J=7.0, 4.9 Hz, 1H), 0.64 (td, J=7.0, 4.9 Hz, 1H); LRMS (ESI): 397.22 [M+H]$^+$.

Example 81 Benzyl 3-fluoro-3-((trans-2-phenylcyclopropyl)amino)methyl)piperidine-1-carboxylate (A81)

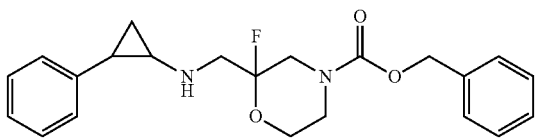 [SMILES: O=C(OCc1ccccc1)N1CCOC(F)(CNC2CC2c2ccccc2)C1]

benzyl 4-fluoro-4-formylpiperidine-1-carboxylate was replace with benzyl 3-fluoro-3-formylpiperidine-1-carboxylate, the remaining raw materials, reagents The preparation method was the same as in Example 1 to give the product A81 (yield: 77%). $^1$H NMR (400 MHz, DMSO-$d_6$) δ 7.32 (dq, J=6.0, 3.2 Hz, 5H), 7.26-7.11 (m, 5H), 6.44 (d, J=12.3 Hz, 1H), 4.63 (d, J=12.5 Hz, 1H), 4.11 (dd, J=25.1, 12.5 Hz, 1H), 3.76 (d, J=12.5 Hz, 1H), 3.38-3.18 (m, 2H), 3.02 (dd, J=25.2, 12.4 Hz, 1H), 2.75 (dd, J=25.3, 12.5 Hz, 1H), 2.74 (s, 1H), 1.98-1.80 (m, 3H), 1.70 (d, J=13.2 Hz, 1H), 1.57 (dd, J=25.1, 13.2 Hz, 1H), 0.94 (s, 1H), 0.70 (s, 1H); LRMS (ESI): 383.21 [M+H]$^+$.

Example 82 N-((4-Fluoro-1-(phenylsulfonyl)piperidin-4-yl)methyl)-trans-2-phenylcyclopropylamine (A82)

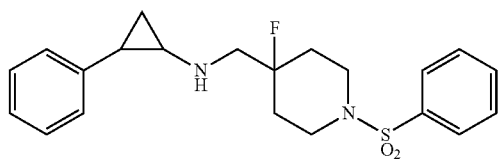 [SMILES: O=S(=O)(c1ccccc1)N1CCC(F)(CNC2CC2c2ccccc2)CC1]

3-phenylpropionyl chloride was replaced with benzenesulfonyl chloride, while other raw materials, reagents and the preparation method were the same as those in example 8 to provide product A82 (yield: 74%). $^1$H NMR (400 MHz, DMSO-$d_6$) δ 7.92-7.84 (m, 2H), 7.63 (hept, J=2.5 Hz, 3H), 7.26-7.11 (m, 5H), 3.79 (dt, J=12.4, 7.1 Hz, 2H), 3.35 (dt, J=12.4, 7.2 Hz, 2H), 2.72-2.64 (m, 2H), 1.75 (ddt, J=25.1, 13.1, 7.0 Hz, 2H), 1.67-1.49 (m, 3H), 0.89 (td, J=7.0, 5.0 Hz, 1H), 0.63 (td, J=6.9, 5.0 Hz, 1H); LRMS (ESI): 389.16 [M+H]$^+$.

Example 83 2-(4-Fluoro-4-(((trans-2-phenylcyclohexyl)amino)methyl)piperidin-1-yl)ethanol (A83)

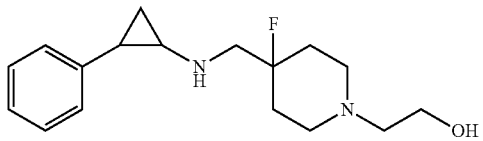 [SMILES: OCCN1CCC(F)(CNC2CC2c2ccccc2)CC1]

bromomethylbenzene was replaced with 2-bromoethanol, while other raw materials, reagents and the preparation method were the same as those in example 6 to provide product A83 (yield: 55%). $^1$H NMR (400 MHz, DMSO-$d_6$) δ 7.26-7.11 (m, 5H), 4.25 (t, J=5.0 Hz, 1H), 3.53 (td, J=7.2, 5.0 Hz, 2H), 3.08 (dt, J=12.5, 7.2 Hz, 2H), 2.74-2.64 (m, 2H), 2.60 (s, 1H), 2.49 (dt, J=12.2, 7.2 Hz, 4H), 2.00-1.89 (m, 1H), 1.94-1.82 (m, 2H), 1.42 (ddt, J=25.1, 13.2, 7.0 Hz, 2H), 0.95 (td, J=6.9, 5.0 Hz, 1H), 0.68 (td, J=7.0, 5.0 Hz, 1H); LRMS (ESI): 293.20 [M+H]$^+$.

Example 84 N-(4-Fluoro-4-(((trans-2-phenylcyclopropyl)amino)methyl)cyclohexyl)acetamide (A84)

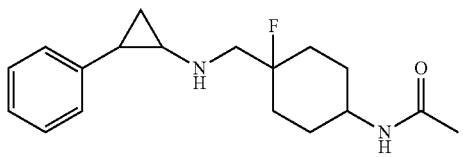 [SMILES: CC(=O)NC1CCC(F)(CNC2CC2c2ccccc2)CC1]

benzyl 4-fluoro-4-formylpiperidine-1-carboxylate was replaced with N-(4-fluoro-4-formylcyclohexyl)acetamide, while other raw materials, reagents and the preparation method were the same as those in example 1 to provide product A84 (yield: 65%). $^1$H NMR (400 MHz, DMSO-$d_6$) δ 7.26-7.11 (m, 5H), 5.49 (s, 1H), 3.44 (p, J=7.0 Hz, 1H), 2.72-2.61 (m, 2H), 2.60 (s, 1H), 2.33-2.18 (m, 2H), 1.99 (s, 3H), 1.95-1.75 (m, 3H), 1.77-1.66 (m, 2H), 1.67 (dd, J=5.8, 4.3 Hz, 1H), 1.61 (dt, J=12.3, 6.8 Hz, 1H), 0.99 (td, J=7.0, 5.0 Hz, 1H), 0.66 (td, J=7.0, 5.0 Hz, 1H); LRMS (ESI): 305.21 [M+H]$^+$.

Example 85 N-Benzyl-4-fluoro-4-(((trans-2-phenylcyclopropyl)amino)methyl)cyclohexylamine (A85)

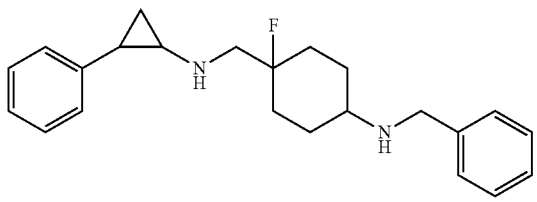 [SMILES: FC1(CNC2CC2c2ccccc2)CCC(NCc2ccccc2)CC1]

benzyl 4-fluoro-4-formylpiperidine-1-carboxylate was replaced with 4-(benzylamino)-1-fluorocyclohexane-1-carbaldehyde, while other raw materials, reagents and the preparation method were the same as those in example 1 to provide product A85 (yield: 72%). $^1$H NMR (400 MHz, DMSO-$d_6$) δ 7.37-7.11 (m, 10H), 4.09 (s, 2H), 2.72-2.57 (m, 3H), 2.09-1.98 (m, 2H), 1.98-1.83 (m, 5H), 1.67-1.49 (m, 4H), 0.99 (td, J=7.0, 4.9 Hz, 1H), 0.66 (td, J=6.9, 5.0 Hz, 1H); LRMS (ESI): 353.23 [M+H]$^+$.

Example 86 N-(4-Fluoro-4-(((trans-2-phenylcyclopropyl)amino)methyl)cyclohexyl)aniline (A86)

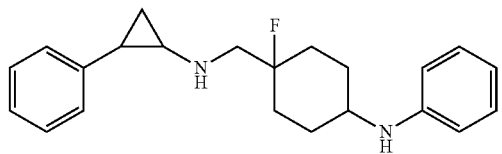 [SMILES: FC1(CNC2CC2c2ccccc2)CCC(Nc2ccccc2)CC1]

benzyl 4-fluoro-4-formylpiperidine-1-carboxylate was replaced with 1-fluoro-4-(anilino)cyclohexane-1-carbaldehyde, while other raw materials, reagents and the preparation method were the same as those in example 1 to provide product A86 (yield: 64%). $^1$H NMR (400 MHz, DMSO-$d_6$) δ 7.26-7.12 (m, 5H), 7.17-7.03 (m, 2H), 6.74-6.60 (m, 3H), 6.26 (s, 1H), 3.06 (p, J=7.0 Hz, 1H), 2.76-2.64 (m, 2H), 2.60 (s, 1H), 1.97-1.71 (m, 5H), 1.53 (ddt, J=25.3, 11.6, 6.4 Hz, 2H), 1.42 (dq, J=12.7, 6.9 Hz, 2H), 0.95 (td, J=6.9, 5.0 Hz, 1H), 0.68 (td, J=7.0, 5.0 Hz, 1H); LRMS (ESI): 339.22 [M+H]$^+$.

Example 87 N-(4-Fluoro-4-(((trans-2-phenylcyclopropyl)amino)methyl)cyclohexyl)benzenesulfonamide (A87)

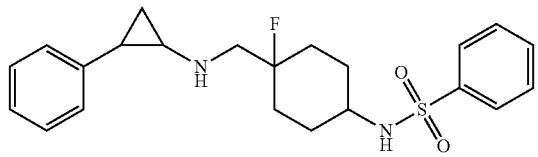 [SMILES: O=S(=O)(NC1CCC(F)(CNC2CC2c2ccccc2)CC1)c1ccccc1]

benzyl 4-fluoro-4-formylpiperidine-1-carboxylate was replaced with N-(4-fluoro-4-formylcyclohexyl)benzenesulfonamide, while other raw materials, reagents and the preparation method were the same as those in example 1 to provide product A87 (yield: 68%). $^1$H NMR (400 MHz, DMSO-$d_6$) δ 7.86-7.77 (m, 2H), 7.68-7.55 (m, 4H), 7.26-7.11 (m, 5H), 3.05 (p, J=7.0 Hz, 1H), 2.75 (q, J=7.0 Hz, 1H), 2.66 (s, 1H), 2.60 (s, 1H), 1.93-1.74 (m, 5H), 1.68-1.57 (m, 1H), 1.62-1.44 (m, 3H), 0.94 (td, J=7.0, 5.1 Hz, 1H), 0.67 (td, J=6.9, 5.0 Hz, 1H); LRMS (ESI): 403.18 [M+H]$^+$.

Example 88 (1r, 4r)-4-fluoro-4-(((trans-2-phenylcyclopropyl)amino)methyl)cyclohexylamine (A88)

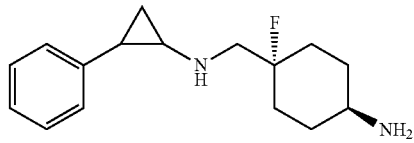

tert-butyl 4-fluoro-4-formylpiperidine-1-carboxylate was replaced with tert-butyl ((1r,4r)-4-fluoro-4-formylcyclohexyl)carbamate, while other raw materials, reagents and the preparation method were the same as those in example 2 to provide product A88 (yield: 72%). ¹H NMR (400 MHz, DMSO-d₆) δ 7.26-7.11 (m, 5H), 2.83 (p, J=7.0 Hz, 1H), 2.76-2.64 (m, 2H), 2.60 (s, 1H), 1.91-1.69 (m, 5H), 1.62-1.44 (m, 2H), 1.47-1.32 (m, 2H), 1.30 (s, 2H), 0.90 (td, J=6.9, 5.0 Hz, 1H), 0.67 (td, J=7.0, 5.0 Hz, 1H); LRMS (ESI): 263.18 [M+H]⁺.

Example 89 (1-Methylpiperidin-4-yl)methyl 4-fluoro-4-(((trans-2-phenylcyclopropyl)amino) methyl)piperidine-1-carboxylate (A89)

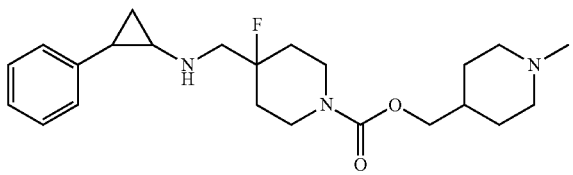 [SMILES: CN1CCC(COC(=O)N2CCC(F)(CNC3CC3c3ccccc3)CC2)CC1]

3-phenylpropionyl chloride was replaced with (1-methylpiperidin-4-yl)methyl chloroformate, while other raw materials, reagents and the preparation method were the same as those in examples 8.1 and 5.4 to provide the dihydrochloride of product A89 (yield: 66%). ¹H NMR (400 MHz, MeOD) δ 7.33 (tt, J=7.9, 1.5 Hz, 2H), 7.30-7.22 (m, 1H), 7.26-7.19 (m, 2H), 4.08 (d, J=15.2 Hz, 4H), 3.62-3.51 (m, 4H), 3.29-3.14 (m, 2H), 3.08 (p, J=4.2 Hz, 2H), 3.03 (dd, J=13.0, 2.5 Hz, 1H), 2.88 (s, 3H), 2.64 (ddd, J=10.3, 6.6, 3.6 Hz, 1H), 2.09-1.95 (m, 5H), 1.94-1.76 (m, 2H), 1.76-1.58 (m, 3H), 1.41 (dt, J=7.9, 6.7 Hz, 1H); LRMS (ESI): 404.26 [M+H]⁺.

Example 90 (1-Benzylpiperidin-4-yl)methyl 4-fluoro-4-(((trans-2-phenylcyclopropyl)amino) methyl)piperidine-1-carboxylate (A90)

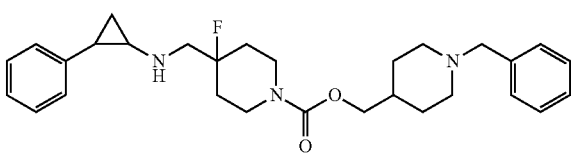 [SMILES: O=C(OCC1CCN(Cc2ccccc2)CC1)N1CCC(F)(CNC2CC2c2ccccc2)CC1]

3-phenylpropionyl chloride was replaced with (1-benzylpiperidin-4-yl)methyl chloroformate, while other raw materials, reagents and the preparation method were the same as those in examples 8.1 and 5.4 to provide the dihydrochloride of product A90 (yield: 57%). ¹H NMR (400 MHz, MeOD) δ 7.57 (dd, J=6.7, 2.9 Hz, 2H), 7.52-7.46 (m, 3H), 7.31 (tt, J=8.3, 1.6 Hz, 2H), 7.26-7.22 (m, 1H), 7.22-7.17 (m, 2H), 4.32 (s, 2H), 4.06 (d, J=16.2 Hz, 4H), 3.56 (s, 1H), 3.54-3.45 (m, 3H), 3.28-2.95 (m, 5H), 2.61 (ddd, J=10.3, 6.6, 3.6 Hz, 1H), 2.04-1.92 (m, 5H), 1.91-1.75 (m, 2H), 1.74-1.64 (m, 2H), 1.60 (ddd, J=10.4, 6.8, 4.4 Hz, 1H), 1.39 (dt, J=7.8, 6.7 Hz, 1H); LRMS (ESI): 478.29 [M+H]⁺.

Example 91 4-((4-(((4-fluoro-4-(((trans-2-phenylpropyl)amino)methyl)piperidine-1-carbonyl)oxo) methyl)piperidin-1-yl)methyl)benzoic Acid (A91)

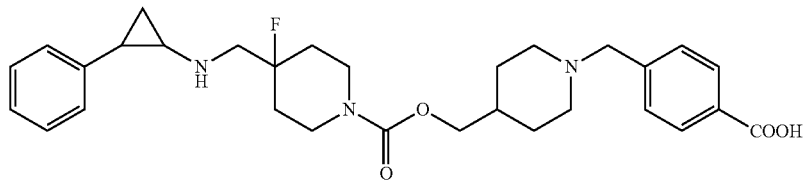 [SMILES: O=C(O)c1ccc(CN2CCC(COC(=O)N3CCC(F)(CNC4CC4c4ccccc4)CC3)CC2)cc1]

Tert-butyl 4-fluoro-4-((trans-2-phenylcyclopropyl) amino)methyl)piperidine-1-carboxylate was replaced with (1-(tert-butoxycarbonyl)piperidine-4-yl)methyl 4-fluoro-4-(((trans-2-phenylcyclopropyl)amino)methyl)piperidine-1-carboxylate, while other raw materials, reagents and the preparation method were the same as those in example 5 to provide hydrochloride salt of product A91 (yield 35%). ¹H NMR (500 MHz, D₂O) δ 7.98 (d, J=8.2 Hz, 2H), 7.51 (d, J=8.1 Hz, 2H), 7.28 (t, J=7.5 Hz, 2H), 7.24-7.19 (m, 1H), 7.12 (d, J=7.2 Hz, 2H), 4.27 (s, 2H), 3.91-3.88 (m, 4H), 3.48-3.39 (m, 4H), 3.15-3.03 (m, 2H), 3.00-2.90 (m, 3H), 2.50 (ddd, J=10.4, 6.7, 3.6 Hz, 1H), 1.99-1.81 (m, 5H), 1.69 (td, J=13.3, 5.0 Hz, 1H), 1.62 (td, J=13.3, 5.1 Hz, 1H), 1.48 (ddd, J=11.0, 7.0, 4.4 Hz, 1H), 1.45-1.37 (m, 2H), 1.34 (q, J=7.2 Hz, 1H); LRMS (ESI): 524.28 [M+H]⁺.

Example 92 N-((4-Fluoro-1-(piperidin-4-ylmethyl) sulfonyl)piperidin-4-yl)methyl)-trans-2-phenylcyclopropylamine (A92)

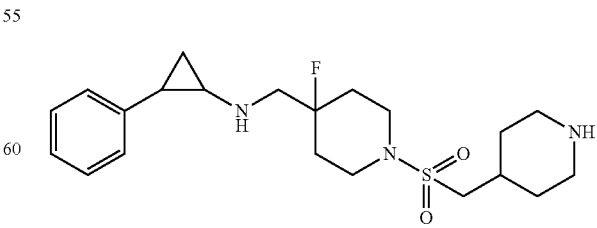

3-phenylpropionyl chloride was replaced with tert-butyl 4-((chlorosulfonyl)methyl)piperidine-1-carboxylic acid, while other raw materials, reagents and the preparation method were the same as those in examples 8.1 and 5.4 to provide the dihydrochloride of product A92 (yield: 68%). ¹H NMR (500 MHz, MeOD) δ 7.31 (t, J=7.5 Hz, 2H), 7.24 (d, J=7.5 Hz, 1H), 7.20 (d, J=7.3 Hz, 2H), 3.79-3.71 (m, 2H), 3.58 (d, J=20.1 Hz, 2H), 3.51 (dt, J=12.6, 3.4 Hz, 3H), 3.36-3.23 (m, 4H), 3.16-2.99 (m, 3H), 2.62 (ddd, J=10.3, 6.6, 3.6 Hz, 1H), 2.30 (dd, J=14.7, 3.7 Hz, 2H), 2.10-1.86 (m, 6H), 1.61 (ddd, J=10.8, 6.8, 4.4 Hz, 1H), 1.39 (q, J=7.0 Hz, 1H); LRMS (ESI): 410.22 [M+H]⁺.

Example 93 N-((4-Fluoro-1-(methylsulfonyl)piperidin-4-yl)methyl)-trans-2-phenylcyclopropylamine (A93)

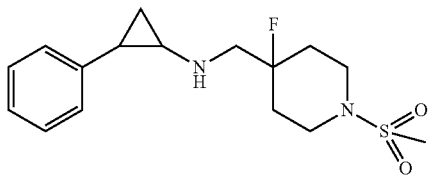 [SMILES: CS(=O)(=O)N1CCC(F)(CNC2CC2c2ccccc2)CC1]

3-phenylpropionyl chloride was replaced with methylsulfonyl chloride, while other raw materials, reagents and the preparation method were the same as those in examples 8.1 and 5.4 to provide the dihydrochloride of product A93 (yield: 80%). ¹H NMR (400 MHz, DMSO-d₆) δ 9.71 (s, 2H), 7.33-7.28 (m, 2H), 7.25-7.21 (m, 1H), 7.21-7.17 (m, 2H), 3.54-3.42 (m, 4H), 2.99-2.93 (m, 3H), 2.92 (s, 3H), 2.64 (ddd, J=10.1, 6.4, 3.5 Hz, 1H), 2.14-2.04 (m, 2H), 1.97-1.87 (m, 1H), 1.87-1.77 (m, 1H), 1.66 (ddd, J=10.4, 6.1, 4.4 Hz, 1H), 1.27 (dt, J=7.7, 6.3 Hz, 1H); LRMS (ESI): 327.15 [M+H]⁺.

Example 94 Azetidin-3-ylmethyl 4-fluoro-4-(((trans-2-phenylcyclopropyl)amino)methyl)piperidine-1-carboxylate (A94)

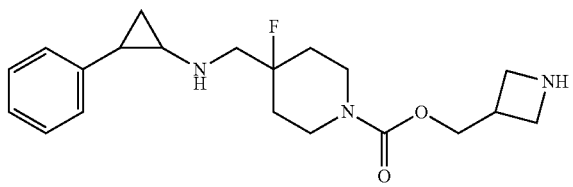 [SMILES: O=C(OCC1CNC1)N1CCC(F)(CNC2CC2c2ccccc2)CC1]

3-phenylpropionyl chloride was replaced with tert-butyl 3-(((chloroformyl)oxy)methyl)azetidin-1-carboxylic acid, while other raw materials, reagents and the preparation method were the same as those in examples 8.1 and 5.4 to provide the dihydrochloride of product A94 (yield: 70%). ¹H NMR (400 MHz, DMSO-d₆) δ 7.27-7.10 (m, 5H), 4.13 (dt, J=12.5, 7.1 Hz, 2H), 3.88 (d, J=7.0 Hz, 2H), 3.43 (dd, J=11.1, 7.0 Hz, 2H), 3.15-3.02 (m, 4H), 2.71-2.56 (m, 4H), 2.01-1.86 (m, 3H), 1.75-1.58 (m, 2H), 0.99 (td, J=7.0, 5.1 Hz, 1H), 0.67 (td, J=7.0, 5.0 Hz, 1H); LRMS (ESI): 362.22 [M+H]⁺.

Example 95 Piperidin-4-yl 4-fluoro-4-(((trans-2-phenylcyclopropyl)amino)methyl)piperidine-1-carboxylate (A95)

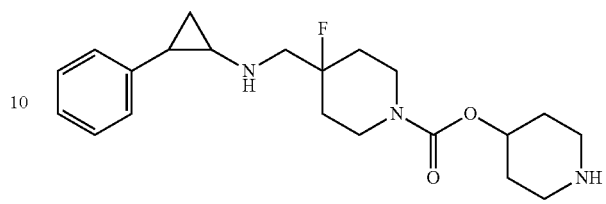

3-phenylpropionyl chloride was replaced with tert-butyl 4-((chloroformyl)oxo)piperidine-1-carboxylic acid, while other raw materials, reagents and the preparation method were the same as those in examples 8.1 and 5.4 to provide the dihydrochloride of product A95 (yield: 65%). ¹H NMR (400 MHz, DMSO-d6) δ 7.26-7.11 (m, 5H), 4.82 (p, J=7.0 Hz, 1H), 4.13 (dt, J=12.5, 7.1 Hz, 2H), 3.11 (dt, J=12.5, 7.1 Hz, 2H), 2.90 (dt, J=12.4, 7.1 Hz, 2H), 2.72-2.56 (m, 5H), 2.02-1.84 (m, 3H), 1.77-1.53 (m, 4H), 1.29 (dq, J=13.9, 7.1 Hz, 2H), 0.99 (td, J=7.0, 5.0 Hz, 1H), 0.67 (td, J=7.0, 5.0 Hz, 1H); LRMS (ESI): 376.23 [M+H]⁺.

Example 96 4-((4-Fluoro-4-(((trans-2-phenylcyclopropyl)amino)methyl)piperidin-1-yl)methyl)benzonitrile (A96)

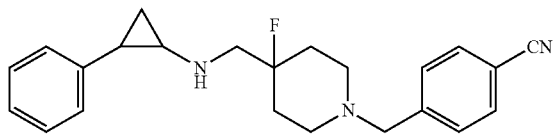 [SMILES: N#Cc1ccc(CN2CCC(F)(CNC3CC3c3ccccc3)CC2)cc1]

bromomethylbenzene was replaced with 4-(bromomethyl)benzonitrile, while other raw materials, reagents and the preparation method were the same as those in example 6 to provide product A96 (yield: 62%). ¹H NMR (400 MHz, MeOD) δ 7.91-7.83 (m, 4H), 7.35-7.30 (m, 2H), 7.28-7.24 (m, 1H), 7.24-7.19 (m, 2H), 4.52 (s, 2H), 3.67 (d, J=20.1 Hz, 2H), 3.54 (d, J=12.4 Hz, 2H), 3.44-3.34 (m, 2H), 3.10 (dt, J=7.8, 4.0 Hz, 1H), 2.70-2.60 (m, 1H), 2.40-2.20 (m, 4H), 1.64 (dt, J=11.0, 6.0 Hz, 1H), 1.42 (dt, J=7.8, 6.8 Hz, 1H); LRMS (ESI): 364.21 [M+H]⁺.

Example 97 N-((4-Fluoro-1-(piperidin-4-ylmethyl)piperidin-4-yl)methyl)-trans-2-phenylcyclopropylamine (A97)

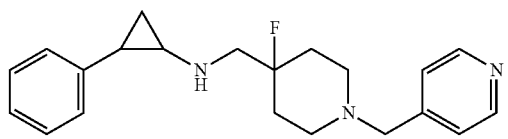 [SMILES: FC1(CNC2CC2c2ccccc2)CCN(Cc2ccncc2)CC1]

bromomethylbenzene was replaced with 4-(bromomethyl)piperidine, while other raw materials, reagents and the preparation method were the same as those in example 6 to provide product A97 (yield: 73%). ¹H NMR (400 MHz, DMSO-d$_6$) δ 8.46 (d, J=5.1 Hz, 2H), 7.40 (d, J=5.1 Hz, 2H), 7.26-7.11 (m, 5H), 4.33 (s, 2H), 2.97 (dt, J=12.5, 7.1 Hz, 2H), 2.72-2.57 (m, 3H), 2.33 (dt, J=12.5, 7.1 Hz, 2H), 1.95-1.73 (m, 3H), 1.56 (ddt, J=25.1, 13.2, 7.2 Hz, 2H), 0.99 (td, J=7.0, 5.0 Hz, 1H), 0.67 (td, J=7.0, 5.0 Hz, 1H); LRMS (ESI): 340.21 [M+H]$^+$.

Example 98 N-((4-Fluoro-1-(thiophen-3-ylmethyl) piperidin-4-yl)methyl)-trans-2-phenylcyclopropylamine (A98)

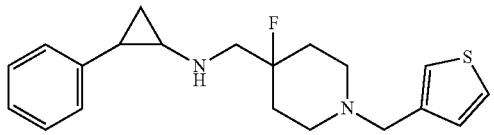 [SMILES: FC1(CNC2CC2c2ccccc2)CCN(Cc2ccsc2)CC1]

bromomethylbenzene was replaced with 3-(bromomethyl)thiophene, while other raw materials, reagents and the preparation method were the same as those in example 6 to provide product A98 (yield: 75%). $^1$H NMR (400 MHz, DMSO-d$_6$) δ 7.31-7.11 (m, 6H), 6.96-6.87 (m, 2H), 3.69 (s, 2H), 3.04 (dt, J=12.5, 7.1 Hz, 2H), 2.72-2.57 (m, 3H), 2.34 (dt, J=12.5, 7.2 Hz, 2H), 1.95-1.74 (m, 3H), 1.56 (ddt, J=25.1, 13.2, 7.0 Hz, 2H), 0.99 (td, J=7.0, 5.0 Hz, 1H), 0.67 (td, J=7.0, 5.0 Hz, 1H); LRMS (ESI): 345.17 [M+H]$^+$.

Example 99 (1-(Cyclopropylmethyl)piperidin-4-yl) methyl 4-fluoro-4-(((trans-2-phenylcyclopropyl) amino)methyl)piperidine-1-formate (A99)

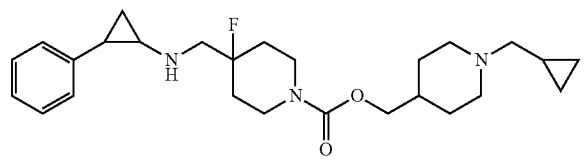 [SMILES: O=C(OCC1CCN(CC2CC2)CC1)N1CCC(F)(CNC2CC2c2ccccc2)CC1]

3-phenylpropionyl chloride was replaced with (1-(cyclopropylmethyl)piperidin-4-yl)methyl chloroformate, while other raw materials, reagents and the preparation method were the same as those in examples 8.1 and 5.4 to provide the dihydrochloride of product A99 (yield: 60%). $^1$H NMR (400 MHz, MeOD) δ 7.34-7.28 (m, 2H), 7.26-7.22 (m, 1H), 7.22-7.17 (m, 2H), 4.15-3.98 (m, 4H), 3.78-3.66 (m, 2H), 3.55 (d, J=20.2 Hz, 2H), 3.25-3.10 (m, 2H), 3.10-2.96 (m, 5H), 2.61 (ddd, J=10.3, 6.6, 3.6 Hz, 1H), 2.09-1.94 (m, 5H), 1.92-1.65 (m, 4H), 1.61 (ddd, J=10.5, 6.8, 4.4 Hz, 1H), 1.39 (dt, J=7.9, 6.7 Hz, 1H), 1.16 (ddtd, J=12.4, 9.7, 7.3, 4.5 Hz, 1H), 0.80-0.74 (m, 2H), 0.46 (dt, J=6.3, 4.7 Hz, 2H); LRMS (ESI): 404.26 [M+H]$^+$.

Example 100 N-(2-Aminophenyl)-4-((4-fluoro-4-(((trans-2-phenylcyclopropyl)amino)methyl)piperidin-1-yl)) benzoylamide (A100)

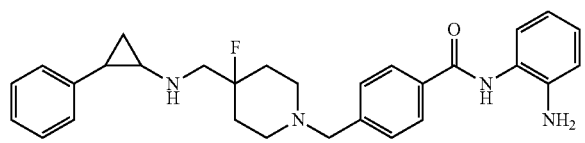 [SMILES: Nc1ccccc1NC(=O)c1ccc(CN2CCC(F)(CNC3CC3c3ccccc3)CC2)cc1]

bromomethylbenzene was replaced with t-butyl(2-(4-(bromomethyl)benzamide)phenyl)carbamate, while other raw materials, reagents and the preparation method were the same as those in example 6 to provide product A100 (yield: 45%). $^1$H NMR (400 MHz, MeOD) δ 8.21 (d, J=7.9 Hz, 2H), 7.86 (d, J=8.0 Hz, 2H), 7.60-7.46 (m, 4H), 7.33 (t, J=7.4 Hz, 2H), 7.24 (dd, J=14.2, 7.2 Hz, 3H), 4.55 (s, 2H), 3.68 (d, J=20.0 Hz, 2H), 3.57 (d, J=10.4 Hz, 2H), 3.47-3.36 (m, 2H), 3.14-3.06 (m, 1H), 2.71-2.64 (m, 1H), 2.45-2.21 (m, 4H), 1.70-1.62 (m, 1H), 1.43 (dd, J=13.9, 7.0 Hz, 1H); LRMS (ESI): 473.26 [M+H]$^+$.

Example 101 Tert-Butyl 4-((4-(((2-(5-bromothien-2-yl))cyclopropyl)amino)methyl)-4-fluoropiperidin-1-yl)methyl)benz Oate (A101)

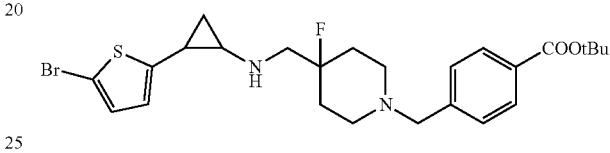

trans-2-phenylcyclopropylamine was replaced with trans-2-(5-bromothien-2-yl)cyclopropylamine, and benzyl 4-fluoro-4-formylpiperidine-1-carboxylate was replaced with t-butyl 4-((4-fluoro-4-formylpiperidin-1-yl)methyl) benzoate, while other raw materials, reagents and the preparation method were the same as those in example 1 to provide product A101 (yield: 61%). $^1$H NMR (400 MHz, DMSO-d$_6$) δ 7.96-7.90 (m, 2H), 7.34 (dt, J=8.4, 1.1 Hz, 2H), 7.00 (d, J=8.4 Hz, 1H), 6.77 (d, J=8.4 Hz, 1H), 3.57 (t, J=1.0 Hz, 2H), 3.18 (ddd, J=25.1, 14.5, 4.9 Hz, 1H), 3.04 (dt, J=7.5, 4.9 Hz, 1H), 2.96 (ddd, J=25.1, 14.6, 4.9 Hz, 1H), 2.87 (ddd, J=12.1, 6.2, 4.3 Hz, 2H), 2.81 (dtd, J=7.5, 6.4, 5.7 Hz, 1H), 2.59-2.49 (m, 3H), 2.11-1.93 (m, 4H), 1.89 (td, J=6.4, 1.3 Hz, 2H), 1.55 (s, 6H). LRMS (ESI): 523.14 [M+H]$^+$.

Example 102 Tert-Butyl 4-((4-(((2-(5-bromothien-2-yl))cyclopropyl)amino)methyl)-4-fluoropiperidin-1-yl)methyl)benzoic Acid (A102)

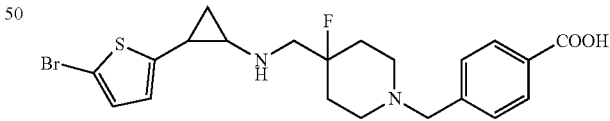

trans-2-phenylcyclopropylamine was replaced with trans-2-(5-bromothiophen-2-yl)cyclopropylamine, while other raw materials, reagents and the preparation method were the same as those in example 5 to provide product A102 (yield: 73%). $^1$H NMR (400 MHz, DMSO-d$_6$) δ 7.99-7.93 (m, 2H), 7.37 (dt, J=8.4, 1.1 Hz, 2H), 7.02 (d, J=8.4 Hz, 1H), 6.71 (d, J=8.4 Hz, 1H), 3.55 (t, J=1.0 Hz, 2H), 3.16 (ddd, J=25.1, 14.4, 5.0 Hz, 1H), 3.08 (dt, J=7.3, 4.9 Hz, 1H), 3.01 (ddd, J=25.1, 14.4, 4.9 Hz, 1H), 2.91-2.78 (m, 3H), 2.61 (ddd, J=12.3, 6.4, 4.1 Hz, 2H), 2.48 (td, J=6.4, 5.6 Hz, 1H), 2.11-1.85 (m, 6H). LRMS (ESI): 467.07 [M+H]$^+$.

Example 103 Methyl 4-((4-(((2-(5-bromothien-2-yl))cyclopropyl)amino)methyl)-4-fluoropiperidin-1-yl)methyl)benzoate (A103)

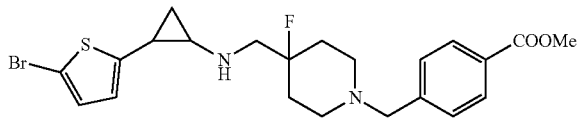 [SMILES: COC(=O)c1ccc(CN2CCC(F)(CNC3CC3c3ccc(Br)s3)CC2)cc1]

trans-2-phenylcyclopropylamine was replaced with trans-2-(5-bromothiophen-2-yl)cyclopropylamine, while other raw materials, reagents and the preparation method were the same as those in example 3 to provide product A103 (yield: 67%). $^1$H NMR (400 MHz, DMSO-d$_6$) δ 7.96-7.90 (m, 2H), 7.34 (dt, J=8.4, 1.1 Hz, 2H), 7.03 (d, J=8.4 Hz, 1H), 6.68 (d, J=8.4 Hz, 1H), 3.89 (s, 2H), 3.55 (t, J=1.0 Hz, 2H), 3.16 (ddd, J=25.1, 14.4, 5.0 Hz, 1H), 3.08 (dt, J=7.3, 4.9 Hz, 1H), 3.01 (ddd, J=25.1, 14.4, 5.0 Hz, 1H), 2.91-2.78 (m, 3H), 2.61 (ddd, J=12.1, 6.4, 4.2 Hz, 2H), 2.48 (td, J=6.4, 5.6 Hz, 1H), 2.11-1.85 (m, 6H). LRMS (ESI): 481.09 [M+H]$^+$.

Example 104 Ethyl 4-((4-(((2-(5-bromothien-2-yl))cyclopropyl)amino)methyl)-4-fluoropiperidin-1-yl)methyl)benzoate (A104)

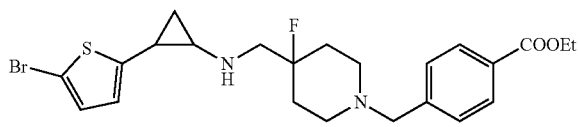 [SMILES: CCOC(=O)c1ccc(CN2CCC(F)(CNC3CC3c3ccc(Br)s3)CC2)cc1]

trans-2-phenylcyclopropylamine was replaced with trans-2-(5-bromothien-2-yl)cyclopropylamine, and benzyl 4-fluoro-4-formylpiperidine-1-carboxylate was replaced with ethyl 4-((4-fluoro-4-formylpiperidin-1-yl)methyl)benzoate, while other raw materials, reagents and the preparation method were the same as those in example 1 to provide product A104 (yield: 75%). $^1$H NMR (400 MHz, DMSO-d$_6$) δ 7.96-7.89 (m, 2H), 7.35 (dt, J=8.4, 1.1 Hz, 2H), 7.03 (d, J=8.4 Hz, 1H), 6.68 (d, J=8.4 Hz, 1H), 4.44-4.27 (m, 2H), 3.58 (dt, J=12.8, 1.1 Hz, 1H), 3.52 (dt, J=12.8, 1.1 Hz, 1H), 3.22 (ddd, J=25.3, 14.6, 4.9 Hz, 1H), 3.07 (dt, J=7.3, 4.8 Hz, 1H), 3.02-2.88 (m, 1H), 2.91-2.82 (m, 3H), 2.59 (ddd, J=12.3, 6.1, 4.5 Hz, 2H), 2.53 (td, J=6.4, 5.6 Hz, 1H), 2.11-1.93 (m, 4H), 1.89 (td, J=6.4, 1.3 Hz, 2H), 1.39 (t, J=7.0 Hz, 3H). LRMS (ESI): 495.10 [M+H]$^+$.

Example 105 Tert-butyl 4-((4-fluoro-4-(((2-(5-(4-fluorophenyl)thiophen-2-yl)cyclopropyl)amino)methyl)piperidin-1-yl) methyl)benzoate (A105)

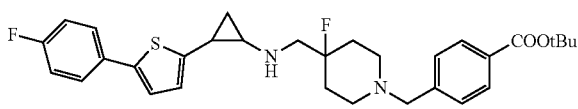

trans-2-phenylcyclopropylamine was replaced with trans-2-(5-(4-fluorophenyl)thiophen-2-yl)cyclopropylamine, while other raw materials, reagents and the preparation method were the same as those in example 101 to provide product A105 (yield: 71%). $^1$H NMR (400 MHz, DMSO-d$_6$) δ 7.96-7.90 (m, 2H), 7.63-7.55 (m, 2H), 7.31 (dt, J=8.5, 1.0 Hz, 2H), 7.21-7.13 (m, 3H), 6.73 (d, J=8.4 Hz, 1H), 3.57 (t, J=1.0 Hz, 2H), 3.20 (ddd, J=25.1, 14.6, 4.8 Hz, 1H), 3.01 (dt, J=7.3, 4.9 Hz, 1H), 2.97-2.78 (m, 4H), 2.58 (ddd, J=12.3, 6.3, 4.2 Hz, 2H), 2.28 (td, J=6.4, 5.6 Hz, 1H), 2.07 (ddd, J=13.6, 6.4, 4.2 Hz, 1H), 2.02 (dd, J=13.5, 4.2 Hz, 1H), 2.02-1.94 (m, 1H), 1.98-1.89 (m, 2H), 1.92-1.85 (m, 1H), 1.55 (s, 7H). LRMS (ESI): 539.25 [M+H]$^+$.

Example 106 Tert-butyl 4-((4-(((2-(5-(4-chlorophenyl)thiophen-2-yl)cyclopropyl)amino)methyl-4-fluoropiperidin-1-yl) methyl)benzoate (A106)

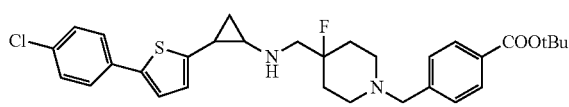

trans-2-phenylcyclopropylamine was replaced with trans-2-(5-(4-chlorophenyl)thiophen-2-yl)cyclopropylamine, while other raw materials, reagents and the preparation method were the same as those in example 106 to provide product A106 (yield: 77%). $^1$H NMR (400 MHz, DMSO-d$_6$) δ 7.96-7.90 (m, 2H), 7.54-7.47 (m, 2H), 7.42-7.36 (m, 2H), 7.31 (dt, J=8.4, 1.0 Hz, 2H), 7.19 (d, J=8.4 Hz, 1H), 6.74 (d, J=8.4 Hz, 1H), 3.57 (t, J=1.0 Hz, 2H), 3.20 (ddd, J=25.1, 14.7, 4.9 Hz, 1H), 3.01 (dt, J=7.3, 4.8 Hz, 1H), 2.97-2.78 (m, 4H), 2.58 (ddd, J=12.1, 6.4, 4.2 Hz, 2H), 2.28 (td, J=6.4, 5.6 Hz, 1H), 2.11-1.86 (m, 6H), 1.55 (s, 7H). LRMS (ESI): 555.22 [M+H]$^+$.

Example 107 Tert-butyl 4-((4-fluoro-4-(((2-(5-(4-(trifluoromethyl)phenyl)thiophen-2-yl)cyclopropyl)amino)methyl)piperidin-1-yl)methyl)benzoate (A107)

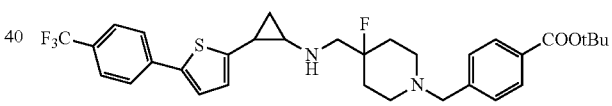

trans-2-phenylcyclopropylamine was replaced with trans-2-(5-(4-(trifluoromethylphenyl)thiophen-2-yl)cyclopropylamine, while other raw materials, reagents and the preparation method were the same as those in example 101 to provide product A107 (yield: 66%). $^1$H NMR (400 MHz, DMSO-d$_6$) δ 7.97-7.90 (m, 2H), 7.77-7.70 (m, 2H), 7.64-7.58 (m, 2H), 7.37-7.28 (m, 3H), 6.91 (d, J=8.4 Hz, 1H), 3.59 (dt, J=12.6, 0.9 Hz, 1H), 3.53 (dt, J=12.6, 1.0 Hz, 1H), 3.23-3.10 (m, 1H), 3.08-2.82 (m, 5H), 2.49 (ddd, J=12.3, 6.3, 4.4 Hz, 2H), 2.29 (td, J=6.5, 5.6 Hz, 1H), 2.11-1.93 (m, 5H), 1.89 (t, J=6.4 Hz, 2H), 1.55 (s, 7H). LRMS (ESI): 589.24 [M+H]$^+$.

Example 108 Tert-butyl 4-((4-fluoro-4-(((2-(5-phenylthiophen-2-yl)cyclopropyl)amino)methyl)piperidin-1-yl)methyl)benzoate (A108)

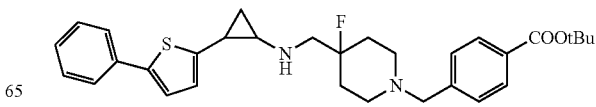

trans-2-phenylcyclopropylamine was replaced with trans-2-(5-phenylthiophen-2-yl)cyclopropylamine, while other raw materials, reagents and the preparation method were the same as those in example 108 to provide product A108 (yield: 73%). $^1$H NMR (400 MHz, DMSO-d$_6$) δ 7.96-7.90 (m, 2H), 7.78-7.70 (m, 2H), 7.49-7.40 (m, 3H), 7.32 (dd, J=8.4, 1.5 Hz, 3H), 6.88 (d, J=8.4 Hz, 1H), 3.59 (dt, J=12.6, 0.9 Hz, 1H), 3.53 (dt, J=12.6, 1.0 Hz, 1H), 3.18 (ddd, J=25.3, 14.5, 5.1 Hz, 1H), 3.07-2.95 (m, 1H), 2.99-2.92 (m, 1H), 2.91-2.79 (m, 3H), 2.53-2.42 (m, 3H), 2.11-1.90 (m, 4H), 1.89 (t, J=6.4 Hz, 2H), 1.55 (s, 7H). LRMS (ESI): 521.26 [M+H]$^+$.

Example 109 tert-Butyl 4-((4-fluoro-4-(((2-(5-(naphthalen-1-yl)thiophen-2-yl)cyclopropyl)amino)methyl)piperidine-1-yl)methyl)benzoate (A109)

trans-2-phenylcyclopropylamine was replaced with trans-2-(5-(naphthalen-1-yl)thiophen-2-yl)cyclopropylamine, while other raw materials, reagents and the preparation method were the same as those in example 101 to provide product A109 (yield: 77%). $^1$H NMR (400 MHz, DMSO-d$_6$) δ 8.06-7.99 (m, 1H), 7.98-7.89 (m, 4H), 7.69 (dd, J=7.9, 0.8 Hz, 1H), 7.61 (t, J=7.8 Hz, 1H), 7.52 (pd, J=7.4, 1.5 Hz, 2H), 7.37-7.28 (m, 3H), 6.88 (d, J=8.4 Hz, 1H), 3.59 (dt, J=12.6, 0.9 Hz, 1H), 3.53 (dt, J=12.6, 1.0 Hz, 1H), 3.17 (ddd, J=25.1, 14.3, 5.1 Hz, 1H), 3.10-2.95 (m, 2H), 2.94 (ddd, J=12.1, 6.2, 4.3 Hz, 2H), 2.85 (dtd, J=7.3, 6.3, 5.6 Hz, 1H), 2.59 (ddd, J=12.1, 6.1, 4.4 Hz, 2H), 2.29 (td, J=6.4, 5.6 Hz, 1H), 2.11-1.96 (m, 4H), 1.99-1.87 (m, 2H), 1.55 (s, 7H). LRMS (ESI): 571.27 [M+H]$^+$.

Example 110 Piperidin-4-ylmethyl 4-fluoro-4-(((2-(5-(4-(trifluoromethyl)phenyl)thiophen-2-yl)cyclopropyl)amino)methyl) piperidine-1-carboxylate (A110)

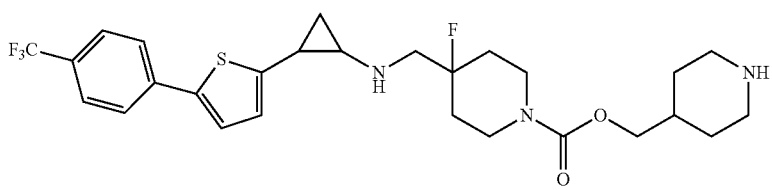 [SMILES: O=C(OCC1CCNCC1)N1CCC(F)(CNC2CC2c2ccc(-c3ccc(C(F)(F)F)cc3)s2)CC1]

trans-2-phenylcyclopropylamine was replaced with trans-2-(5-(4-(trifluoromethylphenyl)thiophen-2-yl)cyclopropylamine, while other raw materials, reagents and the preparation method were the same as those in example 43 to provide product A110 (yield: 55%). $^1$H NMR (400 MHz, DMSO-d$_6$) δ 7.68-7.62 (m, 2H), 7.57-7.51 (m, 2H), 7.30 (d, J=8.4 Hz, 1H), 6.81 (d, J=8.4 Hz, 1H), 4.23 (dd, J=10.6, 6.2 Hz, 1H), 4.02 (ddd, J=12.1, 6.5, 4.1 Hz, 2H), 3.83 (dd, J=10.4, 6.2 Hz, 1H), 3.70 (ddd, J=11.9, 6.4, 4.0 Hz, 2H), 3.35 (p, J=4.1 Hz, 1H), 3.20 (ddd, J=25.3, 14.6, 4.9 Hz, 1H), 3.08 (dt, J=7.5, 4.9 Hz, 1H), 3.04-2.95 (m, 1H), 2.99-2.91 (m, 2H), 2.84 (dtd, J=7.5, 6.3, 5.6 Hz, 1H), 2.75 (ddt, J=14.5, 6.4, 4.1 Hz, 2H), 2.46 (td, J=6.4, 5.6 Hz, 1H), 2.06 (dddd, J=25.1, 13.6, 6.4, 4.1 Hz, 2H), 2.00-1.81 (m, 5H), 1.63-1.53 (m, 2H), 1.51-1.41 (m, 2H). LRMS (ESI): 540.22 [M+H]$^+$.

Example 111 Piperidin-4-ylmethyl 4-(((2-(5-bromothien-2-yl)cyclopropyl)amino)methyl)-4-fluoropiperidine-1-carboxylate (A111)

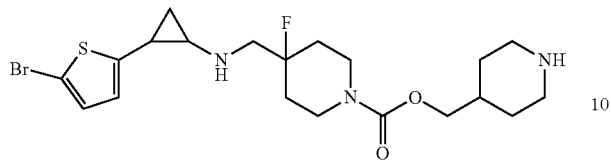

trans-2-phenylcyclopropylamine was replaced with trans-2-(5-bromothiophen-2-yl)cyclopropylamine, while other raw materials, reagents and the preparation method were the same as those in example 43 to provide product A111 (yield: 65%). $^1$H NMR (400 MHz, DMSO-d$_6$) δ 7.02 (d, J=8.4 Hz, 1H), 6.72 (d, J=8.4 Hz, 1H), 4.25 (dd, J=10.4, 6.2 Hz, 1H), 4.02 (ddd, J=12.1, 6.5, 4.1 Hz, 2H), 3.83 (dd, J=10.4, 6.2 Hz, 1H), 3.69 (ddd, J=12.1, 6.4, 4.0 Hz, 2H), 3.35 (p, J=4.1 Hz, 1H), 3.15 (ddd, J=25.3, 14.5, 5.0 Hz, 1H), 3.09-2.97 (m, 1H), 3.01-2.92 (m, 3H), 2.85-2.71 (m, 3H), 2.48 (td, J=6.4, 5.6 Hz, 1H), 2.06 (dddd, J=25.3, 13.6, 6.4, 4.1 Hz, 2H), 1.99-1.80 (m, 5H), 1.64-1.54 (m, 2H), 1.50-1.40 (m, 2H). LRMS (ESI): 474.11 [M+H]$^+$.

Example 112 Piperidin-4-ylmethyl 4-fluoro-4-(((2-(6-(4-methoxyphenyl)pyridin-3-yl)cyclopropyl)amino)methyl)piperidine-1-carboxylate (A112)

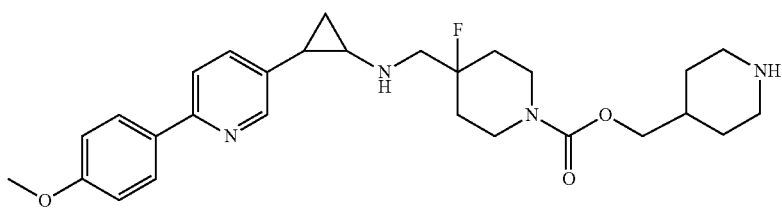 [SMILES: COc1ccc(-c2ccc(C3CC3NCC3(F)CCN(C(=O)OCC4CCNCC4)CC3)cn2)cc1]

trans-2-phenylcyclopropylamine was replaced with trans-2-(6-(4-methoxyphenyl)pyridin-3-yl)cyclopropylamine, while other raw materials, reagents and the preparation method were the same as those in example 43 to provide product A112 (yield: 63%). $^1$H NMR (400 MHz, DMSO-d$_6$) δ 8.40 (d, J=1.8 Hz, 1H), 7.83-7.76 (m, 2H), 7.66 (d, J=8.5 Hz, 1H), 7.41 (dd, J=8.4, 1.8 Hz, 1H), 7.03-6.97 (m, 2H), 4.08 (dd, J=10.6, 6.2 Hz, 1H), 4.06-3.96 (m, 3H), 3.83 (s, 2H), 3.68 (ddd, J=12.1, 6.4, 4.0 Hz, 2H), 3.37 (p, J=4.1 Hz, 1H), 3.18 (ddd, J=25.1, 14.7, 4.8 Hz, 1H), 3.11-2.97 (m, 2H), 3.00-2.92 (m, 2H), 2.76 (ddt, J=14.5, 6.4, 4.1 Hz, 2H), 2.40 (td, J=6.4, 5.6 Hz, 1H), 2.09 (dddd, J=25.3, 13.6, 6.4, 4.1 Hz, 2H), 2.01-1.78 (m, 6H), 1.65-1.55 (m, 2H), 1.52-1.42 (m, 2H). LRMS (ESI): 497.28 [M+H]$^+$.

Example 113 Piperidin-4-ylmethyl 4-(((2-(5-cyclopropylthien-2-yl)cyclopropyl)amino)methyl)-4-fluoropiperidine-1-carboxylate (A113)

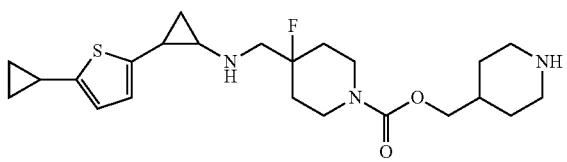 [SMILES: O=C(OCC1CCNCC1)N1CCC(F)(CNC2CC2c2ccc(C3CC3)s2)CC1]

trans-2-phenylcyclopropylamine was replaced with trans-2-(5-cyclopropylthiophen-2-yl)cyclopropylamine, while other raw materials, reagents and the preparation method were the same as those in example 43 to provide product A113 (yield: 67%). ¹H NMR (400 MHz, DMSO-d₆) δ 6.75 (q, J=8.4 Hz, 2H), 4.25 (dd, J=10.5, 6.3 Hz, 1H), 4.02 (ddd, J=12.1, 6.4, 4.0 Hz, 2H), 3.83 (dd, J=10.6, 6.2 Hz, 1H), 3.69 (ddd, J=12.1, 6.5, 4.1 Hz, 2H), 3.22-3.11 (m, 1H), 3.14-3.08 (m, 1H), 3.09-2.92 (m, 4H), 2.85-2.71 (m, 3H), 2.38 (td, J=6.4, 5.5 Hz, 1H), 2.32 (p, J=5.8 Hz, 1H), 2.06 (dddd, J=25.3, 13.6, 6.4, 4.1 Hz, 2H), 1.99-1.87 (m, 2H), 1.91-1.80 (m, 3H), 1.63-1.53 (m, 6H), 1.49-1.39 (m, 2H). LRMS (ESI): 436.24 [M+H]⁺.

Example 114 Piperidin-4-ylmethyl 4-(((2-(5-((4-cyanophenyl)ethynyl)thiophen-2-yl)cyclopropyl)amino)methyl)-4-fluoropiperidine-1-carboxylate (A114)

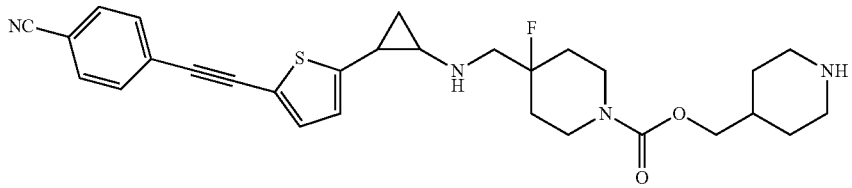 [SMILES: N#Cc1ccc(C#Cc2ccc(C3CC3NCC3(F)CCN(C(=O)OCC4CCNCC4)CC3)s2)cc1]

trans-2-phenylcyclopropylamine was replaced with trans-4-((5-(2-aminocyclopropyl)thiophen-2-yl)ethynyl)benzonitrile, while other raw materials, reagents and the preparation method were the same as those in example 43 to provide product A114 (yield: 51%). ¹H NMR (400 MHz, DMSO-d₆) δ 7.65-7.59 (m, 2H), 7.59-7.53 (m, 2H), 7.24 (d, J=8.4 Hz, 1H), 6.85 (d, J=8.4 Hz, 1H), 4.08 (dd, J=10.5, 6.3 Hz, 1H), 4.07-3.97 (m, 3H), 3.68 (ddd, J=12.1, 6.5, 4.1 Hz, 2H), 3.37 (p, J=4.1 Hz, 1H), 3.18 (ddd, J=25.1, 14.1, 5.2 Hz, 1H), 3.11-2.98 (m, 2H), 3.01-2.88 (m, 3H), 2.76 (ddt, J=14.5, 6.4, 4.1 Hz, 2H), 2.39 (td, J=6.4, 5.6 Hz, 1H), 2.09 (dddd, J=25.3, 13.6, 6.6, 4.2 Hz, 2H), 2.01-1.80 (m, 5H), 1.60 (dtd, J=13.4, 6.4, 4.2 Hz, 2H), 1.47 (dtd, J=13.4, 6.3, 4.2 Hz, 2H). LRMS (ESI): 521.23 [M+H]⁺.

Example 115 Piperidin-4-ylmethyl 4-fluoro-4-(((2-(6-phenylpyridin-3-yl)cyclopropyl)amino)methyl)piperidine-1-carboxylate (A115)

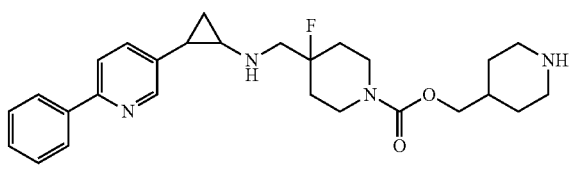 [SMILES: O=C(OCC1CCNCC1)N1CCC(F)(CNC2CC2c2ccc(-c3ccccc3)nc2)CC1]

trans-2-phenylcyclopropylamine was replaced with trans-2-(6-phenylpyridin-3-yl)cyclopropylamine, while other raw materials, reagents and the preparation method were the same as those in example 43 to provide product A115 (yield: 68%). ¹H NMR (400 MHz, DMSO-d₆) δ 8.45 (d, J=1.9 Hz, 1H), 8.02-7.94 (m, 2H), 7.69 (d, J=8.4 Hz, 1H), 7.45 (dd, J=8.4, 2.0 Hz, 1H), 7.44-7.34 (m, 3H), 4.15 (dd, J=10.4, 6.2 Hz, 1H), 4.03 (ddd, J=12.0, 6.5, 4.1 Hz, 2H), 3.93 (dd, J=10.5, 6.3 Hz, 1H), 3.69 (ddd, J=12.1, 6.4, 4.2 Hz, 2H), 3.36 (p, J=4.1 Hz, 1H), 3.27-3.19 (m, 1H), 3.23-3.10 (m, 1H), 3.05 (ddd, J=25.3, 14.7, 4.9 Hz, 1H), 2.98 (dt, J=6.3, 4.1 Hz, 1H), 2.98-2.92 (m, 1H), 2.77 (ddt, J=14.5, 6.4, 4.1 Hz, 2H), 2.40 (td, J=6.4, 5.6 Hz, 1H), 2.09 (dddd, J=25.1, 13.4, 6.4, 4.1 Hz, 2H), 2.03-1.92 (m, 2H), 1.95-1.79 (m, 4H), 1.59 (dtd, J=12.8, 6.3, 4.1 Hz, 2H), 1.46 (dtd, J=13.2, 6.2, 4.0 Hz, 2H). LRMS (ESI): 467.27 [M+H]⁺.

Example 116 Piperidin-4-ylmethyl 4-(((2-(6-(4-ethylphenoxy)pyridin-3-yl)cyclopropyl)amino)methyl)-4-fluoropyridine-1-carboxylate (A116)

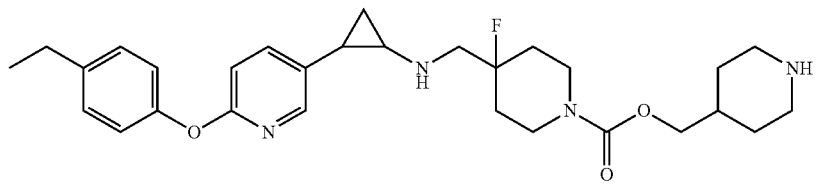 [SMILES: CCc1ccc(Oc2ccc(C3CC3NCC3(F)CCN(C(=O)OCC4CCNCC4)CC3)cn2)cc1]

trans-2-phenylcyclopropylamine was replaced with trans-2-(6-(4-ethylphenoxy)pyridin-3-yl)cyclopropylamine, while other raw materials, reagents and the preparation method were the same as those in example 43 to provide product A116 (yield: 64%). $^1$H NMR (400 MHz, DMSO-d$_6$) δ 7.97 (d, J=1.9 Hz, 1H), 7.61-7.55 (m, 2H), 7.36 (dd, J=8.4, 1.8 Hz, 1H), 7.12 (dt, J=8.4, 1.1 Hz, 2H), 7.01 (d, J=8.4 Hz, 1H), 4.23 (dd, J=10.4, 6.2 Hz, 1H), 4.03 (ddd, J=12.1, 6.4, 4.2 Hz, 2H), 3.82 (dd, J=10.5, 6.3 Hz, 1H), 3.69 (ddd, J=12.1, 6.5, 4.1 Hz, 2H), 3.35 (p, J=4.1 Hz, 1H), 3.28-3.12 (m, 2H), 3.06 (ddd, J=25.3, 14.7, 4.8 Hz, 1H), 2.96 (ddt, J=14.6, 6.4, 4.1 Hz, 2H), 2.80-2.63 (m, 3H), 2.59-2.48 (m, 1H), 2.40 (td, J=6.4, 5.6 Hz, 1H), 2.09 (dddd, J=25.3, 13.6, 6.4, 4.1 Hz, 2H), 2.03-1.81 (m, 6H), 1.64-1.54 (m, 2H), 1.46 (dtd, J=13.4, 6.3, 4.2 Hz, 2H), 1.24 (t, J=7.2 Hz, 3H). LRMS (ESI): 511.30 [M+H]$^+$.

Example 117 Piperidin-4-ylmethyl 4-fluoro-4-(((2-(6-(3-(trifluoromethyl)phenyl)pyridin-3-yl)cyclopropyl)amino)methyl)pyridine-1-carboxylate (A117)

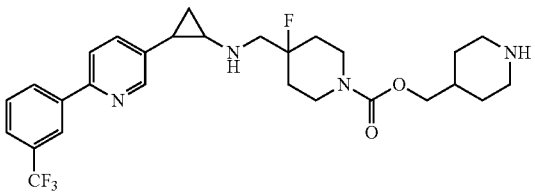 [SMILES: O=C(OCC1CCNCC1)N1CCC(F)(CNC2CC2c2ccc(-c3cccc(C(F)(F)F)c3)nc2)CC1]

trans-2-phenylcyclopropylamine was replaced with trans-2-(6-(3-(trifluoromethyl)phenyl)pyridin-3-yl)cyclopropylamine, while other raw materials, reagents and the preparation method were the same as those in example 43 to provide product A117 (yield: 71%). $^1$H NMR (400 MHz, DMSO-d$_6$) δ 8.46 (d, J=1.9 Hz, 1H), 8.34 (t, J=2.2 Hz, 1H), 7.86 (ddd, J=7.7, 2.2, 1.2 Hz, 1H), 7.77 (ddd, J=7.9, 2.2, 1.3 Hz, 1H), 7.72-7.63 (m, 2H), 7.47 (dd, J=8.4, 2.0 Hz, 1H), 4.08 (dd, J=10.4, 6.2 Hz, 1H), 4.08-3.97 (m, 3H), 3.68 (ddd, J=12.1, 6.5, 4.2 Hz, 2H), 3.37 (p, J=4.1 Hz, 1H), 3.18 (ddd, J=25.1, 14.7, 4.8 Hz, 1H), 3.06 (dtd, J=7.5, 6.4, 5.6 Hz, 1H), 3.04-2.91 (m, 3H), 2.76 (ddt, J=14.5, 6.4, 4.1 Hz, 2H), 2.20 (td, J=6.5, 5.7 Hz, 1H), 2.08 (dddd, J=25.3, 13.6, 6.4, 4.1 Hz, 2H), 2.00-1.78 (m, 6H), 1.65-1.55 (m, 2H), 1.47 (dtd, J=13.2, 6.2, 4.0 Hz, 2H). LRMS (ESI): 535.26 [M+H]$^+$.

Example 118 Piperidin-4-ylmethyl 4-fluoro-4-(((2-(6-(4-fluorophenyl)pyridin-3-yl)cyclopropyl)amino)methyl)piperidine-1-carboxylate (A118)

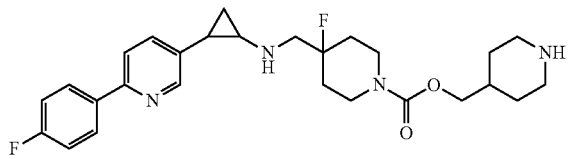 [SMILES: O=C(OCC1CCNCC1)N1CCC(F)(CNC2CC2c2ccc(-c3ccc(F)cc3)nc2)CC1]

trans-2-phenylcyclopropylamine was replaced with trans-2-(6-(4-fluorophenyl)pyridin-3-yl)cyclopropylamine, while other raw materials, reagents and the preparation method were the same as those in example 43 to provide product A118 (yield: 75%). $^1$H NMR (400 MHz, DMSO-d$_6$) δ 8.41 (d, J=1.8 Hz, 1H), 8.18-8.11 (m, 2H), 7.66 (d, J=8.5 Hz, 1H), 7.42 (dd, J=8.4, 1.8 Hz, 1H), 7.20-7.12 (m, 2H), 4.14 (dd, J=10.6, 6.2 Hz, 1H), 4.03 (ddd, J=12.1, 6.4, 4.0 Hz, 2H), 3.83 (dd, J=10.4, 6.2 Hz, 1H), 3.69 (ddd, J=12.1, 6.5, 4.1 Hz, 2H), 3.35 (p, J=4.1 Hz, 1H), 3.16 (ddd, J=25.3, 14.7, 4.9 Hz, 1H), 3.09-2.96 (m, 1H), 3.00-2.90 (m, 3H), 2.75 (ddt, J=14.5, 6.4, 4.1 Hz, 2H), 2.40 (td, J=6.4, 5.6 Hz, 1H), 2.07 (dddd, J=25.1, 13.5, 6.4, 4.0 Hz, 2H), 1.97 (ddd, J=13.4, 6.4, 4.0 Hz, 1H), 1.96-1.86 (m, 3H), 1.89-1.81 (m, 2H), 1.64-1.54 (m, 2H), 1.45 (dtd, J=13.2, 6.3, 4.0 Hz, 2H). LRMS (ESI): 485.26 [M+H]$^+$.

Example 119 Piperidin-4-ylmethyl 4-(((2-(6-(4-chlorophenyl)pyridin-3-yl)cyclopropyl)amino)methyl)-4-fluoropyridine-1-carboxylate (A119)

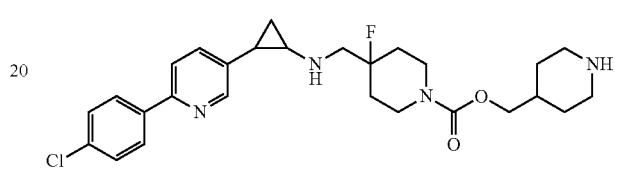

trans-2-phenylcyclopropylamine was replaced with trans-2-(6-(4-chlorophenyl)pyridin-3-yl)cyclopropylamine, while other raw materials, reagents and the preparation method were the same as those in example 43 to provide product A119 (yield: 71%). $^1$H NMR (400 MHz, DMSO-d$_6$) δ 8.41 (d, J=1.9 Hz, 1H), 7.85-7.79 (m, 2H), 7.68 (d, J=8.4 Hz, 1H), 7.46-7.35 (m, 3H), 4.14 (dd, J=10.4, 6.2 Hz, 1H), 4.02 (ddd, J=12.1, 6.4, 4.2 Hz, 2H), 3.82 (dd, J=10.4, 6.2 Hz, 1H), 3.69 (ddd, J=12.1, 6.4, 4.0 Hz, 2H), 3.35 (p, J=4.1 Hz, 1H), 3.15 (ddd, J=25.3, 14.7, 4.9 Hz, 1H), 3.09-2.90 (m, 4H), 2.75 (ddt, J=14.5, 6.4, 4.1 Hz, 2H), 2.40 (td, J=6.4, 5.6 Hz, 1H), 2.07 (dddd, J=25.1, 13.5, 6.4, 4.1 Hz, 2H), 2.01-1.88 (m, 2H), 1.92-1.85 (m, 2H), 1.89-1.81 (m, 2H), 1.58 (dtd, J=12.8, 6.3, 4.0 Hz, 2H), 1.45 (dtd, J=13.4, 6.3, 4.2 Hz, 2H). LRMS (ESI): 501.24 [M+H]$^+$.

Example 120 Piperidin-4-ylmethyl 4-(((2-(6-(3,5-dimethylphenyl)pyridin-3-yl)cyclopropyl)amino)methyl)-4-fluoropyridine-1-carboxylate (A120)

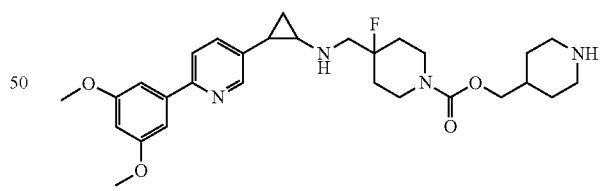

trans-2-phenylcyclopropylamine was replaced with trans-2-(6-(3,5-methoxyphenyl)pyridin-3-yl)cyclopropylamine, while other raw materials, reagents and the preparation method were the same as those in example 43 to provide product A120 (yield: 61%). $^1$H NMR (400 MHz, DMSO-d$_6$) δ 8.40 (d, J=1.9 Hz, 1H), 7.68 (d, J=8.4 Hz, 1H), 7.34 (dd, J=8.4, 2.0 Hz, 1H), 7.19 (d, J=2.0 Hz, 2H), 6.58 (t, J=2.2 Hz, 1H), 4.23 (dd, J=10.4, 6.2 Hz, 1H), 4.04 (ddd, J=12.1, 6.4, 4.0 Hz, 2H), 3.86-3.80 (m, 1H), 3.81 (s, 5H), 3.68 (ddd, J=12.1, 6.5, 4.1 Hz, 2H), 3.35 (p, J=4.1 Hz, 1H), 3.18 (ddd, J=25.3, 14.7, 4.9 Hz, 1H), 3.06 (dtd, J=7.3, 6.2, 5.4 Hz, 1H), 3.04-2.95 (m, 1H), 2.99-2.91 (m, 2H), 2.75 (ddt, J=14.5, 6.4, 4.1 Hz, 2H), 2.21 (td, J=6.5, 5.7 Hz, 1H), 2.09 (dddd, J=25.3, 13.6, 6.4, 4.1 Hz, 2H), 2.00-1.78 (m, 6H), 1.59 (dtd, J=13.4, 6.3, 4.0 Hz, 2H), 1.45 (dtd, J=13.4, 6.3, 4.1 Hz, 2H). LRMS (ESI): 527.30 [M+H]⁺.

Example 121 Piperidin-4-ylmethyl 4-(((2-(6-bromopyridin-3-yl)cyclopropyl)amino)methyl)-4-fluoropiperidine-1-carboxylate (A121)

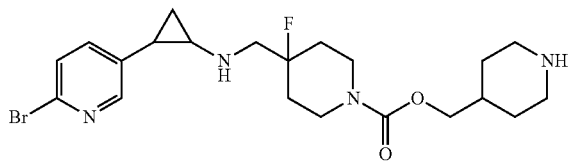 [SMILES: O=C(OCC1CCNCC1)N1CCC(F)(CNC2CC2c2ccc(Br)nc2)CC1]

trans-2-phenylcyclopropylamine was replaced with trans2-(6-bromopyridin-2-yl)cyclopropylamine, while other raw materials, reagents and the preparation method were the same as those in example 43 to provide product A121 (yield: 62%). ¹H NMR (400 MHz, DMSO-d₆) δ 8.18 (d, J=1.8 Hz, 1H), 7.49 (d, J=8.4 Hz, 1H), 7.34 (dd, J=8.4, 1.8 Hz, 1H), 4.25 (dd, J=10.4, 6.2 Hz, 1H), 4.02 (ddd, J=12.1, 6.4, 4.2 Hz, 2H), 3.82 (dd, J=10.6, 6.2 Hz, 1H), 3.68 (ddd, J=12.1, 6.4, 4.2 Hz, 2H), 3.35 (p, J=4.1 Hz, 1H), 3.15 (ddd, J=25.1, 14.7, 4.9 Hz, 1H), 3.08-2.94 (m, 2H), 2.98-2.89 (m, 2H), 2.76 (ddt, J=14.5, 6.4, 4.1 Hz, 2H), 2.23 (td, J=6.4, 5.6 Hz, 1H), 2.06 (dddd, J=25.1, 13.4, 6.4, 4.1 Hz, 2H), 2.01-1.89 (m, 2H), 1.90 (dd, J=6.4, 4.1 Hz, 0H), 1.90 (s, 1H), 1.91-1.80 (m, 3H), 1.64-1.54 (m, 2H), 1.45 (dtd, J=13.4, 6.3, 4.1 Hz, 2H). LRMS (ESI): 469.15 [M+H]⁺.

Example 122 Piperidin-4-ylmethyl 4-(((2-(2-chlorothiazol-5-yl)cyclopropyl)amino)methyl)-4-fluoropiperidine-1-carboxylate (A122)

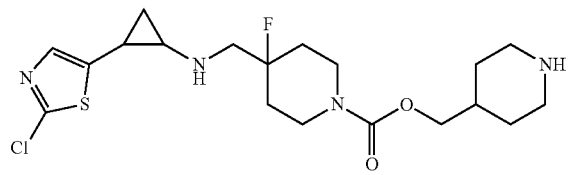 [SMILES: O=C(OCC1CCNCC1)N1CCC(F)(CNC2CC2c2cnc(Cl)s2)CC1]

trans-2-phenylcyclopropylamine was replaced with trans-2-(2-chlorothiazol-5-yl)cyclopropylamine, while other raw materials, reagents and the preparation method were the same as those in example 43 to provide product A122 (yield: 65%). ¹H NMR (400 MHz, DMSO-d₆) δ 7.35 (s, 1H), 4.16 (dd, J=10.6, 6.2 Hz, 1H), 4.04 (ddd, J=12.1, 6.4, 4.2 Hz, 2H), 3.94 (dd, J=10.4, 6.2 Hz, 1H), 3.69 (ddd, J=12.1, 6.4, 4.2 Hz, 2H), 3.20-3.07 (m, 2H), 3.10-2.87 (m, 5H), 2.82-2.72 (m, 3H), 2.16-1.88 (m, 6H), 1.84 (hept, J=6.2 Hz, 1H), 1.64-1.54 (m, 2H), 1.50-1.40 (m, 2H). LRMS (ESI): 431.16 [M+H]⁺.

Example 123 Piperidin-4-ylmethyl 4-fluoro-4-(((2-(2-(4-fluorophenyl)thiazol-5-yl)cyclopropyl)amino)methyl)piperidine-1-carboxylate (A123)

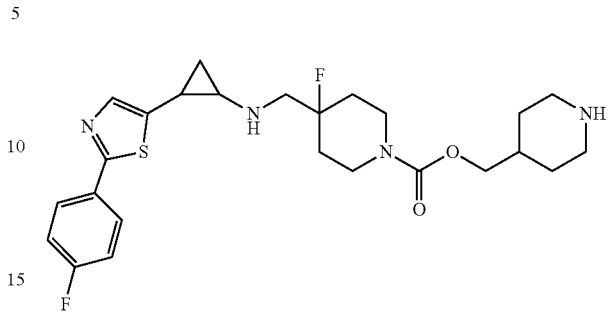

trans-2-phenylcyclopropylamine was replaced with trans-2-(2-(4-fluorophenyl)thiazol-5-yl)cyclopropylamine, while other raw materials, reagents and the preparation method were the same as those in example 43 to provide product A123 (yield: 70%). ¹H NMR (400 MHz, DMSO-d₆) δ 7.70-7.62 (m, 2H), 7.58 (s, 1H), 7.26-7.18 (m, 2H), 4.13 (dd, J=10.5, 6.3 Hz, 1H), 4.03 (ddd, J=12.1, 6.4, 4.0 Hz, 2H), 3.82 (dd, J=10.5, 6.3 Hz, 1H), 3.69 (ddd, J=12.1, 6.5, 4.1 Hz, 2H), 3.35 (p, J=4.1 Hz, 1H), 3.16 (ddd, J=25.1, 14.6, 4.9 Hz, 1H), 3.09-2.97 (m, 1H), 3.00-2.90 (m, 4H), 2.93-2.85 (m, 1H), 2.75 (ddt, J=14.5, 6.4, 4.1 Hz, 2H), 2.09 (ddd, J=13.4, 6.4, 4.0 Hz, 1H), 2.08-1.97 (m, 3H), 2.00-1.81 (m, 3H), 1.64-1.54 (m, 2H), 1.45 (dtd, J=13.4, 6.3, 4.2 Hz, 2H). LRMS (ESI): 491.22 [M+H]⁺.

Example 124 Piperidin-4-ylmethyl 4-(((2-(2-(4-chlorophenyl)thiazol-5-yl)cyclopropyl)amino)methyl)-4-fluoropiperidine-1-carboxylate (A124)

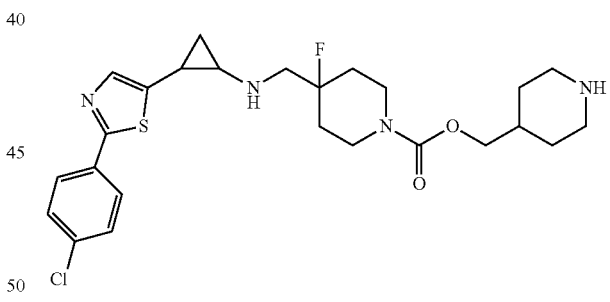

trans-2-phenylcyclopropylamine was replaced with trans-2-(2-(4-chlorophenyl)thiazol-5-yl)cyclopropylamine, while other raw materials, reagents and the preparation method were the same as those in example 43 to provide product A124 (yield: 71%). ¹H NMR (400 MHz, DMSO-d₆) δ 8.05-7.99 (m, 2H), 7.60-7.50 (m, 3H), 4.13 (dd, J=10.4, 6.2 Hz, 1H), 4.02 (ddd, J=12.1, 6.4, 4.2 Hz, 2H), 3.82 (dd, J=10.6, 6.2 Hz, 1H), 3.69 (ddd, J=12.1, 6.5, 4.1 Hz, 2H), 3.35 (p, J=4.1 Hz, 1H), 3.16 (ddd, J=25.1, 14.5, 5.1 Hz, 1H), 3.09-2.97 (m, 1H), 3.01-2.94 (m, 2H), 2.97-2.90 (m, 2H), 2.93-2.85 (m, 1H), 2.75 (ddt, J=14.5, 6.4, 4.1 Hz, 2H), 2.09 (ddd, J=13.4, 6.4, 4.0 Hz, 1H), 2.08-1.99 (m, 3H), 2.02-1.81 (m, 3H), 1.64-1.54 (m, 2H), 1.45 (dtd, J=13.4, 6.3, 4.2 Hz, 2H). LRMS (ESI): 507.19 [M+H]⁺.

Example 125 Piperidin-4-ylmethyl 4-fluoro-4-(((2-(2-phenylthiazol-5-yl)cyclopropyl)amino)methyl)piperidine-1-carboxylate (A125)

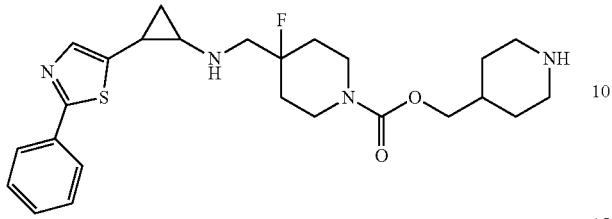

trans-2-phenylcyclopropylamine was replaced with trans-2-(2-phenylthiazol-5-yl)cyclopropylamine, while other raw materials, reagents and the preparation method were the same as those in example 43 to provide product A125 (yield: 69%). $^1$H NMR (400 MHz, DMSO-$d_6$) δ 7.96-7.90 (m, 2H), 7.58 (s, 1H), 7.53-7.41 (m, 3H), 4.14 (dd, J=10.4, 6.2 Hz, 1H), 4.03 (ddd, J=12.1, 6.5, 4.1 Hz, 2H), 3.83 (dd, J=10.4, 6.2 Hz, 1H), 3.70 (ddd, J=11.9, 6.4, 4.0 Hz, 2H), 3.35 (p, J=4.1 Hz, 1H), 3.16 (ddd, J=25.1, 14.4, 5.0 Hz, 1H), 3.09-2.97 (m, 1H), 3.01-2.94 (m, 2H), 2.97-2.90 (m, 2H), 2.93-2.85 (m, 1H), 2.76 (ddt, J=14.5, 6.4, 4.1 Hz, 2H), 2.09 (ddd, J=13.5, 6.5, 4.1 Hz, 1H), 2.08-1.99 (m, 3H), 2.01-1.81 (m, 3H), 1.64-1.54 (m, 2H), 1.45 (dtd, J=13.2, 6.3, 4.0 Hz, 2H). LRMS (ESI): 473.23 [M+H]$^+$.

Example 126 Piperidin-4-ylmethyl 4-fluoro-4-(((2-(2-(4-methoxyphenyl)thiazol-5-yl)cyclopropyl)amino)methyl)piperidine-1-carboxylate (A126)

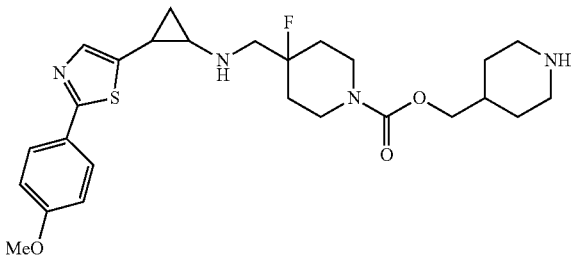 [SMILES: COc1ccc(-c2ncc(C3CC3NCC3(F)CCN(C(=O)OCC4CCNCC4)CC3)s2)cc1]

trans-2-phenylcyclopropylamine was replaced with trans-2-(2-(4-methoxyphenyl)thiazol-5-yl)cyclopropylamine, while other raw materials, reagents and the preparation method were the same as those in example 43 to provide product A126 (yield: 67%). $^1$H NMR (400 MHz, DMSO-$d_6$) δ 8.11-8.05 (m, 2H), 7.57 (s, 1H), 7.25-7.19 (m, 2H), 4.15 (dd, J=10.5, 6.3 Hz, 1H), 4.02 (ddd, J=12.1, 6.5, 4.1 Hz, 2H), 3.86-3.80 (m, 1H), 3.81 (s, 3H), 3.69 (ddd, J=12.1, 6.4, 4.0 Hz, 2H), 3.36 (p, J=4.1 Hz, 1H), 3.16 (ddd, J=25.1, 14.6, 4.9 Hz, 1H), 3.09-2.85 (m, 6H), 2.75 (ddt, J=14.5, 6.4, 4.1 Hz, 2H), 2.09 (ddd, J=13.6, 6.5, 4.2 Hz, 1H), 2.08-2.00 (m, 2H), 2.03-1.92 (m, 2H), 1.96-1.80 (m, 2H), 1.63-1.53 (m, 2H), 1.50-1.40 (m, 2H). LRMS (ESI): 503.24 [M+H]$^+$.

Example 127 Piperidin-4-ylmethyl 4-(((2-(2-(3,5-dimethoxyphenyl)thiazol-5-yl)cyclopropyl)amino)methyl-4-fluoropiperidine-1-carboxylate (A127)

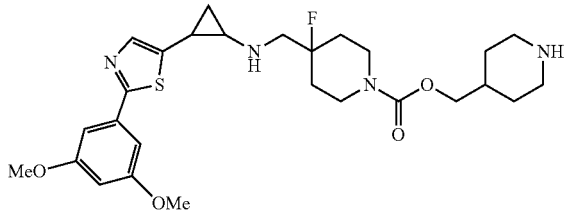 [SMILES: COc1cc(OC)cc(-c2ncc(C3CC3NCC3(F)CCN(C(=O)OCC4CCNCC4)CC3)s2)c1]

trans-2-phenylcyclopropylamine was replaced with trans-2-(2-(3,5-dimethoxyphenyl)thiazol-5-yl)cyclopropylamine, while other raw materials, reagents and the preparation method were the same as those in example 43 to provide product A127 (yield: 59%). $^1$H NMR (400 MHz, DMSO-$d_6$) δ 7.56 (s, 1H), 7.10 (d, J=2.2 Hz, 2H), 6.59 (t, J=2.2 Hz, 1H), 4.13 (dd, J=10.4, 6.2 Hz, 1H), 4.03 (ddd, J=12.1, 6.4, 4.2 Hz, 2H), 3.86-3.80 (m, 1H), 3.81 (s, 4H), 3.69 (ddd, J=12.1, 6.5, 4.1 Hz, 2H), 3.35 (p, J=4.1 Hz, 1H), 3.16 (ddd, J=25.1, 14.2, 5.2 Hz, 1H), 3.09-2.85 (m, 6H), 2.75 (ddt, J=14.5, 6.4, 4.1 Hz, 2H), 2.09 (ddd, J=13.6, 6.4, 4.0 Hz, 1H), 2.08-1.96 (m, 3H), 1.95 (ddd, J=13.6, 6.5, 4.2 Hz, 1H), 1.95-1.81 (m, 2H), 1.64-1.54 (m, 2H), 1.50-1.40 (m, 2H). LRMS (ESI): 533.25 [M+H]$^+$.

Example 128 Piperidin-4-ylmethyl 4-fluoro-4-(((1R,2S)-2-phenylcyclopropyl)amino)methyl)piperidine-1-carboxylate ((1R, 2S)-A43)

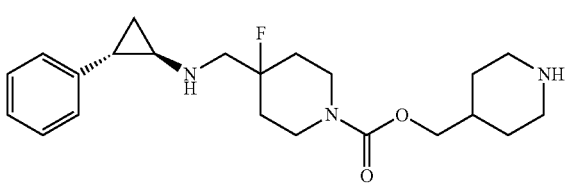 [SMILES: O=C(OCC1CCNCC1)N1CCC(F)(CN[C@@H]2C[C@H]2c2ccccc2)CC1]

trans-2-phenylcyclopropylamine was replaced with (1R, 2S)-2-phenylcyclopropylamine, while other raw materials, reagents and the preparation method were the same as those in example 43 to provide product (1R,2S)-A43 (yield: 49%). $^1$H NMR (400 MHz, D$_2$O) δ 7.32 (t, J=7.4 Hz, 2H), 7.24 (t, J=7.3 Hz, 1H), 7.16 (d, J=7.3 Hz, 2H), 3.95 (d, J=6.0 Hz, 4H), 3.47 (d, J=20.5 Hz, 2H), 3.38 (d, J=13.0 Hz, 2H), 3.12 (t, J=12.0 Hz, 2H), 3.01-2.87 (m, 3H), 2.53 (ddd, J=10.3, 6.6, 3.5 Hz, 1H), 2.04-1.85 (m, 5H), 1.79-1.70 (m, 1H), 1.65 (td, J=13.7, 5.1 Hz, 1H), 1.55-1.33 (m, 4H); LRMS (ESI): 390.25 [M+H]$^+$.

Example 129 Piperidin-4-ylmethyl 4-fluoro-4-(((1S, 2R)-2-phenylcyclopropyl)amino)methyl)piperidine-1-carboxylate ((1S, 2R)-A43)

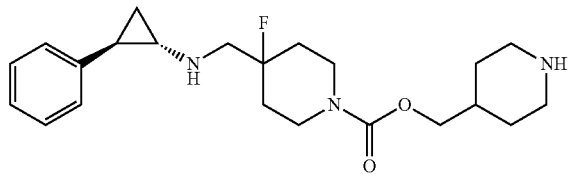 [SMILES: O=C(OCC1CCNCC1)N1CCC(F)(CN[C@H]2C[C@@H]2c2ccccc2)CC1]

trans-2-phenylcyclopropylamine was replaced with (1S, 2R)-2-phenylcyclopropylamine, while other raw materials, reagents and the preparation method were the same as those in example 43 to provide product (1S,2R)-A43 (yield: 52%). $^1$H NMR (400 MHz, D$_2$O) δ 7.31 (t, J=7.4 Hz, 2H), 7.24 (t, J=7.3 Hz, 1H), 7.15 (d, J=7.2 Hz, 2H), 3.94 (d, J=5.9 Hz, 4H), 3.47 (d, J=20.5 Hz, 2H), 3.38 (d, J=12.8 Hz, 2H), 3.12 (t, J=12.4 Hz, 2H), 2.95 (ddd, J=19.8, 10.5, 7.1 Hz, 3H), 2.52 (ddd, J=10.3, 6.7, 3.6 Hz, 1H), 2.04-1.86 (m, 5H), 1.74 (td, J=13.3, 5.0 Hz, 1H), 1.64 (td, J=13.7, 5.2 Hz, 1H), 1.55-1.33 (m, 4H); LRMS (ESI): 390.25 [M+H]$^+$.

Example 130 (1-Benzylpiperidin-4-yl)methyl 4-fluoro-4-(((1R,2S)-2-phenylcyclopropyl)amino)methyl)piperidin-1-carboxylate ((1R, 2S)-A90)

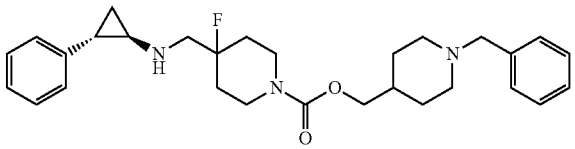 [SMILES: O=C(OCC1CCN(Cc2ccccc2)CC1)N1CCC(F)(CN[C@@H]2C[C@H]2c2ccccc2)CC1]

trans-2-phenylcyclopropylamine was replaced with (1R, 2S)-2-phenylcyclopropylamine, while other raw materials, reagents and the preparation method were the same as those in example 90 to provide product (1R,2S)-A90 (yield: 44%). $^1$H NMR (500 MHz, MeOD) δ 7.58 (dd, J=6.6, 2.8 Hz, 2H), 7.51-7.45 (m, 3H), 7.31 (t, J=7.4 Hz, 2H), 7.25-7.21 (m, 1H), 7.21-7.18 (m, 2H), 4.31 (s, 2H), 4.05 (d, J=13.7 Hz, 4H), 3.58-3.46 (m, 4H), 3.24-3.13 (m, 2H), 3.09-2.99 (m, 3H), 2.62 (ddd, J=10.3, 6.6, 3.6 Hz, 1H), 2.08-1.77 (m, 7H), 1.69 (td, J=15.0, 3.5 Hz, 2H), 1.64-1.58 (m, 1H), 1.39 (dd, J=14.5, 6.8 Hz, 1H); LRMS (ESI): 478.29 [M+H]$^+$.

Example 131 4-((4-Fluoro-4-((((1R,2S)-2-phenylcyclopropyl)amino)methyl)piperidin-1-yl)methyl)benzoate ((1R,2S)-A5)

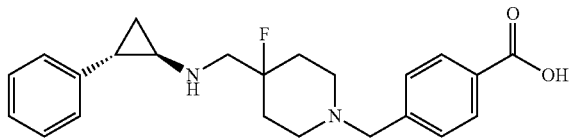 [SMILES: O=C(O)c1ccc(CN2CCC(F)(CN[C@@H]3C[C@H]3c3ccccc3)CC2)cc1]

trans-2-phenylcyclopropylamine was replaced with (1R, 2S)-2-phenylcyclopropylamine, while other raw materials, reagents and the preparation method were the same as those in example 5 to provide product (1R,2S)-A5 (yield: 22%). $^1$H NMR (400 MHz, DMSO-d$_6$) δ 8.02-7.93 (m, 2H), 7.50 (dt, J=7.4, 1.2 Hz, 2H), 7.26-7.10 (m, 5H), 3.54 (d, J=1.5 Hz, 2H), 3.11 (dt, J=12.6, 7.2 Hz, 2H), 2.76-2.62 (m, 2H), 2.62-2.49 (m, 3H), 2.05-1.82 (m, 3H), 1.45 (ddt, J=25.1, 13.2, 7.1 Hz, 2H), 0.95 (td, J=7.0, 4.9 Hz, 1H), 0.71 (td, J=7.0, 5.0 Hz, 1H); LRMS (ESI): 383.21 [M+H]$^+$.

Example 132 4-((4-Fluoro-4-((((1S,2R)-2-phenylcyclopropyl)amino)methyl)piperidin-1-yl)methyl)benzoate ((1S,2R)-A5)

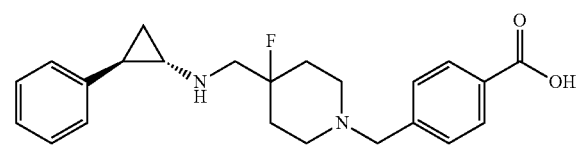 [SMILES: O=C(O)c1ccc(CN2CCC(F)(CN[C@H]3C[C@@H]3c3ccccc3)CC2)cc1]

trans-2-phenylcyclopropylamine was replaced with (1S, 2R)-2-phenylcyclopropylamine, while other raw materials, reagents and the preparation method were the same as those in example 90 to provide product (1S,2R)-A5 (yield: 24%). $^1$H NMR (400 MHz, DMSO-d$_6$) δ 8.00-7.93 (m, 2H), 7.44 (dt, J=7.4, 1.2 Hz, 2H), 7.26-7.11 (m, 5H), 3.54 (d, J=1.5 Hz, 2H), 3.11 (dt, J=12.6, 7.2 Hz, 2H), 2.76-2.64 (m, 2H), 2.62-2.49 (m, 3H), 2.05-1.85 (m, 3H), 1.45 (ddt, J=25.1, 13.2, 7.2 Hz, 2H), 0.95 (td, J=7.0, 4.9 Hz, 1H), 0.71 (td, J=7.0, 5.0 Hz, 1H); LRMS (ESI): 383.21 [M+H]$^+$.

Pharmacological Activity Test Example
Example 1 Activity Test at Molecular Level:
1. LSD1 In Vitro Activity Assay
Screening method: lysine-specific demethylase 1 (LSD1) activity screening
Instrument: microplate reader Envision™ (PerkinElmer, USA).
MATERIALS: Human recombinant LSD1, the LSD1 protein fragment fused with GST (aa158-end) was expressed and purified by *E. coli* expression system by the laboratory in house.
LSD1 Activity Detection Kit LANCE Ultra LSD1 Histone H3-Lysine 4 Demethylase Assay was purchased from Perkin Elmer;
The H3 polypeptide substrate ARTK(me1)QTARKSTG-GKAPRKQLA-GG-K(Biotin)-NH2 was synthesized by Jill Biochemical Company.
Principle: LSD1 specifically removes the methylation modification at the K4 lysine on the H3 polypeptide substrate, making it a substrate without methylation modification. The method employs a histone H3 methylated polypeptide (1-24) as a substrate to introduce a biotin label in the C segment of the substrate. LSD1 initiates the reaction with the participation of FAD to remve the methylation modification on the substrate H3K4. The Eu-labeled H3K4 background antibody binds to the substrate by antigen-antibody reaction, while the streptavidin-labeled receptor is bounded by the specific interaction of streptavidin and biotin. This allows the Eu-labeled donor to interact with the streptavidin-labeled receptor. In fluorescence resonance energy transfer, when two fluorophores are brought close due to biomolecular interaction, part of the energy captured by the cryptate at the time of excitation will be released, the emission wavelength of which is 620 nm; the other part of the energy is transferred to the receptor (acceptor), the emission wavelength of which is 665 nm. The 665 nm emission is only produced by FRET caused by the donor. Therefore, when biomolecules interact, there are two excitation lights at 620 nm and 665 nm; when there is no interaction, there is only one excitation light at 620 nm. The LSD1 demethylation activity was reflected by detecting the ratio of the fluorescence signals at the two emission wavelengths of 665 nm and 620 nm. Meanwhile, a blank control was set to determine the strength of the enzyme activity. ORY-1001 and GSK-2879552 were employed as positive inhibitors in the experiment.

Sample processing: Samples were dissolved in DMSO, stored at low temperature, and the concentration of DMSO in the final system was controlled within a range that won't affect the activity of the assay.

The activity of the sample was tested by primary screening at a single concentration, for example 20 μM. For samples exhibiting activity under certain conditions, for example, the inhibition rate (% Inhibition) being greater than 50, the active dose-dependent relationship, i.e., the IC50 value, was obtained by nonlinearly fitting the sample activity vs sample concentration, the software used for the calculation was Graphpad Prism 5, the model used for fitting was sigmoidal dose-response (variable slope), and for most inhibitor screening models, the bottom and top of the fitted curve were set to 0 and 100.

Experimental Results:

| Compound | $IC_{50}$ (nM) | Compound | $IC_{50}$ (nM) |
|---|---|---|---|
| A1 | 1.04 ± 0.10 | A93 | 560.90 ± 21.35 |
| A2 | 6.97 ± 0.73 | A94 | 70.35 ± 7.23 |
| A3 | 164.16 ± 18.20 | A95 | 36.98 ± 0.57 |
| A4 | 23.27 ± 0.52 | A96 | 93.96 ± 5.35 |
| A5 | 7.83 ± 0.46 | A97 | 304.50 ± 9.40 |
| A6 | 52.71 ± 1.40 | A98 | 72.02 ± 0.72 |
| A7 | 202.05 ± 30.62 | A99 | 64.27 ± 6.23 |
| A8 | 51.83 ± 1.80 | A100 | 513.76 ± 155.03 |
| A9 | 55.86 ± 18.77 | A101 | 532.09 ± 264.03 |
| A10 | 4.08 ± 1.00 | A102 | 69.28 ± 16.03 |
| A11 | 9.50 ± 0.38 | A103 | 80.49 ± 36.13 |
| A12 | 24.14 ± 2.96 | A104 | 140 ± 30 |
| A13 | 263.65 ± 10.82 | A105 | 206.67 ± 29.83 |
| A14 | 42.37 ± 18.19 | A106 | 357.21 ± 93.56 |
| A15 | 21.94 ± 1.40 | A107 | 424.72 ± 100.68 |
| A16 | 56.35 ± 1.34 | A108 | 296.57 ± 40.38 |
| A17 | 48.96 ± 4.45 | A109 | 747.11 ± 115.79 |
| A18 | 80.27 ± 6.70 | A110 | 52.92 ± 7.51 |
| A19 | 173.75 ± 38.54 | A111 | 16.17 ± 3.33 |
| A22 | 118.80 ± 4.24 | A112 | 121.60 ± 2.97 |
| A43 | 44.91 ± 1.77 | A113 | 108.60 ± 0.57 |
| A89 | 115.03 ± 8.21 | A114 | 22.97 ± 2.50 |
| A90 | 24.72 ± 0.61 | A115 | 125.30 ± 3.75 |
| A91 | 384.45 ± 54.64 | A116 | 18.03 ± 2.77 |
| A92 | 21.52 ± 1.88 | A117 | 78.92 ± 21.14 |
| (1R,2S)-A43 | 49.72 ± 8.04 | A118 | 68.75 ± 2.16 |
| (1S,2R)-A43 | 118.30 ± 0.63 | (1R,2S)-A5 | 1295.50 ± 352.85 |
| GSK-2879552 | 1222.08 ± 327.03 | (1S,2R)-A5 | 1846.50 ± 78.59 |

2. MAOA and MAOB In Vitro Activity Experiments

Screening method: Monoamine oxidase MAOA and MAOB activity screening

Instrument: microplate reader Envision™ (PerkinElmer, USA).

MATERIALS: Human recombinant MAOA, purchased from Promega; human recombinant MAOB, purchased from Sigma;

The MAOA and MAOB activity assay kit MAO-Glo was purchased from Promega. Principle: This method uses a specific luciferin derivative as a substrate, MAOA or MAOB can catalyze the conversion of substrate to luciferin methyl ester, and the product, luciferin methyl ester can produce fluorescence under the action of luciferase, thus reflecting the activity of MAOA or MAOB by the intensity of the fluorescent signal. Meanwhile, a blank control was set to determine the strength of the enzyme activity. Tranylcypromine (TCP) was employed as a positive inhibitor in the experiment.

Sample processing: Samples were dissolved in DMSO, stored at low temperature, and the concentration of DMSO in the final system was controlled within a range that won't affect the activity of the assay.

The activity of the sample was tested by primary screening at a single concentration, for example 100 μM. For samples exhibiting activity under certain conditions, for example, the inhibition rate (% Inhibition) being greater than 50, the active dose-dependent relationship, i.e., the $IC_{50}$ value, was obtained by nonlinearly fitting the sample activity vs the sample concentration, the software used for the calculation was Graphpad Prism 5, the model used for the fit was sigmoidal dose-response (variable slope), and for most inhibitor screening models, the bottom and top of the fitted curve were set to 0 and 100.

Experimental Results:

| Compound | $IC_{50}$ (μM)-MAOA | $IC_{50}$ (μM)-MAOB |
|---|---|---|
| GSK-2879552 | >100 | >100 |
| A1 | >100 | >100 |
| A2 | >100 | >100 |
| A3 | >100 | 12.78 ± 1.35 |
| A4 | >100 | >100 |
| A5 | >100 | >100 |
| A6 | >100 | >100 |
| A7 | >100 | >100 |
| A8 | >100 | >100 |
| A9 | >100 | 45.35 ± 0.35 |
| A10 | >100 | 18.01 ± 1.24 |
| A11 | >100 | >100 |
| A12 | >100 | 6.34 ± 0.51 |
| A13 | >100 | 3.81 ± 0.48 |
| A14 | >100 | 4.35 ± 0.51 |
| A15 | >100 | >100 |
| A16 | >100 | 10.41 ± 0.34 |
| A17 | >100 | 3.95 ± 0.08 |
| A18 | >100 | 177.30 ± 9.05 |
| A19 | >100 | 68.44 ± 9.72 |
| A20 | >100 | 22.14 ± 2.03 |
| A43 | 42.05 ± 10.47 | >100 |
| (1R,2S)-A5 | >100 | >100 |
| (1S,2R)-A5 | >100 | >100 |
| (1R,2S)-A43 | 29.68 ± 10.72 | >100 |
| (1S,2R)-A43 | 35.02 ± 6.68 | >100 |
| TCP | 11.55 ± 3.82 | 7.00 ± 0.75 |

Example 2 Activity Test on Cell Level:

1. CD86 Gene Expression Activation Test:

Experimental Principle:

Quantitative Real-time PCR is a method for measuring the total amount of the product after each polymerase chain reaction (PCR) cycle by using fluorescent chemicals in a DNA amplification reaction. Quantitative analysis of a specific DNA sequence in a sample to be tested was conducted by internal reference method or external reference method. There is a linear relationship between the Ct value of the template and the initial copy number of the template during the exponential phase of PCR amplification, which serves as a basis for quantification.

MATERIALS: Leukemia cell line MV4-11: pediatric acute lymphocytic leukemia, immuno-biphenotype, AF4-MLL fusion t(4,11), which is a sensitive cell line in which LSD1 inhibitors activate CD86 expression (Analytical Biochemistry 442 (2013)) 104-106).

Experimental Method:
1. 350 w/mL MV4-11 cells were accurately counted in a 12-well plate at 900 μL per well.
2. 3 μL of the test compound or positive compound was added to 147 μL of medium, mixed well, and 100 μL was taken and added to the 12-well plate with the cells, mixed, and incubated at 37° C., for 24 h in an incubator in 5% $CO_2$.
3. The sample was transferred to a 1.5 mL EP tube, centrifuged at 2000 rpm for 3 min, and the supernatant was removed. 500 mL of trizol was added for lysis and allowed to stand for 3 min.
4. 100 μL of chloroform was added and the EP tube was vigorously shaken for 15 s, and allowed to stand for 3 min, 12000 rpm, 15 min.
5. The supernatant was sucked into a new EP tube, and 200 μL of isopropanol was added, and placed in a −20° C. refrigerator for 15 min, 12000 rpm, 10 min.
6. The supernatant was removed, and 500 μL of 4° 75% ethanol was added and mixed, the mixture was centrifuged at 7,500 rpm for 10 min.
7. The supernatant was removed, and the EP tube was air-dried in a fume hood. 20-30 μL of RNase inactivated deionized water was added and mixed to measure the RNA concentration.
8. All samples were uniformly adjusted to 750 ng/8 μL, and RT-kit enzyme and substrate were added, reverse transcription was performed for 15 min under 42°, and enzyme inactivated at 85° for 2 min.
9. 100 μL of deionized water was added to the EP tube and mixed.
10. The QPCR sample was prepared at a ratio of 7.6 μL sample+0.65 μL forward primer+0.65 μL reverse primer+11.1 μL SYBR and placed in an eight-tube tube, centrifuged at 1500 rpm for 1 min, and then QPCR was started.
11. the data was collected and 2^(−ΔΔct) method was used to calculate the activation fold (BLOOD, 8 Aug. 2013 VOLUME 122, NUMBER 6).
Experimental Results:

| Compound | Activation ratio (10 nM) | Activation ratio (100 nM) | $EC_{50}$ (nM) |
|---|---|---|---|
| A1 | 2.26 ± 0.13 | 12.56 ± 0.92 | — |
| A2 | 6.33 ± 0.96 | 6.18 ± 0.57 | 0.81 ± 0.12 |
| A3 | 2.16 ± 0.05 | 6.80 ± 0.43 | — |
| A4 | 10.31 ± 0.91 | 10.77 ± 0.05 | 1.47 ± 0.37 |
| A5 | 1.05 ± 0.08 | 5.13 ± 1.02 | — |
| A6 | 2.71 ± 0.36 | 8.36 ± 0.61 | — |
| A8 | 1.89 ± 0.19 | 13.08 ± 1.22 | — |
| A9 | 1.99 ± 0.39 | 8.20 ± 0.20 | — |
| A10 | 1.86 ± 0.24 | 8.90 ± 1.65 | — |
| A11 | 7.71 ± 0.98 | 32.36 ± 4.27 | — |
| A12 | 7.36 ± 0.18 | 34.32 ± 9.95 | — |
| A14 | 2.15 ± 0.12 | 16.24 ± 2.14 | — |
| A15 | 12.51 ± 4.38 | 8.63 ± 0.93 | — |
| A16 | 9.02 ± 0.88 | 14.44 ± 1.06 | — |
| A17 | 2.47 ± 0.01 | 5.63 ± 0.61 | — |
| A18 | 3.20 ± 0.08 | 26.27 ± 1.03 | — |
| GSK-2879552 | 1.79 ± 0.37 | 9.76 ± 2.23 | — |

2. Test of Inhibitory Activities of Compound on Growth by MTS Method

Experimental Principle:
MTS assay detects the inhibitory effect of the tested compound to the growth of leukemia cells MV (4:11). The principle is that succinate dehydrogenase in mitochondria in living cells can reduce exogenous thiazole blue to insoluble blue crystal Formazan.

MATERIALS: Leukemia cell line MV4-11: pediatric acute lymphocytic leukemia, immuno-biphenotype, AF4-MLL fusion t (4,11), which is a cell line sensitive to the growth inhibiting LSD1 inhibitor (Cancer cell. 2012, 17; 21(4): 473-487).

Experimental Method:
1. MV4-11 cells in logarithmic growth phase were accurately counted at 16000 cells/mL, and the diluted cell solution was added to 96-well plates at 90 μL per well.
2. Fresh medium was taken and sequentially added to a 96-well plate with cell fluid at 90 μL per well.
3. In the compound plate, 10 mM of the test compound, the positive compounds ORY-1001 and GSK2879552 were sequentially diluted with a DMSO in a 3-time gradient, 8 points for each.
4. 2 μL of the diluted compound was respectively added to a 96-well plate containing 98 μL of blank medium, and for DMSO group, 98 μL of blank medium was added into 2 μL of DMSO, and mixed for further use.
5. The compound mixed with the medium was separately added to a 96-well plate in which cells were plated, in triplicate, 20 μL per well, and were mixed. The blank group was added with 200 μL of IMDM medium, and the DMSO group was added with 180 μL of the cell-containing medium in DMSO diluted with the medium.
6. Incubating for 10 days in an incubator at 37° C., 5% $CO_2$;
7. After 10 days, MTS was added and the values were read after 2.5 h of incubation.

Experimental Results:

| | MTS | |
|---|---|---|
| Compound | 3 D (μM) | 10 D (μM) |
| GSK-2879552 | >20 | 1.03 ± 0.36 |
| A1 | >20 | 0.037 ± 0.012 |
| A2 | >20 | 0.026 ± 0.0061 |
| A4 | >20 | 0.090 ± 0.028 |
| A6 | >20 | 1.02 ± 2.44 |
| A8 | >20 | 0.27 ± 0.37 |
| A9 | >20 | 1.16 ± 0.15 |
| A10 | >20 | 0.60 ± 1.09 |
| A11 | >20 | 0.21 ± 5.39 |
| A12 | >20 | 0.96 ± 3.85 |
| A14 | 8.17 ± 0.35 | 13.03 ± 0.42 |
| A15 | >20 | 0.33 ± 0.16 |
| A16 | >20 | 10.38 ± 2.41 |
| A18 | >20 | 3.00 ± 5.19 |
| A19 | >20 | 2.57 ± 1.66 |
| A20 | >20 | 0.52 ± 0.41 |
| A43 | >20 | 0.37 ± 0.12 |
| A90 | >20 | 0.030 ± 0.006 |
| A91 | >20 | 1.70 ± 0.83 |
| A92 | >20 | 0.132 ± 0.055 |
| A93 | >20 | 0.239 ± 0.004 |
| A94 | >20 | 0.039 ± 0.011 |
| A95 | >20 | 1.237 ± 0.844 |
| A96 | >20 | 0.159 ± 0.074 |
| A97 | >20 | 0.079 ± 0.041 |
| A98 | >20 | 0.064 ± 0.026 |
| A101 | 2.21 ± 0.63 | >20 |
| A102 | >20 | >20 |
| A105 | 1.95 ± 0.60 | 8.35 ± 0.71 |
| A106 | 1.71 ± 0.22 | 9.99 ± 1.50 |
| A107 | 0.75 ± 0.15 | 12.96 ± 1.90 |
| A108 | 2.64 ± 0.97 | 11.92 ± 2.04 |
| A109 | 2.1 ± 0.12 | 4.70 ± 1.68 |

-continued

| Compound | MTS | |
|---|---|---|
| | 3 D (µM) | 10 D (µM) |
| A110 | 2.59 ± 0.14 | 5.93 ± 0.35 |
| A111 | >20 | 19.86 ± 0.86 |
| A112 | >20 | >20 |
| A113 | >20 | >20 |
| A114 | 15.26 ± 0.78 | 7.84 ± 0.35 |
| A115 | >20 | 11.030 ± 0.978 |
| A116 | 19.43 ± 7.38 | 7.407 ± 2.533 |
| A117 | 15.41 ± 3.71 | 6.508 ± 2.016 |

-continued

| Compound | MTS | |
|---|---|---|
| | 3 D (µM) | 10 D (µM) |
| A118 | >20 | 10.219 ± 2.775 |
| (1R,2S)-A5 | >20 | 0.290 ± 0.190 |
| (1S,2R)-A5 | >20 | 3.77 ± 1.19 |
| (1R,2S)-A43 | >20 | 0.109 ± 0.079 |
| (1S,2R)-A43 | >20 | 0.960 ± 0.444 |

Example 3 Evaluation of Chronic Efficacy at the Animal Level:

Inhibitory Effect of LSD1 Inhibitor on the Growth of Subcutaneous Transplantation Tumor in Nude Mice of Human Acute Myeloid Leukemia MV4-11

Preparation method: the drug was accurately weighed, added with physiological saline, and prepared into 0.3 mg/ml, and the dosage volume was 10 ml/kg.

Animals: Balb/c nude mice, female, weighing 17-20 g, were purchased from Beijing Weitong Lihua Experimental Animal Technology Co., Ltd., and the number of animals per group was 5.

Cell line: MV4-11 cell line was used to inoculate at the right axilla of the nude mice, and the inoculation amount was $5 \times 10_6$/animal. The experiment can start after the transplanted tumor was formed.

Experimental Method:

For female nude mice weighing 20±3 g, MV4-11 cells were inoculated into the right axilla of nude mice at a inoculation amount of $5 \times 10^6$/mouse. After tumor formation, the diameter of the transplanted tumor was measured with a vernier caliper. And after the tumor has grown into 100-300 mm³, the animals were divided into model control group and drug-administered group according to body weight and tumor volume, with 5 mouse in each group. The model control group was given an equal amount of blank solvent. Oral gavage was used daily after grouping for 21 days.

Tumor weight inhibition rate %=$(Wc-W_T)/Wc \times 100\%$

Note: Wc: tumor weight of control group, $W_T$: tumor weight of treatment group.

Data processing: Data were expressed as mean±standard deviation, and statistical methods were T-TEST two-tailed analysis for significant analysis.

Experimental Results:

| Group | Tumor weight (g) | | | | | | Tumor inhibition rate (%) |
|---|---|---|---|---|---|---|---|
| | 1 | 2 | 3 | 4 | 5 | mean ± SD | |
| NS (solvent) qd p.o | 0.46 | 1.15 | 1.23 | 1.60 | 0.73 | 1.15 ± 0.46 | — |
| NS (solvent) qd p.o | 1.24 | 1.74 | 1.84 | 0.92 | 0.58 | | |
| GSK2879552 10 mg/kg qd p.o | 0.22 | 1.19 | 0.00 | 1.25 | 0.10 | 0.55 ± 0.55 | 51.96 |
| A1 50 mg/kg qd p.o | 0.05 | 1.82 | 0.07 | 0.61 | 0.11 | 0.53 ± 0.68 | 53.70 |
| A4 1 mg/kg qd p.o | 0.82 | 0.43 | — | 0.47 | — | 0.57 ± 0.18 | 50.10 |
| A43 5 mg/kg qd p.o | 0.68 | 0.65 | 0.59 | 0.02 | 0.01 | 0.39 ± 0.31 | 63.21 |
| (1R,2S)-A43 10 mg/kg qd p.o | 0.09 | 0.37 | 0.23 | 0.04 | 0.03 | 0.15 ± 0.13 | 85.66 |
| (1R,2S)-A90 10 mg/kg qd p.o | 0.27 | 0.01 | 0.37 | 0.08 | 0.04 | 0.15 ± 0.14 | 85.47 |

Example 4 Pharmacokinetic Experiment in Mouse

Experimental Method:

GSK2879552 15 µL of plasma sample was taken in a centrifuge tube, and 60 µL methanol:acetonitrile (1:1, v/v) was added, vortexed for 1 min, and centrifuged (11000 rpm) for 5 min, and then 20 µL of the supernatant was taken, added with 80 µL of water, vortexed and analyzed. The linear range of GSK2879552 was 0.3-12500 ng/mL.

A1 15 µL of plasma sample was taken in a centrifuge tube, and 60 µL methanol:acetonitrile (1:1, v/v) was added, vortexed for 1 min, and centrifuged (11000 rpm) for 5 min, and then 20 µL of the supernatant was taken and added with 80 µL of water, vortexed and analyzed. The linear range of A1 was 3.0-25000 ng/mL.

A2 15 µL of plasma sample was taken in a centrifuge tube, and 60 µL methanol:acetonitrile (1:1, v/v) was added, vortexed for 1 min, and centrifuged (11000 rpm) for 5 min, and then 20 µL of the supernatant was taken and added with 40 µL of water, vortexed and analyzed. The linear range of A2 was 0.3-5000 ng/mL.

A4 15 µL of plasma sample was taken in a centrifuge tube, and 60 µL methanol:acetonitrile (1:1, v/v) was added, vortexed for 1 min, and centrifuged (11000 rpm) for 5 min, and then 20 µL of the supernatant was taken and added with 40 µL of water, vortexed, and analyzed. The linear range of A4 was 1.0-5000 ng/mL.

The experimental methods of A43, A90, (1R, 2S)-A43 and (1R, 2S)-A90 are the same as A1.

Experimental Results:

Summary table of pharmacokinetic parameters of GSK2879552, A1, A2, A4, A43, A90, (1R, 2S)-A43 and (1R, 2S)-A90

| Compound | method of administration | $T_{1/2}$ (h) | $T_{max}$ (h) | $C_{max}$ (ng/mL) | $AUC_{last}$ (h*ng/mL) | $AUC_{INF\_obs}$ (h*ng/mL) | $CL_{\_obs}$ (mL/min/kg) | $MRT_{INF\_obs}$ (h) | $Vss_{\_obs}$ (mL/kg) | F % |
|---|---|---|---|---|---|---|---|---|---|---|
| GSK2879552 | p.o. | 4.24 | 0.167 | 9177 | 5353 | 5362 | — | 1.18 | — | 60.7 |
|  | i.v. | 4.36 | 0.083 | 7740 | 4409 | 4418 | 37.7 | 0.96 | 2180 |  |
| A1 | p.o. | 9.10 | 0.083 | 7197 | 11360 | 12882 | — | 10.2 | — | 43.7 |
|  | i.v. | 3.39 | 0.083 | 16700 | 14623 | 14724 | 11.3 | 3.77 | 2558 |  |
| A2 | p.o. | 4.11 | 0.167 | 544 | 645 | 650 | — | 2.78 | — | 23.5 |
|  | i.v. | 4.72 | 0.083 | 2020 | 1372 | 1381 | 121 | 1.90 | 13725 |  |
| A4 | p.o. | 6.67 | 0.250 | 470 | 1535 | 1630 | — | 7.19 | — | 73.0 |
|  | i.v. | 6.71 | 0.083 | 932 | 1052 | 1105 | 151 | 5.69 | 51527 |  |
| A43 | p.o. | 1.05 | 0.250 | 867 | 1229 | 1234 | — | 1.54 | — | 70.0 |
|  | i.v. | 1.86 | — | — | 878 | 890 | 187 | 1.24 | 13977 |  |
| A90 | p.o. | 1.93 | 0.167 | 3484 | 5216 | 5481 | — | 2.52 | — | 95.3 |
|  | i.v. | 3.99 | — | — | 2736 | 2761 | 60.4 | 4.00 | 14711 |  |
| (1R,2S)-A43 | p.o. | 7.96 | 0.250 | 1257 | 2500 | 2566 | — | 3.65 | — | 74.4 |
|  | i.v. | 6.98 | — | — | 1680 | 1712 | 97.4 | 3.18 | 18567 |  |
| (1R,2S)-A90 | p.o. | 5.15 | 0.250 | 2950 | 7219 | 7431 | — | 5.46 | — | 74.8 |
|  | i.v. | 3.23 | — | — | 4826 | 4843 | 34.4 | 2.93 | 6049 |  |

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A fluorine-substituted cyclopropylamine compound having a structure represented by the following general formula I, and a racemate, R-isomer, S-isomer, pharmaceutically acceptable salt, or a mixture thereof:

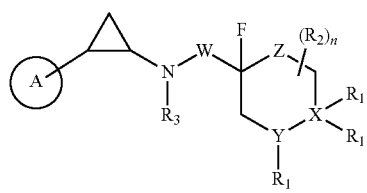

Formula I wherein:

A is selected from the group consisting of a substituted or unsubstituted aromatic ring and a substituted or unsubstituted 5-12 membered aromatic heterocyclic ring containing 1 to 4 heteroatoms selected from the group consisting of oxygen, sulfur and nitrogen, wherein each of the substituted benzene ring or substituted aromatic heterocycles comprises 1 to 3 substituents;

wherein the substituent on the substituted aromatic ring or substituted aromatic heterocyclic ring is independently selected from hydrogen, isotope of hydrogen, halogen, an unsubstituted or substituted C1-C12 straight or branched alkyl, unsubstituted or substituted C1-C12 straight or branched alkoxy, unsubstituted or substituted C2-C12 straight or branched unsaturated hydrocarbon group, unsubstituted C3-C6 cycloalkyl, C1-C6 straight or branched alkyl substituted by C1-C6 alkoxy, C1-C6 straight or branched alkyl substituted by C3-C6 cycloalkyl, hydroxy, cyano, nitro, C1-C6 straight or branched hydroxyalkyl or thiol, oxygen (=O), unsubstituted or substituted C6-C12 aryl, unsubstituted or substituted C6-C12 aryloxy, unsubstituted or substituted phenyloxy, carboxy, acetyl, and sulfonyl; the substituent is selected from the group consisting of halogen, a C1-C4 straight or branched alkyl, halogen-substituted C1-C4 straight or branched alkyl, C1-C4 alkyloxy, cyano-substituted phenyl;

or any two substituents on the substituted aromatic ring or substituted aromatic heterocyclic ring may be linked together with their adjacent carbon or hetero atom to form a 5-7 membered heterocyclic ring comprising 1 to 3 heteroatoms selected from N, O or S, and the 5-7 membered heterocyclic ring is optionally substituted by substituents selected from the group consisting of hydrogen, hydrogen isotope, halogen, C1-C6 straight or branched alkyl unsubstituted or substituted with 1-3 halogens, C1-C6 straight or branched alkoxy unsubstituted or substituted by 1 to 3 halogens, and hydroxyl;

each $R_1$ is independently selected from the group consisting of a substituted or unsubstituted aryl, substituted or unsubstituted heteroaryl, hydrogen, substituted or unsubstituted C1-C6 alkyl, —$SO_2Ra$, —NC(O)Ra, —$(CH_2)_m$C(O)ORa, —C(O)O$(CH_2)_m$Ra, —C(O)ORa, —C(O)Ra, —$(CH_2)_m$ORa, —C(O)NRaRb, —C(S)NRaRb, —CORa, —NRcRd, substituted or unsubstituted amino, substituted or unsubstituted urea, substituted or unsubstituted amide, substituted or unsubstituted sulfonamide, substituted or unsubstituted arylalkyl and substituted or unsubstituted heteroarylalkyl, wherein m is an integer from 1 to 3; the substituent is selected from the group consisting of halogen, hydroxy, carboxy, cyano, amino, C1-C4 alkyl, halogen-substituted C1-C4 alkyl, C1-C4 alkyl ester group, C1-C4 alkylsulfonyl, aminophenylamide

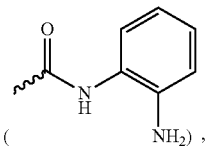

( $NH_2$), arylalkyl, and aryl;

each Ra is independently hydrogen, a substituted or unsubstituted phenyl, substituted or unsubstituted phenylmethyl, 3,5-dimethylisoxazol-4-yl, 1,2-dimethyl-1H-imidazol-4-yl, substituted or unsubstituted C3-C7 cycloalkyl, substituted or unsubstituted C3-C7 heterocyclic group, substituted or unsubstituted C3-C7 heterocycloalkyl, substituted or unsubstituted C1-C6 alkyl, substituted or unsubstituted C1-C6 alkenyl, substituted or unsubstituted C1-C4 alkoxy, substituted or unsubstituted C1-C3 alkylamino, —NHPh, substituted or unsubstituted 5-10 membered heteroaryl, substituted or unsubstituted arylalkyl, and substituted or unsubstituted heteroarylalkyl; the substituent is selected from the group consisting of: a C1-C4 alkyl, halogen-substituted C1-C4 alkyl, phenyl-substituted C1-C4 alkyl, C1-C4 alkyl ester group, C3-C7 cyclic group, C3-C7 cyclic group alkyl, C3-C7 heterocyclic group, benzyl-substituted C3-C7 heterocycloalkyl, aryl, halogen, C1-C4 alkoxy, C1-C4 halogenoalkyl, carboxyl, and a carboxyl-substituted benzyl group;

Rb is hydrogen or a C1-C3 alkyl, or when attached to the same atom,

Ra and Rb together form a 5- or 6-membered heterocycloalkyl ring;

Rc and Rd are each independently selected from hydrogen, a substituted or unsubstituted C1-C3 straight or branched alkyl, substituted or unsubstituted C3-C5 cycloalkyl, substituted or unsubstituted C1-C3 alkoxy, substituted or unsubstituted 4- to -6-membered heterocyclic group, substituted or unsubstituted C1-C3 alkylacyl, substituted or unsubstituted arylacyl, substituted or unsubstituted arylsulfonyl, substituted or unsubstituted benzyl, substituted or unsubstituted aryl; the C1-C3 straight or branched alkyl is optionally substituted by one or more selected from the group consisting of methylsulfonyl, a C1-C3 alkoxy, C1-C3 alkoxycarbonyl group, aryl; and the heterocyclic group contains one heteroatom selected from the group consisting of oxygen, sulfur and nitrogen;

$R_2$ is hydrogen or COOH;

$R_3$ is a C1-C4 alkyl, acyl, —C(O)CF$_3$ or hydrogen;

W is —(CH$_2$)$_{1-4}$ or —CH(Re)(CH$_2$)$_{0-3}$, wherein Re is CN or C1-C4 alkyl;

Y is N, C or none;

X is N or C;

Z is O or (CH$_2$)$_q$, wherein q is 0-2, and when q is 0, Z represents a bond;

n is 0-3;

with the proviso that when Z is O, Y is N and X is C.

2. The fluorine-substituted cyclopropylamine compound, or a racemate, R-isomer, S-isomer, pharmaceutically acceptable salt, or a mixture thereof of claim 1, wherein A is a substituted or unsubstituted benzene ring, or a substituted or unsubstituted 5-12 membered aromatic heterocyclic ring containing 1 to 4 heteroatoms selected from the group consisting of oxygen, sulfur and nitrogen, wherein each of the substituted benzene ring or substituted aromatic heterocycles comprises 1 to 3 substituents;

wherein the substituent on the substituted aromatic ring or substituted aromatic heterocyclic ring is independently selected from the group consisting of hydrogen, hydrogen isotope, halogen, carboxyl, nitro, a C1-C4 alkyl, C1-C4 alkanoyl, C1-C4 alkoxy, cyano, oxygen (=O), sulfonyl.

3. The fluorine-substituted cyclopropylamine compound, or a racemate, R-isomer, S-isomer, pharmaceutically acceptable salt, or a mixture thereof of claim 1, wherein each $R_1$ is independently selected from: a substituted or unsubstituted aryl, substituted or unsubstituted heteroaryl, hydrogen, substituted or unsubstituted C1-C4 alkyl, —SO$_2$Ra, —NC(O)Ra, —(CH$_2$)$_m$C(O)ORa, —C(O)ORa, —C(O)Ra, —(CH$_2$)$_m$ORa, —C(O)NRaRb, —NRcRd, substituted or unsubstituted arylalkyl, and substituted or unsubstituted heteroarylalkyl, wherein m is an integer of 1-3;

each Ra is independently hydrogen, a substituted or unsubstituted phenyl, substituted or unsubstituted phenylmethyl, substituted or unsubstituted C3-C7 cycloalkyl, substituted or unsubstituted C1-C4 alkyl, substituted or unsubstituted C1-C4 alkenyl, substituted or unsubstituted C1-C4 alkoxy, substituted or unsubstituted C1-C3 alkylamino, —NHPh, or substituted or unsubstituted 5-10 membered heteroaryl;

Rb is hydrogen or C1-C3 alkyl;

Rc and Rd are each independently selected from hydrogen, a C1-C3 straight or branched alkyl, substituted or unsubstituted C3-C5 cycloalkyl, substituted or unsubstituted C1-C3 alkoxy, substituted or unsubstituted 4- to -6-membered heterocyclic group, substituted or unsubstituted C1-C3 alkylacyl, substituted or unsubstituted arylacyl, substituted or unsubstituted arylsulfonyl, substituted or unsubstituted benzyl, substituted or unsubstituted aryl; the heterocyclic group contains one heteroatom selected from the group consisting of oxygen, sulfur and nitrogen;

the substituent is selected from the group consisting of a C1-C8 alkyl, C2-C8 alkenyl, C2-C8 alkynyl, C3-C8 cycloalkyl, 3- to 12-membered heterocyclic group, aryl, heteroaryl, halogen, hydroxy, carboxy (—COOH), C1-C8 aldehyde group, C2-C10 acyl, C2-C10 ester group, amino, and alkoxy.

4. The fluorine-substituted cyclopropylamine compound, or the racemate, R-isomer, S-isomer, pharmaceutically acceptable salts thereof, or the mixtures thereof of claim 1, wherein X is N, and $R_1$ attached to X is selected from a substituted or unsubstituted: aryl, heteroaryl, aralkyl, and heteroarylalkyl, wherein the substituent is selected from the group consisting of a C1-C8 alkyl, C2-C8 alkenyl, C2-C8 alkynyl, C3-C8 cycloalkyl, 3- to 12-membered heterocyclic group, aryl, heteroaryl, halogen, hydroxy, carboxy (—COOH), C1-C8 aldehyde group, C2-C10 acyl, C2-C10 ester group, amino, and alkoxy.

5. The fluorine-substituted cyclopropylamine compound, or a racemate, R-isomer, S-isomer, pharmaceutically acceptable salt, or a mixture thereof of claim 1, wherein X is N, and $R_1$ attached to X is selected from a substituted or unsubstituted: aryl C1-C4 alkyl, and heteroaryl C1-C4 alkyl, wherein the substituent is selected from the group consisting of C1-C8 alkyl, C2-C8 alkenyl, C2-C8 alkynyl, C3-C8 cycloalkyl, 3- to 12-membered heterocyclic group, aryl, heteroaryl, halogen, hydroxy, carboxy (—COOH), C1-C8 aldehyde group, C2-C10 acyl, C2-C10 ester group, amino, and alkoxy.

6. The fluorine-substituted cyclopropylamine compound, or a racemate, R-isomer, S-isomer, pharmaceutically acceptable salt, or a mixture thereof of claim 1, wherein W is —(CH$_2$)$_{1-2}$.

7. The fluorine-substituted cyclopropylamine compound, or a racemate, R-isomer, S-isomer, pharmaceutically acceptable salt, or a mixture thereof of claim 1, wherein the structure of compound is shown in formula (1R, 2S)-Ia or formula (1R, 2S)-Ib.

formula (1R, 2S)-Ia

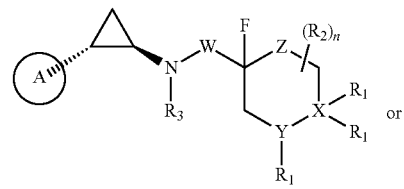

or formula (1S, 2R)-Ia

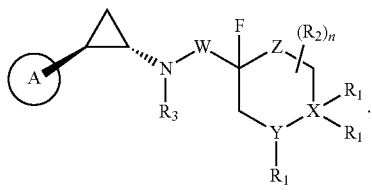

8. The fluorine-substituted cyclopropylamine compound, or a racemate, R-isomer, S-isomer, pharmaceutically acceptable salt, or a mixture thereof of claim 1, wherein the fluorine-substituted cyclopropylamine compound is selected from the following compounds:

| No. | Name | Structure |
|---|---|---|
| A1 | Benzyl 4-fluoro-4-((trans-2-phenylcyclopropyl)amino)methyl)piperidine-1-carboxylate | 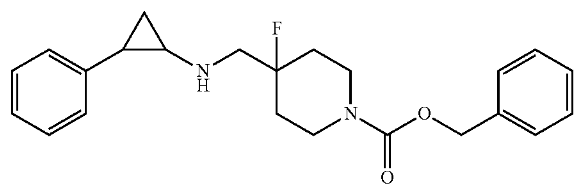 |
| A2 | N-((4-fluoropiperidin-4-yl)methyl)-trans-2-phenylcyclopropylamine | 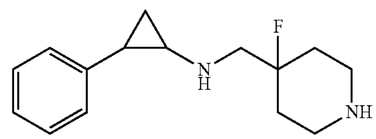 [SMILES: FC1(CNC2CC2c2ccccc2)CCNCC1] |
| A3 | Methyl 4-((4-fluoro-4-(((trans-2-phenylcyclopropyl)amino)methyl)piperidin-1-yl)methyl)benzoate | 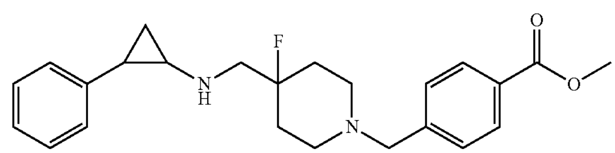 [SMILES: COC(=O)c1ccc(CN2CCC(F)(CNC3CC3c3ccccc3)CC2)cc1] |
| A4 | (1s, 4s)-4-fluoro-4-(((trans-2-phenylcyclopropyl)amino)methyl)cyclohexylamine | 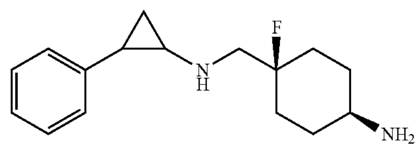 [SMILES: N[C@H]1CC[C@](F)(CNC2CC2c2ccccc2)CC1] |
| A5 | 4-((4-fluoro-4-(((trans-2-phenylcyclopropyl)amino)methyl)piperidin-1-yl)methyl)benzoic acid | 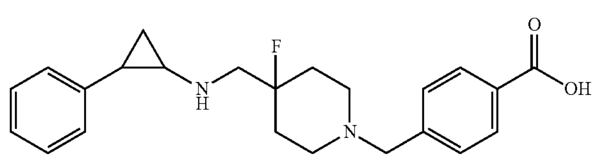 [SMILES: O=C(O)c1ccc(CN2CCC(F)(CNC3CC3c3ccccc3)CC2)cc1] |
| A6 | N-((1-benzyl-4-fluoropiperidin-4-yl)methyl)-trans-2-phenylcyclopropylamine | 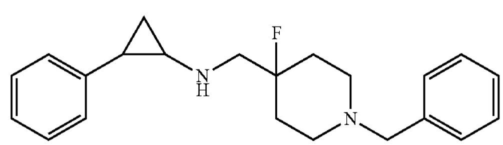 [SMILES: FC1(CNC2CC2c2ccccc2)CCN(Cc2ccccc2)CC1] |
| A7 | Methyl 3-(4-fluoro-4-(((trans-2-phenylcyclopropyl)amino)methyl)piperidin-1-yl)-propionate | 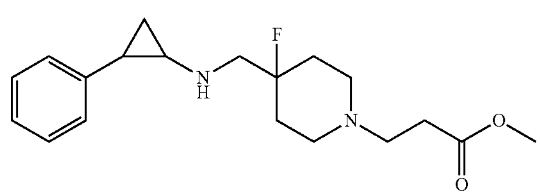 [SMILES: COC(=O)CCN1CCC(F)(CNC2CC2c2ccccc2)CC1] |

-continued

| No. | Name | Structure |
|---|---|---|
| A8 | 1-(4-fluoro-4-(((trans-2-phenylcyclopropyl)amino)methyl)piperidin-1-yl)-3-phenyl-1-propanone | 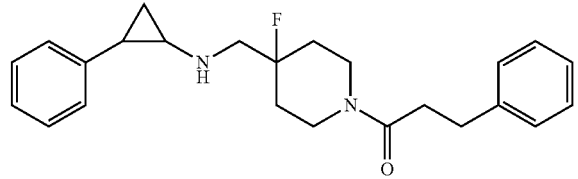 [SMILES: O=C(CCc1ccccc1)N1CCC(F)(CNC2CC2c2ccccc2)CC1] |
| A9 | Phenyl 4-fluoro-4-((trans-2-phenylcyclopropyl)amino)methyl)piperidine-1-carboxylate | 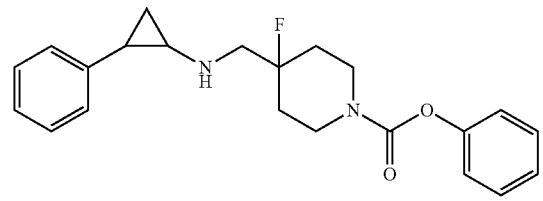 [SMILES: O=C(Oc1ccccc1)N1CCC(F)(CNC2CC2c2ccccc2)CC1] |
| A10 | 3-cyclohexyl-1-(4-fluoro-4-(((trans-2-phenylcyclopropyl)amino)methyl)piperidin-1-yl)-1-propanone | 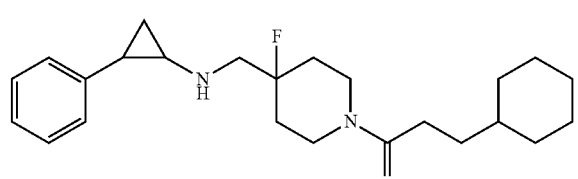 |
| A11 | 4-fluoro-N-methyl-4-(((trans-2-phenylcyclopropyl)amino)methyl)cyclohexane-1-amine | 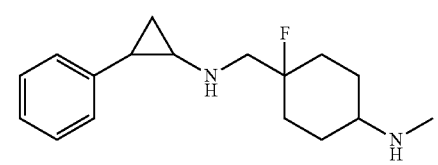 [SMILES: CNC1CCC(F)(CNC2CC2c2ccccc2)CC1] |
| A12 | N-((4-fluoro-1-(3-phenylpropyl)piperidin-4-yl)methyl)-trans-2-phenylcyclopropylamine | 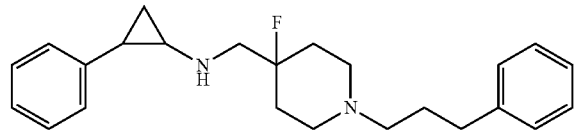 [SMILES: FC1(CNC2CC2c2ccccc2)CCN(CCCc2ccccc2)CC1] |
| A13 | N-((1-([1,1'-biphenyl]-4-methyl)-4-fluoropiperidin-4-yl)methyl)-trans-2-phenylcyclopropylamine | 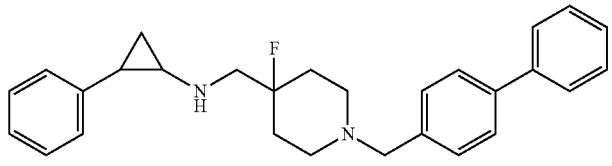 [SMILES: FC1(CNC2CC2c2ccccc2)CCN(Cc2ccc(-c3ccccc3)cc2)CC1] |
| A14 | N-((1-(3-cyclohexylpropyl)-4-fluoropiperidin-4-yl)methyl)-trans-2-phenylcyclopropylamine | 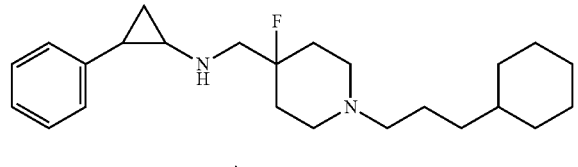 |
| A15 | N-((4-fluoro-1-methylpiperidin-4-yl)methyl)-trans-2-phenylcyclopropylamine | 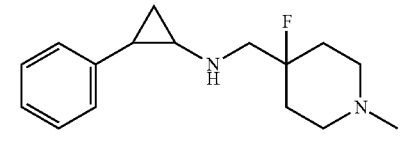 |
| A16 | N-((4-fluoro-1-(4-(methylsulfonyl)benzyl)piperidin-4-yl)methyl)-trans-2-phenylcyclopropylamine | 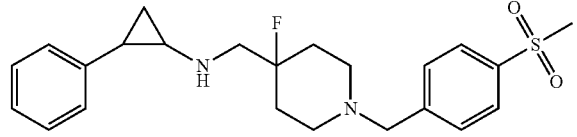 [SMILES: CS(=O)(=O)c1ccc(CN2CCC(F)(CNC3CC3c3ccccc3)CC2)cc1] |

-continued

| No. | Name | Structure |
|---|---|---|
| A17 | N-((4-fluoro-1-(naphthyl-2-methyl)piperidin-4-yl)methyl)-trans-2-phenylcyclopropylamine | 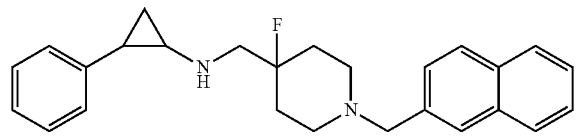 [SMILES: FC1(CNC2CC2c2ccccc2)CCN(Cc2ccc3ccccc3c2)CC1] |
| A18 | N-((1-fluorocyclohexyl)methyl)-trans-2-phenylcyclopropylamine | 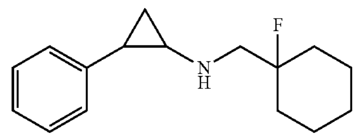 [SMILES: FC1(CNC2CC2c2ccccc2)CCCCC1] |
| A19 | Benzyl (4-fluoro-4-((trans-2-phenylcyclopropyl)amino)methyl)cyclohexyl)carbamate | 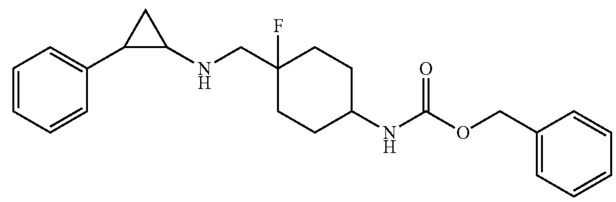 [SMILES: O=C(NC1CCC(F)(CNC2CC2c2ccccc2)CC1)OCc1ccccc1] |
| A20 | N-((4-fluoro-1-phenylpiperidin-4-yl)methyl)-trans-2-phenylcyclopropylamine | 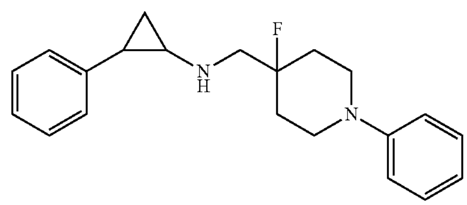 [SMILES: FC1(CNC2CC2c2ccccc2)CCN(c2ccccc2)CC1] |
| A21 | Cyclohexylmethyl 4-fluoro-4-(((trans-2-phenylcyclopropyl)amino)methyl)piperidine-1-carboxylate | 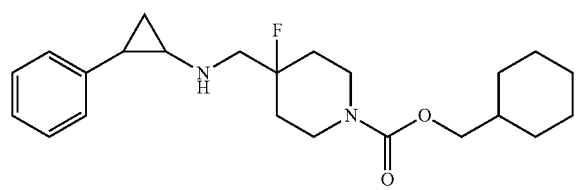 [SMILES: O=C(OCC1CCCCC1)N1CCC(F)(CNC2CC2c2ccccc2)CC1] |
| A22 | Pyridin-4-ylmethyl 4-fluoro-4-(((trans-2-phenylcyclopropyl)amino)methyl)piperidine-1-carboxylate | 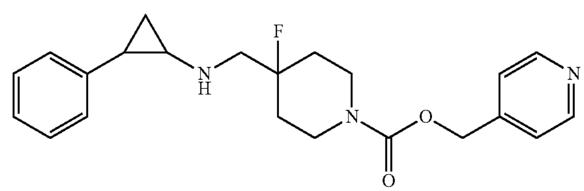 [SMILES: O=C(OCc1ccncc1)N1CCC(F)(CNC2CC2c2ccccc2)CC1] |
| A23 | Phenethyl 4-fluoro-4-(((trans-2-phenylcyclopropyl)amino)methyl)piperidine-1-carboxylate | 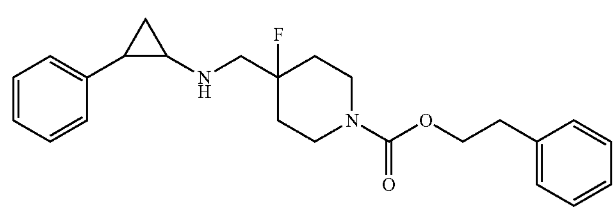 [SMILES: O=C(OCCc1ccccc1)N1CCC(F)(CNC2CC2c2ccccc2)CC1] |
| A24 | Ethyl 4-fluoro-4-(((trans-2-phenylcyclopropyl)amino)methyl)piperidine-1-carboxylate | 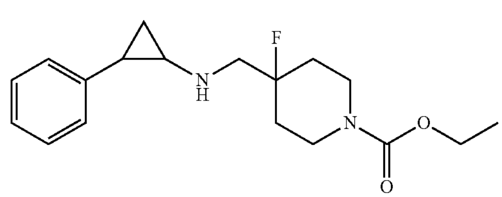 [SMILES: CCOC(=O)N1CCC(F)(CNC2CC2c2ccccc2)CC1] |

| No. | Name | Structure |
|---|---|---|
| A25 | (1H-indol-5-yl)methyl 4-fluoro-4-(((trans-2-phenylcyclopropyl)amino)methyl)piperidine-1-carboxylate | 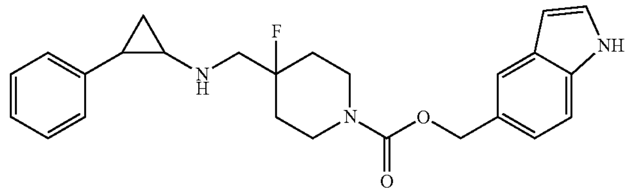 [SMILES: O=C(OCc1ccc2[nH]ccc2c1)N1CCC(F)(CNC2CC2c2ccccc2)CC1] |
| A26 | 1-(4-Fluoro-4-(((trans-2-phenylcyclopropyl)amino)methyl)pyridin-1-yl)-1-ethanone) | 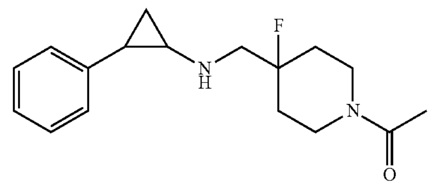 [SMILES: CC(=O)N1CCC(F)(CNC2CC2c2ccccc2)CC1] |
| A27 | Thiophen-2-ylmethyl-4-fluoro-4-(((trans-2-phenylcyclopropyl)amino)methyl)piperidine-1-carboxylate | 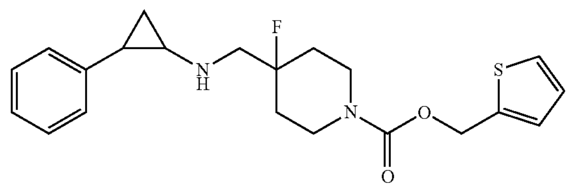 |
| A28 | Furan-2-ylmethyl-4-fluoro-4-(((trans-2-phenylcyclopropyl)amino)methyl)piperidine-1-carboxylate | 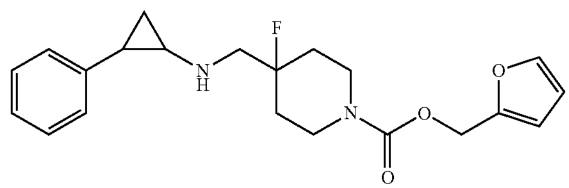 [SMILES: O=C(OCc1ccco1)N1CCC(F)(CNC2CC2c2ccccc2)CC1] |
| A29 | 4-fluorobenzyl-4-fluoro-4-(((trans-2-phenylcyclopropyl)amino)methyl)piperidine-1-carboxylate | 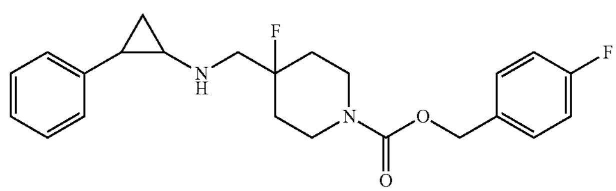 [SMILES: O=C(OCc1ccc(F)cc1)N1CCC(F)(CNC2CC2c2ccccc2)CC1] |
| A30 | 4-chlorobenzyl-4-fluoro-4-(((trans-2-phenylcyclopropyl)amino)methyl)piperidine-1-carboxylate | 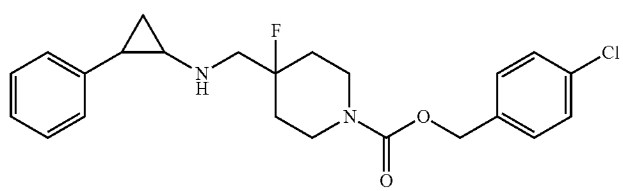 [SMILES: O=C(OCc1ccc(Cl)cc1)N1CCC(F)(CNC2CC2c2ccccc2)CC1] |
| A31 | 4-bromobenzyl-4-fluoro-4-(((trans-2-phenylcyclopropyl)amino)methyl)piperidine-1-carboxylate | 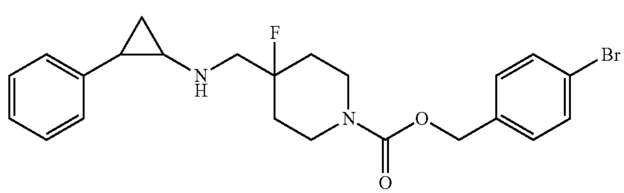 [SMILES: O=C(OCc1ccc(Br)cc1)N1CCC(F)(CNC2CC2c2ccccc2)CC1] |
| A32 | 4-methoxybenzyl-4-fluoro-4-(((trans-2-phenylcyclopropyl)amino)methyl)piperidine-1-carboxylate | 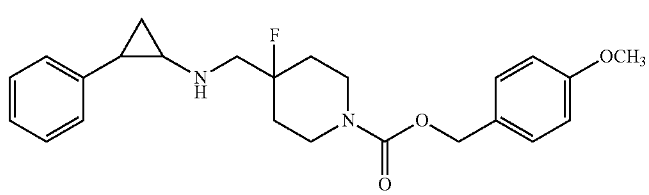 [SMILES: COc1ccc(COC(=O)N2CCC(F)(CNC3CC3c3ccccc3)CC2)cc1] |

-continued

| No. | Name | Structure |
|---|---|---|
| A33 | 4-trifluoromethylbenzyl-4-fluoro-4-(((trans-2-phenylcyclopropyl)amino)methyl)piperidine-1-carboxylate | 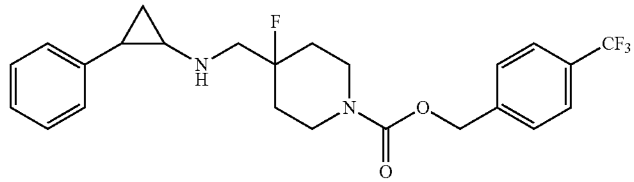 [SMILES: O=C(OCc1ccc(C(F)(F)F)cc1)N1CCC(F)(CNC2CC2c2ccccc2)CC1] |
| A34 | 3,5-Dimethoxybenzyl-4-fluoro-4-(((trans-2-phenylcyclopropyl)amino)methyl)piperidine-4-carboxylate | 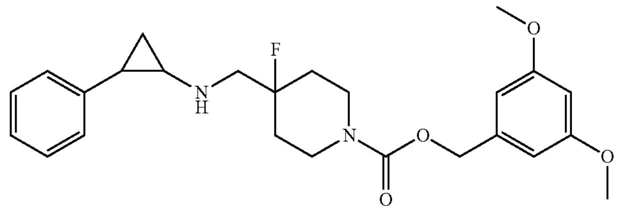 [SMILES: COc1cc(COC(=O)N2CCC(F)(CNC3CC3c3ccccc3)CC2)cc(OC)c1] |
| A35 | 4-((4-Fluoro-4-(((trans-2-phenylcyclopropyl)amino)methyl)piperidine-1-carbonyloxy)methyl)benzoic acid | 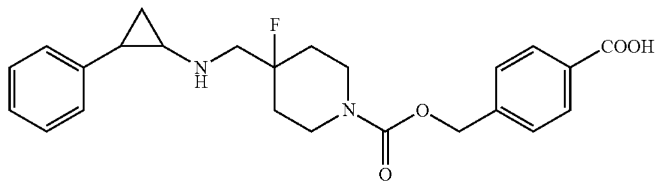 [SMILES: O=C(O)c1ccc(COC(=O)N2CCC(F)(CNC3CC3c3ccccc3)CC2)cc1] |
| A36 | (E)-1-(4-fluoro-4-(((trans-2-phenylcyclopropyl)amino)methyl)piperidin-1-yl)-3-phenyl-2-ene-1-propanone | 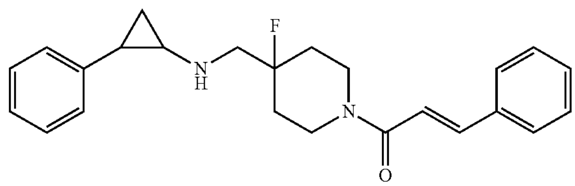 [SMILES: O=C(/C=C/c1ccccc1)N1CCC(F)(CNC2CC2c2ccccc2)CC1] |
| A37 | N-benzyl-4-fluoro-4-(((trans-2-phenylcyclopropyl)amino)methyl)piperidine-1-thioamide | 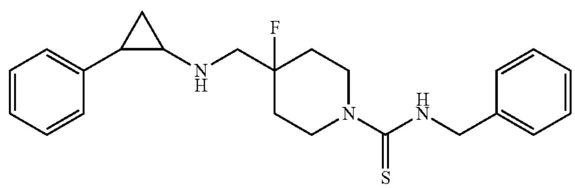 |
| A38 | N-benzyl-4-fluoro-4-(((trans-2-phenylcyclopropyl)amino)methyl)piperidine-1-carboxamide | 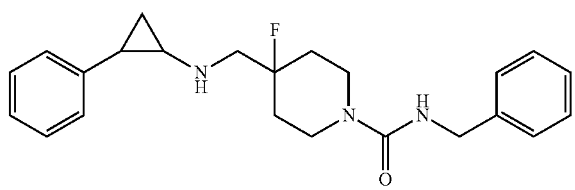 |
| A39 | N-((1-((benzyloxy)methyl)-4-fluoropiperidin-4-yl)methyl)-trans-2-phenylcyclopropylamine | 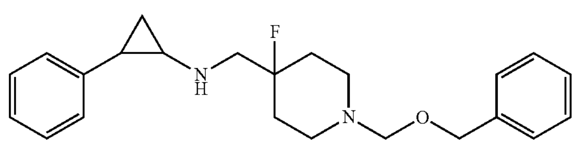 [SMILES: FC1(CNC2CC2c2ccccc2)CCN(COCc2ccccc2)CC1] |
| A40 | Benzyl 4-fluoro-4-(((trans-2-phenylcyclopropyl)amino)methyl)cyclohexane-1-carboxylate | 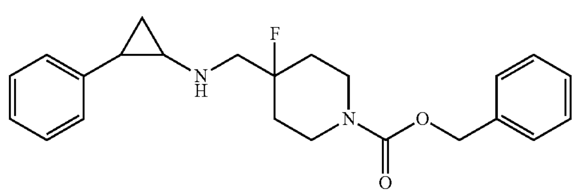 [SMILES: O=C(OCc1ccccc1)N1CCC(F)(CNC2CC2c2ccccc2)CC1] |

-continued

| No. | Name | Structure |
|---|---|---|
| A41 | Cyclopentylmethyl-4-fluoro-4-(((trans-2-phenylcyclopropyl)amino)methyl)piperidine-1-carboxylate | 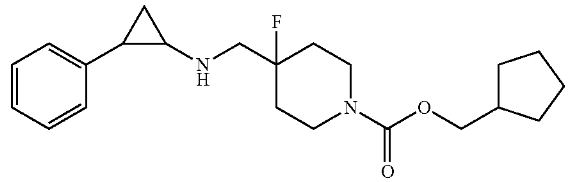 [SMILES: O=C(OCC1CCCC1)N1CCC(F)(CNC2CC2c2ccccc2)CC1] |
| A42 | Cyclobutylmethyl-4-fluoro-4-(((trans-2-phenylcyclopropyl)amino)methyl)piperidine-1-carboxylate | 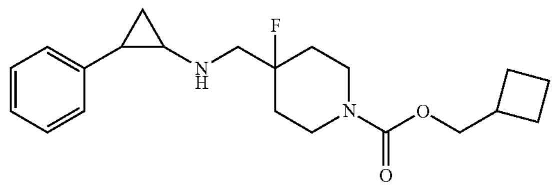 [SMILES: O=C(OCC1CCC1)N1CCC(F)(CNC2CC2c2ccccc2)CC1] |
| A43 | Piperidin-4-ylmethyl-4-fluoro-4-(((trans-2-phenylcyclopropyl)amino)methyl)piperidine-1-carboxylate | 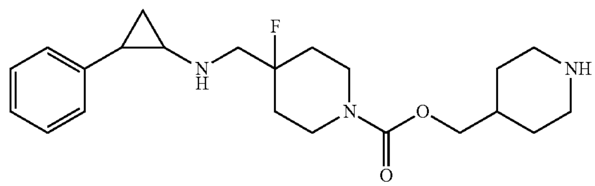 [SMILES: O=C(OCC1CCNCC1)N1CCC(F)(CNC2CC2c2ccccc2)CC1] |
| A44 | 3-chlorobenzyl-4-fluoro-4-(((trans-2-phenylcyclopropyl)amino)methyl)piperidine-1-carboxylate | 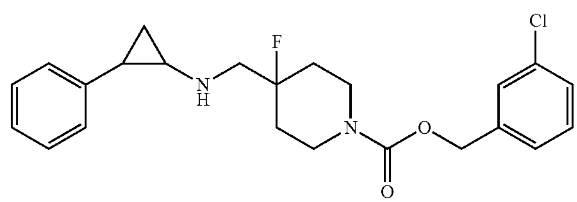 [SMILES: O=C(OCc1cccc(Cl)c1)N1CCC(F)(CNC2CC2c2ccccc2)CC1] |
| A45 | 2-chlorobenzyl-4-fluoro-4-(((trans-2-phenylcyclopropyl)amino)methyl)piperidine-1-carboxylate | 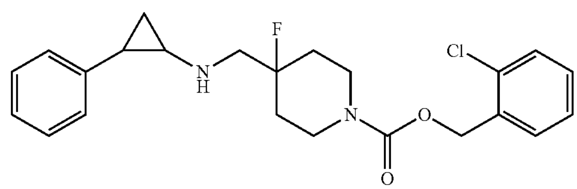 [SMILES: O=C(OCc1ccccc1Cl)N1CCC(F)(CNC2CC2c2ccccc2)CC1] |
| A46 | (4-fluoro-4-((trans-2-phenylcyclopropyl)amino)methyl)piperidin-1-yl)(phenyl)methanone | 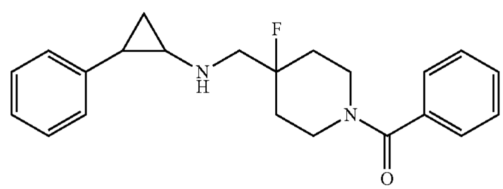 [SMILES: O=C(c1ccccc1)N1CCC(F)(CNC2CC2c2ccccc2)CC1] |
| A47 | 4-tert-butylbenzyl 4-fluoro-4-(((trans-2-phenylcyclopropyl)amino)methyl)piperidine-1-carboxylate | 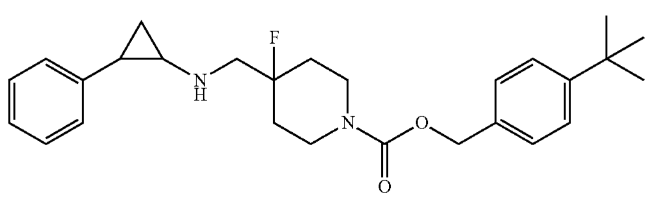 [SMILES: CC(C)(C)c1ccc(COC(=O)N2CCC(F)(CNC3CC3c3ccccc3)CC2)cc1] |
| A48 | Benzyl 4-fluoro-2-methyl-4-((trans-2-phenylcyclopropyl)amino)methyl)piperidine-1-carboxylate | 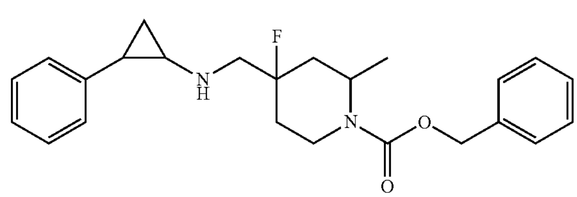 [SMILES: CC1CC(F)(CNC2CC2c2ccccc2)CCN1C(=O)OCc1ccccc1] |

-continued

| No. | Name | Structure |
|---|---|---|
| A49 | Benzyl 4-fluoro-2,6-dimethyl-4-((trans-2-phenylcyclopropyl)amino)methyl)piperidine-1-carboxylate | 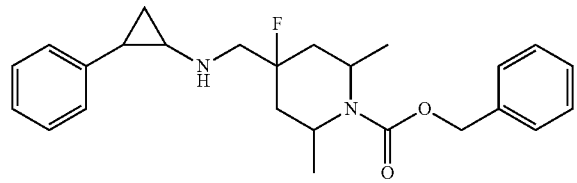 |
| A50 | Benzyl 4-fluoro-4-((trans-2-(naphthalen-2-yl)cyclopropyl)amino)methyl)piperidine-1-carboxylate | 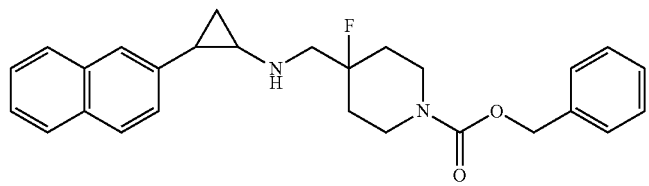 [SMILES: O=C(OCc1ccccc1)N1CCC(F)(CNC2CC2c2ccc3ccccc3c2)CC1] |
| A51 | Benzyl 4-fluoro-4-((trans-2-(benzothiophen-5-yl)cyclopropyl)amino)methyl)piperidine-1-carboxylate | 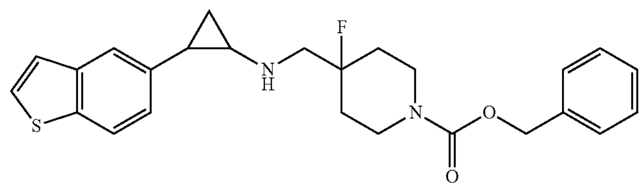 [SMILES: O=C(OCc1ccccc1)N1CCC(F)(CNC2CC2c2ccc3sccc3c2)CC1] |
| A52 | Benzyl 4-fluoro-4-((trans-2-(pyridin-4-yl)cyclopropyl)amino)methyl)piperidine-1-carboxylate | 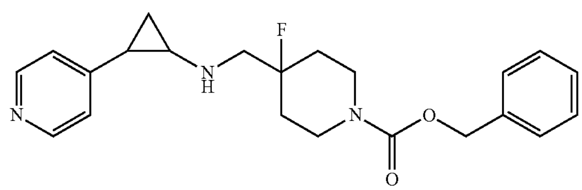 [SMILES: O=C(OCc1ccccc1)N1CCC(F)(CNC2CC2c2ccncc2)CC1] |
| A53 | Benzyl 4-fluoro-4-((trans-2-(1H-indol-5-yl)cyclopropyl)amino)methyl)piperidine-1-carboxylate | 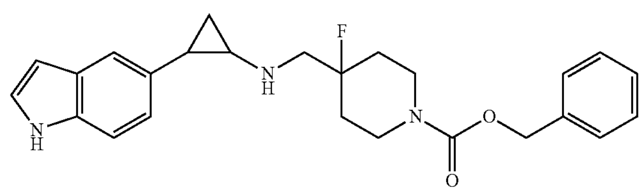 [SMILES: O=C(OCc1ccccc1)N1CCC(F)(CNC2CC2c2ccc3[nH]ccc3c2)CC1] |
| A54 | Benzyl 4-fluoro-4-((trans-2-(1-methyl-1H-indol-5-yl)cyclopropyl)amino)methyl)piperidine-1-carboxylate | 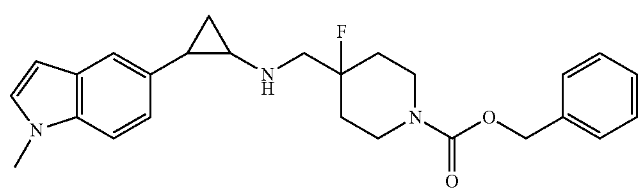 [SMILES: Cn1ccc2cc(C3CC3NCC3(F)CCN(C(=O)OCc4ccccc4)CC3)ccc21] |
| A55 | Benzyl 4-fluoro-4-((trans-2-(indoline-5-yl)cyclopropyl)amino)methyl)piperidine-1-carboxylate | 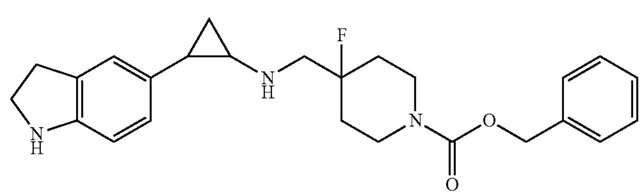 [SMILES: O=C(OCc1ccccc1)N1CCC(F)(CNC2CC2c2ccc3c(c2)CCN3)CC1] |
| A56 | Benzyl 4-fluoro-4-((trans-2-(1-(phenylsulfonyl)indoline-5-yl)cyclopropyl)amino)methyl)piperidine-1-carboxylate | 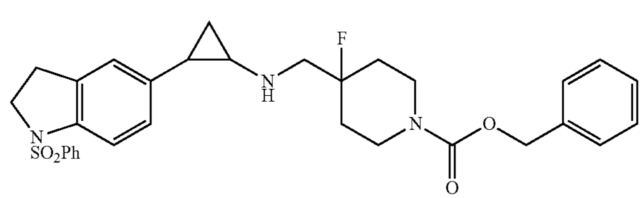 |

-continued

| No. | Name |
|---|---|
| A57 | Benzyl 4-fluoro-4-((trans-2-(1H-indol-3-yl)cyclopropyl)amino)methyl)piperidine-1-carboxylate |
| A58 | Benzyl 4-fluoro-4-((trans-2-(imidazo[1,2-α]pyridin-3-yl)cyclopropyl)amino)methyl)piperidine-1-carboxylate |
| A59 | Benzyl 4-fluoro-4-((trans-2-(2,3-dihydrobenzofuran-5-yl)cyclopropyl)amino)methyl)piperidine-1-carboxylate |
| A60 | benzyl 4-fluoro-4-((trans-2-(chroman-6-yl)cyclopropyl)amino)methyl)piperidine-1-carboxylate |
| A61 | benzyl 4-fluoro-4-(((trans-2-(2-oxo-1,2,3,4-tetrahydroquinolin-6-yl)cyclopropyl)amino)methyl)piperidine-1-carboxylate |
| A62 | Benzyl 4-fluoro-4-((trans-2-(thiophen-3-yl)cyclopropyl)amino)methyl)piperidine-1-carboxylate |
| A63 | Benzyl 4-fluoro-4-((trans-2-(furan-3-yl)cyclopropyl)amino)methyl)piperidine-1-carboxylate |
| A64 | Benzyl 4-fluoro-4-((trans-2-(thiazol-2-yl)cyclopropyl)amino)methyl)piperidine-1-carboxylate |

| No. | Name | Structure |
|---|---|---|
| A65 | Benzyl 4-fluoro-4-((trans-2-(4-fluorophenyl)cyclopropyl)amino)methyl)piperidine-1-carboxylate | 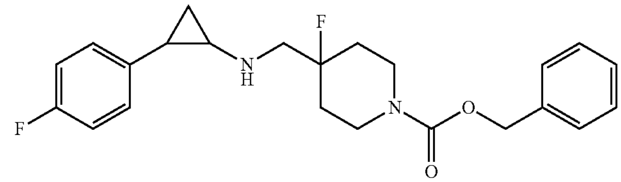 [SMILES: O=C(OCc1ccccc1)N1CCC(F)(CNC2CC2c2ccc(F)cc2)CC1] |
| A66 | Benzyl 4-fluoro-4-((trans-2-(4-cyanophenyl)cyclopropyl)amino)methyl)piperidine-1-carboxylate | 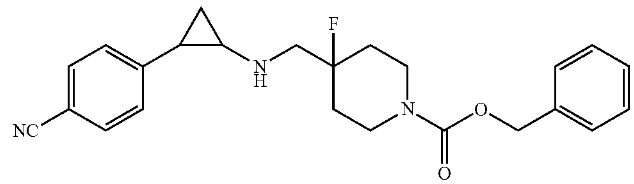 [SMILES: N#Cc1ccc(C2CC2NCC2(F)CCN(C(=O)OCc3ccccc3)CC2)cc1] |
| A67 | Benzyl 4-fluoro-4-((trans-2-(4-methoxyphenyl)cyclopropyl)amino)methyl)piperidine-1-carboxylate | 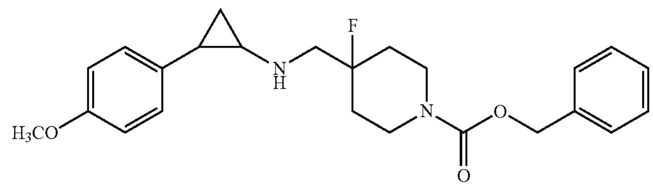 [SMILES: COc1ccc(C2CC2NCC2(F)CCN(C(=O)OCc3ccccc3)CC2)cc1] |
| A68 | Benzyl 4-fluoro-4-((trans-2-(2-acetylphenyl)cyclopropyl)amino)methyl)piperidine-1-carboxylate | 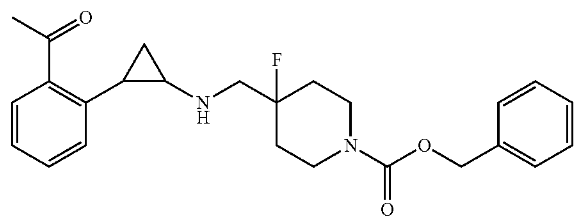 [SMILES: CC(=O)c1ccccc1C1CC1NCC1(F)CCN(C(=O)OCc2ccccc2)CC1] |
| A69 | Benzyl 4-fluoro-4-((trans-2-([1,1'-biphenyl]-4-yl)cyclopropyl)amino)methyl)piperidine-1-carboxylate | 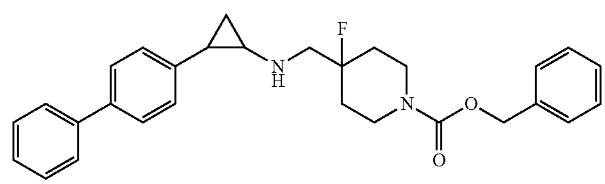 [SMILES: O=C(OCc1ccccc1)N1CCC(F)(CNC2CC2c2ccc(-c3ccccc3)cc2)CC1] |
| A70 | Benzyl 4-fluoro-4-((trans-2-(4-methylphenyl)cyclopropyl)amino)methyl)piperidine-1-carboxylate | 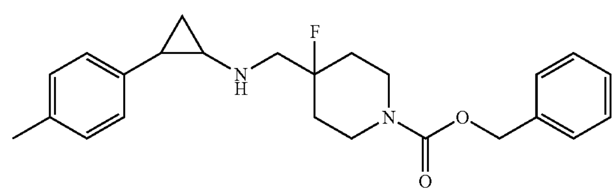 [SMILES: Cc1ccc(C2CC2NCC2(F)CCN(C(=O)OCc3ccccc3)CC2)cc1] |
| A71 | Benzyl 4-fluoro-4-((trans-2-(4-nitrophenyl)cyclopropyl)amino)methyl)piperidine-1-carboxylate | 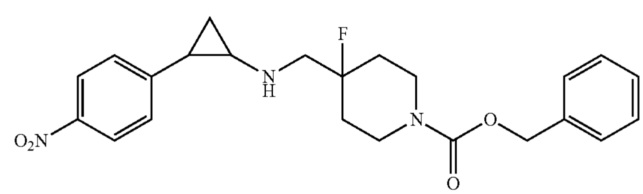 [SMILES: O=C(OCc1ccccc1)N1CCC(F)(CNC2CC2c2ccc([N+](=O)[O-])cc2)CC1] |
| A72 | 4-(trans-2-((1-((benzyloxy))carbonyl)-4-fluoropiperidin-4-yl)methyl)amino)cyclopropyl)benzoic acid | 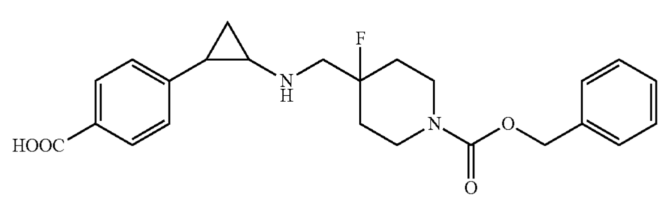 [SMILES: O=C(O)c1ccc(C2CC2NCC2(F)CCN(C(=O)OCc3ccccc3)CC2)cc1] |

-continued

| No. | Name | Structure |
|---|---|---|
| A73 | Benzyl 4-fluoro-4-(((trans-2-(3,4-difluorophenyl)cyclopropyl)amino)methyl)piperidine-1-carboxylate | 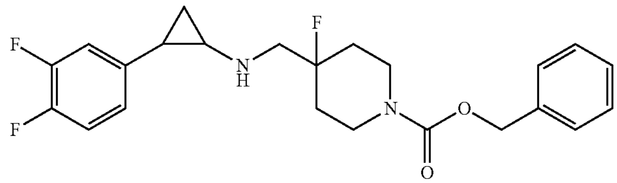 [SMILES: O=C(OCc1ccccc1)N1CCC(F)(CNC2CC2c2ccc(F)c(F)c2)CC1] |
| A74 | Benzyl 4-fluoro-4-((2,2,2-trifluoro-N-(trans-2-phenylcyclopropyl)acetamido)methyl)piperidine-1-carboxylate | 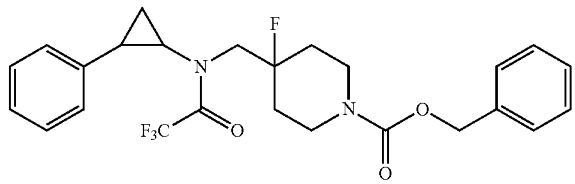 [SMILES: O=C(OCc1ccccc1)N1CCC(F)(CN(C(=O)C(F)(F)F)C2CC2c2ccccc2)CC1] |
| A75 | Benzyl 4-fluoro-4-((methyl(trans-2-phenyl-cyclopropyl)amino)methyl)piperidine-1-carboxylate | 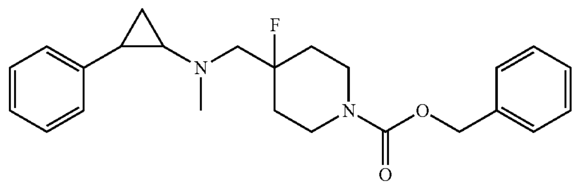 [SMILES: CN(CC1(F)CCN(C(=O)OCc2ccccc2)CC1)C1CC1c1ccccc1] |
| A76 | Benzyl 4-fluoro-4-(1-((trans-2-phenylcyclopropyl)amino)ethyl)piperidine-1-carboxylate | 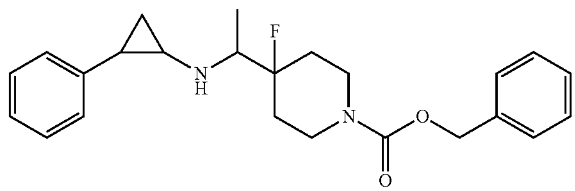 [SMILES: CC(NC1CC1c1ccccc1)C1(F)CCN(C(=O)OCc2ccccc2)CC1] |
| A77 | Benzyl 4-fluoro-4-((N-(trans-2-phenylcyclopropyl)acetamido)methyl)piperidine-1-carboxylate | 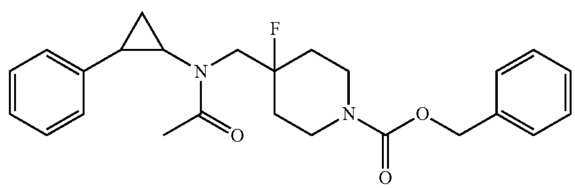 [SMILES: CC(=O)N(CC1(F)CCN(C(=O)OCc2ccccc2)CC1)C1CC1c1ccccc1] |
| A78 | 3-fluoro-3-(((trans-2-phenylcyclopropyl)amino)methyl)azetidin-1-carboxylate | 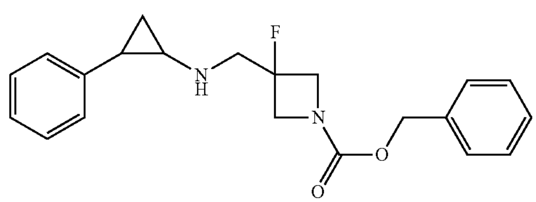 [SMILES: O=C(OCc1ccccc1)N1CC(F)(CNC2CC2c2ccccc2)C1] |
| A79 | 2-fluoro-2-(((trans-2-phenylcyclopropyl)amino)methyl)morpholine-4-carboxylate | 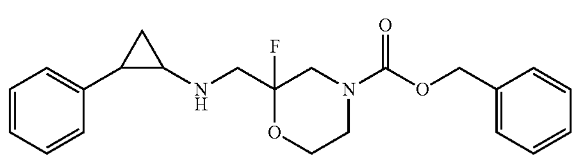 [SMILES: O=C(OCc1ccccc1)N1CCOC(F)(CNC2CC2c2ccccc2)C1] |
| A80 | Benzyl 4-fluoro-4-(2-((trans-2-phenylcyclopropyl)amino)ethyl)piperidine-1-carboxylate | 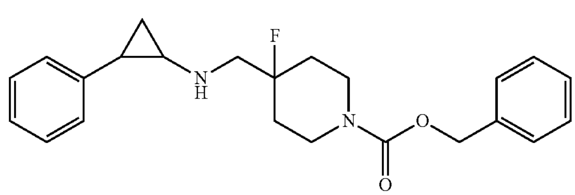 |

-continued

| No. | Name | Structure |
|---|---|---|
| A81 | Benzyl 3-fluoro-3-((trans-2-phenylcyclopropyl)amino)methyl)piperidine-1-carboxylate | 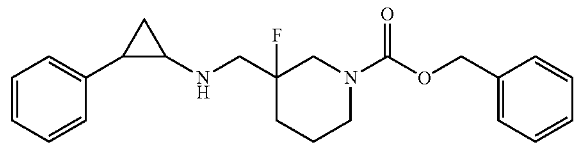 [SMILES: O=C(OCc1ccccc1)N1CCCC(F)(CNC2CC2c2ccccc2)C1] |
| A82 | N-((4-fluoro-1-(phenylsulfonyl)piperidin-4-yl)methyl)-trans-2-phenylcyclopropylamine | 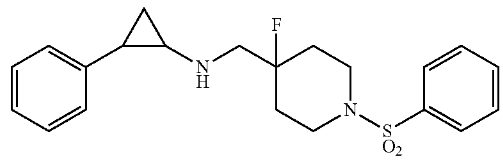 [SMILES: O=S(=O)(c1ccccc1)N1CCC(F)(CNC2CC2c2ccccc2)CC1] |
| A83 | 2-(4-Fluoro-4-(((trans-2-phenylcyclohexyl)amino)methyl)piperidin-1-yl)ethanol | 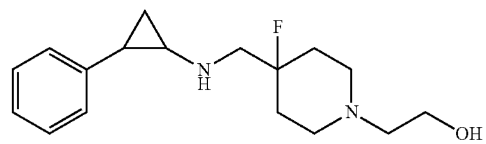 [SMILES: OCCN1CCC(F)(CNC2CC2c2ccccc2)CC1] |
| A84 | N-(4-fluoro-4-(((trans-2-phenylcyclopropyl)amino)methyl)cyclohexyl)acetamide | 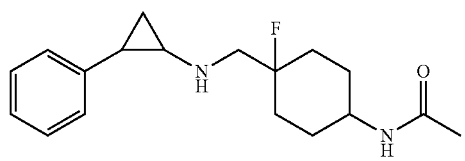 [SMILES: CC(=O)NC1CCC(F)(CNC2CC2c2ccccc2)CC1] |
| A85 | N-benzyl-4-fluoro-4-(((trans-2-phenylcyclopropyl)amino)methyl)cyclohexylamine | 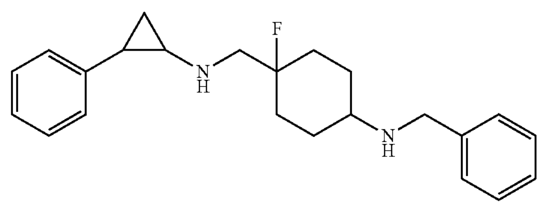 [SMILES: FC1(CNC2CC2c2ccccc2)CCC(NCc2ccccc2)CC1] |
| A86 | N-(4-fluoro-4-(((trans-2-phenylcyclopropyl)amino)methyl)cyclohexyl)aniline | 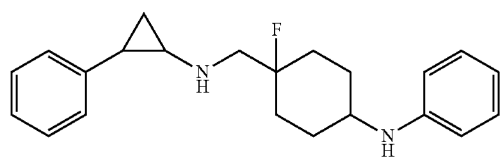 [SMILES: FC1(CNC2CC2c2ccccc2)CCC(Nc2ccccc2)CC1] |
| A87 | N-(4-Fluoro-4-(((trans-2-phenylcyclopropyl)amino)methyl)cyclohexyl)benzenesulfonamide | 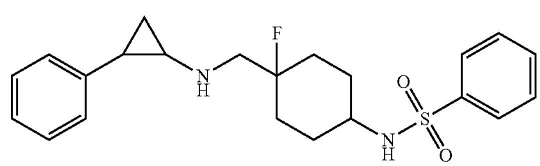 [SMILES: O=S(=O)(NC1CCC(F)(CNC2CC2c2ccccc2)CC1)c1ccccc1] |
| A88 | (1r,4r)-4-fluoro-4-(((trans-2-phenylcyclopropyl)amino)methyl)cyclohexylamine | 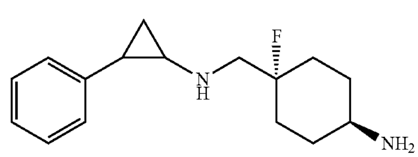 [SMILES: N[C@H]1CC[C@@](F)(CNC2CC2c2ccccc2)CC1] |
| A89 | (1-methylpiperidin-4-yl)methyl 4-fluoro-4-(((trans-2-phenylcyclopropyl)amino)methyl)piperidine-1-carboxylate | 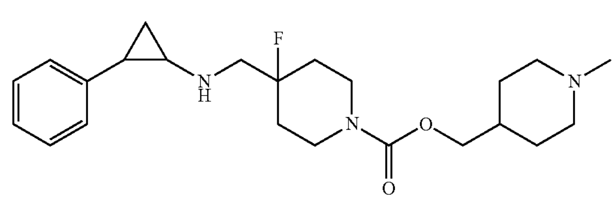 [SMILES: CN1CCC(COC(=O)N2CCC(F)(CNC3CC3c3ccccc3)CC2)CC1] |

| No. | Name | Structure |
|---|---|---|
| A90 | (1-benzylpiperidin-4-yl)methyl 4-fluoro-4-(((trans-2-phenylcyclopropyl)amino)methyl)piperidine-1-carboxylate | 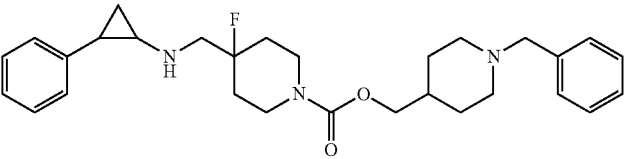 [SMILES: O=C(OCC1CCN(Cc2ccccc2)CC1)N1CCC(F)(CNC2CC2c2ccccc2)CC1] |
| A91 | 4-((4-(((4-Fluoro-4-(((trans-2-phenylcyclopropyl)amino)methyl)piperidine-1-carbonyl)oxo)methyl)piperdin-1-yl)methyl)benzoic acid | 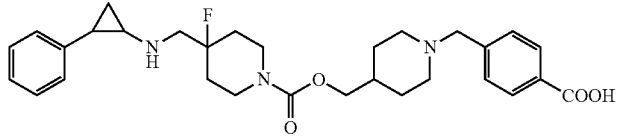 [SMILES: O=C(O)c1ccc(CN2CCC(COC(=O)N3CCC(F)(CNC4CC4c4ccccc4)CC3)CC2)cc1] |
| A92 | N-((4-fluoro-1-(piperidin-4-ylmethyl)sulfonyl)piperidin-4-yl)methyl)-trans-2-phenylcyclopropylamine | 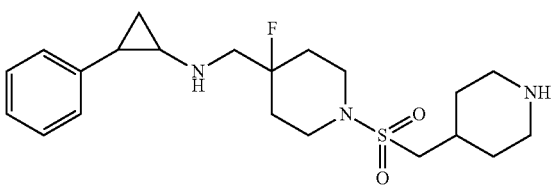 [SMILES: O=S(=O)(CC1CCNCC1)N1CCC(F)(CNC2CC2c2ccccc2)CC1] |
| A93 | N-((4-fluoro-1-(methylsulfonyl)piperidin-4-yl)methyl)-trans-2-phenylcyclopropylamine | 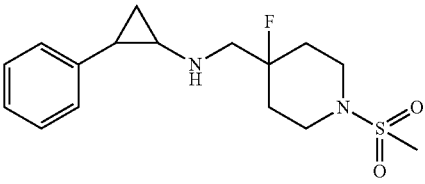 [SMILES: CS(=O)(=O)N1CCC(F)(CNC2CC2c2ccccc2)CC1] |
| A94 | Azetidin-3-ylmethyl 4-fluoro-4-(((trans-2-phenylcyclopropyl)amino)methyl)piperidine-1-carboxylate | 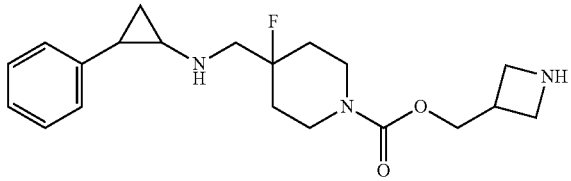 [SMILES: O=C(OCC1CNC1)N1CCC(F)(CNC2CC2c2ccccc2)CC1] |
| A95 | Piperidin-4-yl 4-fluoro-4-(((trans-2-phenylcyclopropyl)amino)methyl)piperidine-1-carboxylate | 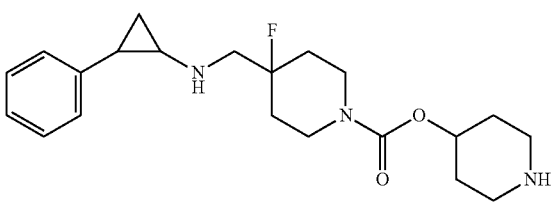 [SMILES: O=C(OC1CCNCC1)N1CCC(F)(CNC2CC2c2ccccc2)CC1] |
| A96 | 4-((4-Fluoro-4-(((trans-2-phenylcyclopropyl)amino)methyl)piperidin-1-yl)methyl)benzonitrile | 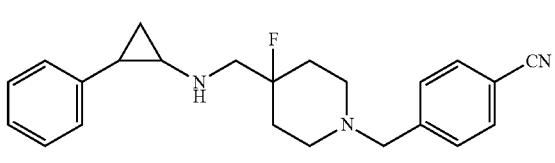 [SMILES: N#Cc1ccc(CN2CCC(F)(CNC3CC3c3ccccc3)CC2)cc1] |
| A97 | N-((4-fluoro-1-(piperidin-4-ylmethyl)piperidin-4-yl)methyl)-trans-2-phenyl cyclopropylamine | 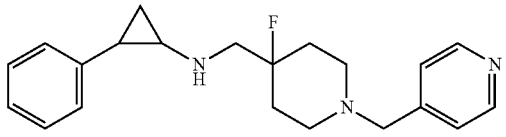 [SMILES: FC1(CNC2CC2c2ccccc2)CCN(Cc2ccncc2)CC1] |
| A98 | N-((4-fluoro-1-(thien-3-ylmethyl)piperidin-4-yl)methyl)-trans-2-phenylcyclopropylamine | 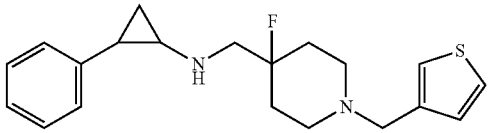 [SMILES: FC1(CNC2CC2c2ccccc2)CCN(Cc2ccsc2)CC1] |

-continued

| No. | Name | Structure |
|---|---|---|
| A99 | (1-(cyclopropylmethyl)piperidin-4-yl)methyl 4-fluoro-4-(((trans-2-phenylcyclopropyl)amino)methyl)piperidine-1-carboxylate | 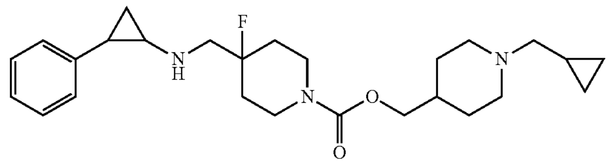 [SMILES: O=C(OCC1CCN(CC2CC2)CC1)N1CCC(F)(CNC2CC2c2ccccc2)CC1] |
| A100 | N-(2-Aminophenyl)-4-((4-fluoro-4-(((trans-2-phenylcyclopropyl)amino)methyl)piperidin-1-yl)methyl)benzamide | 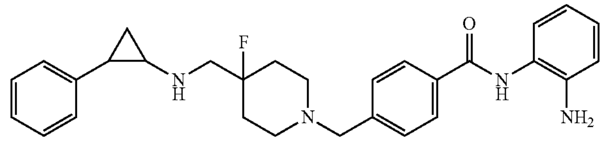 [SMILES: Nc1ccccc1NC(=O)c1ccc(CN2CCC(F)(CNC3CC3c3ccccc3)CC2)cc1] |
| A101 | tert-Butyl 4-((4-((2-(5-bromothien-2-yl))cyclopropyl)amino)methyl)-4-fluoropiperidin-1-yl)methyl)benzoate | 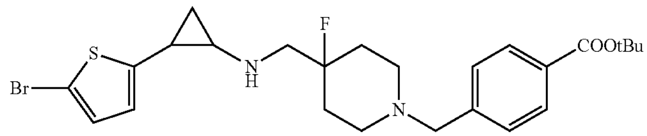 |
| A102 | 4-((4-(((2-(5-Bromothiophen-2-yl))cyclopropyl)amino)methyl)-4-fluoropiperidin-1-yl)methyl)benzoic acid | 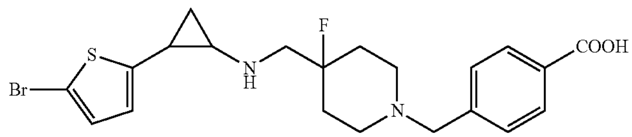 [SMILES: O=C(O)c1ccc(CN2CCC(F)(CNC3CC3c3ccc(Br)s3)CC2)cc1] |
| A103 | Methyl 4-((4-(((2-(5-bromothiophen-2-yl))cyclopropyl)amino)methyl)-4-fluoropiperidin-1-yl)methyl)benzoate | 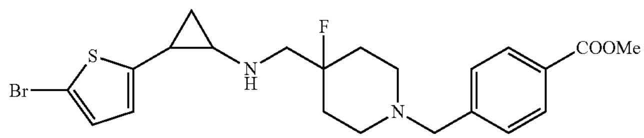 [SMILES: COC(=O)c1ccc(CN2CCC(F)(CNC3CC3c3ccc(Br)s3)CC2)cc1] |
| A104 | Ethyl 4-((4-(((2-(5-bromothiophen-2-yl))cyclopropyl)amino)methyl)-4-fluoropiperidin-1-yl)methyl)benzoate | 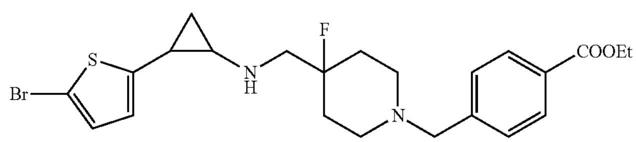 [SMILES: CCOC(=O)c1ccc(CN2CCC(F)(CNC3CC3c3ccc(Br)s3)CC2)cc1] |
| A105 | tert-Butyl 4-((4-fluoro-4-(((2-(5-(4-fluorophenyl)thiophen-2-yl)cyclopropyl)amino)methyl)piperidin-1-yl)methyl)benzoate | 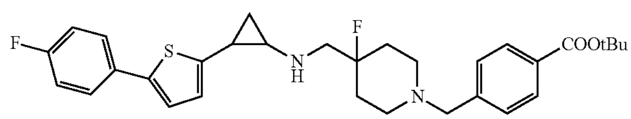 |
| A106 | tert-Butyl 4-((4-(((2-(5-(4-chlorophenyl)thiophen-2-yl)cyclopropyl)amino)methyl)-4-fluoropiperidin-1-yl)methyl)benzoate | 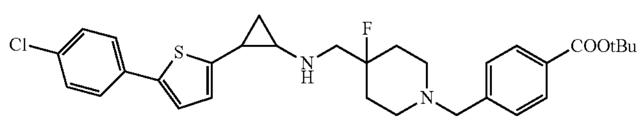 |
| A107 | tert-Butyl 4-((4-fluoro-4-(((2-(5-(4-((trifluoromethyl)phenyl)thiophen-2-yl)cyclopropyl)amino)methyl)piperidine-1-yl)methylbenzoate | 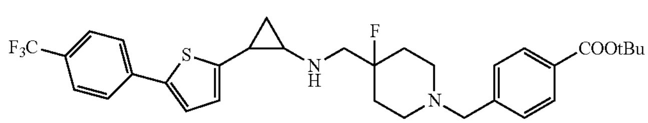 |
| A108 | tert-Butyl 4-((4-fluoro-4-(((2-(5-phenylthiophen-2-yl)cyclopropyl)amino)methyl)piperidin-1-yl)methyl)benzoic acid | 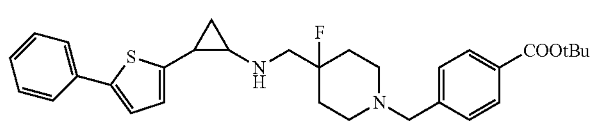 |
| A109 | tert-Butyl 4-((4-fluoro-4-(((2-(5-(naphthalen-1-yl)thiophen-2-yl)cyclopropyl)amino)methyl)piperidin-1-yl)methyl)benzoate | 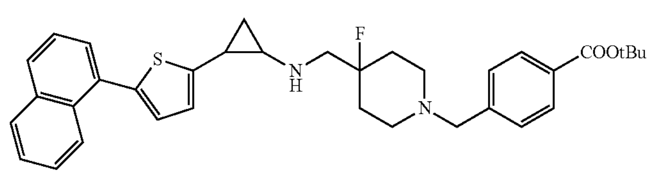 |

| No. | Name | Structure |
|---|---|---|
| A110 | Piperidin-4-ylmethyl 4-fluoro-4-(((2-(5-(4-(trifluoromethyl) phenyl)thiophen-2-yl)cyclopropyl) amino)methyl)piperdine-1-carboxylate | 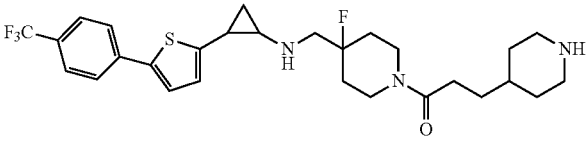 [SMILES: O=C(CCC1CCNCC1)N1CCC(F)(CNC2CC2c2ccc(-c3ccc(C(F)(F)F)cc3)s2)CC1] |
| A111 | Piperidin-4-ylmethyl 4-(((2-(5-bromothien-2-yl)cyclopropyl) amino)methyl)-4-fluoropiperidine-1-carboxylate | 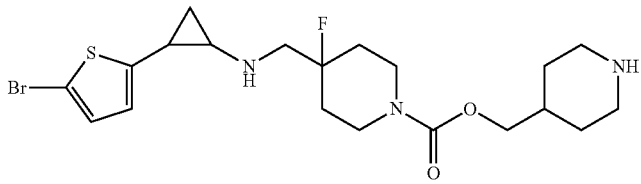 [SMILES: O=C(OCC1CCNCC1)N1CCC(F)(CNC2CC2c2ccc(Br)s2)CC1] |
| A112 | Piperidin-4-ylmethyl 4-fluoro-4-(((2-(6-(4-methoxyphenyl) pyridin-3-yl)cyclopropyl)amino) methyl)piperidin-1-carboxylate | 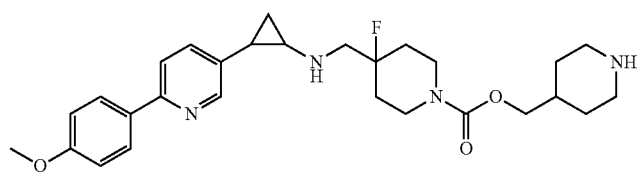 [SMILES: COc1ccc(-c2ccc(C3CC3NCC3(F)CCN(C(=O)OCC4CCNCC4)CC3)cn2)cc1] |
| A113 | Piperidin-4-ylmethyl 4-(((2-(5-cyclopropylthiophen-2-yl) cyclopropyl)amino)methyl)-4-fluoropiperidine-1-carboxylate | 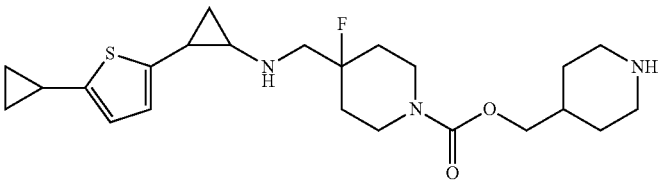 [SMILES: O=C(OCC1CCNCC1)N1CCC(F)(CNC2CC2c2ccc(C3CC3)s2)CC1] |
| A114 | Piperidin-4-ylmethyl 4-(((2-(5-((4-cyanophenyl)ethynyl) thiophen-2-yl)cyclopropyl)amino) methyl)-4-fluoropiperidine-1-carboxylate | 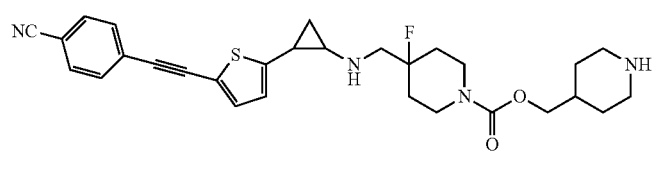 [SMILES: N#Cc1ccc(C#Cc2ccc(C3CC3NCC3(F)CCN(C(=O)OCC4CCNCC4)CC3)s2)cc1] |
| A115 | Piperidin-4-ylmethyl 4-fluoro-4-(((2-(6-phenylpyridin-3-yl) cyclopropyl)amino)methyl)piperidine-1-carboxylate | 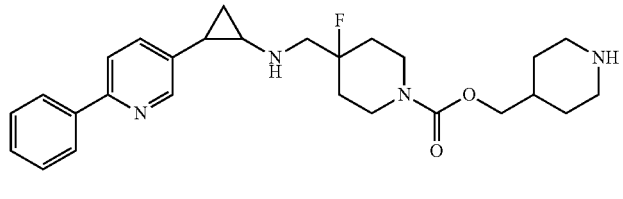 [SMILES: O=C(OCC1CCNCC1)N1CCC(F)(CNC2CC2c2ccc(-c3ccccc3)nc2)CC1] |
| A116 | Piperidin-4-ylmethyl 4-(((2-(6-(4-ethylphenoxy)pyridin-3-yl)cyclopropyl)amino)methyl)-4-fluoropiperidine-1-carboxylate | 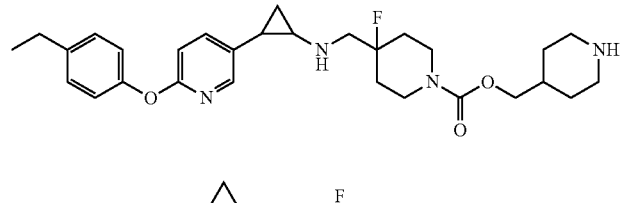 |
| A117 | Piperidin-4-ylmethyl 4-fluoro-4-(((2-(6-(3-(trifluoromethyl) phenyl)pyridin-3-yl)cyclopropyl) amino)methyl)piperidine-1-carboxylate | 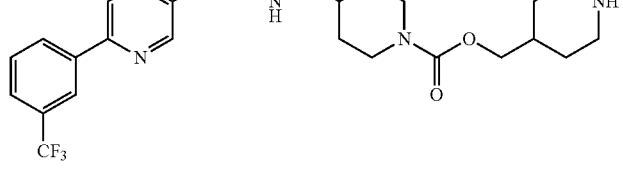 |

| No. | Name | Structure |
|---|---|---|
| A118 | Piperidin-4-ylmethyl 4-fluoro-4-(((2-(6-(4-fluorophenyl)pyridin-3-yl)cyclopropyl)amino)methyl)piperidine-1-carboxylate | 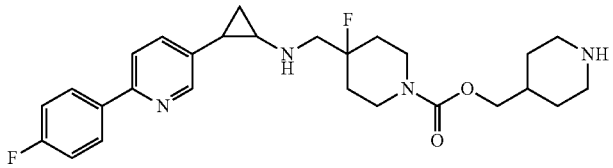 [SMILES: O=C(OCC1CCNCC1)N1CCC(F)(CNC2CC2c2ccc(-c3ccc(F)cc3)nc2)CC1] |
| A119 | Piperidin-4-ylmethyl 4-(((2-(6-(4-chlorophenyl)pyridin-3-yl)cyclopropyl)amino)methyl)-4-fluoropiperidine-1-carboxylate | 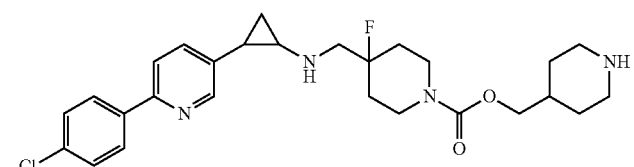 |
| A120 | Piperidin-4-ylmethyl 4-(((2-(6-(3,5-dimethoxyphenyl)pyridin-3-yl)cyclopropyl)amino)methyl)-4-fluoropiperidine 1-carboxylate | 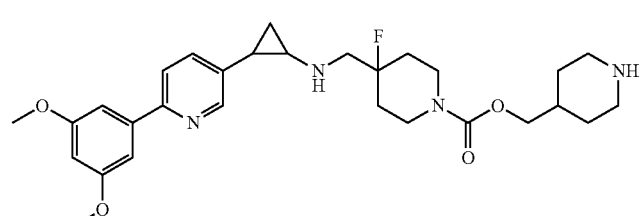 |
| A121 | Piperidin-4-ylmethyl 4-(((2-(6-bromopyridin-3-yl)cyclopropyl)amino)methyl)-4-fluoropiperidine-1-carboxylate | 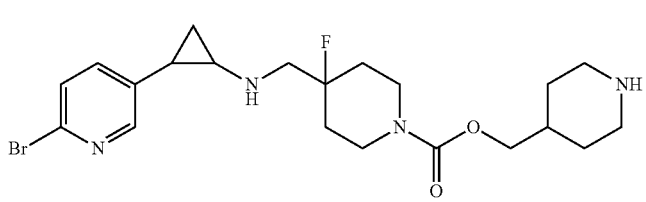 [SMILES: O=C(OCC1CCNCC1)N1CCC(F)(CNC2CC2c2ccc(Br)nc2)CC1] |
| A122 | Piperidin-4-ylmethyl 4-(((2-(2-chlorothiazol-5-yl)cyclopropyl)amino)methyl)-4-fluoropiperidine-1-carboxylate | 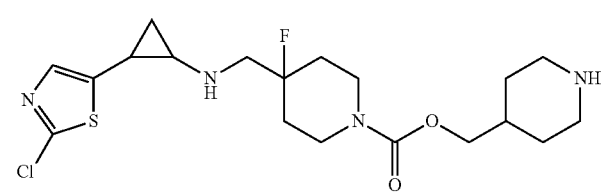 [SMILES: O=C(OCC1CCNCC1)N1CCC(F)(CNC2CC2c2cnc(Cl)s2)CC1] |
| A123 | Piperidin-4-ylmethyl 4-fluoro-4-(((2-(2-(4-fluorophenyl)thiazol-5-yl)cyclopropyl)amino)methyl)piperidine-1-carboxylate | 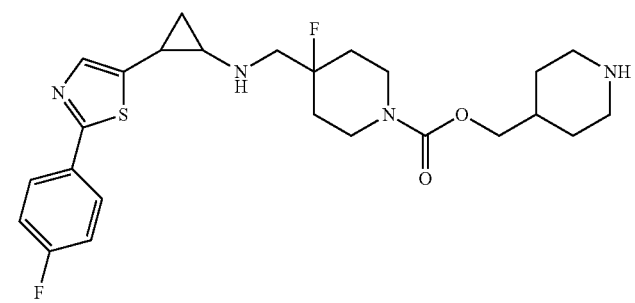 [SMILES: O=C(OCC1CCNCC1)N1CCC(F)(CNC2CC2c2cnc(-c3ccc(F)cc3)s2)CC1] |
| A124 | Piperidin-4-ylmethyl 4-(((2-(2-(4-chlorophenyl)thiazol-5-yl)cyclopropyl)amino)methyl)-4-fluoropiperidine-1-carboxylate | 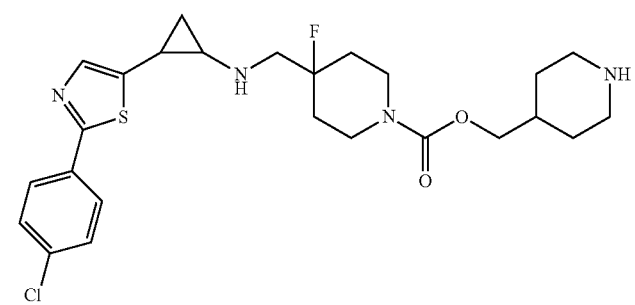 [SMILES: O=C(OCC1CCNCC1)N1CCC(F)(CNC2CC2c2cnc(-c3ccc(Cl)cc3)s2)CC1] |

-continued

| No. | Name | Structure |
|---|---|---|
| A125 | Piperidin-4-ylmethyl 4-fluoro-4-(((2-(2-phenylthiazol-5-yl)cyclopropyl)amino)methyl)piperidine-1-carboxylate | 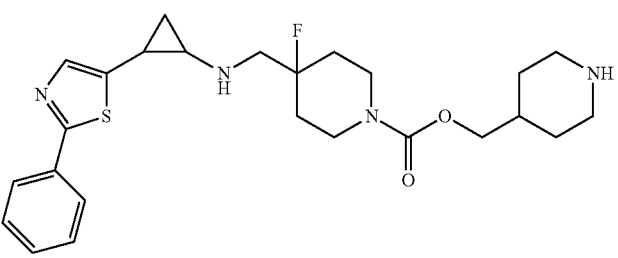 [SMILES: O=C(OCC1CCNCC1)N1CCC(F)(CNC2CC2c2cnc(-c3ccccc3)s2)CC1] |
| A126 | Piperidin-4-ylmethyl 4-fluoro-4-(((2-(2-(4-methoxyphenyl)thiazol-5-yl)cyclopropyl)amino)methyl)piperidin-1-carboxylate | 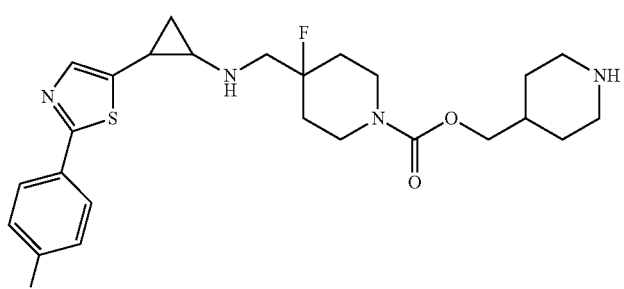 |
| A127 | Piperidin-4-ylmethyl 4-(((2-(2-(3,5-dimethoxyphenyl)thiazol-5-yl)cyclopropyl)amino)methyl)-4-fluoropiperidine-1-carboxylate | 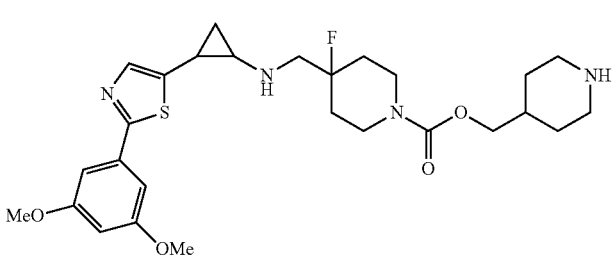 [SMILES: COc1cc(OC)cc(-c2ncc(C3CC3NCC3(F)CCN(C(=O)OCC4CCNCC4)CC3)s2)c1] |
| (1R,2S)-A43 | Piperidin-4-ylmethyl 4-fluoro-4-((((1R,2S)-2-phenylcyclopropyl)amino)methyl)piperidine-1-carboxylate | 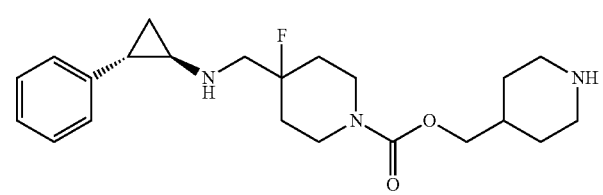 [SMILES: O=C(OCC1CCNCC1)N1CCC(F)(CN[C@@H]2C[C@H]2c2ccccc2)CC1] |
| (1S,2R)-A43 | Piperidin-4-ylmethyl 4-fluoro-4-((((1S,2R)-2-phenylcyclopropyl)amino)methyl)piperidine-1-carboxylate | 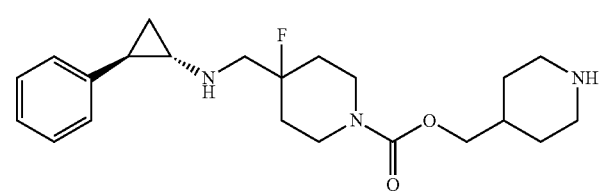 [SMILES: O=C(OCC1CCNCC1)N1CCC(F)(CN[C@H]2C[C@@H]2c2ccccc2)CC1] |
| (1R,2S)-A90 | (1-Benzylpiperidin-4-yl)methyl 4-fluoro-4-((((1R,2S)-2-phenylcyclopropyl)amino)methyl)piperidine-1-carboxylate | 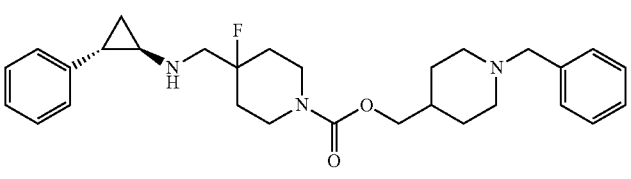 [SMILES: O=C(OCC1CCN(Cc2ccccc2)CC1)N1CCC(F)(CN[C@@H]2C[C@H]2c2ccccc2)CC1] |
| (1R,2S)-A5 | 4-((4-fluoro-4-((((1R,1S)-2-phenylcyclopropyl)amino)methyl)piperidin-1-yl)methyl)benzoic acid | 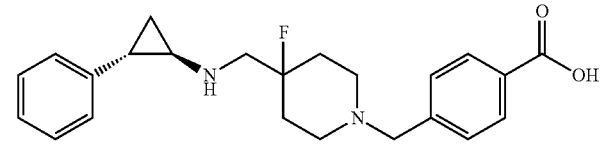 [SMILES: O=C(O)c1ccc(CN2CCC(F)(CN[C@@H]3C[C@H]3c3ccccc3)CC2)cc1] |

| No. | Name | Structure |
|---|---|---|
| (1S,2R)-A5 | 4-((4-fluoro-4-((((1S,2R)-2-phenylcyclopropyl)amino)methyl)piperidin-1-yl)methyl)benzoic acid | 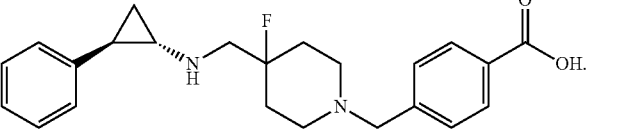 |

9. The fluorine-substituted cyclopropylamine compound, or a racemate, R-isomer, S-isomer, pharmaceutically acceptable salt, or a mixture thereof of claim 1, wherein, the pharmaceutically acceptable salt is prepared by reacting a compound of formula I with an inorganic or organic acid, the inorganic acid is hydrochloric acid, hydrobromic acid, sulfuric acid, nitric acid, aminosulfonic acid or phosphoric acid, and the organic acid is citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalene disulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, p-anilinesulfonic acid, 2-acetoxybenzoic acid or isethionic acid; or sodium, potassium, calcium, aluminum or ammonium salts formed from the compound of formula I with an inorganic base; or a salt formed from the compound of formula I with an organic base, and the salt is selected from methanamine salt, ethylamine salt or ethanolamine salt.

10. A pharmaceutical composition comprising one or more of a therapeutically effective amount of the fluorine-substituted cyclic amine compound, or the pharmaceutically acceptable salt, racemate, R-isomer or S-isomer of claim 1, and optionally one or more pharmaceutically acceptable carriers, excipients, adjuvants, auxiliary substances, and/or diluents.

11. A lysine-specific demethylase 1 (LSD1) inhibitor comprising a therapeutically effective amount of the fluorine-substituted cyclopropylamine compound, pharmaceutically acceptable salt, racemic, R-isomer, S-isomer thereof of claim 1.

12. The fluorine-substituted cycloamine compound, racemate, R-isomer, S-isomer or pharmaceutically acceptable salt thereof of claim 1 for the treatment of malignant tumor disease associated with methylase 1 (LSD1); and the disease is a cancer associated with lysine-specific demethylase 1 (LSD1), wherein the cancer is selected from the group consisting of brain cancer (glioma), glioblastoma, leukemia, Bannayan-Zonana syndrome, Cowden's disease, cerebellar dysplastic ganglioneuroma, breast cancer, inflammatory breast cancer, Wilms' tumor, Ewing Sarcoma, rhabdomyosarcoma, ependymoma, medulloblastoma, colon cancer, head and neck cancer, kidney cancer, lung cancer, liver cancer, melanoma, kidney cancer, ovarian cancer, pancreatic cancer, prostate cancer, sarcoma, osteosarcoma, giant cell tumor of thyroid gland and bone.

* * * * *